US008603493B2

(12) United States Patent
De La Mata De La Mata et al.

(10) Patent No.: US 8,603,493 B2
(45) Date of Patent: Dec. 10, 2013

(54) CARBOSILANE DENDRIMERS, PREPARATION METHOD THEREOF AND USE OF SAME

(75) Inventors: Francisco De La Mata De La Mata, Madrid (ES); Rafael Gómez Ramírez, Madrid (ES); Juan Carlos Flores Serrano, Madrid (ES); Ernesto De Jesús Alcañiz, Madrid (ES); Paula Ortega López, Madrid (ES); Ma Ángeles Muñoz Fernández, Madrid (ES); Jesús Francisco Bermejo Martin, Madrid (ES); Ma Jesus Serramía Lobera, Madrid (ES); Gerónimo Fernández Gómez-Chacón, Madrid (ES); Louis Chonco Jiménez, Madrid (ES); Maria Isabel Clemente Mayoral, Madrid (ES); José Luis Jiménez Fuentes, Madrid (ES)

(73) Assignee: Dendrico, S.L., Madrid (ES)

( * ) Notice: Subject to any disclaimer, the term of this patent is extended or adjusted under 35 U.S.C. 154(b) by 1063 days.

(21) Appl. No.: 11/989,157

(22) PCT Filed: Jul. 21, 2006

(86) PCT No.: PCT/ES2006/070111
§ 371 (c)(1),
(2), (4) Date: Sep. 10, 2009

(87) PCT Pub. No.: WO2007/010080
PCT Pub. Date: Jan. 25, 2007

(65) Prior Publication Data
US 2010/0034789 A1   Feb. 11, 2010

(30) Foreign Application Priority Data

Jul. 22, 2005   (ES) .................................. 200501810

(51) Int. Cl.
*A61K 9/00* (2006.01)
(52) U.S. Cl.
USPC ......................................................... 424/400
(58) Field of Classification Search
None
See application file for complete search history.

(56) References Cited

U.S. PATENT DOCUMENTS

| | | | | |
|---|---|---|---|---|
| 5,677,410 | A * | 10/1997 | Mager et al. | 528/15 |
| 5,834,020 | A * | 11/1998 | Margerum et al. | 424/484 |
| 6,184,313 | B1 * | 2/2001 | Roovers et al. | 525/474 |
| 2003/0216590 | A1 * | 11/2003 | Becke et al. | 556/81 |
| 2004/0009500 | A1 | 1/2004 | Benters et al. | |
| 2004/0040554 | A1 * | 3/2004 | Matsuoka et al. | 127/30 |
| 2006/0108320 | A1 * | 5/2006 | Lazovsky et al. | 216/2 |

FOREIGN PATENT DOCUMENTS

| | | | |
|---|---|---|---|
| EP | 1 302 475 A1 | | 4/2003 |
| EP | 1302475 A1 | * | 4/2003 |
| WO | WO 03/033027 A2 | | 4/2003 |
| WO | WO 03033027 A2 | * | 4/2003 |

OTHER PUBLICATIONS

Lang et al.. Siloxane and Carbosiloxane Based Dendrimers: Synthesis, Reaction Chemistry, and Potential Applications. Adv. Mater. 2001, 13(20):1523-1540.*
K. Inoue. Functional dendrimers, hyperbranched and star polymers. Prog. Polym. Sci. 25 (2000):453-571.*
Paula Ortega et al. Novel Water-Soluble Carbosilane Dendrimers: Synthesis and Biocompatibility. Eur. J. Inorg. Chem. 2006, 1388-1396. Published Online: Feb. 6, 2006.*
Lang et al. Siloxane and Carbosiloxane Basesd Dendrimers: Synthesis, Reaction Chyemistry, and Potential Applications. Adv. Mater. 2001, 13, 13(20):1523-1540.*
Inoue, K. Functional dendrimers, hyperbranched and star polymers. Prog. Polym. Sci. 25 (2000): 453-571.*
Zeng et al. Dendrimers in Supramolecular Chemistry: From Molecular Recognition to Self-Assembly. Chem. Rev. 1997, 97, 1681-1712.*
Osburn et al. Molecular engineering of organic reagents and catalysts using soluble polymers. Prog. Polym. Sci. 26 (2001):2015-2081.*
International Search Report for priority International Application No. PCT/ES2006/070111 mailed Nov. 23, 2006.
Van Heerbeecker, R. et al. "Divergent synthesis of carbosilane wedges as dendritic building blocks: a new strategy towards core functionalized carbosilane dendrimers". Tetrahedron Letters, 1999, vol. 40, pp. 7127-7130.
Beerens, H. et al. "Low-generation carbosilane dendrimerse as core for star polymers using a Ru-ROMP Catalyst". Journal of Molecular Catalysis A: Chemical, 2000, vol. 151, pp. 279-282.
Luhmann, B. et al. "Water Soluble Carbosiloxane Dendrimers". Phosphorus, Sulfur and Silicon, 2001, vol. 169, pp. 157-160.
Aulenta, F. et al. "Dendrimers: a new class of nanoscopic containers and delivery devices". European Polymer Journal, 2003, vol. 39, pp. 1741-1771.

* cited by examiner

*Primary Examiner* — Robert A Wax
*Assistant Examiner* — Olga V Tcherkasskaya
(74) *Attorney, Agent, or Firm* — Klauber & Jackson LLC

(57) ABSTRACT

Novel carbosilane dendrimers, their preparation and their uses. The dendrimers of the invention have secondary, tertiary and quaternary amino groups at their branch ends. Their possible uses include vehicles for carrying anionic-charged molecules in the blood, such as nucleic acids, among them ODN and RNAi, and other anionic drugs with which they have the capacity of interacting, protecting them from interaction with plasma protein and/or increasing their penetration rate in target cells. In the cases where the bond is long-lasting, the dendrimers of the invention can be used to fix anionic molecules to surfaces. Their uses also include their administration as active ingredients to prevent or treat diseases caused by micro-organisms with whose structure and/or life cycle they interfere.

99 Claims, 43 Drawing Sheets
(7 of 43 Drawing Sheet(s) Filed in Color)

1G-[Si(OCH$_2$-(C$_6$H$_3$)-3,5-(OCH$_2$CH$_2$NMe$_3^+$I$^-$)$_2$)]$_4$ (22)   2G-[Si(O(CH$_2$)$_2$N(Me)(CH$_2$)$_2$NMe$_3^+$I$^-$)]$_8$ (26)

1G-[Si(OCH$_2$CH$_2$Me$^+_3$I$^-$)$_2$]$_4$ (19)   3G-[Si(OCH$_2$CH$_2$Me$^+_3$I$^-$)]$_{16}$ (27)

A

B

U87-MG+NN

U87-MG+NN16

Ctrl

1:1

1:2

1:4

1:8

SK-N-MC+NN16

Ctrl

1:1

1:2

1:4

1:8

CARBOSILANE DENDRIMERS, PREPARATION METHOD THEREOF AND USE OF SAME

CROSS-REFERENCE TO RELATED APPLICATIONS

This application is the National Stage of International Application No. PCT/ES2006/070111, filed Jul. 21, 2006, which International Application claims priority to ES P200501810, filed Jul. 22, 2005.

FIELD OF THE INVENTION

The invention relates to three-dimensional molecules called dendrimers, specifically to those of carbosilane type with terminal moieties which contain primary, secondary, tertiary or quaternary amino groups, to the processes for their preparation and to their use. Among the fields wherein their use is possible, their use as vehicles for nucleic acids and other molecules with pharmacological activity with negative charge is highlighted, as it permits increasing the half-life of said drugs and their bioavailability and decreasing the dose necessary to achieve the desired biological effect. The prevention or the treatment of diseases produced by micro-organisms with whose structure and/or life cycle they interfere is another of the applications of the dendrimers of the invention.

BACKGROUND

Dendrimers have received great attention in recent years due to their possible use in applications as varied as catalysis on a nanoscale, chemical sensors, unimolecular micelles, imitation of the enzyme function, molecule encapsulation, molecular recognition, diagnostic agents and also as vehicles for carrying of genes and drugs. Excellent reviews which include all these applications are published in the bibliography.[1,31-38]

One of the areas wherein the dendrimers have been most studied is Gene Therapy (introduction of genetic material in a cell with therapeutic purposes). Until now, the most widely used vectors for carrying nucleic acids have been viral ones. However, the use of viral vectors has been associated to the appearance of some problems such as adverse immunological effects, lymphoproliferative effects related to the deregulation of oncogenes in the human genome[2], etc. To attempt to resolve these problems other types of non-viral vehicles have been developed such as cationic liposomes, polymers and also, as has been mentioned, dendrimers. Each of these cationic systems forms electrostatic complexes with the nucleic acids which are called, respectively, lipoplexes polyplexes or dendriplexes.

The use of liposomes as transfection agents was initially described in 1987.[3] The method most used for the distribution of genes has been encapsulation in cationic lipids, to the point that some of these derivatives such as Cytofectin™ or Lypofectin™ are commercially available. These derivatives, however, have also shown secondary effects such as inflammatory reaction of the lungs and problems such as lack of transfection in the presence of serum.[4]

With regard to conventional degradable polymers, their use as vehicles has the main drawback of their thermodynamic instability, which makes the active species have a very short in vivo half-life.[5]

The greatest advantage of the dendrimers on the moiety of non-viral vehicles lies in a uniform structure and the possibility of modifying in versatile manner the skeleton and surface thereof, which allows the precise characterization of the complex (nucleic acid/vector) and a systematic research of the transfection process. The first publication which described the use of dentritic molecules as transfection agents appeared in 1993 describing the use of dendrimers called PAMAM[6] (polyamidoamine), and since then a great quantity of studies have been carried out.[7,39,40]. The use of these dendrimers as vehicles is based on the fact that at physiological pH some of the terminal groups are protonated giving the PAMAM dendrimer a net positive charge, although some amino groups also remain unprotonated. Good transfection results have also been achieved with these dendrimers, especially with dendrimers of sixth and seventh generation, however, the efficacy of this process can be increased by two or three orders of magnitude when PAMAM dendrimers activated by heat treatment are used, as is the case of Superfect™ or Polyfect™.

Another class of potential transfection agents are dendrimers which contain phosphorous atoms,[8] synthesized by Majoral et al. until the twelfth generation In this case, the surface of the dendrimers has been functionalized with protonated or methylated tertiary amines and have been tested as transfection agents of the luciferase gene of 3T3 cells. The efficacy increases on increasing the dendrimer generation until achieving a constant value between generations three and five. Furthermore, we should highlight that these dendrimers have better transfection efficacy in the presence of serum.

Finally, other macromolecules have been such, such as poly(propylenimine) (PPI)[9] or poly(lysine) dendrimers[10, 41] as systems for the transport of DNA or oligodeoxynucleotides (ODN). For example, dendrimers from low generations of PPI have shown a certain capacity for in vitro transfection with low toxicity, although it has not been possible to use higher generations due to the increase in their toxicity.

For their part, oligonucleotides (ODN) are researched in medical applications in different fields. Thus, for example, antisense ODNs are short synthetic sequences (15-30 bases in length) of DNA or analogous which are complementary (or antisense) to a target sequence (an RNA sequence or the DNA sequence complementary to that from which that RNA could be transcribed); designed to interfere with a biological event, such as the transcription, translation or the cut and splice phenomenon[11]. These molecules are designed to interact as complementary sequences of target mRNA, preventing translation to proteins, by the degradation of the mRNA by the activity of the RNase or interfering with the reading by the ribosome. This is called "antisense therapy". Antisense ODNs have been used in multiple fields since 1978 (antitumour therapy and infectious disease above all), until today when, after a period of doubt, the antisense ODNs have recovered their role as a powerful tool in Molecular Biology, especially from the approval by the American FDA of Formivirsen [12], an antisense ODN indicated in ocular infection by CMV in the context of HIV infection. Another antisense ODN, GEM231, is postulated as a molecule with potential application against different neoplasias[13]. This approach is also being researched for its possible use in isotopic labelling of tumours using Positron Emission Tomography[14]. There is, furthermore, a type of antisense ODN which it is postulated can act at a level of cellular DNA: they are triple helix forming ODNs, some of them designed for their application within the field of HIV[15].

Another totally different field is that of the application of ODN rich in non-methylated CpG sequences as immunomodulators. These sequences lead the immune response to a Th1 profile, characterized by an increased secretion of Interferon, Tumour necrosis factor, interleukine-2, and other factors which increase the immune system's capacity to eliminate pathogens such as virus and bacteria. These ODN interact with receptors of the lymphocyte surface such as those of the Toll-like receptor family. They are being researched to boost immune response in immunodeficient patients and in the context of allergic diseases, characterized by a Th2 balance, with the aim of carrying this profile to Th1[16].

One of the main problems of therapy with ODN is that of achieving adequate levels to attain the therapeutic effect. It is necessary to administer large quantities of ODN to achieve the biological effect, since they have a large affinity to bind to plasma proteins, such as albumin[17]. Binding to plasma proteins and other cell surface proteins is also considered responsible for some of the toxic effects of ODN in vivo (activation of the cascade of the complement, haemolysis, thrombocytopaenia, etc.)[18]. It is therefore believed that the use of a vehicle that prevents said binding to proteins could be translated in the production of greater levels of active ODN, furthermore prolonging the half-life thereof and decreasing its toxicity.

The problem of the interaction with proteins and their binding to them is also present in many other substances used as drugs, since proteins in general (and plasma proteins in particular: albumin, glycoproteins, lipoproteins) show functional groups which are potentially capable of interacting with substances present in the medium, including administered drugs. This bond is a determining factor for the distribution of said drugs, provided that the bound fraction of the drug, as it does not have the capacity to be transferred, does not form part of the vascular-tissue balance ("reservoir"), is not metabolized, is not excreted and has no effect (unless it is determined by said bond).

Plasma protein binding (PPB) is by far the most important and determining factor of drugs distribution, since binding to tissue proteins is, generally, very reduced. This is due, among other things, to the fact that the plasma concentration of proteins is much greater than the interstitial concentration of the tissues, whose proteins, furthermore, have very little mobility and less capacity to bind substances, the latter property of which is particularly notable in the case of albumin, a predominant protein in plasma in normal conditions and whereto acid drugs are mainly bound (although some are also alkaline), whilst the acid glycoproteins bind those alkaline ones.

| Acid Drugs (Albumin) | Alkaline drugs (Albumin - I1 acid glycoprotein) |
|---|---|
| Aspirin | Chlordiazepoxide |
| Furosemide | Diazepam |
| Penicillin | Lidocaine |
| Phenytoin | Quinine |
| Tolbutamide | Amitryptiline |
| Warfarin | |

As the albumin structure from the standpoint of the drug bond is quite complex, two main binding points or locus can be defined:

| POINT I ("of Warfarin"): | POINT II ("of Diazepam"): |
|---|---|
| Chlorothiazide | Benzodiazepines |
| Furosemide | Ibuprofen |
| Nalidixic Acid | Cloxacillin |
| Salicylic Acid | Salicylic Acid |
| Tolbutamide | Tolbutamide |
| Indomethacin | Indomethacin |

Therefore, the problem of binding to plasma proteins does not only affect ODNs, but also almost all commonly used drugs. Many of these problems could also be avoided by the use of a vehicle. It seems clear that the vehicle to develop for this purpose must have a series of characteristics, such as, being:
Non-toxic
Non-immunogenic (unless to be used in vaccination)
Biocompatible
Have functional groups suitable to permit chemical fixation.
Limited corporal accumulation
Maintain the activity of the drug/ODN until reaching the site of action Furthermore, it seems obvious that the vehicle to develop must release the ODN or the drug transported over time, so that this could carry out this action. In this aspect, the development of vehicles which permitted the controlled release of ODN or determined drugs would be very desirable, in order to achieve maintained levels of active substance in the organism and the production of the effect gradually. For all these reasons, the use of dendrimers seems a possibility which meets the desired requirements, as they can act as vehicles of the active substances which would protect them from degradation by plasma enzymes and from interactions with proteins to which they could bind, increasing their blood levels and permitting a higher and/or more prolonged activity. ODNs in particular, like many drugs of interest, are anionic molecules (with negative charge), for which reason use as vehicles thereof of dendrimers with groups which facilitate their interaction and, especially, of those which are of cationic nature at physiological pH is a very suitable option to guarantee the stability of the complex during its transport. Therefore, the invention develops novel dendrimers, specifically of carbosilane type, and provides their use, among others, as vehicles for carrying ODNs and other anionic molecules of interest in the blood and/or in other bodily fluids. This involves a new field since no study has been published to date concerning the use of dendrimers with carbosilane structure, soluble in water as vehicles, although a report has been published on the in vitro biocompatibility of carbosilane dendrimers constituted on ethylene poly(oxide).[21] Furthermore, only three synthetic studies of cationic carbosilane dendrimers have been published to date.[22-24], none of them coinciding with those provided by the invention.

Among the drugs for which the dendrimers can act as vehicles, an interesting group is constituted by the cytotoxic drugs designed for tumour cells[73,74]. When this objective is sought, the dendrimers can be directed at the tumour cells with folic acid, which is overexpressed in the tumour cells, for which reason these dendrimers would have preference for their uptake by said cells with respect to the normal cells. Recently, PAMAM dendrimers modified with folate on their surface have been used as vehicles of boto isotopes in neurone capture therapies in cancer[75]. Furthermore, PAMAM dendrimers conjugated with cisplatin act as macromolecular platin vehicle, an anti-tumour drug, which is released from the dendrimer-platin complex in controlled form, giving rise to a greater accumulation thereof in solid tumours, with less toxicity than the free cisplatin[76]. Another alternative for controlled release is to establish covalent bonds between the dendrimer and the drug by biodegradable bonds at physiological pH, as has been proven with dendrimers with primary amines on the surface and modified partially with 1-bromoacetyl-5-fluorouracil to form a labile amide bond which is hydrolized in vitro at physiological pH, releasing 5-fluorouracil, a powerful antitumour agent, in controlled manner.

Other substances of interest in whose transport dendrimers may be of use are those which become toxic after being irradiated, due to the in situ formation of small quantities of oxygen in singlet state, which has deleterious physiological effects[69]. Articles have been published on dendrimers carrying photosensitive drugs, for example, with 5-aminolevulinic acid in the periphery, supposing these dendrimer agents to be promising in the treatment of keratinocyte tumours[70]. As candidates for the treatment of solid tumours, dendrimers have been evaluated based on polyarylether dendrimers carrying protoporphyrin as photosensitizer[71].

An additional group of drugs for which dendrimers could suppose interesting vehicles is constituted by drugs such as non-steroidal anti-inflammatory drugs, which have secondary effects such as gastrointestinal alterations or nephrotoxicity which could be avoided as they are supplied by transdermal route, instead of through the classic oral or parenteral routes. The data which indicate the presence of dendrimers, bound to the drugs to administer, lead to skin alterations which increase its permeability[72], become good candidates to be used in the transdermal administration of drugs.

The multivalence of the dendrimer's surface functional groups means the great variety of molecules which they can transport even include dendrimers with different functionalities: these are the tectodendrimers, which are being studied due to their great potentiality in possible biomedical applications.

The potentiality of dendrimers for drug transport is not only based on using the possible interactions with an external multivalent dendrimeric surface, but on the fact that the dendrimer's structure can be used to house the molecules which one wants to transport. An example of use of dendrimeric structure cavities is the so-called "dendritic box"[68], wherein a PPI dendrimer is modified on the surface with phenylalanine groups, which protect the external frame making it denser. During the dendrimer growth process, molecules of different sizes are encapsulated in its interior. The dendrimer can carry a different number of molecules according to the size thereof. When the dendrimer is treated with formic acid, the outer frame is opened, allowing the release of the molecules housed therein.

Another group of molecules for which the dendrimers may suppose suitable vehicles are molecules of low molecular weight (such as peptides) against which it is desired to generate an immune response in a subject but which, due to their small size, are scarcely immunogenic or lead to a weak response after being injected in the individual which it is desired to treat. This problem can be resolved by increasing their molecular weight, either by polymerization of by coupling to a high molecular weight vehicle (traditionally to protein). Dendrimers which have a very defined structure and many functional groups capable of binding antigens in their periphery represent a good alternative for manufacturing vaccines which have very defined immunogens and which are highly reproducible. In this line, MAP (multiple antigenic peptide) dendrimers[57,58] have been developed, which are wedge-shaped constructions formed by successive generations of lysine residues. These dendrimers have a large number of primary amines which can be coupled to low molecular weight antigens, with the intention of increasing their immunogenicity, avoiding the need to use vehicle proteins. MAP structures which contain T and B cell stimulating *Plasmodium falciparum* peptides have been used to produce immune responses against this parasite[59]. Furthermore, it has been demonstrated that MAP structures are processed through the antigen-presenting cells in the same way as the antigens derivatives of intracellular structures (such as, for example, virus), giving rise to a potent immune response, including the production of cytotoxic T cells[60]. The dendrimers of the invention, which have at ends of their branches moieties which contain amino groups, may also be of use in vaccination, either because they are coupled to low molecular weight antigens making use of amines present in moieties of ends of their branches, or because said moieties which contain at least one amino group themselves constitute low molecular weight antigens such as those of peptide nature.

MAP structures have also been used to transport non-peptidic antigens such as carbohydrates, haptens, etc., in the context of vaccines. Carbohydrates in particular are a class of important molecules in biological recognition. Glycodendrimers, prepared by mannose-isothiocyanate, sialic acid or lactose binding to the terminal amines of PAMAM dendrimers or lysine dendrimers, have been used as antigens for vaccines[64,65]. In glycodendrimers with the T-associated beta Gal 1-3 alfaGalNAc disaccharide antigen its binding capacity to lectin has also been tested (binding protein to carbohydrates) specific for galactose[66], with the intention of using them to detect tumours which express T antigen receptors and to carry drugs thereto. The glycodendrimers can be used, furthermore, to increase affinity for lectins which are bound to the carbohydrate they have bound[67], which may be of interest for using those glycosilated dendrimers as microbial anti-adhesins, toxin antagonists, or as anti-inflammatory, antiviral and anti-cancer drugs, since the lectin-carbohydrate interactions of carbon have been described in numerous cases in the immune system (in the events that lead to cell activation), in viral and bacterial infections, in relation to cancer and the cell growth, etc. In short, glycosylated dendrimers may imitate the natural glycoconjugates and efficiently interact with the natural receptors of carbohydrates, giving rise to characteristic effects of interaction therewith.

In addition to the possibility of making use of its properties to use them as vehicles, another field related to nucleic acids to which much attention is being paid at present is of the manufacturing of microchips which contain ordered sets of DNA or RNA sequences. When these microchips are manufactured, dendrimers are arising as one of the alternative to coat glass surfaces and make use of their capacity of interaction with the nucleic acids to fix said molecules to the surface of the microchips[63]. The durability of the bond between sequences of nucleotides and dendrimers of the invention makes them suitable to use their capacity of fixing nucleic acids in order to serve as a base for the manufacturing of these DNA or RNA microchips.

Finally, these is also a need to find alternative methods to fight against different pathogens, interfering in their life cycle, a field in which dendrimers are showing themselves to be an interesting alternative. Some previously described dendrimers have shown themselves to be capable of inhibiting the infection caused by different viruses, interfering both with the entry of virus in the cells and in the later steps of viral replication. That is the case, for example, of Herpes Simplex, whose infection is inhibited in vitro by the effect of modified polylysine dendrimers[50,51]. Replication of HIV has also been achieved, both at the level of cell uptake and in the later steps, in this case by the use of covalently modified PAMAM dendrimers, which demonstrated that they were capable of interfering with the retrotranscriptase and integrase of the virus[19,52]. Making use of these properties, vaginal gels have been developed for the prevention of sexually transmitted diseases with dendrimer-based formulations, as is the case of VivaGel™ (Starpharma), whose active ingredient is a polylysine dendrimer functionalized with naphthalene disulfonate moieties which seems to be effective in the prevention of HIV thanks to the capacity of binding to glycoprotein gp120 of the virus surface. Although in the design of antiviral dendrimers there is preference for those which have groups on their surface which imitate those which are present on the cell surface and which, therefore, are capable of competing with the cells for binding to the virus, a dendrimer has also been designed with surface amide groups which function as respiratory syncytial virus inhibitor, thought to be due to the formation of hydrogen bridges between the peripheral groups of the dendrimer with the virus fusion protein, for which reason it is to be expected that dendrimers functionalized with other groups, capable of forming hydrogen bridges with viral proteins involved in the interaction of the cell surface, are also capable of interfering with different virus, inhibiting the infection caused by them.

In other cases, dendrimers have been used as antibacterial agents or to destructure the cell membranes of some fungi. When they are designed for this purpose, there is preference for dendrimers with cationic groups on their surface, such as amines or tetraalkylammonium groups, which facilitate adherence of dendrimers to the bacterial membrane, causing bacteria lysis. This is the case of poly(propylenimine) (PPI) dendrimers with tertiary alkylammonium groups on their surface, which have demonstrated extensive bacterial activity against both Gram positive and Gram negative bacteria[53,54]. These dendrimers have greater bactericide capacity than other hyperbranched polymers. The dendrimers of the invention, also functionalized with moieties which contain amino groups, represent an option to be also used to destructure cell membranes of bacteria or fungus.

It has also been communicated that dendrimers have properties which allow them to act as protein denaturants. Certain types of dendrimers act by decreasing the dielectric constant and the viscosity of the water and disordering its regular structure by the reorganization of the water molecules on the dendrimer surface. This leads to damaging hydrophonic interactions, which is very destabilizing for most tertiary protein structures, causing its denaturing: this is the so-called "chaotropic" effect which have denaturing agents such as urea or guanidine chloride. A very interesting field wherein it is intended to apply this denaturing capacity of proteins is the use to dissolve prionic proteins, such as PrP$^{Sc}$[20]. Prionic proteins are capable of adopting a pathogen structure-formation which cause mortal neuropathies called spongiform encephalopathies (Creutzfeldt-Jakob's disease, mad cow disease", ovine scrapie, etc.). These proteins form aggregates which are located in the brains of the affected individuals and are only soluble in solvents which contain detergents as chaotropic agents (typically 6M guanidine chloride). However, these aggregates can be solubilized by cationic dendrimers such as those of PPI and PAMAM: those of greater generation with greater number of amines on the surface are the most effective. Therefore, the novel dendrimers of the invention, also functionalized with moieties which contain amino groups, provide novel compounds to be used, both to dissolve prionic aggregates and in the therapy of other diseases in whose development the formation of pathogenic protein aggregates also occurs, and, for example, the aggregates of amyloid protein which appear in Alzheimer's disease[55,56].

In short, dendrimers are synthetic polymers with good properties for their use in biological applications: they predictably respond in solution, they can be largely modified to carry multiple ligands with biological activity, they can cross biological barriers and are manufactured with few structural defects. Therefore, their application is being studied in different preventive and therapeutic strategies including their use for the carrying of different drugs, the transfection of oligonucleotidic or polynucleotidic molecules, the design of vaccines, the administration as antibacterial, antifungal, antiviral drugs or even the relief of the symptoms of diseases of different etiology in whose development the formation of protein aggregates such as those originated by prions or the deposits of amyloid protein characteristic of Alzheimer's disease, is involved. The dendrimers of the present invention involve interesting alternatives for these areas of Biomedicine.

GENERAL DESCRIPTION OF THE INVENTION

The invention describes novel branched carbosilane dendrimers with terminal moieties at their branch ends which contain primary, secondary, tertiary or quaternary amino groups which responds to any one of the formulas:

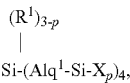

if they are first generation;

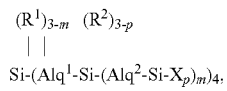

if they are second generation;

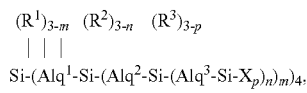

if they are third generation;
or to the corresponding analogous formulas in the case of later generations, wherein the formula corresponding to each generation i would result from substituting $X_p$ in the formula corresponding to the previous generation by a new block of the type:

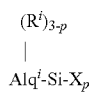

passing the group bound to the same silicon atom as this substitutory block from being represented by $(R^{i-1})_{3-p}$ to being represented by $(R^{i-1})_{3-z}$, formulas wherein:

$Alq^1, Alq^2, Alq^3, \ldots, Alq^i$ represent alkylene moieties of 2 to 4 carbons which are chosen independently from one another according to the length of the branches in each generation;

$R^1, R^2, R^3, \ldots R^{i-1}, R^i$ represent moieties which are chosen independently from one another among methyl and phenyl;

X represents a moiety which contains at least one primary, secondary, tertiary or quaternary amino group;

p is a whole number which varies between 1 and 3;

m, n, ... z are whole numbers which vary independently between 1 and 3

In a preferred embodiment of the invention, the moieties $R^1, R^2, R^3, \ldots R^{i-1}, R^i$ are all identical and correspond to methyl moieties.

In another preferred embodiment of the invention, the moieties $Alq^1, Alq^2, Alq^3, \ldots, Alq^i$ are selected from ethylene and propylene. In another more preferred embodiment of the invention, said moieties are all identical and correspond to propylene moieties.

In another of the preferred embodiments of the invention, the whole numbers m, n, ..., z are identical to one another and have the value 2.

In the most preferred embodiment of the invention, the moieties $R^1, R^2, R^3, \ldots R^{i-1}, R^i$ are all identical and correspond to methyl moieties; the moieties $Alq^1, Alq^2, Alq^3, \ldots, Alq^i$ are identical to one another and correspond to propylene moieties and the whole numbers m, n, ..., j are identical to one another and have the value 2.

X represents any moiety which contains a primary, secondary, tertiary or quaternary amine. From among them, those moieties are preferred wherein X represents either $-OCH_2CH_2N(CH_3)_2$, $-OCH_2-(C_6H_3)-3,5-(OCH_2CH_2N((CH_3)_2)_2$, or $-OCH_2CH_2N(CH_3)CH_2CH_2N(CH_3)_2$, or a $-CH_2CH_2(CH_2)_eNH_2$ group wherein "e" is, a whole number between 0 and 2, in that case preferring that it takes the value 1. Preferred embodiments of the invention are also those wherein X represents the quaternized forms of the previous $-OCH_2CH_2N^+(CH_3)_3I^-$, $-OCH_2-(C_6H_3)-3,5-(OCH_2CH_2N^+(CH_3)_3)I^-)_2$, $-OCH_2CH_2N(CH_3)CH_2CH_2N^+(CH_3)_3I^-$ or $-CH_2CH_2CH_2-N^+H_3Cl^-$.

When X represents $-OCH_2CH_2N(CH_3)_2$, $-OCH_2-(C_6H_3)-3,5-(OCH_2CH_2N(CH_3)_2)_2$, or $-OCH_2CH_2N(CH_3)CH_2CH_2N(CH_3)_2$, or their quaternized forms $-OCH_2CH_2N^+(CH_3)_3I^-$, $-OCH_2-(C_6H_3)-3,5-(OCH_2CH_2N^+(CH_3)_3)I^-)_2$, $-OCH_2CH_2N(CH_3)CH_2CH_2N^+(CH_3)_3I^-$, it is especially preferred that all the branches have terminal moieties which contain amino groups and that the "p" index takes the values 1 or 2, so that each branch would end, respectively, in a single terminal moiety or in two terminal moieties. When X represents $-CH_2CH_2CH_2NH_2$ or its quaternized form $-CH_2CH_2CH_2-N^+H_3Cl^-$, it is especially preferred that all the branches have terminal moieties which contain amino groups and that "p" takes the value 1, so that each branch would end with a single amine moiety.

The scope of the invention also includes the cases wherein X represents an antigenic moiety which contains at least one amino group. A particular case of the previous would be that wherein the antigenic moiety is a peptide.

The invention also relates to a process for preparation of said carbosilane dendrimers, a process which comprises stages of:
a) producing a carbosilane dendrimer skeleton following the steps of:
a1) producing a basic starting carbosilane dendrimer of formula:

where a varies between 0 and 2, according to the length desired for the branches,
making $SiCl_4$ react with $BrMg(CH_2)_aCH=CH_2$;
a2) producing a first generation carbosilane dendrimer precursor of a dendrimer of a later generation making the basic starting carbosilane dendrimer of a1) react with $HSi(R^1)_{3-m}Cl_m$, so that a dendrimer of the following formula is produced:

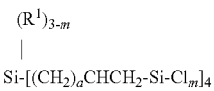

where
m varies between 1 and 3 and is equivalent to the number of branches that can be achieved in the next generation or the number of terminal functional groups which the Cl groups can be replaced by;
$R^1$ represents a phenyl or methyl moiety;
a3) Optionally, producing a second generation carbosilane dendrimer precursor of a dendrimer of a later generation subjecting the derivative with Si—Cl terminal bonds produced in stage a2) to the repetition of stages a1) and a2), i.e.,
i) producing new branches making the corresponding derivative react with Si—Cl terminal bonds with $BrMg(CH_2)_bCH=CH_2$, where "b" varies between 0 and 2, according to the length desired for those branches, and can be the same as or different to the "a" index;
ii) making the carbosilane dendrimer skeleton of the new generation produced in i) react with $HSi(R^2)_{3-n}Cl_n$, where "n" varies between 1 and 3 and can be the same as or different to the "m" index of the previous generation and $R^2$ represents a phenyl or methyl moiety;
a4) optionally, producing carbosilane dendrimers of successive generations precursors of dendrimers of later generations subjecting the derivative with Si—Cl terminal bonds corresponding to the previous generation to that sought on repetition of stage a3) i) using a $BrMg(CH_2)_cCH=CH_2$ reagent and the repetition of stage a3) ii) using a $HSi(R^3)_{3-z}Cl_z$ reagent, reagents wherein "c" varies between 0 and 2 and "z" varies between 1 and 3;
a5) producing the final carbosilane dendrimer skeleton to which moieties will be added in stage b) which contain at least one amino group using in stage a2), a3) or in repetition i-1 of stage a4), depending on whether the dendrimer is of first, second or a generation i, respectively, a $HSi(R^i)_{3-p}Cl_p$ reagent, where "p" varies between 1 and 3 and $R^i$ represents a phenyl or methyl moiety.
b) producing a carbosilane dendrimer with terminal moieties with primary, secondary or tertiary amino groups following one of the following routes:
b1) provoking the alcoholysis of Si—Cl terminal bonds of a carbosilane dendrimer produced in stage a5) reacting it with a primary, secondary or tertiary alcohol-amine in the presence of an excess of an alkali;
b2) previously producing a carbosilane dendrimer with Si—H terminal bonds to which the moieties which contain at least one primary, secondary or tertiary amino group will later bind, making it pass through stages of:

i) producing a derivative with Si—H terminal bonds of a carbosilane dendrimer of any generation making the corresponding carbosilane dendrimer react with Si—Cl bonds with a reagent capable of ceding hydride groups, so that part or all of the Cl atoms are substituted by H atoms;

ii) making the carbosilane dendrimer with Si—H bonds, in the presence of a hydrosilylation catalyst, react with a compound which contains a primary, secondary or tertiary amino group and which has a double carbon-carbon bond at one end, so that the compound is bound to the dendrimer by the end wherein the double bond is found;

c) optionally, producing a carbosilane dendrimer with terminal moieties with quaternized amino groups by the reaction of a dendrimer produced in stage b) with an A-Hal reagent, wherein A represents hydrogen, alkyl of 1 to 10 carbon or aryl atoms and Hal represents Cl, Br, I.

In a preferred embodiment of the process of the invention, indices a, b, ..., k corresponding to reagents $BrMg(CH_2)_a CH=CH_2$, $BrMg(CH_2)_b CH=CH_2$, ..., $BrMg(CH_2)_k CH=CH_2$ are identical to one another and have the value 0, for which purpose the reagent used is the vinylic derivative $BrMg—CH=CH_2$ and the branches have a length of 2 carbons.

In another preferred embodiment of the process of the invention, indices a, b, ..., k corresponding to reagents $BrMg(CH_2)_a CH=CH_2$, $BrMg(CH_2)_b CH=CH_2$, ..., $BrMg(CH_2)_k CH=CH_2$ are identical to one another and have the value 1, for which purpose the reagent used is the allylic derivative $BrMg—CH_2—CH=CH_2$ and the branches have a length of 3 carbons.

In another preferred embodiment of the process of the invention, the moieties $R^1$, $R^2$, ..., $R^i$ are all identical and correspond to methyl moieties.

In another preferred embodiment of the invention, indices n, m, ..., j corresponding to the reagents of general formula $HSi(R^2)_{3-n}Cl_n$, are preferably chosen from 1 and 2. In a particular embodiment of the previous, the number of branches formed in each generation is always the same as and equal to 2, for which reason reagent $HSi(R^2)_{3-n}Cl_n$, when it is used to created a precursor which gives rise to a new generation dendrimer, would be in all cases, $HSi(R^2)_2Cl$, preferably, $HSi(CH_3)_2Cl$, which corresponds to a value of "n" of 1.

In the most preferred embodiment of the invention, the moieties $R^1$, $R^2$, ..., $R^i$ are all identical and correspond to methyl moieties, whilst indices a, b, ..., k corresponding to reagents $BrMg(CH_2)_a CH=CH_2$, $BrMg(CH_2)_b CH=CH_2$, ..., $BrMg(CH_2)_k CH=CH_2$ are identical to one another and have the value 1, for which purpose the branches of the carbosilane dendrimers would have a length of 3 carbons, and the branches created in each new generation would be 2, for which purpose $HSi(CH_3)_2Cl$ would always be used to create a precursor of a new generation. In contrast, when reagent $HSi(R^2)_{3-n}Cl_n$ is used to give rise to a carbosilane dendrimer with Si—Cl terminal bonds from which to produce a carbosilane dendrimer of the invention with amino groups in the branches, it is preferred that the value "n" is chosen from 1 and 2, it being possible to use, therefore, $HSi(CH_3)_2Cl$ as $Si(CH_3)Cl_2$ depending on whether it is desired that the number of terminal groups present per branch is 1 or 2, respectively.

In an embodiment of the invention, the alcohol-amine used to produce the carbosilane dendrimers of the invention from the corresponding derivatives with Si—Cl terminal bonds is chosen among N,N-dimethylethanolamine ($CH_2OH—CH_2—N(CH_3)_2$), 2-[(2-dimethylaminoethyl)methyl]amino ethanol ($CH_2OH—CH_2—N(CH_3)—CH_2—CH_2—N(CH_3)_2$) or 3,5-bis(dimethylaminoethoxy)benzyl alcohol ($CH_2OH—(C_6H_3)—(O—CH_2—CH_2—N(CH_3)_2)_2$). In a preferred embodiment of the previous, the carbosilane dendrimer with Si—Cl bonds is treated with the corresponding stoichiometric quantity of the alcohol-amine chosen, in diethylene ether and in the presence of an excess of triethylamine, so that each of the Si—Cl bonds passes to be a Si—O bond whereby it is bound to the moiety corresponding to the alcohol-amine used. In another embodiment of the invention, the carbosilane dendrimer produced from any one of the previous alcohol-amines is subsequently quaternized by treating it with $CH_3I$ in diethylene ether.

In another embodiment of the invention, the compound which contains a primary, secondary or tertiary amino group, which has a double carbon-carbon bond at one end and which is made to react with a carbosilane dendrimer with Si—H bonds is a primary alkyleneamine of formula $CH_2=CH—(CH_2)_e—NH_2$, wherein the "e" index varies between 0 and 2. In a preferred embodiment of the previous, the primary alkyleneamine is that wherein the "e" index has a value of 1, i.e. allylamine, $CH_2=CH—CH_2—NH_2$. In another embodiment of the invention, the carbosilane dendrimer with terminal moieties $—CH_2—CH_2—CH_2—NH_2$ produced by reaction with the allylamine is quaternized by the addition of HCl in diethylene ether.

In another embodiment of the invention, the compound which contains a primary, secondary or tertiary amino group, which has a double carbon-carbon bond at one end and which is made to react with a carbosilane dendrimer with Si—H bonds is a compound which comprises an alkenyl moiety at one end ($CH_2=CH—(CH_2)_e—$, wherein "e" varies again between 0 and 2) and an amino group (primary, secondary or tertiary) at another different end, the compound additionally comprising a $—R^a—$ moiety between the alkynyl moiety $CH_2=CH—(CH_2)_e$ and the amino group. In a preferred embodiment thereof, the compound used is 4-allyl-2-methoxy-1-(N,N-dimethylaminoethoxy)benzene, ($CH_2=CH—CH_2)C_6H_3(OMe)\{O(CH_2)_2NMe_2\}$.

In preferred embodiments of the method of the invention, the carbosilane dendrimers with Si—H bonds at their ends with which compounds are made to react which contain at least one primary, secondary or tertiary amino group and which have a double carbon-carbon bond at one end are produced in stage b2)i) using $LiAlH_4$ as the reagent capable of ceding hydride groups, which permits converting part or all of the Si—Cl bonds into Si—H bonds, although the use of analogous reagents is included within the scope of the method of the invention, among which we can cite NaH or $NaBH_4$. In said preferred embodiments, the binding of compounds which contain at least one primary, secondary or tertiary amino group at the end wherein they have a double carbon-carbon bond is carried out using the Karstedt catalyst[28] to catalyze the reaction, although the use of other hydrosilylation catalysts is included within the scope of the method of the invention, which permit carrying out the desired binding such as Spiers catalyst[61,62].

In another additional aspect, the invention relates to pharmaceutical compositions which contain the carbosilane dendrimers of the invention. In an embodiment of the invention, the composition contains at least one carbosilane dendrimer of the invention together with at least one another molecule, anionic or polyanionic. In a particular embodiment of the previous, the polyanionic molecule is an oligodeoxyribonucleotide (ODN) or a double chain DNA molecule. In another particular embodiment of the previous, the polyanionic molecule is an RNA molecule, single-stranded or two-stranded, which preferably contains complementary regions associated to one another which allow that said RNA can be used as interference RNA (RNAi). In a further embodiment, the anionic molecule is a drug with tendency to be associated to the plasma proteins or cell membranes which are in contact with it or susceptible to being degraded by any of these proteins.

In a different embodiment from the previous, the carbosilane dendrimer is present in the invention as active substance with the capacity to interfere in the life cycle of pathogenic micro-organisms. In a particular embodiment thereof, the pathogen is a virus, which can be HIV. In another particular embodiment, the pathogenic micro-organism is a bacteria or fungus whose cell wall or membrane is susceptible to being altered by said dendrimer.

In another additional embodiment, the carbosilane dendrimer is present in the invention as active substance with capacity of interfering in the formation or facilitating the dissolution of protein aggregates involved in the development of pathological processes such as the encephalopathies caused by prions or degenerative processes such as Alzheimer's disease.

In a further embodiment, different from the previous ones, a carbosilane dendrimer of the invention present in a pharmaceutical composition has bound to it a peptide or any antigenic moiety and is designed to unleash an immune response which prevents or protects the individual to whom it is supplied against a disease caused by an organism wherein said peptide or antigenic moiety is present.

The dendrimers of the invention and the compositions which contain them may be administered by common administration routes, iontophoresis, transdermal route, injection or inhalation. They are also suitable for forming films to coat prosthesis structures or STENT meshes so that controlled release of at least one dendrimer of the invention or of at least one substance present in the same composition as said dendrimer is produced from them.

In another aspect of the invention, the carbosilane dendrimers are used for the fixation of molecules of anionic or polyanionic character to surfaces. In an embodiment of the invention, the molecules would be sequences of nucleic acids and the surfaces whereto they are fixed, the bases used for the microchips whereto sequences of nucleotides are fixed.

In a further additional aspect, the invention relates to the use of the carbosilane dendrimers of the invention as vehicles for carrying anionic substances in the blood which protect said substances from their interaction with plasma proteins or of the cell membranes which are in contact with it and which are capable of binding to said anionic substances or degrading them. A particular case of this would be that wherein the substance with anionic character at blood pH would be a drug.

In a further additional aspect, the invention relates to the use of the carbosilane dendrimers of the invention as drugs to reduce or eliminate the symptoms of a disease caused by a micro-organism with whose life cycle the dendrimer of the invention is capable of interfering.

In another additional aspect, the invention relates to the use of the carbosilane dendrimers of the invention as transfection vehicles of molecules of anionic or polyanionic character whereto they are bound. A particular case of this would be that wherein the polyanionic molecule is an oligodeoxyribonucleotide (ODN) or an RNA molecule, single-stranded or two-stranded, which preferably contains complementary regions associated with one another which allow said RNA to be used as interference RNA (RNAi). It is especially preferred that cells to transfect are nervous system cells or from cell lines derived therefrom.

The invention will now be described in greater detail with reference to the following figures and the examples stated in the section of the detailed description of the invention.

BRIEF DESCRIPTION OF THE FIGURES

The patent or application file contains at least one drawing executed in color. Copies of this patent or patent application publications with color drawing(s) will be provided by the Office upon request and payment of the necessary fees.

FIG. 9b shows the protein stain of the gel corresponding to 4 hours whose staining with ethydium bromide is shown in FIG. 9a.

FIG. 21B shows a similar analysis of the fluorescence taking a region of interest (ROI) drawn around the nucleus wherein the blue fluorescence (top graphic) and the green fluorescence (bottom graphic) is analysed.

DETAILED DESCRIPTION OF THE INVENTION

Figure 1A:
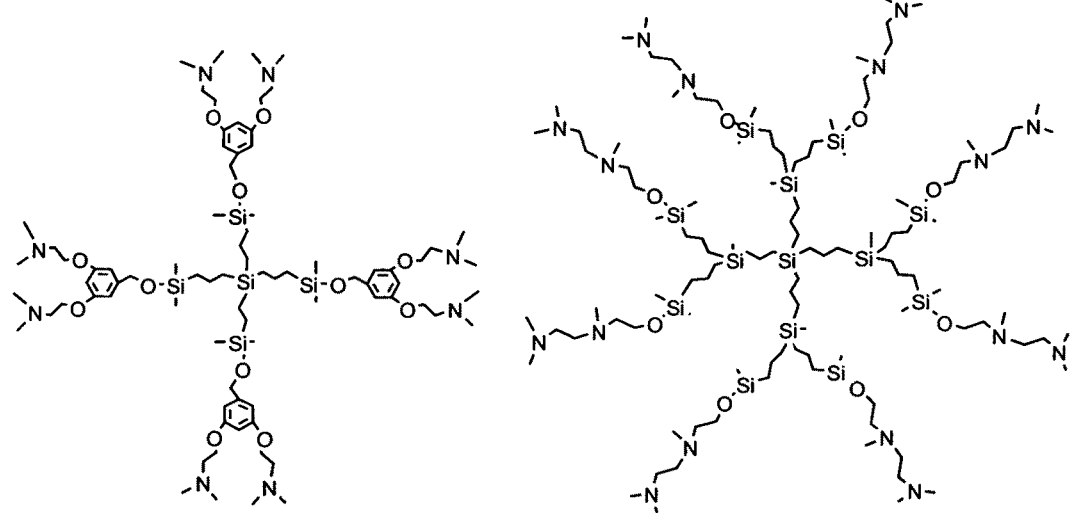
FIG. 1 shows the structure of several carbosilane dendrimers of the invention with unquaternized amine moieties: those synthesized in examples 7, 11, 2, 5 in FIG. 1a and those synthesized in examples 13 and 14 in FIG. 1b.
Figure 1A:
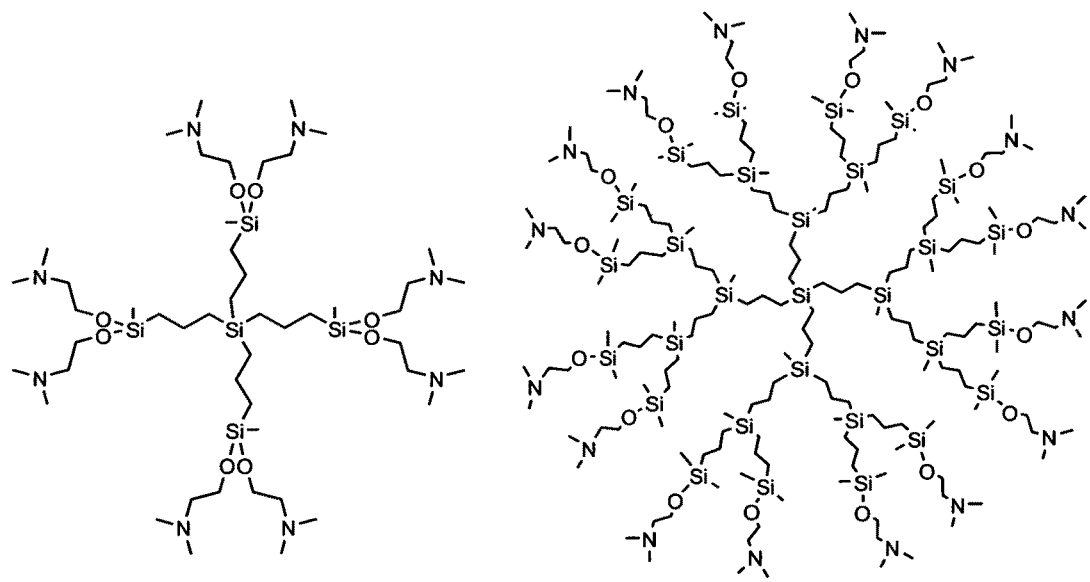

The invention describes novel branched carbosilane dendrimers with primary, secondary, tertiary or quaternary amino groups at the ends of the branches which respond to the formulas:

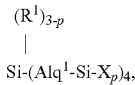

$$\begin{array}{c} (R^1)_{3-p} \\ | \\ Si\text{-}(Alq^1\text{-}Si\text{-}X_p)_4, \end{array}$$

in the case of those of first generation;

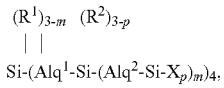

$$\begin{array}{cc} (R^1)_{3-m} & (R^2)_{3-p} \\ | & | \\ Si\text{-}(Alq^1\text{-}Si\text{-}(Alq^2\text{-}Si\text{-}X_p)_m)_4, \end{array}$$

in the case of those of second generation;

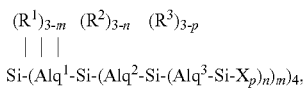

$$\begin{array}{ccc} (R^1)_{3-m} & (R^2)_{3-n} & (R^3)_{3-p} \\ | & | & | \\ Si\text{-}(Alq^1\text{-}Si\text{-}(Alq^2\text{-}Si\text{-}(Alq^3\text{-}Si\text{-}X_p)_n)_m)_4, \end{array}$$

in the case of those of third generation;
generation;
or to the corresponding analogous formulas in the case of later generations, wherein the formula corresponding to each generation i would result from substituting $X_p$ in the formula corresponding to the previous generation by a new block of the type:

$$\begin{array}{c} (R^i)_{3-p} \\ | \\ Alq^i\text{-}Si\text{-}X_p \end{array}$$

passing the group bound to the same silicon atom as this substitutory block from being represented by $(R^{i-1})_{3-p}$ to being represented by $(R^{i-1})_{3-z}$, formulas wherein:

$Alq^1, Alq^2, Alq^3 \ldots, Alq^i$ represent alkylene moieties of 2 to 4 carbons which are chosen independently from one another according to the length of the branches in each generation;

$R^1, R^2, R^3, \ldots R^{i-1}, R^i$ represent methyl and phenyl moieties;

X represents a moiety which contains at least one primary, secondary, tertiary or quaternary amino group;

p is a whole number which varies between 1 and 3;

m, n, . . . , z are whole numbers which vary independently between 1 and 3.

In the most preferred embodiment of the invention, the moieties $R^1, R^2, R^3, \ldots, R^{i-1}, R^i$ are all identical and correspond to methyl moieties; the moieties $Alq^1, Alq^2, Alq^3, \ldots, Alq^i$ are identical to one another and correspond to propylene moieties and the whole numbers m, n, . . . , j are identical to one another and have the value 2. In those conditions, the dendrimers which correspond to that embodiment of the invention can also be represented by the general formula iG-$(X_p)_m$, where:

i: indicates the number of the dendrimer generation
X: indicates the nature of the functional groups situated in the periphery of the dendrimer
p: indicates the number of functional groups in each branch m: indicates the number of terminal functional groups in the dendrimer G: represents the dendrimer carbosilane skeleton which, according to the generation, would correspond to the following formulas:

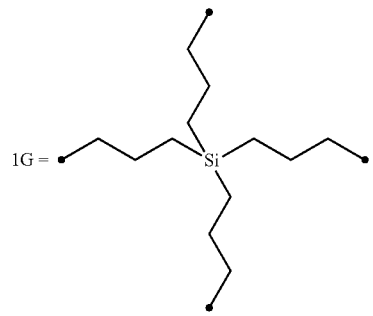

1G =

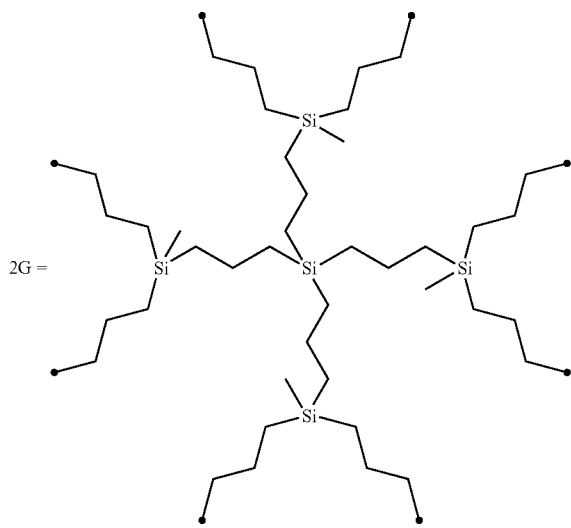

2G =

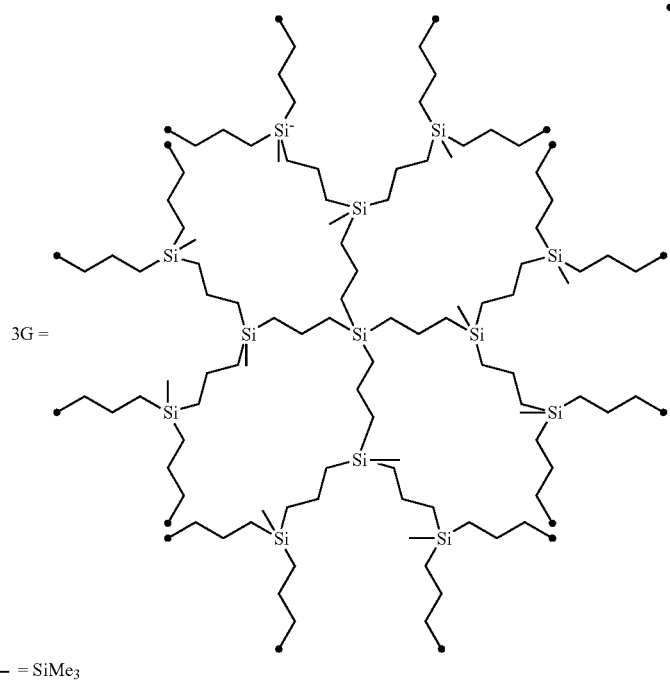

3G =

●—— = SiMe₃ skeletons where the SiMe₃ (Me=CH₃) final ends would be converted into SiMe₂X in the general formula of the dendrimer in the case that "p" was equal to 1 and into SiMeX₂ in the case that "p" was equal to 2.

X represents any moiety which contains a primary, secondary, tertiary or quaternary amine.

As used in the invention, the term dendrimer relates to a three-dimensional macromolecule of tree-like construction.

The term "generation" relates to the number of iterative stages which are necessary for the preparation of the dendrimer.

The term "carbosilane dendrimer" relates to a dendritic molecule with a carbosilane skeleton.

The term "hydrosilylation" relates to the addition of Si—H bonds to double C=C bonds.

As used in the invention, the term "antigenic moiety" relates to a moiety which is bound to a molecule and which is capable of unleashing an immune response in an individual who is supplied the molecule which has that moiety bound.

As used in the invention, the term "peptide" relates to a linear chain of two or more amino acids which are bound by the formation of an amide type link between a carboxyl group of an amino acid and an amino group of the adjacent amino acid.

As previously indicated, the invention also relates to a process for the preparation of the dendrimers of the invention. These organosilane dendrimers of different generations can be prepared with high yields using well known reactions, via divergent processes.[25,42,43,44,45,46] These dendrimers have great versatility which gives them advantages over other derivatives: i) it is possible to modify the length of the branches using vinylic or allylic Grignard derivatives in the metathesis step; ii) it is possible to vary the number of branches of each generation, replacing, for example, HSiCl$_3$ by HSiCH$_3$Cl$_2$; iii) it is possible to incorporate a great variety of functional groups to the periphery of the dendrimer. Furthermore, the carbosilane dendrimers have great chemical inertia, which is very useful for the additional purpose of this invention of using them as vehicles for carrying of anionic molecules (such as ODN and different anionic drugs) in the blood, its protection against interaction with plasma proteins and its uptake in a cell to exercise its action.

As has been commented, in a preferred embodiment of the invention the branches of the different generations are all equal and are the result of the use of the allylic derivative BrMg—CH$_2$—CH═CH$_2$, whilst the branches produced in each generation are also the same in all cases and equal to 2 by use of HSiCH$_3$Cl$_2$. In those conditions, the divergent synthesis process used to generate the different carbosilane dendrimers, could be schematized, until the second generation, in the following way Divergent synthesis

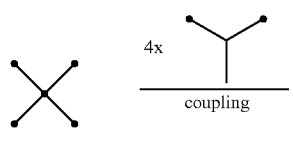

Central nucleus

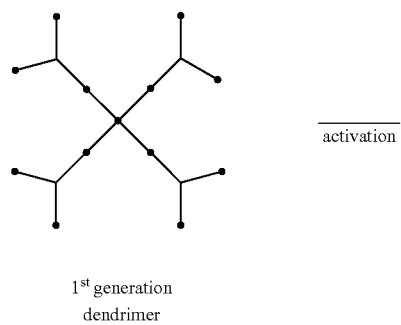

1$^{st}$ generation dendrimer

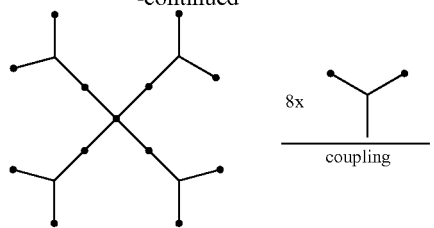

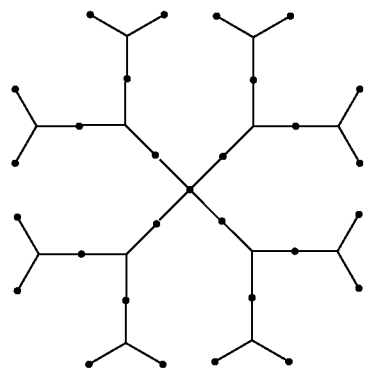

2$^{nd}$ generation dendrimer

Once the skeleton corresponding to the dendrimer precursor of the desired generation is produced, derivatives would be produced with Si—Cl or Si—H terminal bonds from which to produce the carbosilane dendrimers with terminal moieties which contain amino groups of the invention. The process detailed would be the following:

Production of Carbosilane Dendrimers with Terminal Amino Groups

The first step in the synthesis of these derivatives is the preparation of precursor dendrimers which contain Si—Cl or Si—H terminal bonds. The synthesis of these dendrimers has already been published[25,42,43,44,45,46,] and is carried out with high yields. In the examples stated below in the present specification, the dendrimers have grown to a third generation, but the methodology to produce dendrimers of later generations is analogous, for which purpose said dendrimers of later generations and their preparation are also included in the scope of the invention.

In the case of the preferred embodiment of the invention, wherein the branches of each generation are of equal size and correspond to 3-carbon chains and wherein new branches are formed in each generation, leaving a methyl bound to a Si atom in the fourth valency which would be left to saturate, the reactions scheme which would lead to the production of the different precursor carbosilane dendrimers with Si—Cl and Si—H terminal bonds would be represented by Scheme 1:

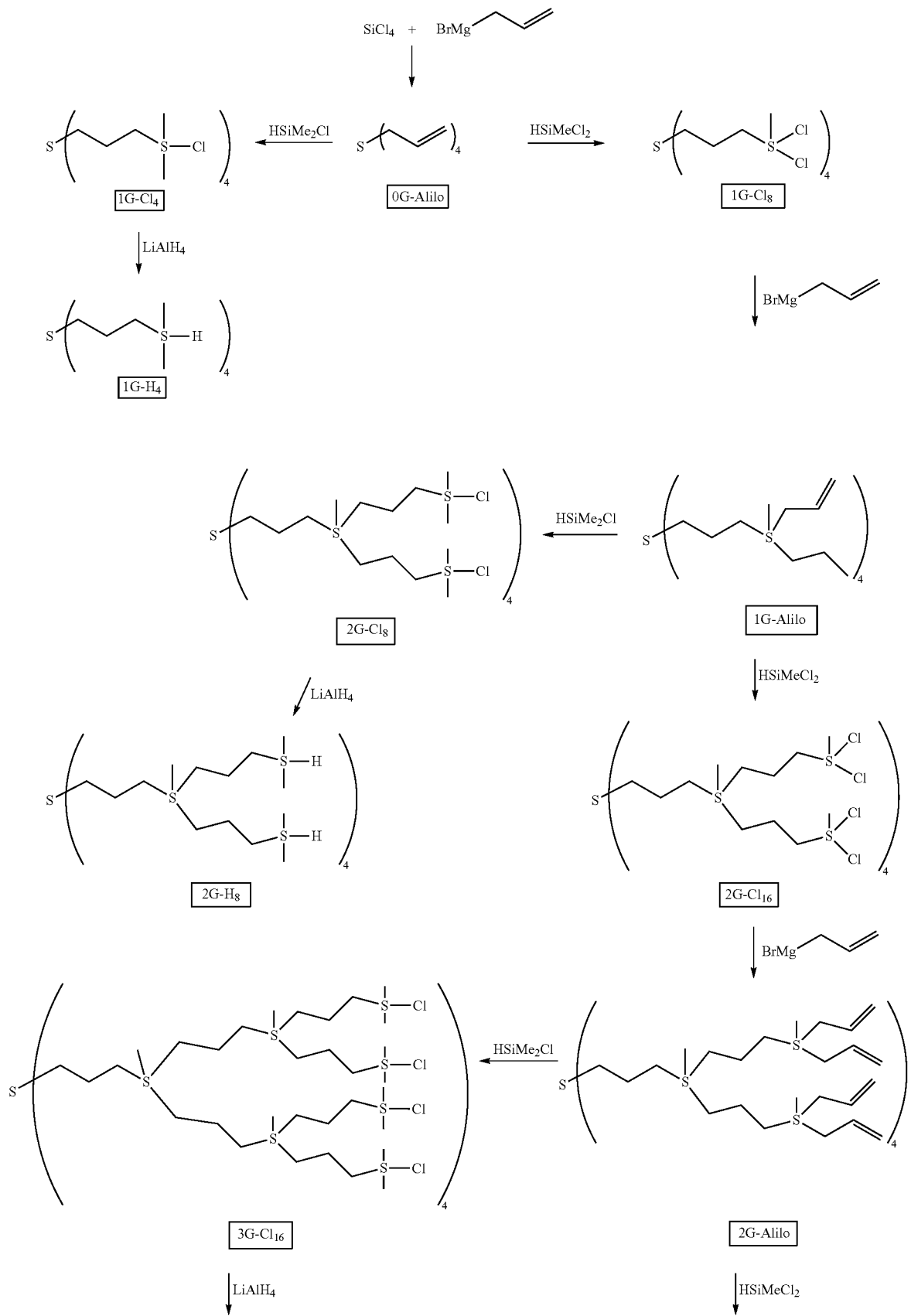

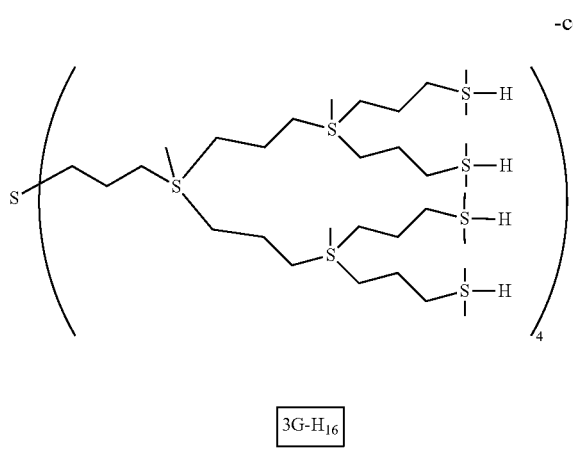

3G-H₁₆

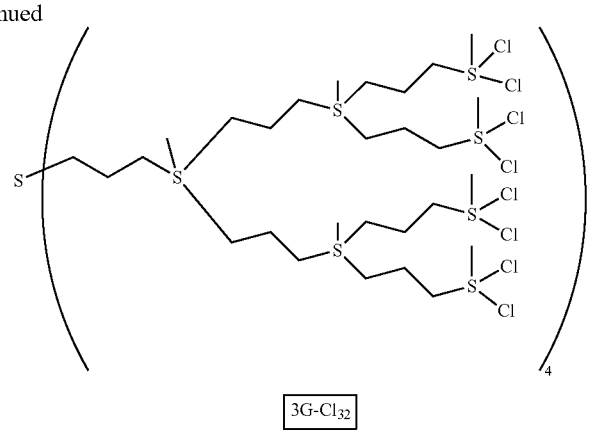

3G-Cl₃₂

The second step consists of binding different amino groups to the surface of these dendrimers using the known reactivity of the Si—Cl and Si—H bonds. With this purpose, two alternative synthetic routes can be followed, depending on the nature of the terminal group present in the carbosilane dendrimer.

1. Alcoholysis Route of Si—Cl Bonds.

This process has used different alcohol-amines in the presence of an alkali such as triethylamine added to remove the hydrogen chloride which is given off in this reaction. The term "alcohol-amine" relates to different amines which contain an alcoholic functionality, similar to the examples described by the following formulas:

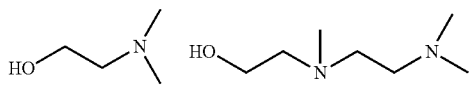

N,N-dimethylethanolamine
2-[(2-(dimethylaminoethyl)methyl]amino ethanol

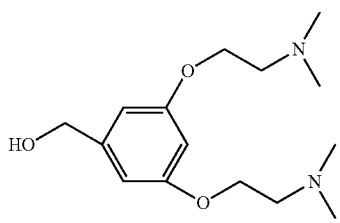 [SMILES: CN(C)CCOc1cc(CO)cc(OCCN(C)C)c1]

3,5-Bis(Dimethylaminoethoxy)benzyl alcohol

In the present invention, the use of these three amines is preferred, but the process of the invention permits functionalizing the periphery of a dendrimer with any other amine which has an alcoholic functionality susceptible of carrying out the alcoholysis process described herein, the functionalization of any of those amines and the carbosilane dendrimers with amine functions produced are also included in the scope of the invention.

The treatment of the carbosilane dendrimers which contain Si—Cl terminal bonds with the stoichiometric quantity of N,N-dimethylethanolamine in diethylene ether and in the presence of an excess of triethylamine leads to the formation of carbosilane dendrimers with terminal amino groups. In general terms, this stage is reproduced in Scheme 2:

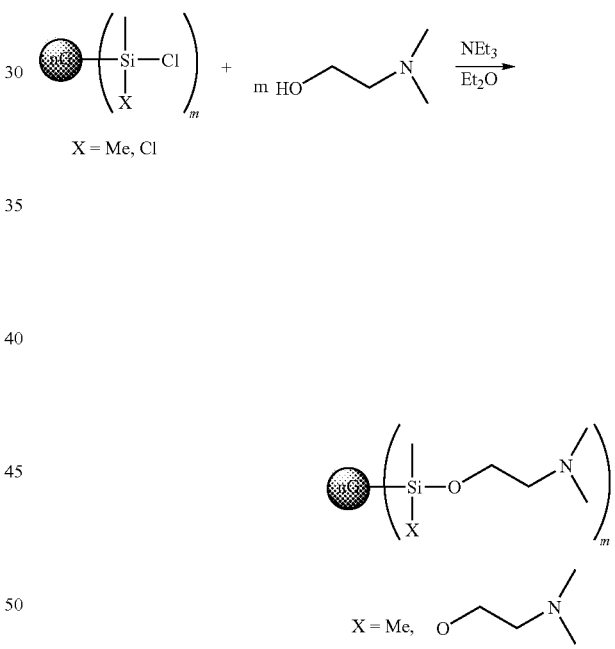

The use of this reaction scheme gave rise to the compounds 1G-[Si(OCH₂CH₂NMe₂)]₄ (1), 1G-[Si(OCH₂CH₂NMe₂)₂]₄ (2), 2G-[Si(OCH₂CH₂NMe₂)]₈ (3), 2G-[Si(OCH₂CH₂NMe₂)₂]₈ (4), 3G-[Si(OCH₂CH₂NMe₂)]₁₆ (5), 3G-[Si(OCH₂CH₂NMe₂)₂]₁₆ (6), whose synthesis process is explained in greater detail in examples 1-6 which are described below.

The substitution of N,N-dimethylethanolamine by other alcohol amine derivatives such as 3,5-(OCH₂CH₂NMe₂)₂—(C₆H₃)CH₂OH or Me₂NCH₂CH₂N(Me)CH₂CH₂OH leads to a similar reaction to that described above for the preparation of the dendrimers. This reaction is reproduced in Scheme 3:

Scheme 3

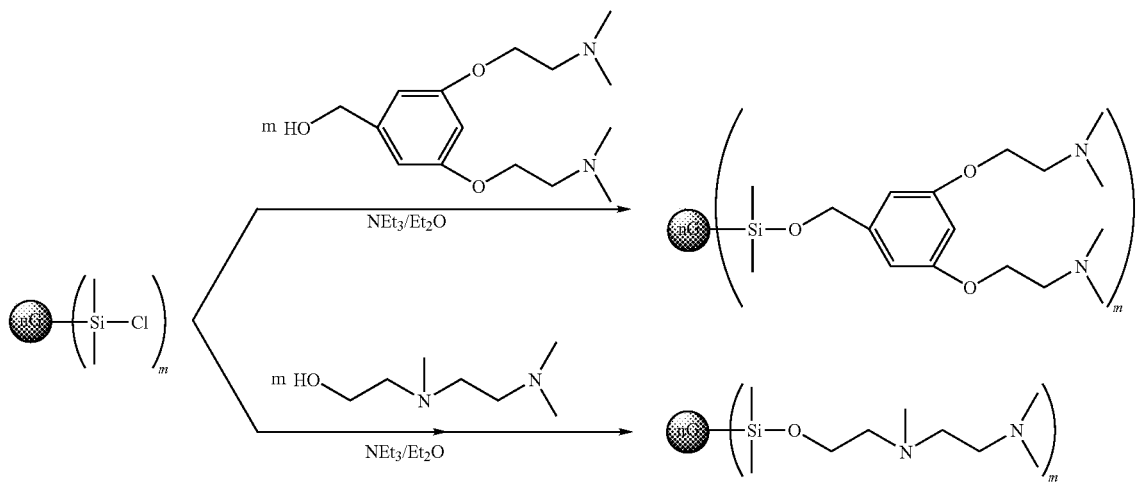

The use of this reaction scheme gave rise to the compounds 1G-[Si(OCH$_2$—(C$_6$H$_3$)-3,5-(OCH$_2$CH$_2$NMe$_2$)$_2$)]$_4$ (7), 2G-[Si(OCH$_2$—(C$_6$H$_3$)-3,5-(OCH$_2$CH$_2$NMe$_2$)$_2$)]$_8$ (8), 3G-[Si(OCH$_2$—(C$_6$H$_3$)-3,5-(OCH$_2$CH$_2$NMe$_2$)$_2$)]$_{16}$ (9), 1G-[Si(OCH$_2$CH$_2$N(Me)CH$_2$CH$_2$NMe$_2$)]$_4$ (10), 2G-[Si(OCH$_2$CH$_2$N(Me)CH$_2$CH$_2$NMe$_2$)]$_8$ (11), 3G-[Si(OCH$_2$CH$_2$N(Me)CH$_2$CH$_2$NMe$_2$)]$_{16}$ (12), whose synthesis process is explained in greater detail in examples 1-6 which are described below.

Quaternization with MeI

The attempts made to quaternize the terminal amino groups of dendrimers 1-12 with the stoichiometric quantity or a small excess of HCl did not lead to the expected result, due to the gradual hydrolysis of the Si—O bonds. However, the treatment of these dendrimers with an excess MeI in diethylene ether quantitatively produces the quaternization of the amino groups in a few hours, causing the precipitation of the iodine salts of the ammonium cations as white-coloured hygroscopic solids in high yields. This reaction is presented in Scheme 4:

Scheme 4

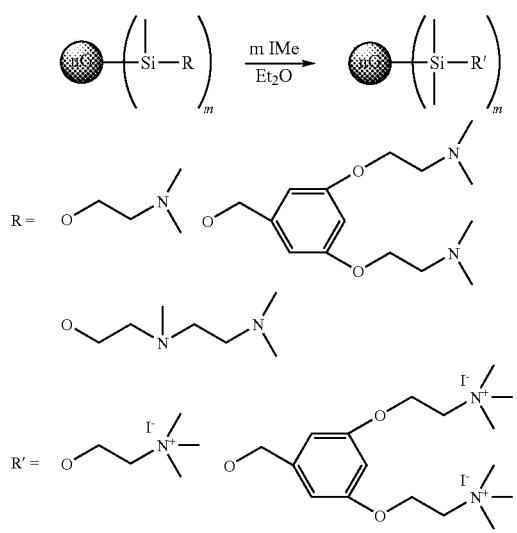

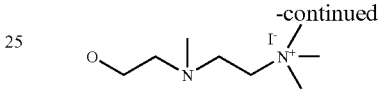
-continued

In this way, the dendrimers listed below have been isolated and characterized: 1G-[Si(OCH$_2$CH$_2$NMe$_3$$^+$I$^-$)]$_4$ (16), 1G-[Si(OCH$_2$CH$_2$NMe$_3$$^+$I$^-$)$_2$]$_4$ (17), 2G-[Si(OCH$_2$CH$_2$NMe$_3$$^+$I$^-$)]$_8$ (18), 2G-[Si(OCH$_2$CH$_2$NMe$_3$$^+$I$^-$)$_2$]$_8$ (19), 3G-[Si(OCH$_2$CH$_2$NMe$_3$$^+$I$^-$)]$_{16}$ (20), 3G-[Si(OCH$_2$CH$_2$NMe$_3$$^+$I$^-$)$_2$]$_{16}$ (21), 1G-[Si(OCH$_2$—(C$_6$H$_3$)-3,5-(OCH$_2$CH$_2$NMe$_3$$^+$I$^-$)$_2$)]$_4$ (22), 2G-[Si(OCH$_2$—(C$_6$H$_3$)-3,5-(OCH$_2$CH$_2$NMe$_3$$^+$I$^-$)$_2$)]8 (23), 3G-[Si(OCH$_2$—(C$_6$H$_3$)-3,5-(OCH$_2$CH$_2$NMe$_3$$^+$I$^-$)$_2$)]$_{16}$ (24), 1G-[Si(OCH$_2$CH$_2$N(Me)CH$_2$CH$_2$NMe$_3$$^+$I$^-$)]$_4$ (25), 2G-[Si(OCH$_2$CH$_2$N(Me)CH$_2$CH$_2$NMe$_3$$^+$I$^-$)]8 (26), 3G-[Si(OCH$_2$CH$_2$N(Me)CH$_2$CH$_2$NMe$_3$$^+$I$^-$)]$_{16}$ (27).

Their synthesis and characterization process is detailed below in examples 16 to 27 which are described later. The details provided herein show that the quaternization of the dimethylamino group is incomplete for some of the third generation dendrimers, specifically 21, 24 and 27: only around 90% of the terminal groups of these complexes have been quaternized. This is the case even in the presence of an excess MeI and leaving the reaction for greater time periods.

In the case of dendrimers 10 and 11, of first and second generation respectively, the addition of an excess MeI to the stoichiometric quantity necessary for the quaternization of all the nitrogen atoms present in the macromolecules leads to the formation of dendrimers 35 (1G-[Si(O(CH$_2$)$_2$N$^+$(Me)$_2$(CH$_2$)$_2$ NMe$_3$$^+$2I$^-$)]$_4$ and 36 (2G-[Si(O(CH$_2$)$_2$N$^+$(Me)$_2$(CH$_2$)$_2$ NMe$_3$$^+$2I$^-$)]$_8$), whose synthesis and characterization process is described, respectively, in examples 48 and 49.

2. Hydrosilylation route of Si—H terminal bonds

The treatment of the carbosilane dendrimers which contain Si—H terminal bonds with allylamine (CH$_2$=CH—CH$_2$—NH$_2$) in the presence of Karstedt catalyst[28] leads to the formation of carbosilane dendrimers with terminal amino groups 1G-[SiCH$_2$CH$_2$CH$_2$NH$_2$]$_4$ (13), 2G-[SiCH$_2$CH$_2$CH$_2$NH$_2$]$_8$ (14), 3G-[SiCH$_2$CH$_2$CH$_2$NH$_2$]$_{16}$ (15) with practically quantitative yields. The reaction whereby they are produced is shown in Scheme 5:

Scheme 4

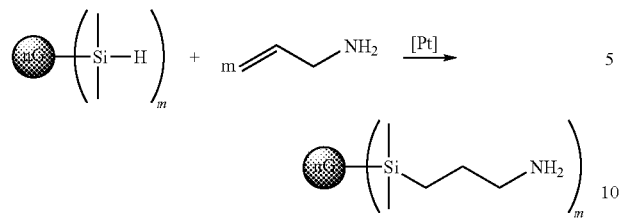

These dendrimers are thermally stable and soluble in organic solvents. Their characterization and purity has been verified by elemental analysis (H, C, N), NMR spectroscopy ($^1$H, $^{13}$C and $^{29}$Si) and mass spectrometry (electrospray or MALDI-TOF MS). Their synthesis and characterization are detailed in examples 13 to 15 which are described below.

This process is also applicable for the synthesis of carbosilane dendrimers which have other different terminal moieties at their branch ends which also contain amino groups, substituting allylamine in the reaction for another compound which contains an amino group and which also contains a terminal carbon which forms a double bond with an adjacent carbon, so that one of the ends of said compound has a $CH_2=CH-$ terminal moiety which leads to the compound being bound to the dendrimer skeleton by a $-CH_2-$ group. Said compound can simply be an alkyleneamine, for example primary, of formula $CH_2=CH-(CH_2)_e-NH_2$, wherein the "e" index varies between 0 and 2 (corresponding the case wherein e=1 specifically to the allylamine), or more complex compounds, which also comprise an alkenyl moiety at one end ($CH_2=CH-(CH_2)_e-$) and an amino group (primary, secondary, tertiary or quaternary) at another different end, the compound additionally comprising a $-R_a-$ moiety between the $CH_2=CH-(CH_2)_e-$ alkenyl moiety and the amino group. Examples 44 and 45 detail the synthesis and characterization of dendrimers 31 (1 G-[Si(($CH_2)_2C_6H_3$(OMe)(O($CH_2)_2NMe_2$))]$_4$) and 32 (2G-[Si(($CH_2)_2C_6H_3$(OMe)(O($CH_2)_2NMe_2$))]$_8$) which contain at their branch ends moieties derivative of one of said compounds, specifically the non-commercial product ($CH_2=CH-CH_2)C_6H_3$(OMe){O($CH_2)_2NMe_2$}, whose prior synthesis is described in example 44.

Quaternization with HCl

The quaternization of dendrimers with $-NH_2$ terminal groups, 13-15, could be performed by the addition of HCl (1M solution in Et$_2$O) in diethylene ether as solvent (Scheme 6).

Scheme 6

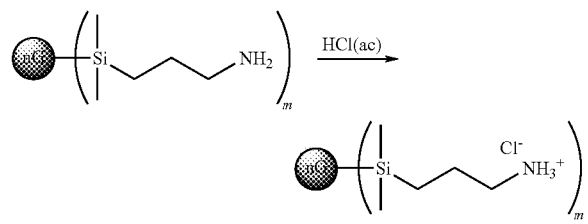

The ionic derivatives 1 G-[SiCH$_2$CH$_2$CH$_2$NH$_3^+$Cl$^-$]$_4$ (28), 2G-[SiCH$_2$CH$_2$CH$_2$NH$_3^+$Cl$^-$]$_8$ (29), 3G-[SiCH$_2$CH$_2$CH$_2$NH$_3^+$Cl$^-$]$_{16}$ (30) were produced following said reaction Scheme 6. Said compounds precipitate as white-Coloured solids and are easily purified by vacuum elimination of the solvent and excess HCl used in the reaction.

These dendrimers are thermally stable and soluble in DMSO, MeOH and H$_2$O. Their characterization and purity has been verified, as with the previously described dendrimers, by elemental analysis (H, C, N), NMR spectroscopy ($^1$H, $^{13}$C and $^{29}$Si) and mass spectroscopy (electrospray or MALDI-TOF MS).

Quaternization with MeI

The quaternization of dendrimers 31 and 32, with $-NMe_2$ terminal groups, was carried out following Scheme 4, wherein, in the case of dendrimers 31 and 32, R would correspond to the moiety $-[(CH_2)_2C_6H_3(OMe)(O(CH_2)_2NMe_2)]$. Dendrimers 31 and 32, therefore, were treated with methyl iodide (abbreviated MeI) in diethylene ether (Et$_2$O), as described in examples 46 and 47, thus producing dendrimers 33 and 34.

Examples of Synthesis of Carbosilane Dendrimers with Terminal Amino Groups

It should be understood that the examples given below are only to illustrate the object of this invention and do not involve any limitations in any way.

The values of the integrals of the signals in the $^1$H-NMR spectrums of the dendrimers which are described only represent the fourth part of the total number of hydrogen atoms.

Examples 1 to 30 which appear below describe the synthesis of carbosilane dendrimers with terminal amino groups which start from precursor dendrimers (1G-Cl$_4$, 1G-Cl$_8$, 1G-H$_4$, 2G-Cl$_8$, 2G-Cl$_{16}$, 1G-H$_8$, 3G-Cl$_4$, 1G-Cl$_8$, 1G-H$_4$,) previously synthesized following the already known processes indicated in Scheme 1. As has been commented, said precursor dendrimers serve as "skeletons" wherefrom the carbosilane dendrimers of the invention are formed, with terminal amino groups, by reacting them with compounds which give rise to the ligands which are converted at the ends of the dendrimer branches. The compounds used for the synthesis of the dendrimers described in Examples 1 to 30 were: allylamine ($CH_2=CH-CH_2-NH_2$) (acquired from Sigma Aldrich), N,N-diethylethanolamine ($CH_2OH-CH_2-N(CH_3)_2$) (acquired from Sigma Aldrich) or 2-[(2-(dimethylaminoethyl)methyl]amino ethanol ($CH_2OH-CH_2-N(CH_3)-CH_2-CH_2-N(CH_3)_2$) (acquired from Sigma Aldrich) or 3,5-bis(dimethylaminoethoxy)benzyl alcohol ($CH_2OH-(C_6H_3)-(O-CH_2-CH_2-N(CH_3)_2)_2$), this latter compound which was not acquired from any commercial establishment and it was necessary to previously synthesize it, as described in Example 7. The details of the reactions wherein these compounds were used to give rise to carbosilane dendrimers of the invention, as well as the quaternization thereof to give rise to additional dendrimers of the invention, are described below in Examples 1 to 30.

EXAMPLES 1 to 12

Example 1

Synthesis of 1G-[Si(OCH$_2$CH$_2$NMe$_2$)]$_4$ (1)

A slight excess of NEt$_3$ (0.86 ml, 6.2 mmol) and N,N-dimethylethanolamine (0.6 ml, 5.97 mmol) was added to a 1G-Cl$_4$ dendrimer solution (0.85 g, 1.49 mmol) in ether (50 ml). The reaction mixture was maintained with constant stirring during 1 h at ambient temperature, after vacuum eliminating the excess NEt$_3$ and the solvent giving rise to a residue which was extracted with ether (30 ml). The resulting suspension was filtered with celite to eliminate the ammonium salt $NEt_3 \cdot HCl$ generated in the reaction and the filtrate was dried giving rise to compound 1 as a pale yellow oil. (0.98 g, 84%).

$^1$H-NMR ($CDCl_3$): δ 3.64 (2H, t, $CH_2O$), 2.40 (2H, t, $CH_2N$), 2.22 (6H, s, $NMe_2$), 1.31 (2H, m, $SiCH_2CH_2CH_2SiO$), 0.60 (2H, m, $SiCH_2CH_2CH_2SiO$), 0.53 (2H, m, $SiCH_2CH_2CH_2SiO$), 0.067 (6H, s, $OSiMe_2$), $^{13}$C{$^1$H}-NMR ($CDCl_3$): δ. 61.5 ($CH_2N$), 60.8 ($CH_2O$), 46.1 ($NMe_2$), 21.3 ($SiCH_2CH_2CH_2SiO$), 18.1, 17.4 ($SiCH_2CH_2CH_2SiO$), −1.7 ($OSiMe_2$). $^{29}$Si{$^1$H}-NMR ($CDCl_3$): δ 0.49 ($G_0$-Si), 17.62 ($G_1$-Si). Elemental analysis of $C_{36}H_{88}N_4O_4Si_5$: Calc.: C, 55.33; H, 11.35; N, 7.17. Obt.: C, 55.16; H, 11.22; N, 7.06.

Example 2

Synthesis of 1G-[Si(OCH$_2$CH$_2$NMe$_2$)$_2$]$_4$ (2)

The first generation dendrimer 2 was prepared following a process similar to that described for 1, starting from 1G-Cl$_8$ (0.54 g, 0.87 mmol), N,N-dimethylethanolamine (0.7 ml, 6.94 mmol) and NEt$_3$ (1.0 ml, 7.2 mmol). In this way, 2 was produced as a colourless oil. (0.75 g, 80%).

$^1$H-NMR ($CDCl_3$): δ 3.74 (4H, t, $CH_2O$), 2.43 (4H, t, $CH_2N$), 2.23 (12H, s, $NMe_2$), 1.31 (2H, m, $SiCH_2CH_2CH_2SiO$), 0.63 (2H, m, $SiCH_2CH_2CH_2SiO$), 0.52 (2H, m, $SiCH_2CH_2CH_2SiO$), 0.09 (3H, s, $OSiMe$), $^{13}$C{$^1$H}-NMR ($CDCl_3$): δ 61.4 ($CH_2N$), 60.7 ($CH_2O$), 46.2 ($NMe_2$), 18.7 ($SiCH_2CH_2CH_2SiO$), 17.7, 17.2 ($SiCH_2CH_2CH_2SiO$), −4.4 ($OSiMe$). $^{29}$Si{$^1$H}-NMR ($CDCl_3$): δ 0.47 ($G_0$-Si), −3.65 ($G_1$-Si), Elemental analysis of $C_{48}H_{116}N_8O_8Si_5$: Calc,: C, 53.68; H, 10.89; N, 10.43. Obt.: C, 53.54; H, 11.33; N, 10.06. MALDI-TOFF-MS: m/z 1095.8 [M+H]+ (Calc, 1095.8).

Example 3

Synthesis of 2G-[Si(OCH$_2$CH$_2$NMe$_2$)]$_8$ (3)

The second generation dendrimer 3 was prepared following a process similar to that described for 1, starting from 2G-Cl$_8$ (0.27 g, 0.18 mmol), N,N-dimethylethanolamine (0.15 ml, 1.47 mmol) and NEt$_3$ (0.25 ml, 1.79 mmol). In this way, 3 was produced as a colourless oil (0.31 g, 90%).

$^1$H-NMR ($CDCl_3$): δ 3.64 (4H, t, $CH_2O$), 2.41 (4H, t, $CH_2N$), 2.23 (12H, s, $NMe_2$), 1.30 (6H, m, $SiCH_2CH_2CH_2SiO$ and $SiCH_2CH_2CH_2Si$ overlapped), 0.65 (4H, m, $SiCH_2CH_2CH_2SiO$), 0.53 (8H, m, moiety of $CH_2Si$), 0.07 (12H, s, $OSiMe_2$), −0.09 (3H, s, SiMe). $^{13}$C{$^1$H}-NMR ($CDCl_3$): δ 61.5 ($CH_2N$), 60.8 ($CH_2O$), 46.1 ($NMe_2$), 21.1 ($SiCH_2CH_2CH_2SiO$), 18.6-17.9 (moiety of —$CH_2$— groups), −1.9 ($OSiMe_2$), −4.9 (SiMe), $^{29}$Si{$^1$H}-NMR ($CDCl_3$): δ 0.93 ($G_1$-Si), 17.6 ($G_2$-Si), $G_0$-Si not observed. Elemental analysis of $C_{88}H_{212}N_8O_8Si_{13}$. Calc.: C, 56.35; H, 11.39; N, 5.97. Obt.: C, 55.98; H, 11.20; N, 5.78.

Example 4

Synthesis of 2G-[Si(OCH$_2$CH$_2$NMe$_2$)$_2$]$_8$ (4)

The second generation dendrimer 4 was prepared following a process similar to that described for 1, starting from 2G-Cl$_{16}$ (0.48 g, 0.30 mmol), N,N-dimethylethanolamine (0.48 ml, 4.77 mmol) and NEt$_3$ (0.7 ml, 5.02 mmol). In this way, 3 was produced as a colourless oil (0.66 g, 90%).

$^1$H-NMR ($CDCl_3$): δ 3.75 (8H, t, $CH_2O$), 2.44 (8H, t, $CH_2N$), 2.24 (24H, s, $NMe_2$), 1.34 (6H, m, $SiCH_2CH_2CH_2SiO$ and $SiCH_2CH_2CH_2Si$ overlapped), 0.64 (4H, m, $SiCH_2CH_2CH_2SiO$), 0.51 (8H, m, moiety of $CH_2Si$), 0.09 (6H, s, $OSiMe$), −0.10 (3H, s, SiMe). $^{13}$C{$^1$H}-NMR ($CDCl_3$): δ 61.4 ($CH_2N$), 60.7 ($CH_2O$), 46.2 ($NMe_2$), 18.6 ($SiCH_2CH_2CH_2SiO$), 17.7-17.0 (moiety of —$CH_2$— groups), −4.4 ($OSiMe$), −4.8 (SiMe). $^{29}$Si{$^1$H}-NMR ($CDCl_3$): δ 0.9 ($G_1$-Si); −3.5 ($G_2$-Si); $G_0$-Si not observed. Elemental analysis of $C_{112}H_{268}N_{16}O_{16}Si_{13}$: Calc.: C, 54.67; H, 10.98; N, 9.11. Obt.: C, 54.20; H, 10.37; N, 9.59.

Example 5

Synthesis of 3G-[Si(OCH$_2$CH$_2$NMe$_2$)]$_{16}$ (5)

The third generation dendrimer 5 was prepared following a process similar to that described for 1, starting from 3G-Cl$_{16}$ (0.20 g, 0.06 mmol), N,N-dimethylethanolamine (0.10 ml, 0.99 mmol) and NEt$_3$ (0.16 ml, 1.14 mmol). In this way, 5 was produced as a pale yellow oil (0.18 g, 74%).

$^1$H-NMR ($CDCl_3$): δ 3.65 (8H, t, $CH_2O$), 2.42 (8H, t, $CH_2N$), 2.24 (24H, s, $NMe_2$), 1.23 (14H, m, $SiCH_2CH_2CH_2SiO$ and $SiCH_2CH_2CH_2Si$ overlapped), 0.64 (8H, m, $SiCH_2CH_2CH_2SiO$), 0.53 (20H, m, moiety of $CH_2Si$), 0.068 (24H, s, $OSiMe_2$), −0.10 (9H, s, SiMe). $^{13}$C{$^1$H}-NMR ($CDCl_3$): δ 61.5 ($CH_2N$), 60.8 ($CH_2O$), 46.1 ($NMe_2$), 21.1 ($SiCH_2CH_2CH_2SiO$), 18.6-17.9 (moiety of —$CH_2$— groups), −1.82 ($OSiMe_2$), −4.8 (SiMe), $^{29}$Si{$^1$H}-NMR ($CDCl_3$): δ 0.95 ($G_2$-Si); 17.95 ($G_3$-Si) $G_0$-Si and $G_1$-Si not observed. Elemental analysis of $C_{198}H_{460}N_{16}O_{16}Si_{29}$. Calc.: C, 56.74; H, 11.41; N, 5.51. Exp.%: C, 56.17; H, 11.28; N, 5.34.

Example 6

Synthesis of 3G-[Si(OCH$_2$CH$_2$NMe$_2$)$_2$]$_{16}$ (6)

The third generation dendrimer 6 was prepared following a process similar to that described for 1, starting from 3G-Cl$_{32}$ (0.19 g, 0.05 mmol), N,N-dimethylethanolamine (0.17 ml, 1.68 mmol) and NEt$_3$ (0.24 ml, 1.79 mmol). In this way, 6 was produced as a pale yellow oil (0.20 g, 72%).

$^1$H-NMR ($CDCl_3$): δ 3.75 (16H, t, $CH_2O$), 2.44 (16H, t, $CH_2N$), 2.24 (48H, s, $NMe_2$), 1.32 (14H, m, $SiCH_2CH_2CH_2SiO$ and $SiCH_2CH_2CH_2Si$ overlapped), 0.66 (8H, m, $SiCH_2CH_2CH_2SiO$), 0.53 (20H, m, moiety of SiCH$_2$), 0.07 (12H, s, $OSiMe_2$), −0.10 (18H, s, SiMe). $^{13}$C{$^1$H}-NMR ($CDCl_3$): δ 61.4 ($CH_2N$), 60.7 ($CH_2O$), 46.1 ($NMe_2$), 18.4-17.4 (moiety of —$CH_2$— groups), −4.7 ($OSiMe_2$), −5.2 (SiMe). Elemental analysis of $C_{240}H_{572}N_{32}O_{32}Si_{29}$. Calc.: C, 55.08; H, 11.02; N, 8.56. Obt.: C, 56.11; H, 11.89; N, 8.13.

Example 7

Synthesis of 1G-[Si(OCH$_2$—(C$_6$H$_3$)-3,5-(OCH$_2$CH$_2$NMe$_2$)$_2$)]$_4$ (7)

7.1. Synthesis of 3,5-(OCH$_2$CH$_2$NMe$_2$)$_2$—(C$_6$H$_3$)—CH$_2$OH

With the purpose of synthesizing dendrimers 7, 8 and 9 (starting dendrimers, in turn, to produce dendrimers 22, 23 and 24), it as necessary to previously synthesize the compound which was later to be used as ligand, 3,5-(OCH$_2$CH$_2$NMe$_2$)$_2$—(C$_6$H$_3$)—CH$_2$. For this, to a solution of 3,5-dihydroxybenzyl alcohol (1.47 g, 10.39 mmol) in acetone as solvent, 2 equivalents of the 2-chloro-N,N dimethylaminoethane hydrochloride (2.98 g, 20.78 mmol), 4.5 equivalents of $K_2CO_3$ (6.43 g, 46.75 mmol), 18-Corona-6 ether corona (0.54 g, 2 mmol) and a spatula tip of KI. The reaction was maintained at reflux during 48 h. After the vacuum elimination of the solvent, it was extracted in $CH_2Cl_2/H_2O$ (2×50 ml). The organic phase was dried with $MgSO_4$ during 1 h. It was then filtered and the solvent was eliminated in a vacuum, producing a pale yellow oil which was washed with hexane (2×10 ml) to eliminate the 18-Corona-6 ether corona. Thus the intended compound was produced as a pale yellow oil (1.53 g, 50%).

NMR-$^1$H(CDCl$_3$): δ 6.48 (2H, m, $C_6H_3$), 6.36 (1H, m, $C_6H_3$), 4.57 (2H, s, $CH_2OH$), 3.99 (4H, t, $CH_2O$—$C_6H_3$), 2.65 (4H, t, $CH_2N$), 2.60 (1H, s, $CH_2OH$), 2.28 (12H, s, $NMe_2$). NMR-$^{13}C\{^1H\}$ (CDCl$_3$): δ 159.9 ($C_6H_3$, $C_{ipso}$ bound to $OCH_2CH_2NMe_2$), 143.8 ($C_6H_3$, $C_{ipso}$ bound to $CH_2OH$), 105.1 and 100.6 ($C_6H_3$), 65.8 ($CH_2O$—$C_6H_3$), 64.9 ($CH_2OH$), 58.2 ($CH_2N$), 45.8 ($NMe_2$). Elemental analysis of $C_{15}H_{26}N_2O_3$. Calc. %: C, 63.80; H, 9.28; N, 9.92. Exp. %: C, 63.50; H, 9.17; N, 9.83.

This compound was used for the synthesis of dendrimers 7, 8 and 9, which is described below.

7.2. Synthesis of dendrimer 7

A slight excess of NEt$_3$ (0.12 ml, 0.87 mmol) and 3,5-$(OCH_2CH_2NMe_2)_2$—$(C_6H_3)$—$CH_2OH$ (0.22 g, 0.378 mmol) was added to a 1G-Cl$_4$ (0.11 g, 0.19 mmol) dendrimer solution in ether (30 ml),. The reaction mixture was maintained with constant stirring during 1 h at ambient temperature, after the vacuum elimination of the excess NEt$_3$ and the solvent giving rise to a residue which was extracted with ether (2×20 ml). The resulting suspension was filtered with celite to eliminate the ammonium salt NEt$_3$-HCl generated in the reaction and the filtrate was dried giving rise to compound 7 as a pale yellow oil (0.23 g, 80%).

$^1$H-NMR (CDCl$_3$): δ 6.45 (2H, m, $C_6H_3$); 6.36 (1H, m, $C_6H_3$); 4.56 (2H, s, $CH_2OSi$); 3.99 (4H, t, $CH_2O$—$C_6H_3$); 2.66 (4H, t, $CH_2N$); 2.28 (12H, s, $NMe_2$); 1.33 (2H, m, $SiCH_2CH_2CH_2SiO$); 0.68 (2H, m, $SiCH_2CH_2CH_2SiO$); 0.55 (2H, m, $SiCH_2CH_2CH_2SiO$); 0.08 (6H, s, $SiMe_2$). $^{13}C\{^1H\}$-NMR (CDCl$_3$): δ 159.8 ($C_6H_3$, $C_{ipso}$ bound to $OCH_2CH_2NMe_2$); 143.2 ($C_6H_3$, $C_{ipso}$ bound to $CH_2OSi$); 104.9 and 100.2 ($C_6H_3$); 65.9 ($CH_2O$—$C_6H_3$); 64.6 ($CH_2OSi$); 58.2 ($CH_2N$); 45.8 ($NMe_2$); 21.2 ($SiCH_2CH_2CH_2SiO$); 17.9, 17.2 ($SiCH_2CH_2CH_2SiO$); −1.89 ($SiMe_2$). Elemental analysis of $C_{80}H_{148}N_8O_{12}Si_5$. Calc.: C, 61.81; H, 9.60; N, 7.21. Obt.: C, 62.10; H, 9.82; N, 7.3.

Example 8

Synthesis of 2G-[Si(OCH$_2$—(C$_6$H$_3$)-3,5-(OCH$_2$CH$_2$NMe$_2$)$_2$)]$_8$ (8)

The second generation dendrimer 8 was prepared following a process similar to that described for 7, starting from 2G-Cl$_8$ (0.27 g, 0.19 mmol); NEt$_3$ (0.22 mL, 1.62 mmol) and 3,5-$(OCH_2CH_2NMe_2)_2$—$(C_6H_3)$—$CH_2OH$ (0.43 g, 1.52 mmol). In this way, 8 was produced as a pale yellow oil (0.54 g; 82%).

$^1$H-NMR (CDCl$_3$): δ 6.45 (4H, m, $C_6H_3$); 6.36 (2H, m, $C_6H_3$); 4.56 (4H, s, $CH_2OSi$); 3.99 (8H, t, $CH_2O$—$C_6H_3$); 2.67 (8H, t, $CH_2N$); 2.29 (24H, s, $NMe_2$); 1.33 (6H, m, $SiCH_2CH_2CH_2SiO$ and $SiCH_2CH_2CH_2Si$), 0.69 (4H, m, $SiCH_2CH_2CH_2SiO$), 0.55 (8H, m, $CH_2$ bound to Si), 0.09 (12H, s, $OSiMe_2$), −0.09 (3H, s, SiMe). $^{13}C\{^1H\}$-NMR (CDCl$_3$): δ 159.0 ($C_6H_3$, $C_{ipso}$ bound to $OCH_2CH_2NMe_2$); 143.3 ($C_6H_3$, $C_{ipso}$ bound to $CH_2OSi$); 104.8 and 100.1 ($C_6H_3$); 65.9 ($CH_2O$—$C_6H_3$); 64.6 ($CH_2OSi$); 58.3 ($CH_2NMe_2$); 45.9 ($NMe_2$), 21.2 ($SiCH_2CH_2CH_2SiO$); 17.9, 17.2 ($SiCH_2CH_2CH_2SiO$ and overlapping signals of $SiCH_2CH_2CH_2Si$); −1.7 ($OSiMe_2$), −4.9 (SiMe). 29Si$\{^1H\}$-NMR (CDCl$_3$): δ 0.93 ($G_1$-Si), 18.7 ($G_2$-Si), $G_0$-Si not observed. Elemental analysis of $C_{176}H_{332}N_{16}O_{24}Si_{13}$. Calc.: C, 61.78; H, 9.78; N, 6.55. Obt.: C, 62.51; H, 9.90; N, 6.75.

Example 9

Synthesis of 3G-[Si(OCH$_2$—(C$_6$H$_3$)-3,5-(OCH$_2$CH$_2$NMe$_2$)$_2$)]$_{16}$ (9)

The third generation dendrimer 9 was prepared following a process similar to that described for 7, starting from 3G-Cl$_{16}$ (0.072 g, 0.022 mmol); NEt$_3$ (0.060 ml, 0.43 mmol) and 3,5-$(OCH_2CH_2NMe_2)_2$—$(C_6H_3)$—$CH_2OH$ (0.101 g, 0.358 mmol). In this way, 9 was produced as a pale yellow oil (0.110 g; 69%).

$^1$H-NMR (CDCl$_3$): δ 6.46 (8H, m, $C_6H_3$); 6.35 (4H, m, $C_6H_3$); 4.56 (8H, s, $CH_2OSi$); 3.97 (16H, t, $CH_2O$—$C_6H_3$); 2.67 (16H, t, $CH_2N$); 2.28 (48H, s, $NMe_2$); 1.33 (14H, m, $SiCH_2CH_2CH_2SiO$ and $SiCH_2CH_2CH_2Si$), 0.69 (8H, m, $SiCH_2CH_2CH_2SiO$), 0.55 (18H, m, $CH_2$ bound to Si), 0.09 (24H, s, $OSiMe_2$), −0.09 (9H, s, SiMe). $^{13}C\{^1H\}$-NMR (CDCl$_3$): □ 160.0 ($C_6H_3$, $C_{ipso}$ bound to $OCH_2CH_2NMe_2$); 143.2 ($C_6H_3$, $C_{ipso}$ bound to $CH_2OSi$); 104.3 and 100.8 ($C_6H_3$); 65.9 ($CH_2O$—$C_6H_3$); 64.6 ($CH_2OSi$); 58.3 ($CH_2NMe_2$); 45.8 ($NMe_2$), 21.1 ($SiCH_2CH_2CH_2SiO$); 17.8, 17.2 ($SiCH_2CH_2CH_2SiO$ and overlapping signals of $SiCH_2CH_2CH_2Si$); −1.8 ($OSiMe_2$), −4.9 (SiMe). Elemental analysis of $C_{368}H_{700}N_{32}O_{48}Si_{29}$. Calc.: C, 61.76; H, 9.86; N, 6.26. Obt.: C, 62.43; H, 9.90; N, 6.80.

Example 10

Synthesis of 1G-[Si(O(CH$_1$))N(Me)(CH$_7$)NMe$_2$)]$_4$ (10)

A slight excess of NEt$_3$ (0.5 ml, 3.58 mmol) and 2-{[2-dimethylamino)ethyl]methylamino}ethanol (0.35 ml, 2.19 mmol) was added to a 1G-Cl$_4$ (0.31 g, 0.54 mmol) dendrimer solution in ether (30 ml),. The reaction mixture was maintained with constant stirring during 12 h at ambient temperature, after the vacuum elimination of the excess NEt$_3$ and the solvent giving rise to a residue which was extracted with ether (2×20 mL). The resulting suspension was filtered with celite to eliminate the ammonium salt NEt$_3$.HCl generated in the reaction and the filtrate was dried giving rise to compound 10 as a colourless oil (0.3 g, 57%).

$^1$H-NMR (CDCl$_3$): δ 3.64 (2H, t, $CH_2O$), 2.51 (4H, m, $CH_2N(Me)$), 2.35 (2H, t, $CH_2N(Me)_2$), 2.26 (3H, s, NMe), 2.19 (6H, s, $NMe_2$), 1.29 (2H, m, $SiCH_2CH_2CH_2SiO$), 0.62 (2H, m, $SiCH_2CH_2CH_2SiO$), 0.59 (2H, m, $SiCH_2CH_2CH_2SiO$), 0.05 (6H, s, $SiMe_2$). $^{13}C\{^1H\}$-NMR (CDCl$_3$): δ 60.8 ($CH_2O$), 59.9 and 56.2 ($CH_2N(Me)CH_2$), 57.5 ($CH_2N(Me)_2$), 45.9 ($NMe_2$), 43.3 (NMe), 21.2 ($SiCH_2CH_2CH_2SiO$), 17.8 ($SiCH_2CH_2CH_2SiO$), 17.2 ($SiCH_2CH_2CH_2SiO$), −2.0 ($SiMe_2$). $^{29}Si\{^1H\}$-NMR (CDCl$_3$): δ 0.49 ($G_0$-Si), 17.59 ($G_1$-Si). Elemental analysis of $C_{48}H_{116}N_8O_4Si_5$. Calc.: C, 57.09; H, 11.58; N, 11.10. Obt.: C, 57.60; H. 11.72; N, 11.20.

Example 11

Synthesis of 2G-[Si(O(CH$_2$N(Me)(CH$_2$)$_2$N(Me)(CH$_2$)$_2$NMe$_2$)]$_8$ (11)

The third generation dendrimer 11 was prepared following a process similar to that described for 10, starting from 2G-Cl$_8$ (1.12 g, 0.77 mmol), NEt$_3$ (1 ml, 7.17 mmol) and 2-{[2-dimethylamino)ethyl]methylamino}ethanol (1 ml, 6.16 mmol). In this way, 11 was produced as a pale yellow oil (1.3 g, 72%).

$^1$H-NMR (CDCl$_3$): δ 3.65 (4H, t, CH$_2$O), 2.51 (8H, m, CH$_2$N(Me)), 2.30 (4H, t, CH$_2$N(Me)$_2$), 2.26 (6H, s, NMe), 2.20 (12H, s, NMe$_2$), 1.31 (6H, m, SiCH$_2$CH$_2$CH$_2$SiO and SiCH$_2$CH$_2$CH$_2$Si), 0.63 (4H, m, SiCH$_2$CH$_2$CH$_2$SiO), 0.59 (8H, m, SiCH$_2$), 0.06 (12H, s, SiMe$_2$), −0.10 (3H, s, SiMe). $^{13}$C{$^1$H}-NMR (CDCl$_3$): δ 60.8 (CH$_2$O), 59.9 and 56.2 (CH$_2$N(Me)CH$_2$), 57.5 (CH$_2$N(Me)$_2$), 45.9 (NMe$_2$), 43.3 (NMe), 21.2 (CH$_2$SiO), 18.7-17.9 (SiCH$_2$CH$_2$CH$_2$SiO and SiCH$_2$CH$_2$CH$_2$Si), −1.79 (OSiMe$_2$), −4.8 (SiMe). $^{29}$Si{$^1$H}-NMR (CDCl$_3$): δ 0.38 (G$_0$-Si), 0.93 (G$_1$-Si), 17.58 (G$_2$-Si). Elemental analysis of C$_{112}$H$_{226}$N$_{16}$O$_8$Si$_{13}$. Calc.: C, 57.67; H, 11.58; N, 9.61. Obt.: C, 57.20; H, 11.40; N, 9.52

Example 12

Synthesis of 3G-[Si(O(CH$_2$N(Me)(CH$_2$)$_2$NMe$_2$)]$_{16}$ (12)

The third generation dendrimer 12 was prepared following a process similar to that described for 10, starting from 3G-Cl$_{16}$ (0.49 g, 0.152 mmol), NEt$_3$ (0.40 ml, 2.86 mmol) and 2-{[2-Dimethylamino)ethyl]methylamino}ethanol (0.39 ml, 2.43 mmol) In this way, 12 was produced as a pale yellow oil (0.51 g, 67%).

$^1$H-NMR (CDCl$_3$): δ 3.65 (8H, t, CH$_2$O), 2.51 (16H, m, CH$_2$N(Me)), 2.36 (8H, t, —CH$_2$N(Me)$_2$), 2.26 (12H, s, NMe), 2.21 (24H, s, NMe$_2$), 1.30 (14H, m, SiCH$_2$CH$_2$CH$_2$SiO and SiCH$_2$CH$_2$CH$_2$Si), 0.63 (8H, m, SiCH$_2$CH$_2$CH$_2$SiO), 0.53 (18H, m, SiCH$_2$), 0.06 (24H, s, SiMe$_2$), −0.10 (9H, s, SiMe). $^{13}$C{$^1$H}-NMR (CDCl$_3$): δ 60.8 (CH$_2$O), 60.0 and 56.2 (CH$_2$N(Me)CH$_2$), 57.4 (CH$_2$N(Me)$_2$), 45.9 (NMe$_2$), 43.3 (NMe), 21.1 (CH$_2$SiO), 18.7-17.8 (SiCH$_2$CH$_2$CH$_2$SiO and SiCH$_2$CH$_2$CH$_2$SiSi), −1.9 (OSiMe$_2$), −4.8 (SiMe). $^{29}$Si{$^1$H}-NMR (CDCl$_3$): δ 0.93 (G$_1$-Si and G$_2$-Si), 17.58 (G$_3$-Si). Elemental analysis of C$_{240}$H$_{572}$N$_{32}$O$_{16}$Si$_{29}$. Calc.: C, 57.91; H, 11.58; N, 9.0 Obt.: C, 57.32; H, 11.38; N, 8.72.

These dendrimers are produced as clear brown coloured oily products, in high yields. All of them are soluble in common water insoluble organic solvents.

The spectroscopic and analytical details of derivatives 1-12 are consistent with the proposed structures which are shown in FIG. 1a. Thus, the signals corresponding to the carbosilane skeleton in the $^1$H-NMR of the previous dendrimers have chemical displacements for the analogous nuclei in the different generations, although the signals become wider and more destructured as the dendrimer generation increases. These characteristics have mainly been attributed to two factors: the polymer-type structure of these derivatives, which gives the nuclei in the different generations very slight differences in their chemical environment and the restriction of mobility of the respective protons in the outermost layers on increasing the generation.[26]

These spectrums show three groups of signals which are assigned to the methylene groups. In the SiCH$_2$CH$_2$CH$_2$Si branches, the central methylene groups are observed at 1.30 ppm, whilst the methylene groups bound directly to the silicon atoms are localized at 0.61 and 0.51 ppm. The centered signal was assigned at 0.61 ppm to the CH$_2$SiO— groups, whilst the signal centered at 0.51 ppm is attributed to the methylene group moiety, based on the increase in intensity of the integral of this last signal on increasing the dendrimer generation and in 1D $^1$H-TOCSY and NOESY experiments. In the $^{13}$C NMR spectrums, the methylene groups of the interior SiCH$_2$CH$_2$CH$_2$Si branches have signals in the range of 21.3-17.4 ppm. The complete assignment of these signals was made with the aid of HMQC experiments. Finally, the —SiMe$_2$— and —SiMe— fragments are easily distinguishable in all the derivatives and generations. The $^{29}$Si NMR spectrums are also in accordance with the proposed formulation, although in these spectrums the innermost silicon atoms are only observed in the first generation dendrimers.

With respect to the characterization of the terminal groups of these dendrimers, here, by way of example, the characterization of these groups is described in derivatives 1-6. The characterization in the moiety of compounds has been done in similar fashion and the details relative to each one of them are reflected in the experimental part of this work.

In dendrimers 1-6, a triplet is observed for the external fragment —OCH$_2$CH$_2$NMe$_2$ localized at 3.64 (for dendrimers 1, 3 and 5) and 3.74 (for dendrimers 2, 4 and 6) which is assigned to —OCH$_2$— groups and another triplet centered at 2.43 ppm in all the cases corresponding to —CH$_2$N— groups. The low field displacement observed in the signal corresponding to —OCH$_2$— groups in dendrimers 2, 4 and 6 is consistent with the presence of two oxygen atoms bound to the silicon atom in these derivatives, although this effect is imperceptible for —CH$_2$N— groups. The methyl groups bound to nitrogen appear in all cases at 2.23 and 46.1 ppm in NMR for $^1$H and $^{13}$C respectively.

The characterization of these compounds was completed with mass spectrometry (electrospray or MALDI-TOF MS) using 1,8,9-trihydroxyanthracene (ditranol) as matrix. However, the molecular peaks could not be observed for the second and third generations, a fact that has been described for many other high molecular weight dendrimers.[27,46-49]

EXAMPLES 13 to 15

Example 13

Synthesis of 1G-[Si(CH$_2$)$_3$NH$_2$]$_4$ (13)

Figure 1B:
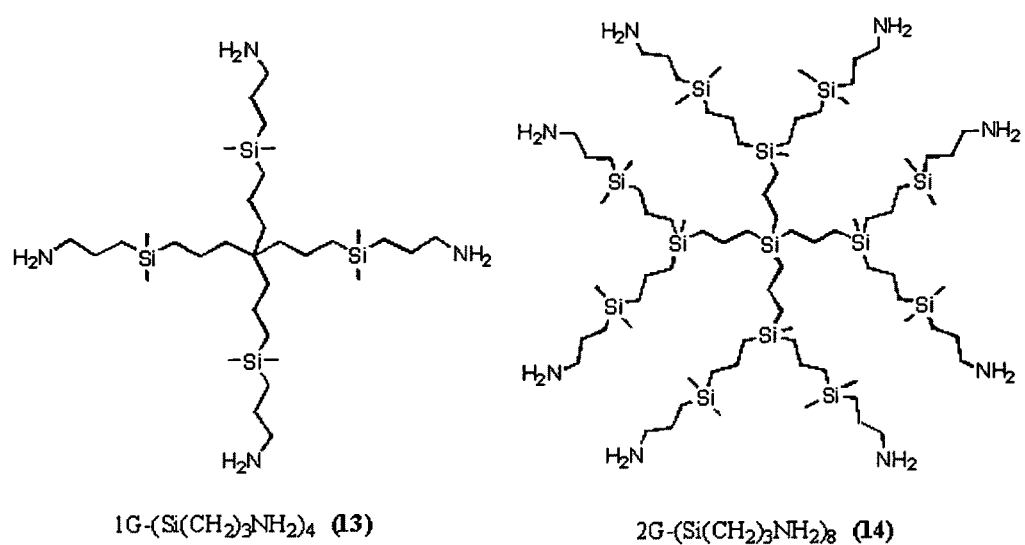

Allylamine (1.5 ml, 19.99 mmol) and two drops of Karstedt catalyst (3-3.5% Pt) were added to a 1G-H$_4$ (0.54 g, 1.23 mmol) dendrimer solution in the minimum quantity of THF (1 ml). The reaction mixture was heated to 120° C. in a vacuum ampoule during 4 h, the reaction mixture was dried to eliminate the solvent and the excess allylamine, the resulting residue was dissolved in CH$_2$Cl$_2$ and was filtered with celite and active carbon. The solution produced was dried by vacuum elimination of the solvent, giving rise to compound 13 as a colourless oil (0.90 g; 83%). The structure of this dendrimer is represented in FIG. 1b.

$^1$H-NMR (CDCl$_3$): δ 2.63 (2H, t, CH$_2$N), 1.34 (4H, m, SiCH$_2$CH$_2$CH$_2$N and SiCH$_2$CH$_2$CH$_2$Si), 1.13 (2H, s, NH$_2$), 0.54-0.44 (8H, m, CH$_2$ bound to Si), −0.06 (6H, s, SiMe$_2$), $^{13}$C{$^1$H}-NMR (CDCl$_3$): δ 45.7 (CH$_2$N), 28.3 (SiCH$_2$CH$_2$CH$_2$N), 20.2, 18.6, 17.6, (SiCH$_2$CH$_2$CH$_2$Si), 12.4 (SiCH$_2$CH$_2$CH$_2$N), −3.3 (SiMe$_2$). $^{29}$Si{$^1$H}-NMR (CDCl$_3$): δ 0.50 (G$_0$-Si), 1.96 (G$_1$-Si). Elemental analysis of C$_{32}$H$_{80}$N$_4$Si$_5$. Calc.: C, 58.14; H, 12.21; N, 8.48. Obt.: C, 57.63; H, 12.27; N, 8.78. Electrospray MS: m/z z=1 661.25 uma [M+H]⁺. (Calc. 661.52 uma).

Example 14

Synthesis of 2G-[Si(CH$_2$)$_3$NH$_2$]$_8$ (14)

The second generation dendrimer 14 was prepared following a process similar to that described for 13, starting from 2G-H$_8$ (0.42 g, 0.36 mmol), allylamine (2 ml, 26.7 mmol), 1 ml of THF and two drops of Karstedt catalyst. In this way, 14 was produced as a colourless oil (0.32 g, 55%). The structure of this dendrimer is represented in FIG. 1b.

$^1$H-NMR (CDCl$_3$): δ 2.63 (4H, t, CH$_2$N), 1.41-1.28 (6H, m, SiCH$_2$CH$_2$CH$_2$Si and SiCH$_2$CH$_2$CH$_2$N), 0.54-0.44 (20H, m, CH$_2$ bound to Si), −0.06 (12H, s, SiMe$_2$), −0.10 (3H, s, SiMe), $^{13}$C{$^1$H}-NMR (CDCl$_3$): δ 45.7 (CH$_2$N), 28.4 (SiCH$_2$CH$_2$CH$_2$N), 20.2, 18.6, 17.6, (SiCH$_2$CH$_2$CH$_2$Si), 12.5 (SiCH$_2$CH$_2$CH$_2$N), −3.1 (SiMe$_2$), −4.8 (SiMe). $^{29}$Si{$^1$H}-NMR (CDCl$_3$): δ 0.92 (G$_1$-Si); 2.00 (G$_2$-Si). Elemental analysis of C$_{80}$H$_{196}$N$_8$Si$_{13}$. Calc.: C, 58.75; H, 12.08; N, 6.85. Obt.: C, 58.16; H, 11.95; N, 6.58. Electrospray MS: m/z z=1 not observed, for z=2 (m/z+1) 818.44 uma [M+H]⁺. (Calc. Z=2 818.8 uma).

Example 15

Synthesis of 3G-[Si(CH$_2$)$_3$NH$_2$]$_{16}$ (15)

The third generation dendrimer 15 was prepared following a process similar to that described for 13, starting from 3G-H$_{16}$ (0.100 g, 0.037 mmol), allylamine (2 ml, 26.7 mmol), 1 ml of THF and two drops of Karstedt catalyst. In this way, 15 was produced as a colourless oil (0.085 g, 64%).

$^1$H-NMR (CDCl$_3$): δ 2.63 (8H, t, CH$_2$N), 1.41-1.28 (22H, m, SiCH$_2$CH$_2$CH$_2$Si and SiCH$_2$CH$_2$CH$_2$N), 0.54-0.44 (36H, m, CH$_2$ bound to Si), −0.06 (24H, s, SiMe$_2$), −0.10 (9H, s, SiMe), $^{13}$C{$^1$H}-NMR (CDCl$_3$): δ 45.7 (CH$_2$N), 28.4 (SiCH$_2$CH$_2$CH$_2$N), 20.2, 18.6, 17.6, (Si SiCH$_2$CH$_2$CH$_2$Si), 12.5 (SiCH$_2$CH$_2$CH$_2$N), −3.1 (SiMe$_2$), −4.8 (SiMe). $^{29}$Si{$^1$H}-NMR (CDCl$_3$): δ 0.92 (G1-Si and G2-Si); 2.00 (G3-Si). Elemental analysis of C$_{176}$H$_{428}$N$_{16}$Si$_{29}$. Calc.: C, 58.98; H, 12.04; N, 6.25. Obt.: C, 58.06; H, 11.84; N, 6.48.

EXAMPLES 16 to 27

Example 16

Synthesis of 1G-[Si(OCH$_2$CH$_2$NMe$_3$⁺I⁻)]$_4$ (16)

0.4 ml of a 2M MeI solution in ether (0.8 mmol) were added to a solution of 1 (0.12 g, 0.15 mmol) in ether (10 ml). The reaction mixture was maintained with constant stirring during 48 h at ambient temperature, then, it was dried to eliminate the excess MeI. The resulting residue was washed with Et$_2$O (2×5 ml) and was vacuum dried to produce compound 16 as a white coloured solid (0.20 g, 96%).

$^1$H-NMR (DMSO): δ 3.94 (2H, m, CH$_2$O), 3.43 (2H, m, CH$_2$N), 3.09 (9H, s, NMe$_3$⁺), 1.29 (2H, m, SiCH$_2$CH$_2$CH$_2$SiO), 0.66 (2H, m, SiCH$_2$CH$_2$CH$_2$SiO), 0.56 (2H, m, CH$_2$Si), 0.11 (6H, s, OSiMe$_2$). $^{13}$C{$^1$H}-NMR (DMSO): δ 65.8 (CH$_2$N), 55.8 (CH$_2$O), 52.6 (NMe$_3$⁺), 19.7 (SiCH$_2$CH$_2$CH$_2$SiO), 16.9, 16.1 (SiCH$_2$CH$_2$CH$_2$SiO), −2.6 (OSiMe$_2$). Elemental analysis of C$_{40}$H$_{100}$N$_4$O$_4$Si$_5$I$_4$. Calc.: C, 35.61; H, 7.47; N, 4.15. Obt.: C, 36.67; H, 7.65; N, 4.42.

Example 17

Synthesis of 1G-[Si(OCH$_2$CH$_2$NMe$_3$⁺I⁻)$_2$]$_4$ (17)

The first generation dendrimer 17 was prepared following a process similar to that described for 16, starting from 2 (0.17 g, 0.16 mmol) and 0.80 ml of a 2M MeI solution in ether (1.6 mmol). In this way, 17 was produced as a white coloured solid (0.29 g, 86%).

$^1$H-NMR (DMSO): δ 4.12 (4H, m, CH$_2$O), 3.54 (4H, m, CH$_2$N), 3.17 (18H, s, NMe$_3$⁺), 1.29 (2H, m, SiCH$_2$CH$_2$CH$_2$SiO), 0.75 (2H, m, SiCH$_2$CH$_2$CH$_2$SiO), 0.54 (2H, m, SiCH$_2$CH$_2$CH$_2$SiO), 0.20 (3H, s, OSiMe). $^{13}$C{$^1$H}-NMR (DMSO): δ 65.8 (CH$_2$N), 56.0 (CH$_2$O), 52.7 (NMe$_3$⁺), 17.3 (SiCH$_2$CH$_2$CH$_2$SiO), 16.5, 15.9 (SiCH$_2$CH$_2$CH$_2$SiO), −5.3 (OSiMe). Elemental analysis of C$_{56}$H$_{140}$N$_8$O$_8$Si$_5$I$_8$. Calc.: C, 30.44; H, 6.39; N, 5.07. Obt.: C, 31.47; H, 6.47; N, 5.19.

Example 18

Synthesis of 2G-[Si(OCH$_2$CH$_2$NMe$_3$⁺I⁻)]$_8$ (18)

The second generation dendrimer 18 was prepared following a process similar to that described for 16, starting from 3 (0.25 g, 0.13 mmol) and 0.6 ml of a 2M MeI solution in ether (1.2 mmol). In this way, compound 18 was produced as a white coloured solid (0.35 g, 87%).

$^1$H-NMR (DMSO): δ 3.96 (4H, m, CH$_2$O), 3.45 (4H, m, CH$_2$N), 3.11 (18H, s, NMe$_3$⁺), 1.29 (6H, m, SiCH$_2$CH$_2$CH$_2$SiO and SiCH$_2$CH$_2$CH$_2$Si), 0.65 (4H, m, SiCH$_2$CH$_2$CH$_2$SiO), 0.52 (8H, m, moiety of SiCH$_2$), 0.11 (12H, s, OSiMe$_2$), −0.10 (3H, s, SiMe). $^{13}$C{$^1$H}-NMR (DMSO): δ 65.7 (CH$_2$N), 55.9 (CH$_2$O), 52.6 (NMe$_3$⁺), 19.7, 17.5, 16.9 and overlapping signals (moiety of —CH$_2$— groups), −2.5 (OSiMe$_2$), −5.3 (SiMe). Elemental analysis of C$_{96}$H$_{236}$N$_8$O$_8$Si$_{13}$I$_8$. Calc.: C, 38.29; H, 7.9; N, 3.72. Obt.: C, 38.87; H, 8.32; N, 3.79.

Example 19

Synthesis of 2G-[Si(OCH$_2$CH$_2$NMe$_3$⁺I⁻)$_2$]$_8$ (19)

The second generation dendrimer 19 was prepared following a process similar to that described for 16, starting from 4 (0.10 g, 0.04 mmol) and 0.5 ml of a 2M MeI solution in ether (1.0 mmol). In this way, compound 19 was produced as a white coloured solid (0.17 g, 87%).

$^1$H-NMR (DMSO): δ (ppm) 4.13 (8H, m, CH$_2$O), 3.56 (8H, m, CH$_2$N), 3.19 (36H, s, NMe$_3$⁺), 1.28 (6H, m, SiCH$_2$CH$_2$CH$_2$SiO and SiCH$_2$CH$_2$CH$_2$Si), 0.72 (4H, m, SiCH$_2$CH$_2$CH$_2$SiO), 0.55 (8H, m, moiety of SiCH$_2$), 0.21 (6H, s, OSiMe), −0.08 (3H, s, SiMe). $^{13}$C{$^1$H}-NMR (DMSO): δ 65.7 (CH$_2$N), 56.0 (CH$_2$O), 52.7 (NMe$_3$⁺), 19.2, 17.2, 16.4 and overlapping signals (moiety of —CH$_2$— groups), −5.2 (OSiMe), −5.6 (SiMe). Elemental analysis of C$_{128}$H$_{316}$N$_{16}$O$_{16}$Si$_{13}$I$_{16}$. Calc.: C, 32.49; H, 6.73; N, 4.74. Obt.: C, 33.32; H, 7.03; N, 4.72.

Example 20

Synthesis of 3G-[Si(OCH$_2$CH$_2$NMe$_3$⁺I⁻)]$_{16}$ (20)

The third generation dendrimer 20 was prepared following a process similar to that described for 16, starting from 5 (0.12 g, 0.03 mmol) and 0.4 ml of a 2M MeI solution in ether (0.8 mmol). In this way, compound 20 was produced as a white coloured solid (0.16 g, 83%).

$^1$H-NMR (DMSO): δ 3.96 (8H, m, CH$_2$O), 3.47 (8H, m, CH$_2$N), 3.13 (36H, s, NMe$_3^+$), 1.28 (14H, m, SiCH$_2$CH$_2$CH$_2$SiO and SiCH$_2$CH$_2$CH$_2$Si), 0.65 (8H, m, SiCH$_2$CH$_2$CH$_2$SiO), 0.52 (20H, m, moiety of SiCH$_2$), 0.10 (24H, s, OSiMe$_2$), −0.08 (9H, s, SiMe). $^{13}$C{$^1$H}-NMR (DMSO): Λ 65.8 (CH$_2$N), 55.9 (CH$_2$O), 52.6 (NMe$_3^+$), 19.7, 17.2, 16.0 and overlapping signals (moiety of —CH$_2$— groups), −2.7 (OSiMe$_2$), −5.5 (SiMe). Elemental analysis of C$_{96}$H$_{236}$N$_8$O$_8$Si$_{13}$I$_8$. Calc.: C, 39.43; H, 8.08; N, 3.54. Obt.: C, 39.19; H, 8.19; N, 3.68.

Example 21

Identification of 3G-[Si(OCH$_2$CH$_2$NMe$_3^+$I$^-$)$_2$]$_{16}$ (21)

The third generation dendrimer 21 was prepared following a process similar to that described for 16, starting from 6 (0.060 g, 0.012 mmol) and 0.2 ml of a 2M MeI solution in ether (0.4 mmol). The 1H-NMR spectrum has broad signals and indicates that approximately 90% of the terminal amino groups have been quaternized, for which purpose the compound 21 was not isolated pure.

$^1$H-NMR (DMSO): δ 4.16 (16H, m, OCH$_2$), 3.60 (16H, m, CH$_2$N), 3.22 (72H, s, NMe$_3^+$I$^-$), 1.27 (14H, m, SiCH$_2$CH$_2$CH$_2$SiO and SiCH$_2$CH$_2$CH$_2$Si), 0.52 (26H, m, SiCH$_2$CH$_2$CH$_2$SiO and moiety of —CH$_2$— groups), 0.07 (24H, s broad, SiMe$_2$), the signal corresponding to SiMe was not observed as it appeared overlapped with the previous signal.

Example 22

Synthesis of 1G-[Si(OCH$_2$—(C$_6$H$_3$)-3,5-(OCH$_2$CH$_2$NMe$_3^+$I$^-$)$_2$)]$_4$ (22)

The first generation dendrimer 22 was prepared following a process similar to that described for 16, starting from 7 (0.1 g, 0.06 mmol) and 0.35 ml of a 2M MeI solution in ether (0.7 mmol). In this way, compound 22 was produced as a white coloured solid (0.14 g, 90%).

$^1$H-NMR (DMSO): δ 6.55 (3H, m, C$_6$H$_3$); 4.58 (2H, s, CH$_2$OSi); 4.42 (4H, t, CH$_2$O—C$_6$H$_3$); 3.77 (4H, t, CH$_2$N); 3.18 (18H, s, NMe$_3^+$); 1.35 (2H, m, SiCH$_2$CH$_2$CH$_2$SiO), 0.70 (2H, m, SiCH$_2$CH$_2$CH$_2$SiO), 0.57 (2H, m, SiCH$_2$CH$_2$CH$_2$SiO), 0.08 (6H, s, SiMe$_2$). $^{13}$C{$^1$H}-NMR (DMSO): δ 157.8 (C$_6$H$_3$, C$_{ipso}$ bound to OCH$_2$CH$_2$NMe$_2$); 143.2 (C$_6$H$_3$, C$_{ipso}$ bound to CH$_2$OSi); 104.9 and 99.6 (C$_6$H$_3$); 63.5 (CH$_2$NMe$_2$); 63.0 (CH$_2$OSi); 61.3 (CH$_2$O—C$_6$H$_3$); 52.7 ($^+$NMe$_3$), 19.9 (SiCH$_2$CH$_2$CH$_2$SiO); 16.9, 16.1 (SiCH$_2$CH$_2$CH$_2$SiO); −2.4 (SiMe$_2$). Elemental analysis of C$_{88}$H$_{172}$I$_8$N$_8$O$_{12}$Si$_5$. Calc.: C, 39.29; H, 6.44; N, 4.17. Obt.: C, 38.90; H, 6.24; N, 4.09.

Example 23

Synthesis of 2G-[Si(OCH$_2$—(C$_6$H$_3$)-3,5-(OCH$_2$CH$_2$NMe$_3^+$I$^-$)]$_8$(23)

The second generation dendrimer 23 was prepared following a process similar to that described for 16, starting from 8 (0.08 g, 0.023 mmol) and 0.20 ml of a 2M MeI solution in ether (0.4 mmol). In this way, compound 23 was produced as a white coloured solid (0.11 g, 85%).

$^1$H-NMR (DMSO): δ 6.58 (6H, m, C$_6$H$_3$); 4.58 (4H, s, CH$_2$OSi); 4.44 (8H, t, CH$_2$O—C$_6$H$_3$); 3.79 (8H, t, CH$_2$N); 3.20 (30H, s, NMe$_3^+$); 1.33 (6H, m, SiCH$_2$CH$_2$CH$_2$SiO and SiCH$_2$CH$_2$CH$_2$Si), 0.67(4H, m, SiCH$_2$CH$_2$CH$_2$SiO), 0.54 (8H, m, CH$_2$ bound to Si), 0.07 (12H, s, OSiMe$_2$), −0.07 (3H, s, SiMe). $^{13}$C{$^1$H}-NMR (DMSO): δ 157.9(C$_6$H$_3$,C$_{ipso}$ bound to OCH$_2$CH$_2$NMe$_2$); 143.2 (C$_6$H$_3$, C$_{ipso}$ bound to CH$_2$OSi); 105.2 and 99.6 (C$_6$H$_3$); 63.5 (CH$_2$NMe$_2$); 63.0 (CH$_2$OSi); 61.4 (CH$_2$O—C$_6$H$_3$); 52.7 (NMe$_3^+$), 19.8 (SiCH$_2$CH$_2$CH$_2$SiO); 17.5, 16.8 (SiCH$_2$CH$_2$CH$_2$SiO and overlapping signals of and SiCH$_2$CH$_2$CH$_2$Si); −2.4 (OSiMe$_2$); −5.5 (SiMe). Elemental analysis of C$_{192}$H$_{380}$I$_{16}$N$_{16}$O$_{24}$Si$_{13}$. Calc.: C, 40.51; H, 6.73; N, 3.94. Obt.: C, 41.20; H, 7.02; N, 4.10.

Example 24

Synthesis of 3G-[Si(OCH$_2$—(C$_6$H$_3$)-3,5-(OCH$_2$CH$_2$NMe$_3^+$I$^-$)$_2$)]$_{16}$ (24)

The third generation dendrimer 24 was prepared following a process similar to that described for 16, starting from 9 (0.084 g, 0.012 mmol) and 0.25 ml of a 2M MeI solution in ether (0.5 mmol). In this way, compound 24 was produced as a white coloured solid (0.080 g, 72%).

$^1$H-NMR (DMSO): δ 6.57 (12H, m, C$_6$H$_3$); 4.58 (8H, s, CH$_2$OSi); 4.44 (16H, t, CH$_2$O—C$_6$H$_3$); 3.78 (16H, t, CH$_2$N); 2.28 (72H, s, NMe$_3^+$); 1.33 (14H, m, SiCH$_2$CH$_2$CH$_2$SiO and SiCH$_2$CH$_2$CH$_2$Si), 0.69 (8H, m, SiCH$_2$CH$_2$CH$_2$SiO), 0.55 (18H, m, CH$_2$ bound to Si), 0.08 (24H, s, OSiMe$_2$), −0.08 (9H, s, SiMe). $^{13}$C{$^1$H}-NMR (CDCl$_3$): δ 158.0 (C$_6$H$_3$, C$_{ipso}$ bound to OCH$_2$CH$_2$NMe$_2$); 143.2 (C$_6$H$_3$, C$_{ipso}$ bound to CH$_2$OSi); 104.9 and 100.12 (C$_6$H$_3$); 63.4 (CH$_2$O—C$_6$H$_3$); 63 (CH$_2$OSi); 61.4 (CH$_2$NMe$_2$); 52.7 (NMe$_3^+{}_3$), 19.9 (SiCH$_2$CH$_2$CH$_2$SiO); 17.5, 16.8 (SiCH$_2$CH$_2$CH$_2$SiO and overlapping signals of SiCH$_2$CH$_2$CH$_2$Si); −2.3 (OSiMe$_2$), −5.5 (SiMe). Elemental analysis of C$_{384}$H$_{748}$I$_{16}$N$_{32}$O$_{48}$Si$_{29}$. Calc.: C, 48.92; H, 8; N, 4.75. Obt.: C, 47.60; H, 7.02; N, 4.35.

Example 25

Identification of 1G-[Si(O(CH$_2$)$_2$N(Me)(CH$_2$)$_2$NMe$_3^+$I$^-$)]$_4$ (25)

The first generation dendrimer 25 was prepared following a process similar to that described for 16, starting from 10 (0.043 g, 0.047 mmoles) and 0.094 ml of a 2M MeI solution in ether (0.188 mmoles). In this way, compound 25 was produced as a white coloured solid. This compound was not isolated pure, observing mixtures due to a non-selective quaternization process wherein both nitrogen atoms can participate, although, compound 25 is the main component of this mixture.

$^1$H-NMR (DMSO): δ 3.98 (2H, m, OCH$_2$CH$_2$N(Me)CH$_2$CH$_2$NMe$_3^+$I$^-$), 3.60 (2H, t, OCH$_2$CH$_2$N(Me)CH$_2$CH$_2$NMe$_3^+$I$^-$), 3.42 (2H, m, OCH$_2$CH$_2$N(Me)CH$_2$CH$_2$NMe$_3^+$I$^-$), 3.11 (9H, s, NMe$_3^+$I$^-$), 2.76 (2H, m, OCH$_2$CH$_2$N(Me)CH$_2$CH$_2$NMe$_3^+$I$^-$), 2.21 (3H, s, NMe), 1.30 (2H, m, SiCH$_2$CH$_2$CH$_2$SiO), 0.61 (2H, m, SiCH$_2$CH$_2$CH$_2$SiO), 0.53 (2H, m, SiCH$_2$CH$_2$CH$_2$SiO), 0.04 (6H, s, SiMe$_2$). $^{13}$C{$^1$H}-NMR (CDCl$_3$): δ 64.8 (OCH$_2$CH$_2$N(Me)CH$_2$CH$_2$NMe$_3^+$I$^-$), 61.0 (OCH$_2$CH$_2$N(Me)CH$_2$CH$_2$NMe$_3^+$I$^-$), 59.5 (OCH$_2$CH$_2$N(Me)CH$_2$CH$_2$NMe$_3^+$I$^-$), 58.3 (OCH$_2$CH$_2$N(Me)CH$_2$CH$_2$NMe$_3^+$I$^-$), 52.2 (NMe$_3^+$I$^-$), 41.3 (NMe), 20.0 (SiCH$_2$CH$_2$CH$_2$SiO), 16.9 and 16.1 (SiCH$_2$CH$_2$CH$_2$SiO), −2.5 (SiMe$_2$).

Example 26

Identification of 2G-[Si(O(CH$_2$)$_2$N(Me)(CH$_2$)$_2$NMe$_3^+$I$^-$)]$_8$ (26)

The second generation dendrimer 26 was prepared following a process similar to that described for 16, starting from 11 (0.19 g, 0.08 mmol) and 0.34 ml of a 2M MeI solution in ether (0.68 mmol). In this way, compound 26 was produced as a pale yellow-coloured solid. This compound was not isolated pure, observing mixtures due to a non-selective quaternization process wherein both nitrogen atoms can participate, although, compound 26 is the main component of this mixture.

$^1$H-NMR (DMSO): δ 4.02 (4H, m, OCH$_2$CH$_2$N(Me)CH$_2$CH$_2$NMe$_3^+$I$^-$), 3.60 (4H, t, OCH$_2$CH$_2$N(Me)CH$_2$CH$_2$NMe$_3^+$I$^-$), 3.42 (4H, m, OCH$_2$CH$_2$N(Me)CH$_2$CH$_2$NMe$_3^+$I$^-$), 3.11 (18H, s, NMe$_3^+$I$^-$), 2.76 (4H, m, OCH$_2$CH$_2$N(Me)CH$_2$CH$_2$NMe$_3^+$I$^-$), 2.21 (6H, s, NMe), 1.30 (4H, m, SiCH$_2$CH$_2$CH$_2$SiO and SiCH$_2$CH$_2$CH$_2$Si), 0.59 (4H, m, SiCH$_2$CH$_2$CH$_2$SiO), 0.51 (8H, m, moiety of —CH$_2$— groups), 0.03 (12H, s, SiMe$_2$), −0.11 (3H, s, SiMe). $^{13}$C{$^1$H}-NMR (CDCl$_3$): δ 64.9 (OCH$_2$CH$_2$N(Me)CH$_2$CH$_2$NMe$_3^+$I$^-$), 61.0 (OCH$_2$CH$_2$N(Me)CH$_2$CH$_2$NMe$_3^+$I$^-$), 59.6 (OCH$_2$CH$_2$N(Me)CH$_2$CH$_2$NMe$_3^+$I$^-$), 58.3 (OCH$_2$CH$_2$N(Me)CH$_2$CH$_2$NMe$_3^+$I$^-$), 52.3 (NMe$_3^+$I$^-$), 41.3 (NMe), 20.0-16.8 (—CH$_2$— groups of the carbosilane skeleton), −2.5 (SiMe$_2$), −5.5 (SiMe).

Example 27

Identification of 3G-[Si(O(CH$_2$)$_2$N(Me)(CH$_2$)$_2$NMe$_3^+$I$^-$)]$_{16}$ (27)

The third generation dendrimer 27 was prepared following a process similar to that described for 16, starting from 20 (0.084 g, 0.017 mmol) and 0.13 ml of a 2M MeI solution in ether (0.27 mmol). In this way, compound 27 was produced as a pale yellow-coloured solid. This compound was not isolated pure, observing mixtures due to a non-selective quaternization process wherein both nitrogen atoms can participate, although, compound 27 is the main component of this mixture.

$^1$H-NMR (DMSO): δ 3.99 (8H, m, OCH$_2$CH$_2$N(Me)CH$_2$CH$_2$NMe$_3^+$I$^-$), 3.60 (8H, t, OCH$_2$CH$_2$N(Me)CH$_2$CH$_2$NMe$_3^+$I$^-$), 3.44 (8H, m, OCH$_2$CH$_2$N(Me)CH$_2$CH$_2$NMe$_3^+$I$^-$), 3.12 (36H, s, NMe$_3^+$I$^-$), 2.76 (8H, m, OCH$_2$CH$_2$N(Me)CH$_2$CH$_2$NMe$_3^+$I$^-$), 2.22 (12H, s, NMe), 1.28 (14H, m, SiCH$_2$CH$_2$CH$_2$SiO and SiCH$_2$CH$_2$CH$_2$Si), 0.51 (26H, m, SiCH$_2$CH$_2$CH$_2$Si 0 and moiety of —CH$_2$— groups), 0.03 (24H, s, SiMe$_2$), −0.11 (9H, s, SiMe). $^{13}$C{$^1$H—NMR (CDCl$_3$): δ 64.9 (OCH$_2$CH$_2$N(Me)CH$_2$CH$_2$NMe$_3^+$I$^-$), 61.0 (OCH$_2$CH$_2$N(Me)CH$_2$CH$_2$NMe$_3^+$I$^-$), 59.6 (OCH$_2$CH$_2$N(Me)CH$_2$CH$_2$NMe$_3^+$I$^-$), 58.3 (OCH$_2$CH$_2$N(Me)CH$_2$CH$_2$NMe$_3^+$I$^-$), 52.3 (NMe$_3^+$I$^-$), 41.3 (NMe), 20.0-16.8 (groups —CH$_2$— of the carbosilane skeleton), −2.5 (SiMe$_2$), −5.5 (SiMe).

In the case of the third generation dendrimers 21, 24 and 27, the quaternization of the dimethylamino group is not complete as demonstrated by the $^1$H-NMR spectrums, from which it can be approximately estimated that around 90% of the terminal dimethylamino group in these complexes have been quaternized, even in the presence of excess MeI and leaving the reaction during greater periods of time.

All these ionic derivatives are insoluble in typical organic solvents, but soluble in DMSO, MeOH and H$_2$O.

Figure 2A:
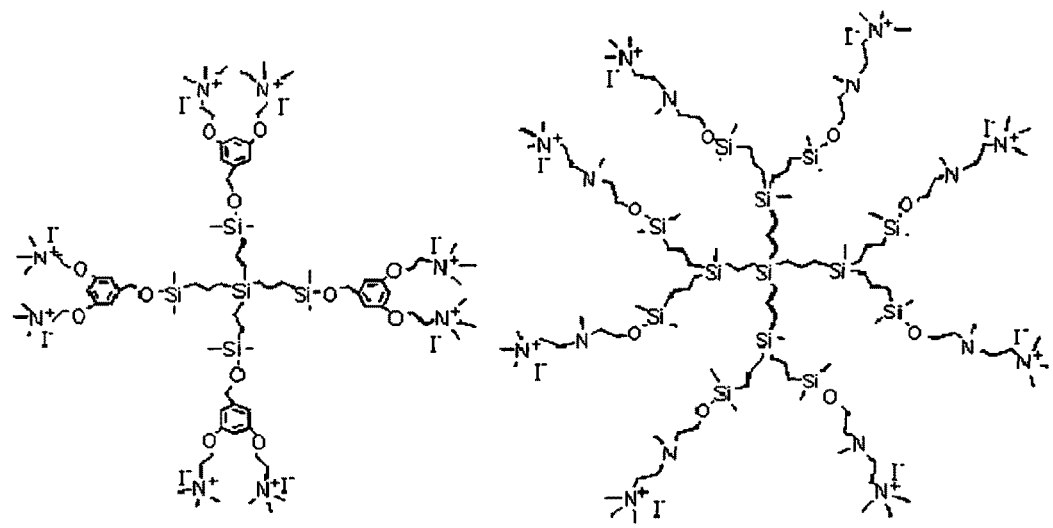
FIG. 2 shows the structure of several carbosilane dendrimers of the invention with quaternized amine moieties, those synthesized in examples 22, 26, 19 and 27 in FIG. 2a and those synthesized in examples 28 and 29 in FIG. 2b.
Figure 2A:
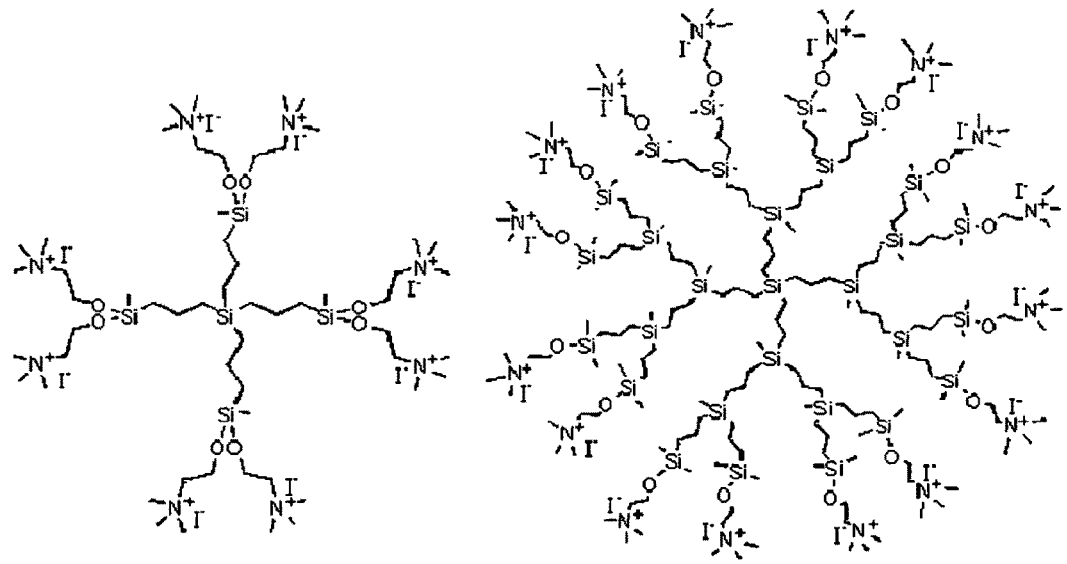

The spectroscopic and analytical information of derivatives 16-27 are consistent with the proposed structures which are shown in FIG. 2a. The signals which appear in the $^1$H-NMR spectrums of these derivatives, made in DMSO as solvent at ambient temperature, are broader than those of their precursors in common organic solvents. This fact has been previously described for other water-soluble carbosilane dendrimers and it has been explained as an effect of dipolar widening as a consequence of the decrease in the mobility of some of these predominantly hydrophobic dendrimers.[29]

The $^1$H and $^{13}$C NMR spectrums of dendrimers 16-27 have identical resonance patterns to those of their precursors 1-12, for the carbosilane skeleton, although an increase in the widening of the signals on increasing the generation is observed.

As with the dendrimers with terminal amino groups, for these derivatives, here it describes in detail the assignment of the signals of the external groups only for derivatives 16-21, having made the assignment in the moiety of derivatives in a similar fashion.

The external groups SiOCH$_2$CH$_2$NMe$_3^+$I$^-$, give rise to broad multiplets centered at 3.94 (for dendrimers 16, 18 and 20) or 4.12 (for dendrimers 17, 19 and 21) assignable to the methylenic protons of —OCH$_2$— groups, and 3.45 (for dendrimers 16, 18 and 20) or 3.56 (for dendrimers 17, 19 and 21) which are assigned to the protons of fragment —CH$_2$N—. The quaternization of the amino group produces a low field displacement of 0.3-0.4 ppm in the —OCH$_2$— signal, whilst the methylene protons of the —CH$_2$N— groups are displaced in 1 ppm approximately. The methyl groups directly bound to nitrogen give $^1$H and $^{13}$C NMR signals centered at 3.18 and 52.6 ppm respectively, which supposes a low field displacement with respect to the signals observed in the dendrimers ending in amino groups 1-6. These variations are in accordance with the presence of a positive charge on the nitrogen atom in the dendrimers ending in ammonium groups 16-21.

EXAMPLES 28 to 30

Example 28

Synthesis of G$_1$[Si(CH$_2$)$_3$NH$_3^+$Cl$^-$]$_4$ (28)

Figure 2B:
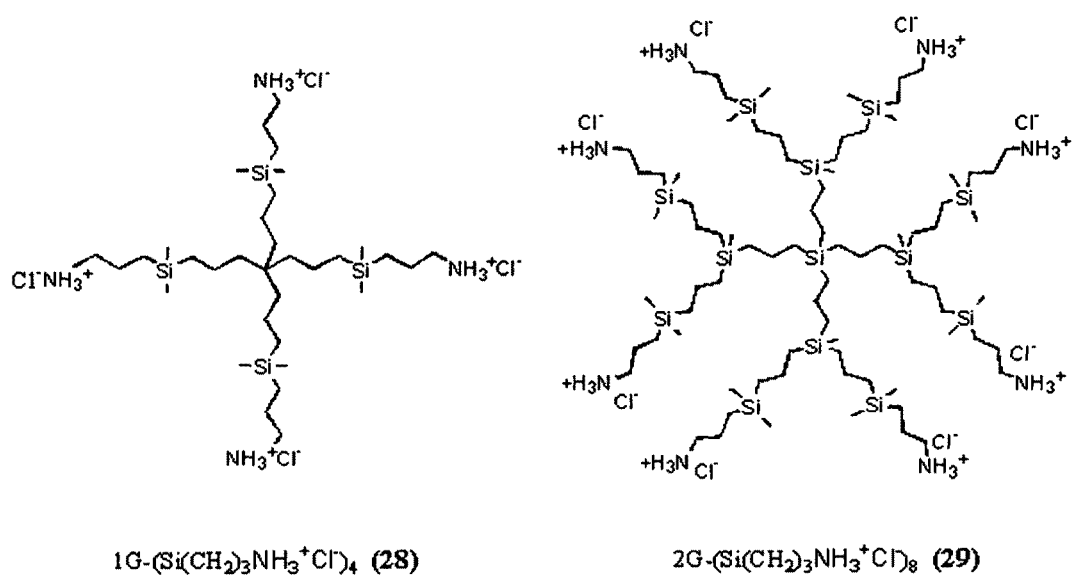

1.2 ml (1.2 mmol) of a 1M solution of HCl in Et$_2$O was added to a solution of compound 13 (0.17 g, 0.26 mmol) in 40 ml of Et$_2$O. The reaction was maintained at ambient temperature and with constant stirring during 2 h after which the appearance of a white-coloured precipitate was observed. The solvent and the excess HCl is eliminated in a vacuum and In this way, 28 was produced as a white solid with a quantitative yield. The structure of this dendrimer is represented in FIG. 2b.

$^1$H-NMR (D$_2$O): δ 2.74 (2H,t, CH$_2$N), 1.45 (2H, m, SiCH$_2$CH$_2$CH$_2$N), 1.19 (2H, m, SiCH$_2$CH$_2$CH$_2$Si), 0.38 (6H, t, CH$_2$Si), −0.19 (6H, s, SiMe$_2$). $^{13}$C{$^1$H}-NMR (D$_2$O): δ 42.0 (CH$_2$N), 21.3 (SiCH$_2$CH$_2$CH$_2$N), 18.8, 18.0, 16.6 (SiCH$_2$CH$_2$CH$_2$Si), 11.2 (SiCH$_2$CH$_2$CH$_2$N), −4.4 (SiMe$_2$). Elemental analysis of C$_{32}$H$_{84}$N$_4$Cl$_4$Si$_5$. Calc.: C, 47.61; H, 10.49; N, 6.94. Obt.: C, 48.57; H, 10.46; N, 6.82.

Example 29

Synthesis of 2G-[Si(CH$_2$)$_3$NH$_3^+$Cl$^-$]$_8$ (29)

The second generation dendrimer 29 was prepared following a process similar to that described for 28, starting from 14 (0.09 g, 0.05 mmol) and 0.6 ml of a 1M solution in ether of HCl (0.06 mmol). In this way, compound 29 was produced as a pale yellow-coloured solid (0.06 g; 55%). The structure of this dendrimer is represented in FIG. 2b.

$^1$H-NMR (D$_2$O): δ 2.74 (2H, t, CH$_2$N), 1.47 (2H, m, SiCH$_2$CH$_2$CH$_2$N), 1.16 (4H, m, SiCH$_2$CH$_2$CH$_2$Si), 0.38 (16H, t, CH$_2$Si), −0.19 (6H, s, SiMe$_2$). −0.22 (3H, s, SiMe). $^{13}$C{$^1$H}-NMR (D$_2$O): δ 42.0 (CH$_2$N), 21.8 (SiCH$_2$CH$_2$CH$_2$N), 2.5-17.0 (SiCH$_2$CH$_2$CH$_2$Si), 12.01 (SiCH$_2$CH$_2$CH$_2$N), 3.23 (SiMe$_2$), −4.2 (SiMe$_2$). Elemental analysis of C$_{80}$H$_{204}$N$_8$Cl$_8$Si$_{13}$. Calc.: C, 49.86; H, 10.67; N, 5.81. Obt.: C, 49.79; H, 10.18; N, 5.76.

Example 30

Synthesis of 3G-[Si(CH$_2$)$_3$NH$_3$$^+$Cl$^-$]$_{16}$ (30)

The third generation dendrimer 30 was prepared following a process similar to that described for 28, starting from 15 (0.060 g, 0.018 mmol), and 0.30 ml of a 1M solution in ether of HCl (0.30 mmol). In this way, 30 was produced as a pale yellow-coloured solid (0.054 g, 78%).

$^1$H-NMR (D$_2$O): δ 2.74 (8H, t, CH$_2$N), 1.45 (8H, m, SiCH$_2$CH$_2$CH$_2$N), 1.20 (14H, m, SiCH$_2$CH$_2$CH$_2$Si) 0.39 (36H, m, CH$_2$ bound to Si), −0.19 (24H, s, SiMe$_2$), −0.10 (9H, s, SiMe), $^{13}$C{$^1$H}-NMR (CDCl$_3$): δ 42.0 (CH$_2$N), 21.3 (SiCH$_2$CH$_2$CH$_2$N), 18.9, 17.9, 16.5, (SiCH$_2$CH$_2$CH$_2$Si), 11.3 (SiCH$_2$CH$_2$CH$_2$N), −4.4 (SiMe$_2$), −4.8 (SiMe). Elemental analysis of C$_{176}$H$_{444}$N$_{16}$Si$_{29}$. Calc.: C, 55.44; H, 11.74; N, 5.88. Obt.: C, 56.16; H, 11.98; N, 6.01.

Biocompatibility Studies of the Novel Dendrimers, Characterization of the Bond to Polyanions and Plasma Proteins and Biological Behaviour of the Dendriplexes As previously indicated, one of the aspects of the invention is constituted by pharmaceutical compositions which contain at least one dendrimer of the invention, either together with another/other substance(s) of anionic character and of pharmaceutical interest to that/those which it accompanies as vehicle to facilitate the transport in the blood flow to the target cells wherein it/they has/have to exercise their effect, protecting it/them from the interaction with plasma proteins to which they could be bound or which could affect their stability, either as active substance with capacity to interact with the life cycle of a micro-organism causing a disease whose effects one aims to prevent, reduce or eliminate by one or more of a dendrimer of the invention. In one of the preferred embodiments of that aspect of the invention, the(s) molecule(s) of anionic character to that/those which one or more dendrimers of the invention serve as vehicle is an oligodeoxyribonucleotide (ODN), preferably an antisense ODN, or a two-stranded DNA molecule of greater length or an interference RNA. The use of a dendrimer of the invention or of compositions which contain them to prevent or treat diseases caused by pathogens or gene failure are also aspects of the invention.

Therefore, it was decided to test the biocompatibility of the novel proposed dendrimers, characterizing their binding to polyanions and plasma proteins and analysing the biological behaviour dendriplex-type complex formed between the dendrimers of the invention and the chosen polyanions. The dendrimers which are selected to perform these tests were:

Dendrimers:

IM8:

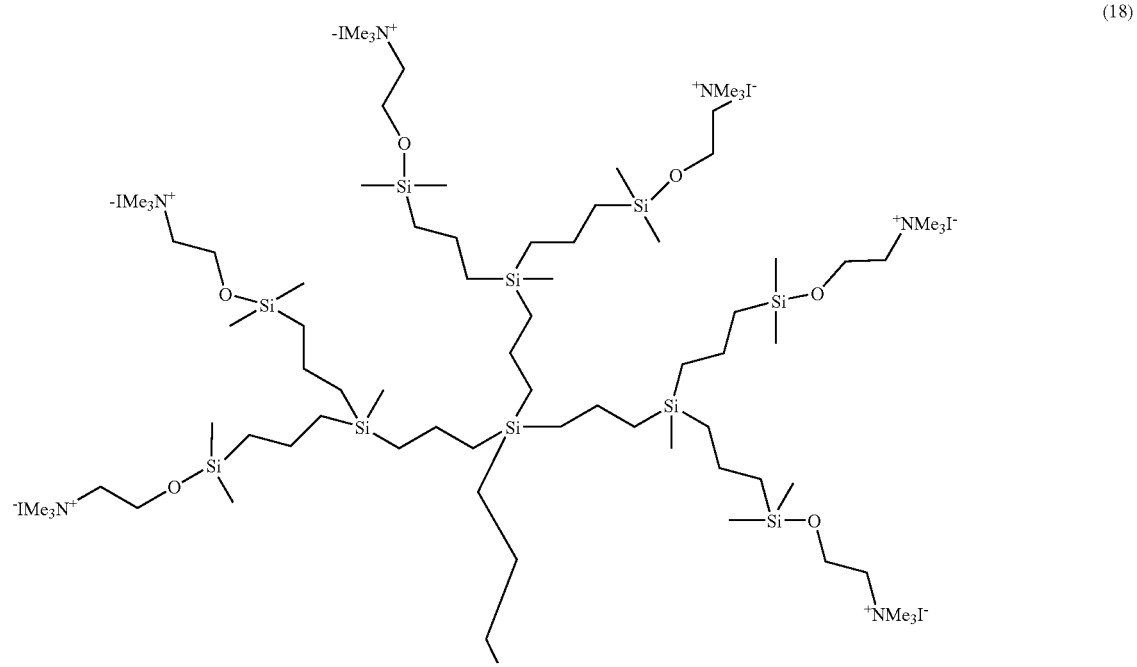

(18)

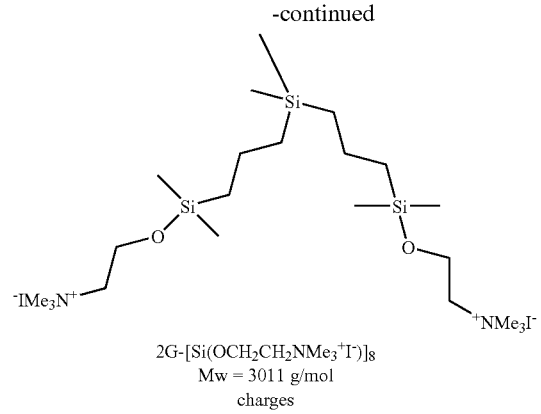
2G-[Si(OCH$_2$CH$_2$NMe$_3^+$I$^-$)]$_8$
Mw = 3011 g/mol
charges
IM16:
(19)
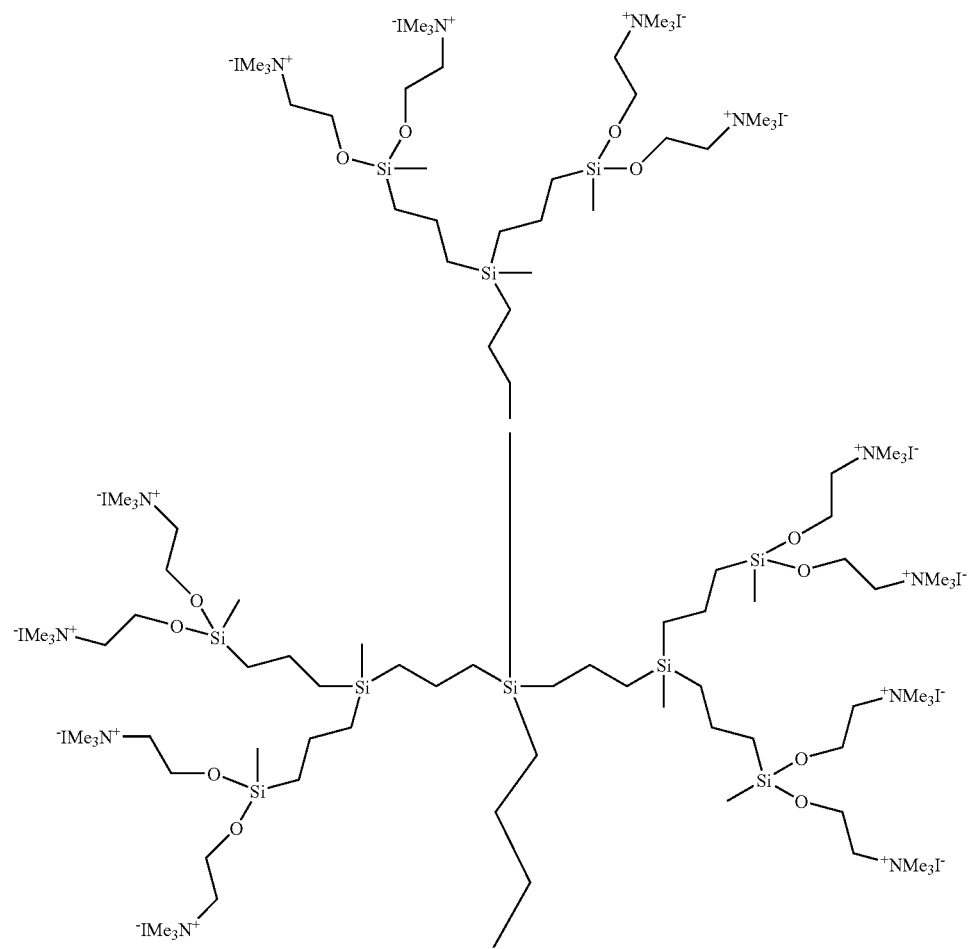

-continued
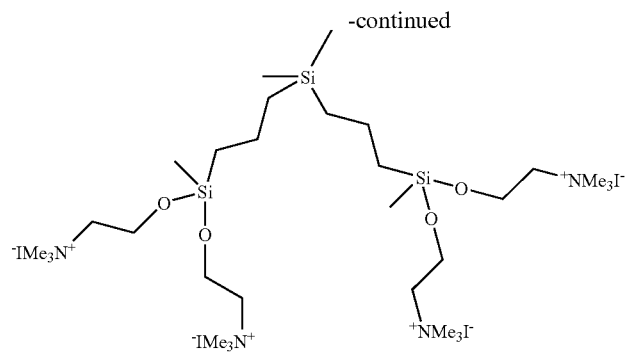
2G-[Si(OCH$_2$CH$_2$NMe$_3^+$I$^-$)$_2$]$_8$
Mw = 4731.59 g/mol 8 positive
16 positive charges
Phe:
(23)
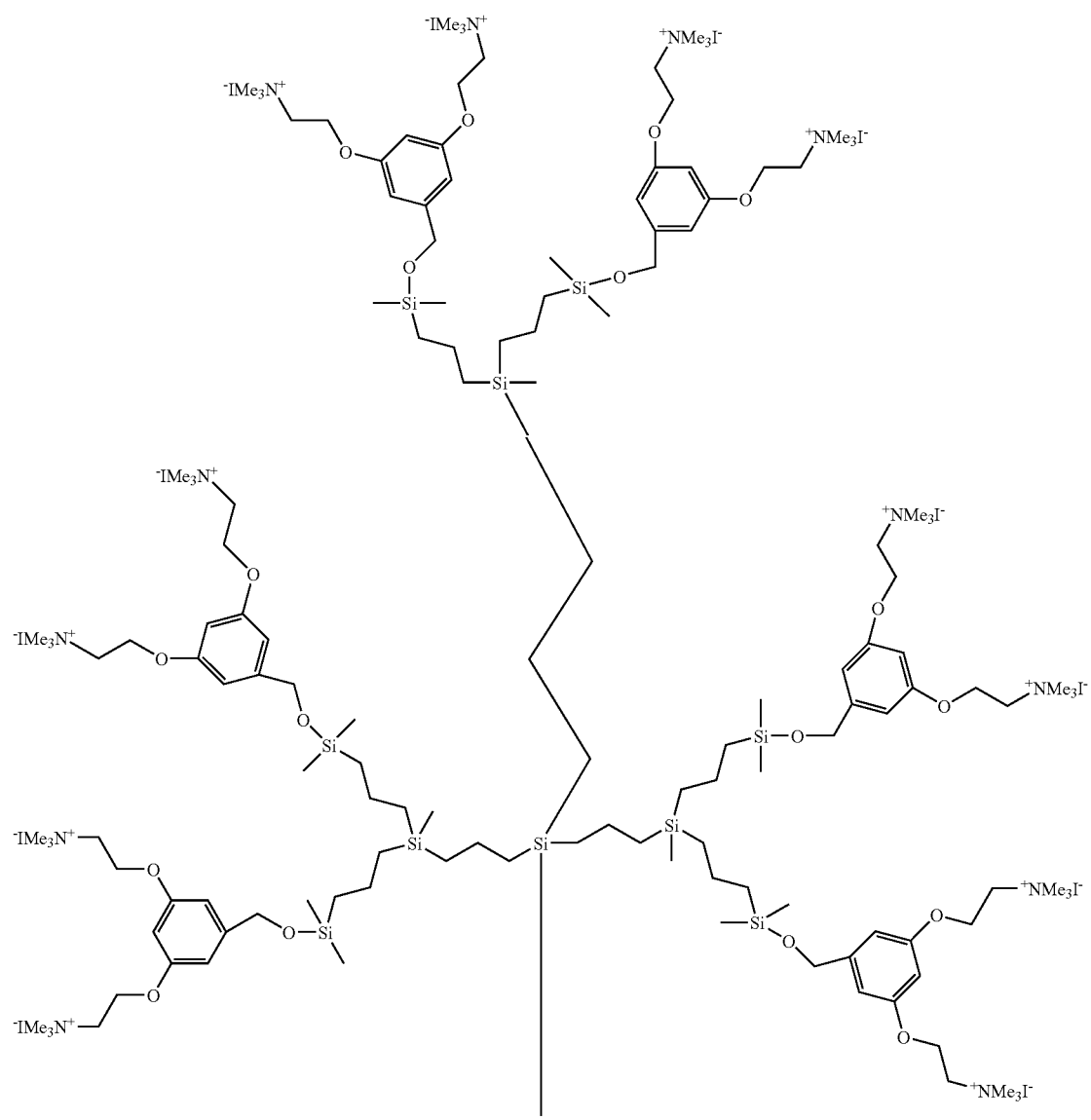

-continued
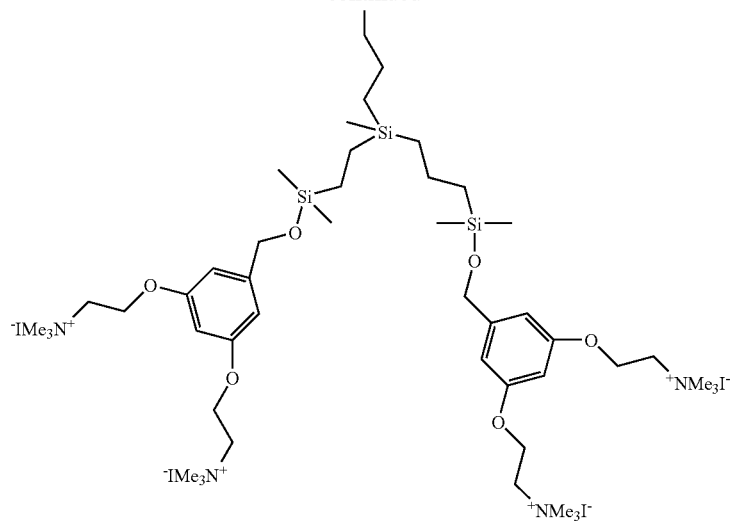
2G-[Si(OCH$_2$-(C$_6$H$_3$)-3,5-(OCH$_2$CH$_2$NMe$_3^+$I$^-$)$_2$)]$_8$
Mw = 5692.80 g/mol
16 positive charges
NN:
(26)
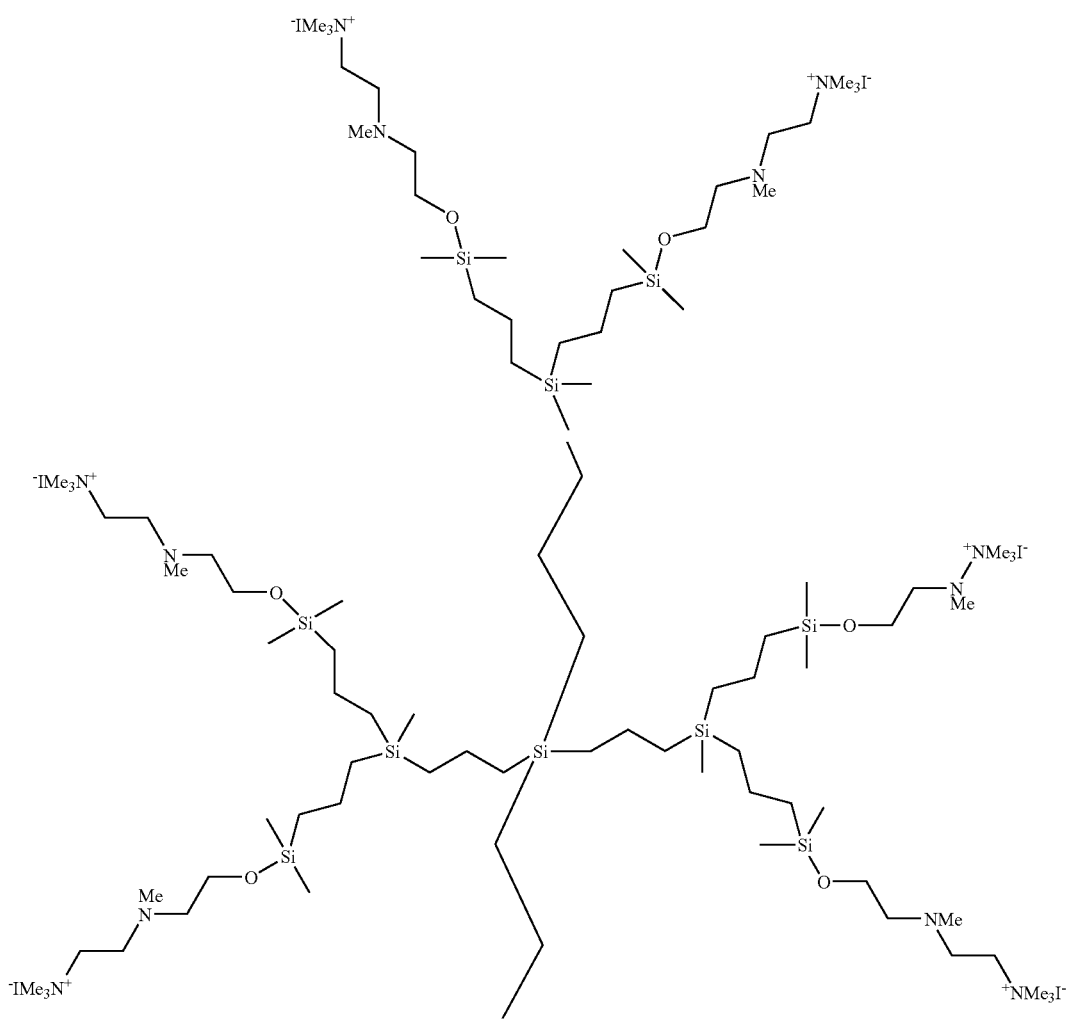

-continued
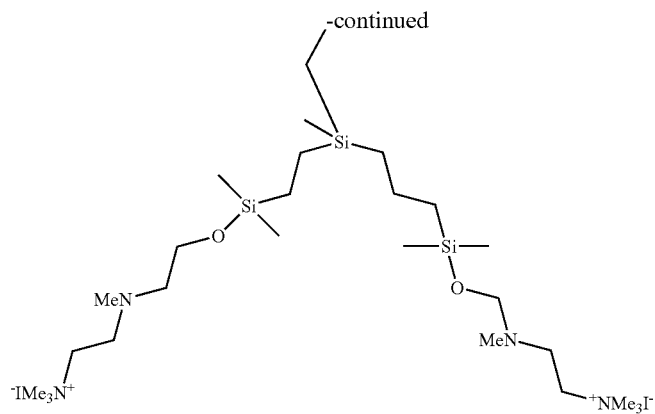
2G-[Si(O(CH$_2$)$_2$N(Me)(CH$_2$)$_2$NMe$_3$$^+$I$^-$)]$_8$
Mw = 3468.08 g/mol
charges
ClNH4:
(29)
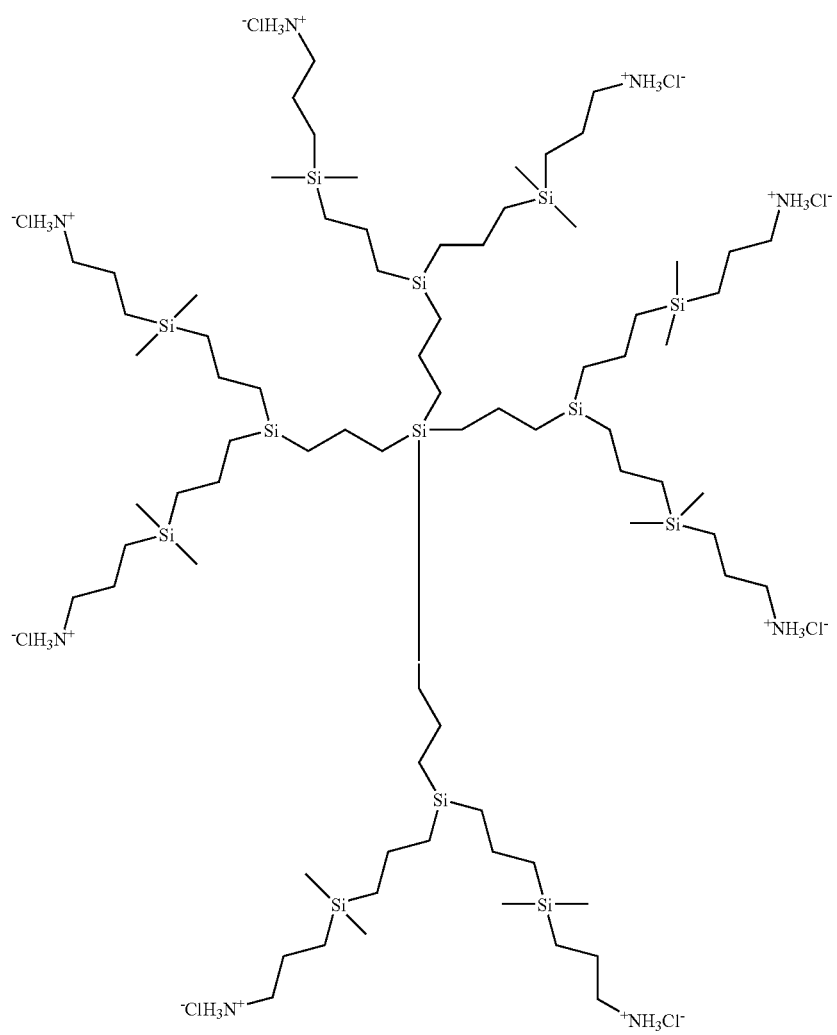
2G-[Si(CH$_2$)$_3$NH$_3$$^+$Cl$^-$]$_8$
Mw = 1927.6 g/mol 8 positive
8 positive charges
G4:

-continued

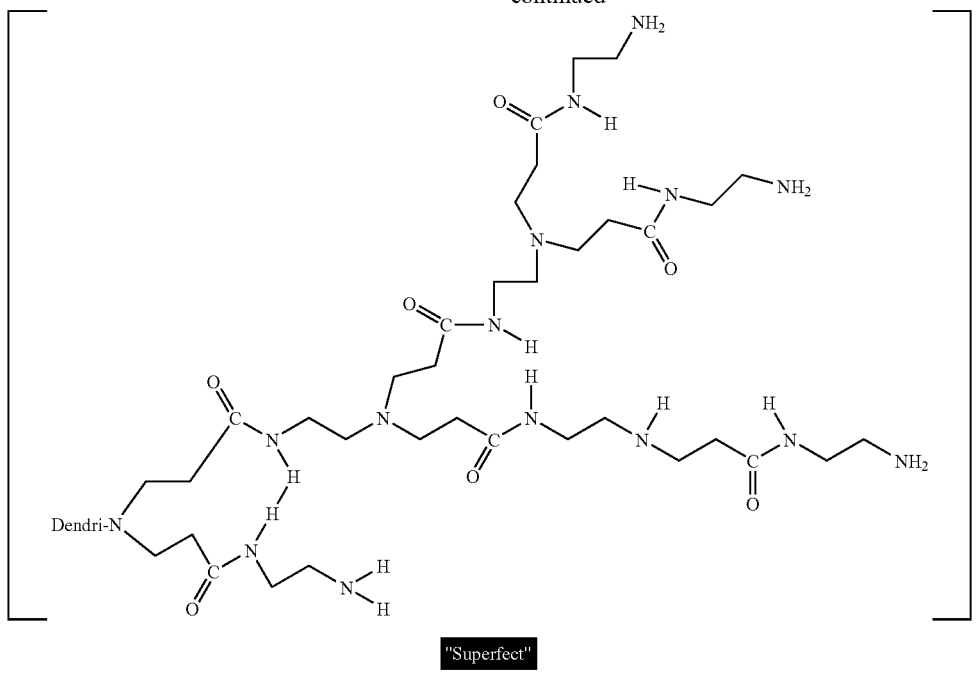

(4TH generation PAMAM dendrimer; Aldrich Chemical Co., Milwaukee, WI)
140 terminal amino group
Mw = 14.215

SF (Superfect® (activated PAMAM dendrimer, Qiagen, Crawley, GB)
140 terminal amino group
Mw = 35.000

The two last ones, Superfect and G4, are commercial PAMAM dendrimers which are used by way of comparison with respect to the carbosilane dendrimers of the invention.

Physicochemical Properties of CBS: Water Solubility

All the carbosilane dendrimers of the invention are water soluble at the concentration used for the starting solutions (2 mg/ml) by gentle stirring, without heating being necessary.

To perform the experiments, all the CBS used were resuspended at that starting concentration (2 µg/µl=2 mg/ml).

Example 31

Complex Formation Between CBS and ODN

ODN Used

The oligonucleotidic sequences used were antisense sequences (complementary) directed against HIV RNA. The length varied from 15 to 28 bases, being of phosphorothioate nature. The specific ODN used and their sequences are shown below in Table 1.

TABLE 1

| NAME | ODN used ANTISENSE SEQUENCES 5'-3' | NUMBER OF BASES | Mw g/mol |
|---|---|---|---|
| A) GF (anti-gag) | CTCTCGCACCCATCTCTCTCCTTCT (SEQ ID NO: 1) | 25 | 8112.5 |

TABLE 1-continued

| NAME | ODN used ANTISENSE SEQUENCES 5'-3' | NUMBER OF BASES | Mw g/mol |
|---|---|---|---|
| B) RF (anti-Rev) | TCGTCGCTGTCTCCGCTTCTTCCTGCCA (SEQ ID NO: 2) | 28 | 9086.0 |
| C) PPT (antim-RNA) | AATTTTCTTTTCGCCCCT (SEQ ID NO: 3) | 18 | 5841.0 |
| D) PPT-TFO (Triple helix former) | TTTTCTTTTGGGGGG (SEQ ID NO: 4) | 15 | 4867.5 |
| E) TAR (anti-TAR) | GCTCCCGGGCTCGACC (SEQ ID NO: 5) | 16 | 5192.0 |

Several of the ODN were used fluorescent at the 5' end. This is indicated by adding the letter F to its notation. Thus, "GF" makes reference to the fluorescent anti-gag ODN at end 5', whilst "RF" makes reference to the anti-Rev ODN fluorescent at end 5'.

All the ODN used were resuspended at a concentration of 1 µg/µl.

Display of the Complexes in Agarose Gels

The use of agarose gels for the study of the complex formation between the PAMAM-type dendrimers and plasma DNA or in the form of ODN by the isotopic labelling thereof is known. Based on this type of approaches, gels were attempted to be made which permitted studying this property without the use, if possible, of radioactive isotopes.

Different agarose concentrations were used to show the migration of the ODN and the dendriplexes, bearing in mind the small size of the ODN used. Finally, a 3% agarose concentration in TAE 1× was chosen as the best. The migration of non-fluorescent ODNs was compared with fluorescent ones, both migrating at the same height but the latter increasing the signal perceived considerably. Using them, it thus avoided the isotopic labelling of the ODN. A double well was manufactured to prepare these gels, to permit load volumes of 60 µl, of which 50 µl was mixture volume of the samples in RPMI and 10 µl load buffer with glycerol. As size marker, a ladder of 100 base pairs was used (Gibco BRL®).

Complex Formation

For the complex formations in all the tests performed, both on gels and on cells the ratio between the number of positive and negative charges in said complex was taken. As published by different authors in studies with PAMAM dendrimers, it is necessary that the complex formed has an excess positive charge to facilitate its binding to the cell membrane glycoproteins, negatively charged, thus starting the endocytosis process. Likewise, an excess of positive charge is added to ensure the formation of the dendrimer-DNA complex. Therefore, the complexes between the CBS dendrimers and the different nucleic acids were formed in excess number of positive charges (provided by the CBS) compared with negative charges (provided by the ODN). Nevertheless, different charge ratios were tested, making the calculations based in the number of dendrimer charges (fixed) and the number of negative charges of the ODN (also fixed). The 2/1 ratio of positive/negative charges was fixed as sufficient in all dendrimers to form the complexes with a total positive charge, although in some experiments a balance was provided of an equal number of negative charges as positive charges or excess negative charges.

For the SF, the charge ratio proposed by the manufacturer was used and for the G4 PAMAM a molar excess of 100 to 1 in favour of the PAMAN type dendrimer was used, according to that proposed by Sato et al. (Clin Cancer Res 2001 November; 7(11):3606-12).

In all the tests, a complex formation volume of 60 µl was used, using phenol red without RPMI serum as support medium.

Electrophoresis of the Complexes Formed

Tests of complex formation were used with the dendrimers of the invention IM8, ClNH$_4$, NN, Phe and IM16.

Figure 3:
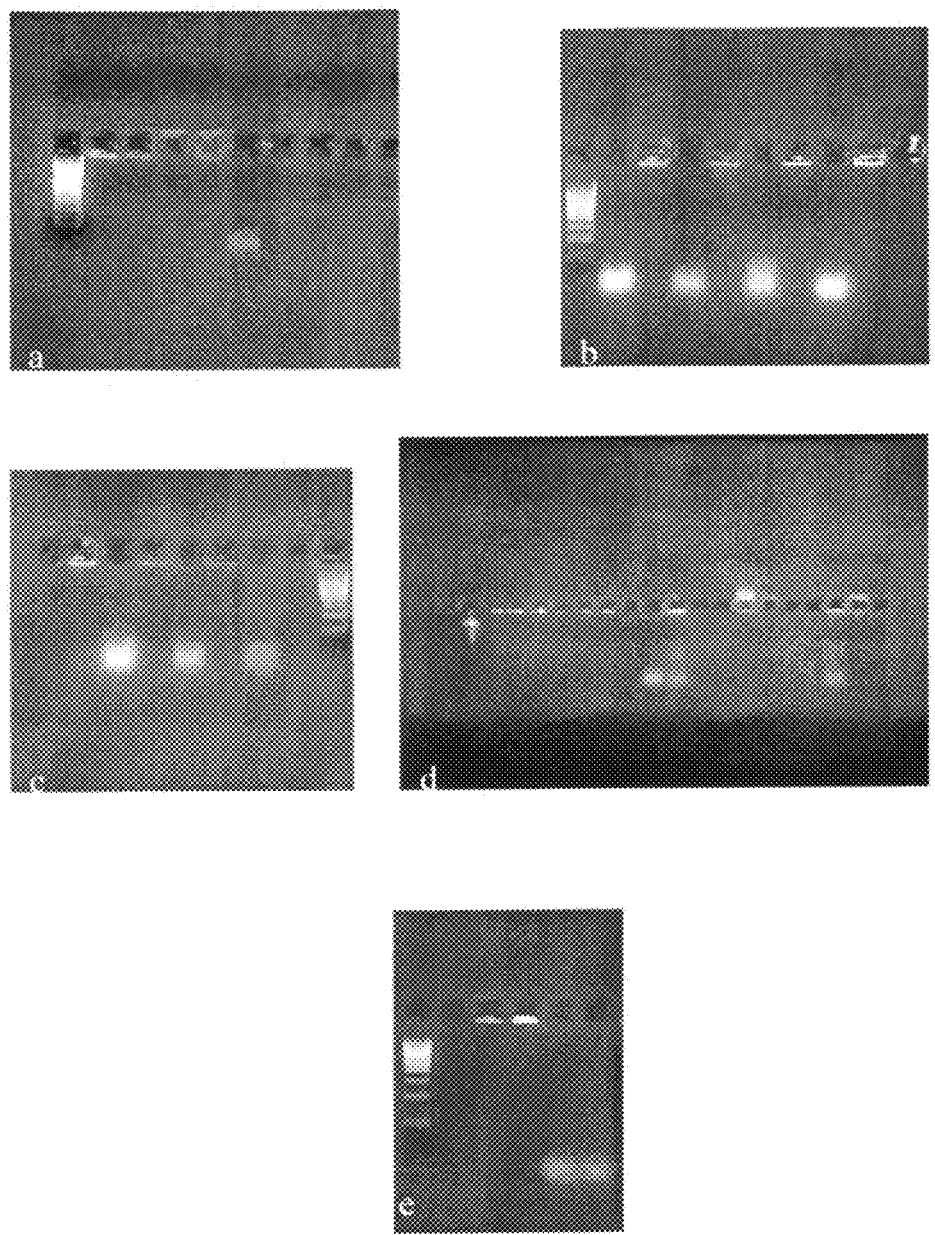
FIG. 3 shows the electrophoresis gels of complex formation between an ODN and IM8 dendrimer (with GF in gel a) and with different ODN in gel b), ClNH4 (c), NN and Phe (d) and IM16 (gel e, which also contains the IM8 samples).

The results of the electrophoresis carried out with the samples resulting from the mixture of different ODN and the different dendrimers shown in FIG. 3. The samples loaded in the different gels which appear in them are the following:

IM8:

FIG. 3a. Complex formation between IM8 and the ODN GF. The samples subjected to electrophoresis were the following:
Lane 1: 100 bp ladder
Lane 2: 4 µl GF+4.52 µl IM8+91.48 µl RPMI (+/−)=2/1
Lane 3: 4 µl GF+9.03 µl IM8+86.97 µl RPMI (+/−)=4/1
Lane 4: 4 µl GF+45.2 µl IM8+50.8 µl RPMI (+/−)=20/1
Lane 5: 4 µl GF+90.4 µl IM8+5.6 µl RPMI (+/−)=40/1
Lane 6: 4 µl GF+96 RPMI
Lane 7: 4.52 µl IM8+95.48 µl RPMI
Lane 8: 9.03 µl IM8+90.97 µl RPMI
Lane 9: 45.2 µl IM8+54.8 µl RPMI
Lane 10: 90.4 µl IM8+9.6 µl RPMI The results of the electrophoresis show that IM8 is capable of retaining the DNA. The greater the charge, the more the complex migrates towards the negative pole, until reaching the limit at which no matter by how much the positive charge is increased (the quantity of dendrimer) it no longer migrates above (probably all the DNA molecules are already forming a complex with the CBS-IM8 or because the size of the gel pore does not allow it).

FIG. 3b: Electrophoresis of samples with IM8 and ODNs of different sizes (charge ratio 2/1). The samples subjected to electrophoresis were the following:
Lane 1: 100 bp ladder
Lane 2: RF: 4.5 µl+56 µl RPMI
Lane 3: RF: 4.5 µl+5.3 µl IM8+50 µl RPMI
Lane 4: PPT 3 µl+57 µl RPMI
Lane 5: PPT 3 µl+3.4 µl IM8+54 µl RPMI
Lane 6: PPT-TFO 2.5 µl+58 µl RPMI
Lane 7: PPT-TFO 2.5 l+2.8 µl IM8+55 µl RPMI
Lane 8: TAR 2.6 µl+57 µl RPMI
Lane 9: TAR 2.6 µl+3 µl IM8+55 µl RPMI The results of the electrophoresis show that IM8 was capable of retaining the migration of all the ODN. This is a first indication that the length of the ODNs is not a determining factor for complex formation.

ClNH4

FIG. 3c. Complex formation between ClNH$_4$ and ODN RF. The samples subjected to electrophoresis were the following:
Lane 1: RPMI control
Lane 2: RF 4.5 µl+3.3 µl ClNH4+52 µl RPMI (+/−)=2
Lane 3: RF 4.5 µl+55 µl RPMI
Lane 4: RF 2.25 µl+3.3 µl ClNH4+55 µl RPMI (+/−)=4
Lane 5: RF 2.25 µl+58 µl RPMI
Lane 6: RF 1.28 µl+3.3 µl ClNH4+56 µl RPMI (+/−)=7
Lane 7: RF 1.28 µl+58 µl RPMI
Lane 8: 3.3 µl ClNH4+57 µl RPMI
Lane 9: 100 bp ladder According to the results produced, ClNH4 is capable of retaining the DNA also with all the charge ratios evaluated.

NN and Phe

FIG. 3d. Complex formation between ODN RF and NN or Phe dendrimers. The samples subjected to electrophoresis were the following:
Lane 1: 4.5 µl RF+6 µl G2 NN+50 µl RPMI (+/−)=2
Lane 2: 4.5 µl RF+21 µl G2 NN+35 µl RPMI (+/−)=7
Lane 3: 1.3 µl RF+6 µl G2 NN+53 µl RPMI (+/−)=7
Lane 4: 2.25 µl RF+3 µl G2 NN+55 µl RPMI (+/−)=2
Lane 5: 2.25 µl RF+10.5 µl G2 NN+48 µl RPMI (+/−)=7
Lane 6: 0.64 µl RF+3 µl G2 NN+56 µl RPMI (+/−)=7
Lane 7: 2.25 µl RF+57 µl RPMI
Lane 8: 4.5 µl RF+5 µl G2 Phe+55 µl RPMI (+/−)=2
Lane 9: 4.5 µl RF+17.5 µl G2 Phe+38 µl RPMI (+/−)=7
Lane 10: 1.3 µl RF+5 µl G2 Phe+54 µl RPMI (+/−)=7
Lane 11: 2.25 µl RF+2.5 µl G2 Phe+55 µl RPMI (+/−)=2
Lane 12: 2.25 µl RF+8.75 µl G2 Phe+50 µl RPMI (+/−)=7
Lane 13: 0.64 µl RF+2.5 µl G2 Phe+57 µl RPMI (+/−)=7

The results of this electrophoresis also demonstrate that both NN and Phe are also capable of forming complexes with the ODN.

IM16

FIG. 3e. Complex formation between ODN PPT, IM8 and IM16 dendrimers and the corresponding monomer from which the dendrimer was formed. The samples subjected to electrophoresis were the following:
Lane 1: 100 bp ladder
Lane 2: PPT 2.57 µl+3 µl IM8+54 µl RPMI
Lane 3: PPT 2.57 µl+2.35 µl IM 16+55 µl RPMI Lane 4: PPT 2.57 μl+1.8 μl monomer+55 μl RPMI
Lane 5: PPT 2.57 μl+57 μl RPMI In the lane wherein the sample was run which contained ODN and IM16 dendrimer, the latter was also capable of retaining the DNA Therefore, the $2^{nd}$ generation CBS tested was capable of retaining the DNA migration towards the positive pole, this being a reflection of the formation of electrostatic formation between CBS and ODN in all cases: the small generation of the CBS tested is not obstacle for retaining the DNA. The dendrimers without DNA, for their part, emit a weak, almost imperceptible signal.

Study of the Integrity of the Dendrimer in the Complex Formed

The synthesis process of the CBS used in this work begins from an initial nucleus of common structure, which is ended functionalizing in the periphery by the use of different functional groups, which are those which provide the positive charge to the dendrimer and determine the differences between themselves, the dendrimeric nucleus being of apolar nature. Since some of the bonds of the functional groups used to the dendrimeric nucleus could be unstable in aqueous solution, tests were performed to determine if the DNA retention in agarose gels and, therefore, the complex formation between the CBS and the DNA could be due to the total dendrimer structure being conserved or in contrast, the terminal functional groups came away from the moiety of the dendrimeric core which are responsible for the DNA retention. For this, gels were used in which complexes were formed between the ODNs and the integral CBS and those formed supposedly between the ODNs and the terminal functional groups with which the carbosilane skeleton had functionalized, in this case quaternized dimethylethanolamine. As has previously been commented, those positively charged molecules, which are bound to the dendrimer as terminal functional groups, are those which give the dendrimer its charge. As control, the mixtures of ODN-dendrimers, ODN-monomers and ODN alone were compared. The corresponding gel is shown in FIG. 3e, to which reference has already been made, wherein the samples compared and subjected to electrophoresis are the following:

Calle1: 100 bp ladder
Lane 2: Control with RPMI medium without dendrimer or oligonucleotide
Lane 3: PPT 2.57 μl+3 μl IM8+54 μl RPMI
Lane 4: PPT 2.57 μl+2.35 μl IM 16+55 μl RPMI
Lane 5: PPT 2.57 μl+1.8 μl monomer+55 μl RPMI
Lane 6: PPT 2.57 μl+57 μl RPMI The result of this test clearly shows that a complete dendrimeric structure is necessary to retain the DNA, monomers not being capable, despite their positive charge of retaining the DNA. Therefore, at these concentrations, the dendrimeric structure was would be maintained whole.

Example 32

Stability of the Dendriplexes at Different pHs

Stability studies were carried out on the complexes a different pHs, to determine how the changes in pH would affect the complex, since there are different anatomic, tissue or cell localizations in which the pH acidifies or alkalinifies. Examples are stomach ambient acid, the alkali of the pancreatic secretions of the small intestine, or at a cellular level, the endosome-lisosome behaviour, where it changes from a physiological pH (7.35-7.45) to an acid pH around 4. It is interesting to know, therefore, in what pH range the DNA complex could be maintained with the different CBS used. The complexes were formed following the habitual process and volumes were added in excess of different solutions at different pHs.

Figure 4:
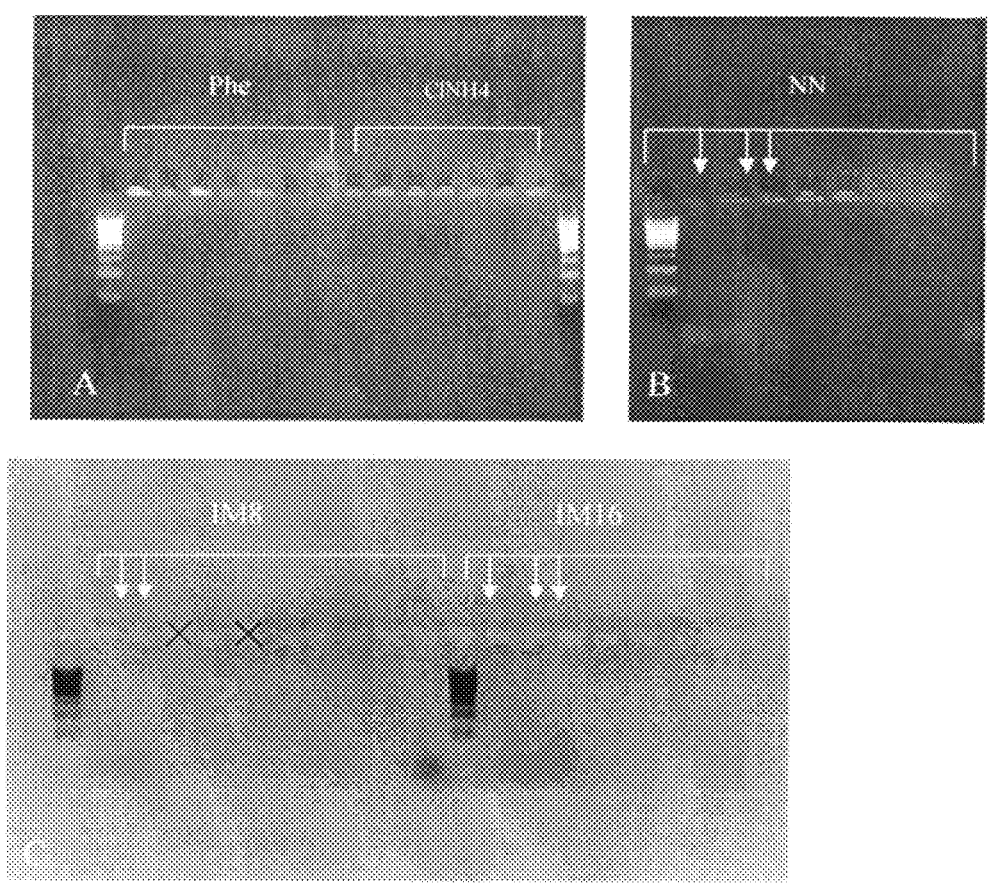
FIG. 4 shows electrophoresis gels of complexes formed between an ODN and dendrimers Phe, ClNH4 (gel A), NN (gel B) and IM8 and IM16 (gel C) at different pH values.

Therefore, for each one of dendrimers Phe, ClNH$_4$, NN, IM8 and IM16, according to Example 31, 7 solutions were prepared of dendriplexes formed with PPT, in a 2/1 charge ratio and with the following pHs: 2.8; 2.7; 4.7; 5.7; 6.4; 7.4; 8:

The results produced are shown in the electrophoresis gels which appear in FIG. 4, wherein the height of the normal ODN migration band is shown with arrows in the lower part of the gels. The samples were loaded from left to right following an increasing pH order. No sample was formed in the wells indicated with an X.

In accordance with the results produced, whilst the complexes formed between dendrimers ClNH$_4$ and Phe and the ODN are stable at all pHs tested, the complexes formed between NN and ODN were labile at acid pH (less than 5.7), as shown by the appearance of a signal in the migration area of the ODN in the wells indicated with arrows in the gel corresponding to FIG. 4b. In the case of IM8 and IM16, something similar occurred: the IM8-ODN complexes are dissociated at pH<4.7; those formed with IM16 are dissociated at pH<5.7. At alkaline pH, however, all the complexes were stable, as no signal appears in the lanes corresponding to pH 7.4 and pH 8.

This means that in an acid environment (stomach, endosome-lisosome) the complex between CBS NN, CBS IM8 and CBS IM16 with ODN will release the latter progressively. This fact would be good for those applications which require the controlled release of pH-dependent ODN. It also means that if the dendrimer was still inside the cell bound to ODN, it would break when it entered the endosome-lisosome compartment. In contrast, in an alkaline environment (small intestine juices) it would be maintained stable.

Example 33

Stability of the Dendriplexes in Aqueous Solution in Accordance with Time

Figure 5:
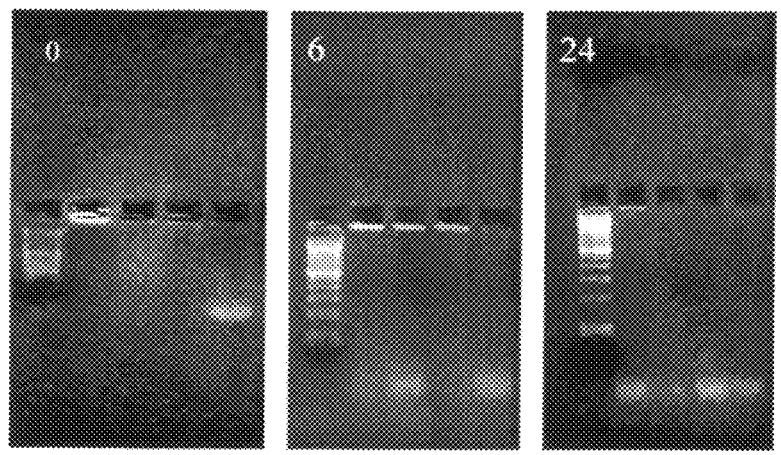
FIG. 5 shows the evolution of dendrimer complexes of the invention and the ODN PPT on remaining in an aqueous solution for 0, 6 or 24 hours.

Different samples of dendriplexes were prepared in aqueous solution formed between the ODN PPT and dendrimers IM8, IM16 and NN at a 2/1 charge ratio according to Example 31 and electrophoresis was performed after different times since the preparation of the samples, specifically 0 hours, 6 hours and 24 hours. During those times, the dendriplexes were maintained in conditions which imitate the physiological conditions: 37° C., in 5% CO$_2$ atmosphere. The results are shown in FIG. 5, wherein the gel of FIG. 5a corresponds to the sample of 0 hours, that of FIG. 5b to the samples after 6 hours and that of FIG. 5c to the samples after 24 hours. In the three cases, a, b and c, the samples appear in the lanes following this order:

Lane 1: 100 bp ladder.
Lane 2: IM8+PPT
Lane 3: IM16+PPT
Lane 4: NN+PPT
Lane 5: PPT The gels show that there is a gradual release over time of the ODN from the dendriplexes formed with any of the three dendrimers considered. This is a good indication for its use in the delayed release of polyanions.

Example 34

Stability of the Dendriplexes in the Presence of Proteins and Detergents

Binding to plasma proteins is one of the obstacles that therapies with ODNs face. Said binding decreases the bioavailability of ODN, making a greater dose necessary to be able to exercise the biological effect desired. This section aims to analyse the influence of the presence of proteins in the medium on the stability of the complex, and if this could in any way protect the ODN of the binding to plasma proteins. These studies were performed with the CBS NN and analysing the behaviour of the dendriplexes formed in the presence of bovine serum albumin (BSA) and of the anionic detergent PBS.

Figure 6:
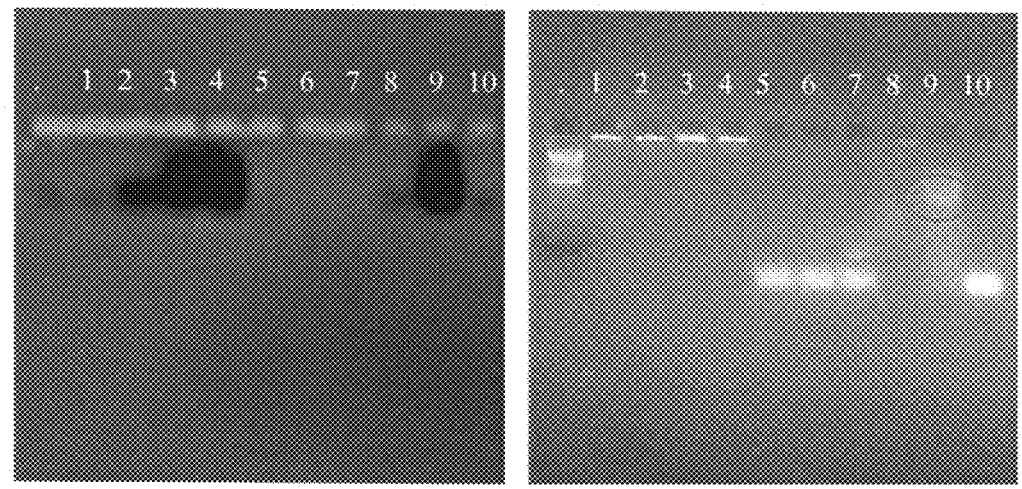
FIG. 6 shows an electrophoresis gel of samples of dendrimer complexes and the ODN TAR in the presence of albumin and SDS. The left part is a stain of the proteins with Paragon blue and the right part a photograph of the stain of the DNA samples with ethydium bromide.

The calculations necessary to put a dendrimer/ODN ratio of 2/1 were made and the following samples were prepared, with the object of exposing the dendriplexes to the presence of different concentrations of bovine serum albumin, complete medium with foetal calf serum or AB complete human serum. The different mixtures produced were tested for DNA and protein migration on a same 3% agarose gel ethydium bromide in its composition. First, a photograph was taken of the gel exposed to ultraviolet light and then it was stained with a 0.5% Paragon blue colouring solution (8-amino-7-(3-nitrophenylazo)-2-(phenacyl)-1-naphthol-3,6-disulfonic acid sodium salt, Beckman Coulter®) during 20 minutes (dye to show the presence of proteins) and the gel was finally unstained with washes of 10% glacial acetic, taking a photograph with digital camera subsequently. The results are shown in FIG. 6, wherein part a corresponds to the stain with Paragon Blue and part b corresponds to the photograph of the gel taken with ultraviolet light. The samples appear in the following order:

Lane: 100 bp ladder
Lane 1: 2.60 µl TAR+3.47 µl NN+25 µl RPMI
Lane 2: 2.60 µl TAR+3.47 µl NN+25 µl RPMI+30 µl PBS-BSA 2%
Lane 3: 2.60 µl TAR+3.47 µl NN+25 µl RPMI+30 µl PBS-BSA 5%
Lane 4: 2.60 µl TAR+3.47 µl NN+25 µl RPMI+30 µl PBS-BSA 10%
Lane 5: 2.60 µl TAR+3.47 µl NN+25 µl RPMI+30 µl SDS 0.5%
Lane 6: 2.60 µl TAR+3.47 µl NN+25 µl RPMI+30 µl SDS 1%
Lane 7: 2.60 µl TAR+3.47 µl NN+25l RPMI+30 µl SDS 2%
Lane 8: 2.60 µl TAR+3.47 µl NN+25 µl RPMI+30 µl Complete medium
Lane 9: 2.60 µl TAR+27 I RPMI+30 µl PBS-BSA 10%
Lane 10: 2.60 µl TAR+27 µl RPMI In first place, it is observed that in all the wells (except that treated with SDS) dark bands appear midway between the free ODN and the well: they are complexes of the Paragon Blue with the bromophenol blue present in the load buffer. Furthermore, in all the lanes wherein the albumin is present there appears a spot corresponding to its stain.

In accordance with the results shown in the gels, the following conclusions can be drawn:

a) ODN forms complexes with the albumin, to which there corresponds a band in the gel stained with ethydium bromide, which has been marked surrounding it.

b) The increasing concentrations of albumin are not capable of dissociating the complex (2,3,4). Furthermore, the albumin should not be sequestrating ODN from the dendrimer-DNA complex, because, if not, it would migrate to the height of the circle.

c) The complex is dissociated in the presence of an anionic detergent (SDS) at all concentrations tested.

Example 35

Stability of the N,N-ODN Dendriplex in the Presence of Serum

With the intention of seeing the stability of the dendriplexes in the presence of serum over time, a test was performed wherein to the samples was added complete medium which contained 10% foetal calf serum (FCS). The following samples were prepared with TAR as ODN:

1. TAR 2.59 µL + NN 3.47 µL + 54 µL RPMI (+/−) = 2/1
2. TAR 2.59 µL + NN 1.73 µL + 55 µL RPMI (+/−) = 1/1
3. TAR 2.59 µL + NN 0.86 µL + 57 µL RPMI (+/−) = 0.5
4. TAR 2.59 µL + 54 µL RPMI

+100 µL COMPLETE MEDIUM

Figure 7:
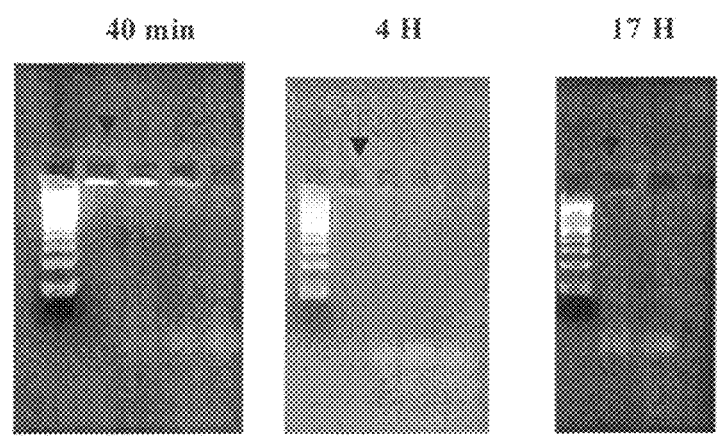
FIG. 7 shows the evolution of samples of dendrimers of the invention and an ODN on being incubated in the presence of complete medium during 40 minutes (40 min), 4 hours (4H) and 17 hours (17 H).

As indicated, 20' after its preparation 100 µl of complete medium were added to samples 1, 2 and 3. From each one of the samples 45 µl aliquots were taken after 40 minutes, 4 hours and 17 hours and they were subjected to electrophoresis in agarose gel. The samples were loaded in the gel following the ordering of its numbering from left to right, having previously situated a 100 bp ladder marker. In the last point (17 hours), only the 2/1 ratio complex was tested against ODN without NN. The results are shown in FIG. 7, wherein there appears a date on each one of the wells corresponding to samples with TAR+NN in 2/1 ratio.

From the previously mentioned details, the following observations can be drawn:

a) After 40 min, it is observed that only the 2/1 charge ratio is capable of completely retaining the ODN, the 1/1, nor of course the 0.5/1, ratio being possible.

b) After 17 h the NN dendrimer releases the ODN which migrates towards the anode.

c) There is no interference of the proteins of the complete medium with the stability of the complex. On the other hand, the ODN released migrates at the same level as the ODN alone, which indicates that the ODN does not form any complexes with any of the proteins existing in the medium (10% foetal calf serum, Antibiotic and L-Glutamine).

In short, in the presence of 10% FCS, the complex and the ODN behave as if the medium used for the mixtures only contained RPMI, does not form complexes with the plasma proteins, and the NN releases to the ODN after 17 h.

It was then checked how the complex and ODN behaved in the presence of human serum. For this, studies were performed with human serum AB.

Figure 8:
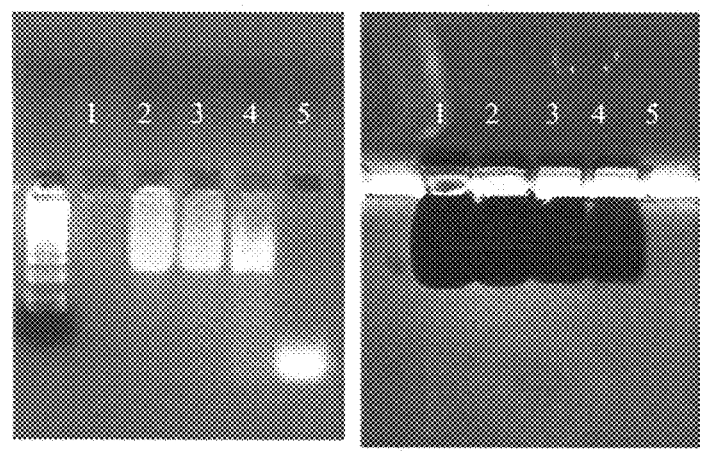
FIG. 8 shows an electrophoresis gel of samples of dendrimers and ODN in the presence of human serum. The left part shows a photo produced with ultraviolet light of DNA samples and the right part shows a stain of the proteins of that gel with Paragon Blue.

In first place, the behaviour of the ODN without dendrimer was checked in the presence of human serum. To do this, samples with the following composition were subjected to electrophoresis:

Lane 0: 100 bp ladder
Lane 1: Control (Serum AB)
Lane 2. 2.6 µL TAR+17 µL RPMI+40 µL Serum AB
Lane 3. 2.6 µL TAR+37 µL RPMI+20 µL Serum AB
Lane 4. 2.6 µL TAR+47 µL RPMI+10 µL Serum AB
Lane 5. 2.6 µL TAR+57 µL RPMI The electrophoresis gels, produced after waiting 20 minutes for a good interaction of the ODN with the serum proteins before loading the samples in the gel, is shown in FIG. 8. In this, part a shows the photograph produced with UV light of the appearance of bands by staining with ethydium bromide and part b shows the same gel treated with Paragon Blue®. The localization of the bands corresponding to the ODN in part a at the same height as the protein bands in part b demonstrated the binding of ODN to human serum proteins.

In second place, the effect of the presence of human serum proteins on the ODN-NN dendriplex was verified. It was attempted to check if the dendrimer would protect the ODN of the binding to proteins; to do this, dendriplexes, ODN and dendrimers without DNA with 3 concentrations of human serum AB were incubated: 20 minutes after performing the mixtures of ODN, dendrimer and RPMI without serum, 100 µL of RPMI were added to the mixture, either pure, or with serum AB at 5%, 10% or 20%. Electrophoresis was performed after 0 hours, 4 hours and 24 hours of the dendrimer and ODN mixture, loading the samples in the following manner:

| 0 hours ... 20' => 100 µL RPMI | | |
| --- | --- | --- |
| Lane 1. | 2.43 µL PPT-TFO + 3.25 µL NN + 54 µL RPMI | PURE |
| Lane 2. | 2.43 µL PPT-TFO + 3.25 µL NN + 54 µL RPMI | 5% |
| Lane 3. | 2.43 µL PPT-TFO + 3.25 µL NN + 54 µL RPMI | 10% |
| Lane 4. | 2.43 µL PPT-TFO + 3.25 µL NN + 54 µL RPMI | 20% |
| Lane 5. | 2.43 µL PPT-TFO + 57 µL RPMI | 5% |
| Lane 6. | 2.43 µL PPT-TFO + 57 µL RPMI | 10% |
| Lane 7. | 2.43 µL PPT-TFO + 57 µL RPMI | 20% |
| Lane 8. | 2.43 µL PPT-TFO + 57 µL RPMI | PURE |

| 4 hours: ... 20' => 100 µL RPMI | | |
| --- | --- | --- |
| Lane 1. | Control (60 µL RPMI) | 20% |
| Lane 2. | 2.43 µL PPT-TFO + 3.25 µL NN + 54 µL RPMI | PURE |
| Lane 3. | 2.43 µL PPT-TFO + 3.25 µL NN + 54 µL RPMI | 5% |
| Lane 4. | 2.43 µL PPT-TFO + 3.25 µL NN + 54 µL RPMI | 10% |
| Lane 5. | 2.43 µL PPT-TFO + 3.25 µL NN + 54 µL RPMI | 20% |
| Lane 6. | 2.43 µL PPT-TFO + 57 µL RPMI | 5% |
| Lane 7. | 2.43 µL PPT-TFO + 57 µL RPMI | 10% |
| Lane 8. | 2.43 µL PPT-TFO + 57 µL RPMI | 20% |
| Lane 9. | 2.43 µL PPT-TFO + 57 µL RPMI | PURE |
| Lane 10. | 3.25 µL NN + 57 µL RPMI | 5% |
| Lane 11. | 3.25 µL NN + 57 µL RPMI | 10% |
| Lane 12. | 3.25 µL NN + 57 µL RPMI | 20% |

| 24 hours ... 20' => 100 µL RPMI | | |
| --- | --- | --- |
| Lane 1. | Control (60 µL RPMI) | 20% |
| Lane 2. | 2.43 µL PPT-TFO + 3.25 µL NN + 54 µL RPMI | PURE |
| Lane 3. | 2.43 µL PPT-TFO + 3.25 µL NN + 54 µL RPMI | 5% |
| Lane 4. | 2.43 µL PPT-TFO + 3.25 µL NN + 54 µL RPMI | 10% |
| Lane 5. | 2.43 µL PPT-TFO + 3.25 µL NN + 54 µL RPMI | 20% |
| Lane 6. | 2.43 µL PPT-TFO + 57 µL RPMI | 5% |
| Lane 7. | 2.43 µL PPT-TFO + 57 µL RPMI | 10% |
| Lane 8. | 2.43 µL PPT-TFO + 57 µL RPMI | 20% |
| Lane 9. | 2.43 µL PPT-TFO + 57 µL RPMI | PURE |
| Lane 10. | 3.25 µL NN + 57 µL RPMI | 5% |
| Lane 11. | 3.25 µL NN + 57 µL RPMI | 10% |
| Lane 12. | 3.25 µL NN + 57 µL RPMI | 20% |

Figure 9A:
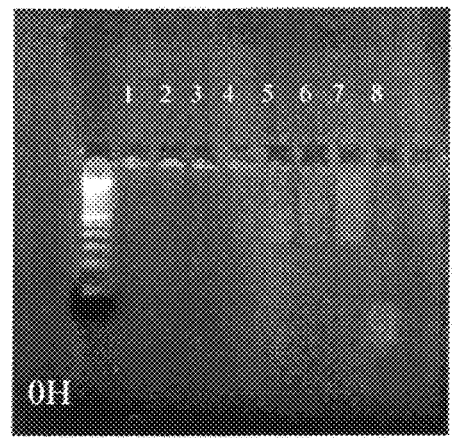
FIG. 9a shows the staining with ethydium bromide of electrophoresis gels corresponding to mixtures of dendrimers and ODN after 0 hours (0H), 4 hours (4H) and 24 hours (24H).
Figure 9A:
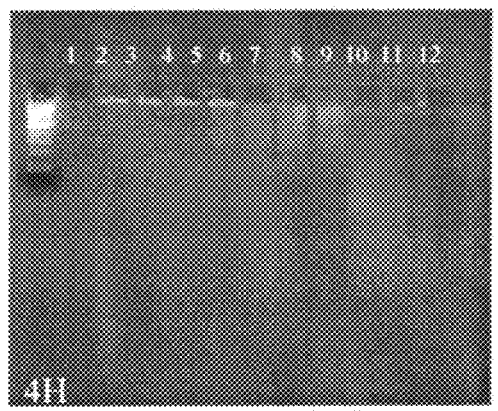
Figure 9A:
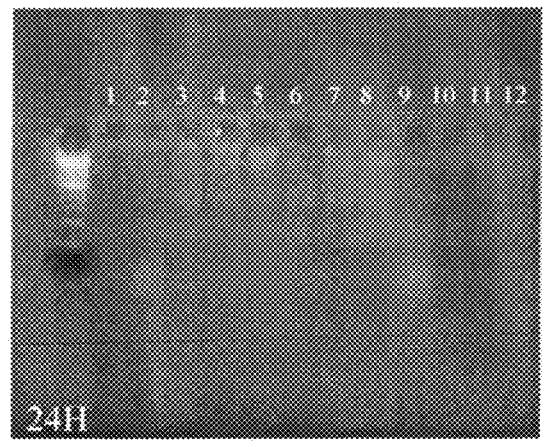
Figure 9B:
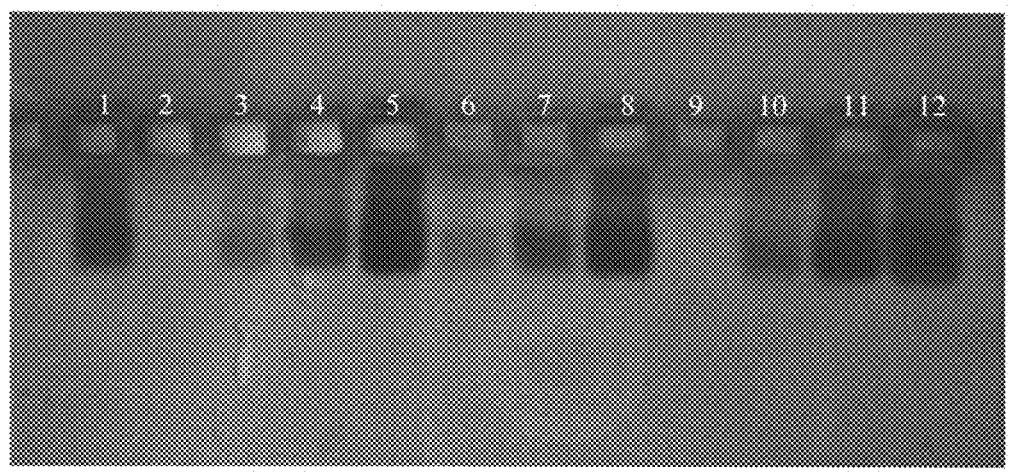

The results of photographing the gels under ultraviolet light is shown in FIG. 9a. FIG. 9b, for its part, shows the staining with Paragon Blue of the gel corresponding to the 4 hour samples.

The results show that the NN+PPT-TFO dendriplex without serum behaves as habitual, releases the ODN after 24 h. After 0 and 4 h: the NN+PPT-TFO in the presence of serum gives a different electrophoresis pattern to PPT-TFO in the presence of serum. The latter gives an elongated and diffuse signal, whilst the dendriplex leaves the ODN in the well (except when the serum is at 20%, which produces a slight leak of ODN and binds to proteins). The protein gels are observed, (of which those corresponding to the 4 hour samples have been shown as an example, although the results were similar in the 0 and 24 hour gels), these run towards the positive pole, (stain which separates it from the well); but it is interesting to observe in the BE gel that proteins form a complex with the ODN when it is alone, without dendrimers. The proteins run at the same height in all experiment circumstances, irrespective of the presence of the dendrimer (which does not manage to retain the protein in the well, does not form a complex with the protein). The presence of protein does not manage to remove ODN from the ODN-dendrimer complex; after 24 h, the complex starts to release ODN, but this does not migrate downwards like the ODN control without serum, instead it is immediately retained in its migration by the proteins, giving the same elongated and diffuse signal as the ODN without NN with serum.

It, therefore, seems that there is a window of between 4 and 24 h in which the dendrimer would protect the ODN of the bond to proteins. After this time it releases it. This would give the ODN time to bind to the dendrimer on passing from the endovascular to the extravascular space, with the certainty that the dendrimer would later release the ODN in controlled manner over time, giving it the opportunity to exercise its action. The main protein of the serum is albumin, which has 2 negative domains which give it a total negative charge, but it also has a positive charge, which binds it to the ODN. The hydrophobic sites of the CBS probably do not interact with the hydrophobic sites of the albumin. Said interaction is necessary to achieve a stable bond between dendrimer and protein, for this reason they do not form complexes; however the electrostatic bond between dendrimer and ODN protects the latter from the bond with the positive site of the albumin.

Example 36

Capacity to Form Complexes with Large-sized DNA

Preliminary tests were carried out with plasmids with CBS IM8, it being capable of forming complexes with the plasmid used, Nf-kappaB-luc. In a similar form to the previous experiments, electrophoresis was carried out with different samples, placing them a ladder type marker which measures up to 5000 pb in the well previous to it. The samples were the following:

Lane 1: 1 µl p+0.58 µl IM8 (+/−)=2/1+28 µl RPMI

Lane 2. 1 µl p+1.74 µl IM8 (+/−)=6/1+28 µl RPMI

Lane 3. 1 µl p+2.9 µl IM8 (+/−)=10/1+27 µl RPMI
Lane 4. 1 µl p+29 µl IM8 (+/−) 100/1+0 µl RPMI
Lane 5. 1 µl p (0.43 µg p)
Lane 6. 2 µl p
where p=plasmid.

Figure 10:
FIG. 10 shows an electrophoresis gel of samples of complexes between the plasmid Nf-kappaB-luc and the IM8 dendrimer.

The electrophoresis photograph is shown in FIG. 10. It demonstrates that the charge ratio A (+/−)=6/1 now manages to retain DNA migration.

Example 37

Capacity of Forming Complexes with siRNA

Preliminary tests were also performed to evaluate the retention capacity of small interfering RNA (siRNA). The following anti-CD4 siRNA was used with this purpose:

```
5'-GAUCAAGAGACUCGUCAGUdGdA-3'     (SEQ ID NO: 6)
``` supplied by Ambion, Inc. The gel used was a matrix gel, a gel prepared with a 25 or 50% agarose and linear acrylamide mixture produced after heating and later labelling of the samples with ethydium bromide. In this case specifically, a 50% matrix, 0.7% agarose and 50% TAE 2× gel was used.

Figure 11:
FIG. 11 shows an electrophoresis gel of tests of complex formation between an RNAi and a dendrimer (IM8) of the invention.
Figure 12:
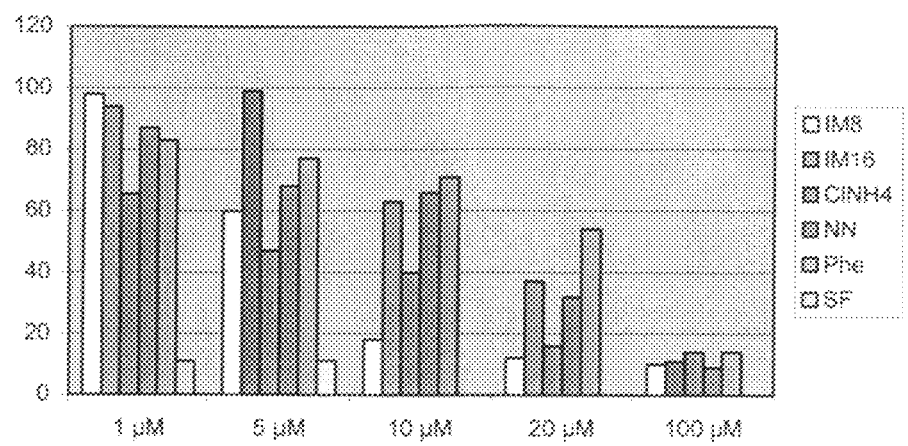
FIG. 12 shows a graphic with the results of mitochondrial activity for concentrations 1, 5, 10, 20 and 100 µM after the incubation of cells with the dendrimers IM8, IM16, ClNH4, NN, Phe and SF, which have their corresponding bar for each concentration placed in the post it occupies in the previous numbering.
Figure 13:
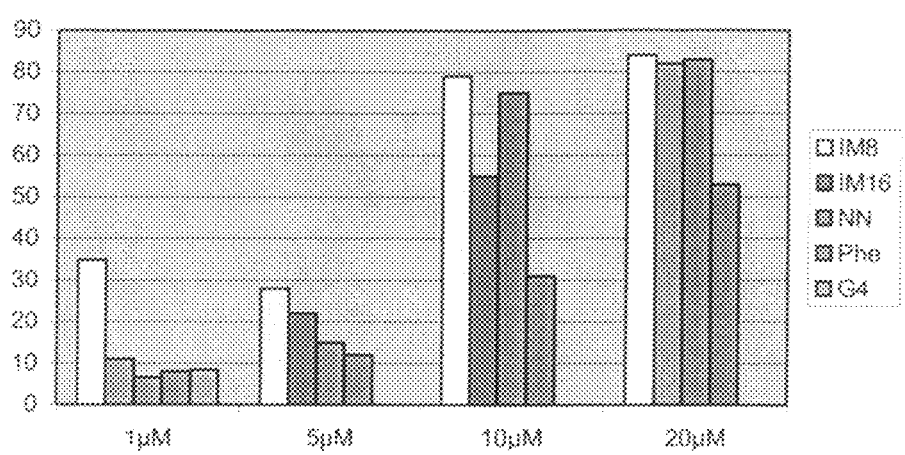
FIG. 13 shows a graphic with the results of haemoglobin release after the incubation of erythrocytes with dendrimers IM8, IM16, NN, Phe and S, at concentrations of 1, 5, 10 and 20 µM. Each bar corresponds to a dendrimer, placed in the order corresponding to the previous numbering and each group of bars corresponds to a concentration, ordered in rising order.

The samples subjected to electrophoresis were the following:
Lane 1: RPMI
Lane 2: 1 µl siRNA+1.58 µl IM8+48 µl RPMI (+/−)=2
Lane 3: 1 µl siRNA+4.74 µl IM8+44 µl RPMI (+/−)=6
Lane 4: 1 µl siRNA+49 µl RPMI The photograph of the electrophoresis gel, shown in FIG. 11, again demonstrates that the complex formation is positive.

Toxicity Tests

The toxicity of the different dendrimers was studied by five different but complementary processes, which provided details on cell functionality, membrane permeability and cell appearance.

Different techniques were used in order to evaluate the viability in different aspects: membrane integrity (stains with Trypan Blue), apoptosis (labelling with anexine-V-PE and DAPI), necrosis (labelling with 7-AAD), MTT reagent (it evaluates mitochondrial toxicity), evaluation of the size and complexity of the cells by flow cytometry, in vivo microscopy to evaluate cell mobility. These techniques were applied for the study of the toxicity of ODN, dendrimers and dendriplexes in peripheral blood mononuclear cells (PBMC). Additionally, the toxicity of the dendrimers on erythrocytes was evaluated by a haemolysis test.

Example 38

Tests on PBMC

Dendrimers Tested

The toxicity of dendrimers IM8, IM16, ClNH4, NN, Phe and the commercial controls SF (Superfect) and G4 were tested. Different quantities were taken of each one of them so that the final concentrations with which the cells were incubated were 1 µM, 5 µM, 10 µM, 20 µM and 100 µM.

Production of Peripheral Blood Mononuclear Cells (PBMC)

The blood came from adult donors or the umbilical cord of health newborns. Said blood was diluted ½ with PBS and it was centrifuged in a Ficoll gradient. After said centrifugation, the PBMC halo was recovered and two subsequent washing-centrifuging cycles were carried out. The resulting PBMC were resuspended in complete culture medium with 10% FCS, antibiotics and glutamine.

Incubation with the Cells

100 µl of 10% complete medium of foetal calf serum, antibiotics and glutamine were added to a volume of 60 µl of RPMI with the corresponding dendrimer tested. 160 µl were then added to the cells seeded in 340 µl, completing a final volume of 500 µl. The cells were incubated in this way for 48 hours and then the effect of the incubation with the dendrimers was evaluated by its visual examination and by the evaluation of the mitochondrial activity.

Results of the Visual Examination

The observations produced from the visual examination are shown below in Table 2.

TABLE 2

Results of the visual examination of PBMC incubated with dendrimers

| | 1 µM | 5 µM | 10 µM | 20 µM | 100 µM |
|---|---|---|---|---|---|
| IM8 | O.K | O.K | Decrease double refraction Increase in mortality | Decease in number of cells | Very few live cells |
| IM16 | O.K | O.K | Cell aggregates + | Cell aggregates ++ | Cell aggregates +++ |
| ClNH4 | O.K | Aggregates + | Many membrane moieties | Few cells with dead appearance | Large brown cell lumps. |
| NN | O.K | O.K | Much better appearance than the previous CBS at this concentration | The number of cells decreases but the appearance improves in relation to previous CBS at this concentration | Very few cells, but better appearance than the previous CBS at this concentration |
| Phe | O.K | O.K | O.K | Few cells | Isolated cells. |
| SF | Aggregates ++ | Aggregates ++++ | Not tested | Not tested | Not tested |
| G4 | O.K | Aggregates + | Aggregates ++ | Aggregates +++. Much mortality | Large dark aggregates. |

From the visual observation it is gathered that the least toxic dendrimers for the lymphocytes were CBS NN and Phe, the two PAMAM dendrimers tested being least toxic.

Mitochondrial Activity: MTT

A curve of mitochondrial activity was performed of the dendrimer concentration after 48 hours. This technique was used to demonstrate intracellular deleterious effects on the inside of the cells. It is a calorimetric test based on the selective capacity of the cells viable for reducing 3-(4,5-dimethylthiazol-2-il)-2,5-diphenyl tetrazolium bromide in insoluble formazan crystals. After 48 hours of incubation of the PBMC with different concentrations of dendrimers in a 96-well plate (100,000/well), the supernatant which contained dendrimer was removed and it was replaced by 200 µl of a culture medium without serum or red phenol (Optimem). To avoid the loss of cells in this step and subsequently of formazan, a modification had been made of the protocol, seeding the PBMC in total human plasma fibronectin (Sigma®) at a concentration of 5-10 µg/ml, so that during the 4-hour incubation they fixed to the bottom of the well. In addition to the 200 µl of Optimem, 20 µl of filtered MTT were added to achieve its sterility (Thiazolyl Blue, Sigma®) in PBS pH 7.4 at a concentration of 5 mg/ml to achieve a final concentration per well of 0.5 mg MTT/ml. After 4 hours of incubation at 37° C. with 5% $CO_2$ atmosphere, the plate was centrifuged at 2000 rpm and the supernatant with the excess MTT that had not reacted was subsequently removed. The formazan crystals were observed under a phase contrast microscope and later dissolved with 200 µl of dimethyl sulfoxide (DMSO). The plate was stirred at 700 rpm in an Eppendorf® stirrer-heater to ensure the correct dissolution of said crystals. The concentration of formazan ([A]) was determined by spectrometry using a plate reader at a wavelength of 570 nm with a reference of 690 nm. The spectrophotometry was calibrated to zero using Optimem without cells. The relative cell viability (%) with respect to the control (untreated cells), based on mitochondrial activity, was calculated based on this formula: [A] test/[A] control×100. Each dendrimer concentration was tested in triplicate, following the guidelines of the ATCC. The results produced are shown below in Table 3.

TABLE 3

Cell viability after incubation with dendrimers according to MTT

|        | 1 µM | 5 µM | 10 µM | 20 µM | 100 µM |
|--------|------|------|-------|-------|--------|
| IM8    | 98   | 60   | 18    | 12    | 10     |
| IM16   | 94   | 99   | 63    | 37    | 11     |
| ClNH4  | 65.5 | 47   | 40    | 16    | 14     |
| NN     | 87   | 68   | 66    | 32    | 9      |
| Phe    | 83   | 77   | 71    | 54    | 14     |
| SF     | 11   | 11   |       |       |        |

From the tests with MTT it is it is gathered that the cells that showed greater mitochondrial viability after being treated with increasing concentrations of CBS or SF were those treated with CBS IM16, CBS NN and CBS Phe. However, if the data are taken as a whole with those of visual observation, it is inferred that whilst IM16 would lead to the formation of cell aggregates, NN and Phe do not do so, the latter being more compatible for lymphocytes.

Example 39

Tests on Erythrocytes

A visual examination was carried out to detect the presence/absence of hemagglutination and quantification of haemoglobin release (haemolysis test) by spectrophotometry. ClNH4 was excluded from the dendrimers of previous Example 38, as the result had been more toxic for lymphocytes, and the results were compared with those produced for a PAMAN type generation 4 dendrimer.

The erythrocytes were obtained after being separated from the PBMC using the same Ficoll gradient cited in the previous Example. They were diluted in PBS to be able to view them individually. The cells were resuspended in 500 µl of PBS and were seeded in a 24-well plate (300,000/well). As positive control, cells treated with 0.2% Triton X-100 were used. Negative control: PBS (blank). The erythrocytes were incubated with different dendrimer concentrations. The presence of hemagglutination, number of cells and release of haemoglobin by hour were evaluated by collecting 100 µl of supernatant and measuring absorbencies by spectrophotometry using a plate reader at a wavelength of 550 nm and 690 nm as reference.

Visual Examination

The observations resulting from the visual examination are shown below in Table 4.

TABLE 4

Visual examination of erythrocytes incubated with dendrimers

|      | 1 µM | 5 µM | 10 µM | 20 µM |
|------|------|------|-------|-------|
| IM8  | O.K  | Ag+  | Ag+   | No cells |
| IM16 | O.K  | Ag++ | Ag++ but more cells than with IM8 | No cells |
| NN   | O.K  | O.K  | Ag+/− | No cells |
| Phe  | Ag+  | Ag+++ | Ag+++ | There are cells but very agglutinated |
| G4   | Ag+  | Ag++ | Fusiform cells | There are cells but they are fusiform |

Ag = agglutination

Quantification of the Release of Haemoglobin After 1 Hour

100% haemolysis in the control of Triton X-100 (the cells treated with Triton were all dead and broken). 7% haemolysis in the negative control of untreated cells. Each well is expressed as the percentage with respect to the O.D. (optical density) of Triton X-100, which is considered 100%; in addition to that percentage 7% of the control is subtracted. In that way the results shown below in Table 5 were obtained:

TABLE 5

Percentage of haemoglobin release after incubation with dendrimers

|       | IM8  | IM16   | NN  | Phe    | G4  |
|-------|------|--------|-----|--------|-----|
| 1 µM  | 34.8 | 11.000 | 6.6 | 8.000  | 8.4 |
| 5 µM  | 28   | 22.000 | 15  | 12.000 | 0   |
| 10 µM | 79   | 55.000 | 75  | 31.000 | 0   |
| 20 µM | 84   | 82.000 | 83  | 53.000 | 0   |

At 5 µM NN and the Phe slightly exceed 10% toxicity, which is what is considered as cut-off point for erythrotoxicity. What happens is that the Phe induces hemagglutination and the NN does not. As a curious detail, IM16 induces less haemolysis and leaves a greater number of cells in the well than IM8, (agrees with that observed for MTT in lymphocytes), but it induces agglutination. All induce hemagglutination except NN. PAMAM G4 induces agglutination and formation changes in the erythrocytes, but not haemolysis.

The order of hemagglutination from greater to lesser is:
G4>Phe>IM16>IM8>NN

As a whole, the well wherein the cells had better appearance, also having almost unappreciable haemolysis, was NN dendrimer.

If the toxicity results on lymphocytes and erythrocytes are taken together, the dendrimer which demonstrated better biocompatibility profiles was NN.

Example 40

Toxicity of the ODN+Dendrimer Complexes in Comparison with the Dendrimer Alone

The toxicity of other dendrimers such as PAMAM is modified (decreased) when they form complexes with DNA. The following experiments attempt to disclose what happens with CBS in terms of toxicity when bound to the ODN.

The evaluation time on this occasion was 72 hours. The toxicity was evaluated on PBMC, produced in the manner described in Example 38.

The following charge ratio was used in all cases: (+/−)=2/1
The dendrimer concentrations used in these experiments to achieve the 2/1 charge ratio (+/−) were:
IM8: 2.96 μg=3.93 μM
IM16: 2.35 μg=1.99 μM
ClNH4: 1.92 μg=3.98 μM
Phe: 2.8 μg=1.96 μM
NN: 3.42 μg=3.94 μM
SF: 0.68 μM
G4: 100 μM
The ODN used was PPT, in the following way:
[ODN PPT] in the complex with the CBS: 2.57 (0.88 μM)
[ODN PPT] in the complex with SF: 0.34 μM
[ODN PPT] in the complex with G4: 1 μM Complex Formation A complex formation volume of 60 μl was used in all the tests, using RPMI with phenol red without serum as support medium. The corresponding quantities of ODN or dendrimer were used to reach the charge ratio (+/−)=2, the positive charge being provided by the dendrimer and the negative by the ODN. The calculations were performed based in the charge number of the dendrimer (fixed) and the number of negative charges of the ODN (also fixed).

Once the ODN and the CBS were added in the RPMI, a time of 20 minutes was waited to ensure complex formation.

In the case of SF, the complexes were formed following the manufacturer's instructions.

Incubation with the Cells

After the time necessary to ensure complex formation, 100 μl of 10% FCS complete medium, antibiotics and glutamine were added to the 60 μl of RPMI with ODN and dendrimer. 160 μl were then added to the cells seeded in 340 μl, completing a final volume of 500 μl. The cells were either incubated with said complexes, a mixture of equal volume which contained ODN without CBS, a mixture which contained dendrimer alone, or with a mixture which contained only RPMI+complete medium which was used as negative control. The cells and/or the supernatant were then collected to be analysed by flow cytometry, confocal microscopy or cell DNA extraction.

Immunofluorescence and Confocal Microscopy

After incubations with the mixtures containing fluorescent ODNs, dendriplexes, dendrimers or RPMI, the cells were treated for the subsequent acquisition of images in the conventional confocal or fluorescence microscope. The cells were adhered to glass slides with wells of 30 mm in diameter by Poly-L-lysine, (PLL) (Sigma®). To do this, the slides were preincubated with 30 μl of PLL during 2 hours in an incubator at 37° C. and 5% CO2. After this incubation, the excess PLL was washed with PBS. The cells from each treatment that were going to be adhered in the PLL were washed twice with PBS and were labelled for 1 minute with 0.8% Trypan Blue (Sigma®) to then show the viable cells. They were again washed twice with PBS. At that time the cells were added to the well (100,000/well), being disposed on the PLL during 1 hour in an incubator at 37° C. and 5% CO2. After this hour, the excess volume was washed with PBS and the cells were treated with recently prepared 3% paraformaldehyde (PFA) (within 2 weeks of its use) during 10 minutes. After these 10 minutes, the excess PFA was washed with PBS and the cells were labelled with antibodies, labelled with fluorochromes and DAPI. The cell membrane was stained first and then the nucleus. A preliminary titering of the antibodies used to determine the best concentrations to use for our test was carried out. In first place a mouse antihuman anti-CD45 IgG1, κ primary antibody was used (BD®); 30 μl of antibody were added to each well, at a dilution of 1 μg/ml; it was incubated for 30 minutes and then the excess was washed with PBS. Then, a secondary antibody of goat anti-mouse IgG-IgM was used (heavy and light chains) conjugated in Texas-Red (Jackson ImmunoResearch®), 30 μl/well at a 1/130 dilution of the stock (stock concentration 1.4 mg/ml). The cells were incubated a further 30 minutes and they were then washed with PBS. Finally, the cell nuclei were stained using DAPI (Vysys®) 10 μl/well during 10 minutes, then washing twice with PBS. The incubations with antibodies and DAPI were performed at ambient temperature. The antibodies were diluted on the same day of use to avoid their degradation with the passage of time and they were centrifuged at 12000 rpm prior to their use to eliminate the presence of aggregates. The dilution of each antibody was performed in blocking medium to decrease non-specific labelling (PBS with 1% bovine serum albumin). Finally, the preparation was mounted using a special medium for fluorescence (DAKO Cytomation Fluorescent Mounting Medium®) with antifading (designed to protect the sample from deterioration caused by lasers). It was then observed and images captured using a Leica TCS SP2 confocal microscope using different excitation lines: 405, 488 and 514 nm and using the lens for optical differential contrast microscopy of the confocal. After the capture of images, it was analysed using Leica® software.

In vivo Confocal Microscopy. In order to examine cell viability after different treatments with ODNs, dendriplexes and dendrimers to which the PBMC was subjected, and studying phenomena such as the capture of fluorescent ODN thereby or evaluating the movement of transfected cells, in vivo confocal microscopy techniques were used. Thus, 2.5 cm crystals were seeded with total human plasma fibronectin (Sigma®) at a use concentration of 5-10 μg/ml being incubated with fibronectin during 1 hour at 37° C. After washing the excess fibronectin on the crystal with PBS, PBMC previously washed with PBS were used and they were incubated at 37° C. with 5% $CO_2$ atmosphere during 30 minutes. The excess cells not adhered were eliminated by washing with PBS. All work with the crystal was performed disposing this on a non-adherent surface (sterilized metallic paper) in a sterile Petri dish and in a laminar flow cabin. Finally, the crystal was included in the chamber for in vivo microscopy of the confocal, in which the cells remained at 37° C. with 5% atmosphere. Before starting any in vivo experiment, the cells were left to recover from handling during 30 minutes in the chamber. After this period, the cells were treated differently:

1. Addition of the fluorescent ODN or dendriplexes with fluorescent ODN and evaluation of the internalization of the cells thereof.
2. Evaluation of the movement capacity of the cells after different challenges with dendrimers, dendriplexes or ODNs.

To do this, sequential captures were take over time (every 30", 1' or 2') of the cells choosing a cut-off in the mid-plane thereof, which included the nucleus. After the acquisition, the images were mounted for process image production.

Staining with Trypan Blue

This technique evaluated the permeability of the cell membrane to Trypan Blue (abbreviation TB). The live cells exclude this stain.

To perform it, a solution was prepared with 0.8% Trypan Blue (Sigma) and the cell pellet produced after centrifuging for 1 minute was treated, proceeding with the subsequent centrifugation-washing of the cells with PBS twice. The cells were observed under an optical microscope and the positive cells were counted for the presence of Trypan Blue (blue cells, dead) in relation to the percentage of negative cells (live cells). To do this, a large field was chosen with at least 100 cells. The results produced are shown below in Table 6.

TABLE 6

Percentage of cells stained with Trypan Blue

|  | TB+ (%) |  | TB+ (%) |
| --- | --- | --- | --- |
| Control | 12.2 | PPT | 11.9 |
| PPT + IM8 | 11.5 | IM8 | 17.1 |
| PPT + IM16 | 14.9 | IM16 | 18.5 |
| PPT + ClNH4 | 15.8 | ClNH4 | 15.7 |
| PPT + Phe | 10.7 | Phe | 11.3 |
| PPT + NN | 13.6 | NN | 10.6 |
| PPT + SF | 72 | SF | 100 |
| PPT + G4 | 80.5 | G4 | 100 | n = 100 cells per count

The greater percentages of mortality corresponded to PAMAM both forming a complex with the ODN and alone. The CBS did not show an increased percentage of TB positive cells with respect to the untreated control cells, scarcely observing differences when the cells were treated with CBS-ODN or with CBS alone.

Flow Cytometry Test

Figure 15:
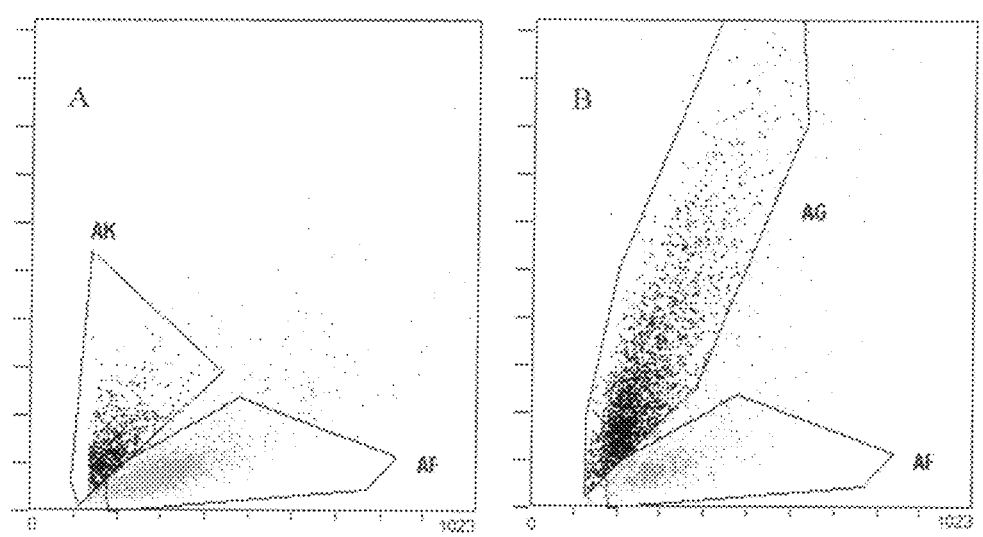
FIG. 15 shows the results of a flow cytometry test wherein the percentages of cells are compared with size and complexity corresponding to cells in apoptosis-necrosis with live cells. The X-axis represents the size and the Y-axis the complexity, the cloud of dark cells corresponding to cells in apoptosis-necrosis. Part A corresponds to PBMC cells treated with CBS dendrimers and part B to PBMC cells treated with PAMAN type dendrimers.
Figure 16:
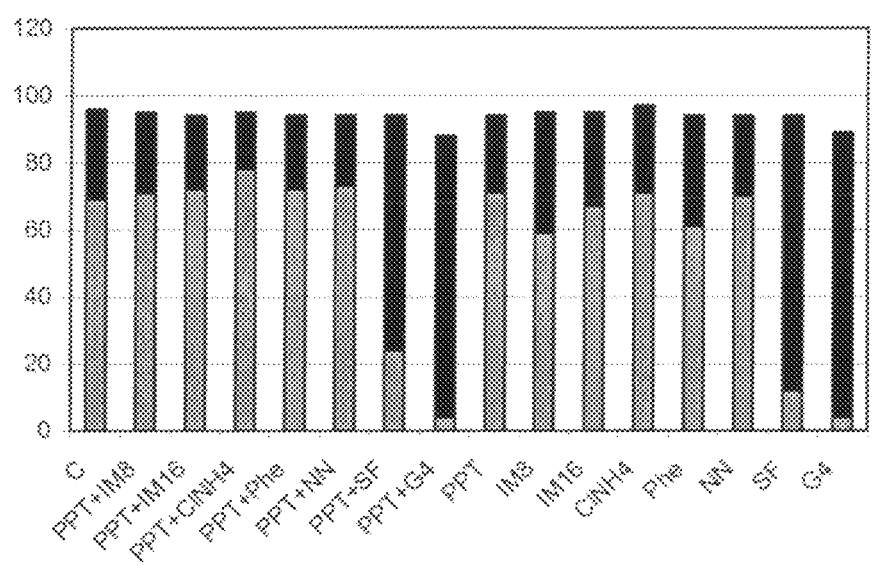
FIG. 16 shows the representation of the percentages of live cells and in apoptosis produced after the flow cytometry tests produced in PBMC cells treated with CMS dendrimers (A) or with a PAMAN type dendrimer (B).

The percentages of cells with size and complexity corresponding to cells in apoptosis-necrosis were compared with the live cells. For this, the size (FW) and the complexity (SD) was evaluated by flow cytometry. To do this, a region was drawn around the cells with FW and SD corresponding to cells in apoptosis-necrosis and another around the cells with FW and SD corresponding to live cells. The percentages of cells present in each slide were compared. The graphics produced are shown in FIG. 15, wherein the X-axis represents the size (FW) and the Y-axis the complexity (SD).

Part A shows a PBMC-type cell population treated with CBS dendrimers and part B a population treated with a PAMAN type dendrimer. The cloud of dark cells corresponds to cells in apoptosis necrosis. The live cells are represented in grey. The numerical percentages were obtained corresponding to each one of the cell types, producing the values shown in Table 7.

TABLE 7

Percentages of live cells and in apoptosis-necrosis

|  | Live cells (%) | Apoptosis-necrosis (%) |  | Live cells (%) | Apoptosis-necrosis (%) |
| --- | --- | --- | --- | --- | --- |
| Control | 69 | 27 | PPT | 71 | 23 |
| PPT + IM8 | 71 | 24 | IM8 | 59 | 36 |
| PPT + IM16 | 72 | 22 | IM16 | 67 | 28 |
| PPT + ClNH4 | 78 | 17 | ClNH4 | 71 | 26 |
| PPT + Phe | 72 | 22 | Phe | 61 | 33 |
| PPT + NN | 73 | 21 | NN | 70 | 24 |
| PPT + SF | 24 | 70 | SF | 12 | 82 |
| PPT + G4 | 4 | 84 | G4 | 4 | 85 |

Figure 14:
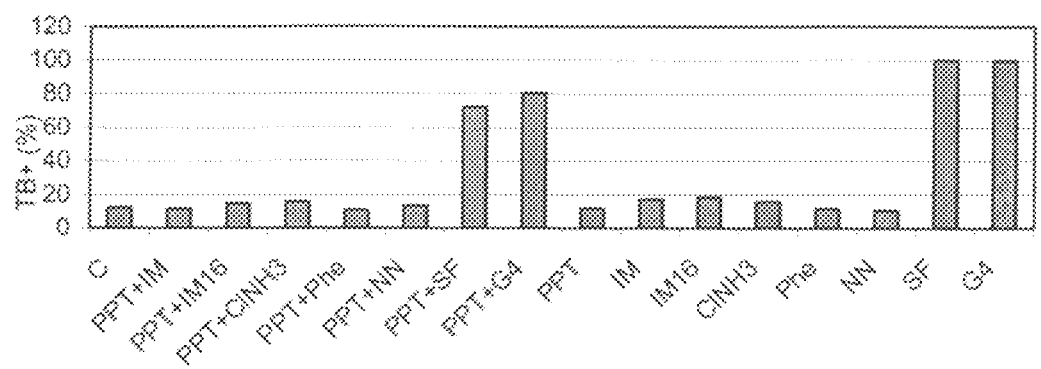
FIG. 14 shows a graphic with the percentages of mortality of cells incubated with different dendriplexes and dendrimers of the invention and stained with Trypan Blue.

These results are graphically represented in FIG. 14, which represents the percentage of dead cells in black and the percentage of live cells in grey. The first bar (C), corresponds to the control.

The greatest percentages of mortality corresponded to PAMAM both forming a complex with ODN and alone. On the other hand, CBS did not show a greater percentage of apoptosis-necrosis with respect to the control of untreated cells, scarcely observing differences when the cells were treated with CBS-ODN or with CBS alone.

Stainings with DAPI

As additional test to check cell viability, the DAPI (Vysys®) vital stain was used, using 10 µl per well during 10 minutes and later washing twice with PBS. The cell nuclei in apoptosis or necrosis show a reduced nuclear size, condensation of the chromatin and nuclear fragmentation.

Figure 17:
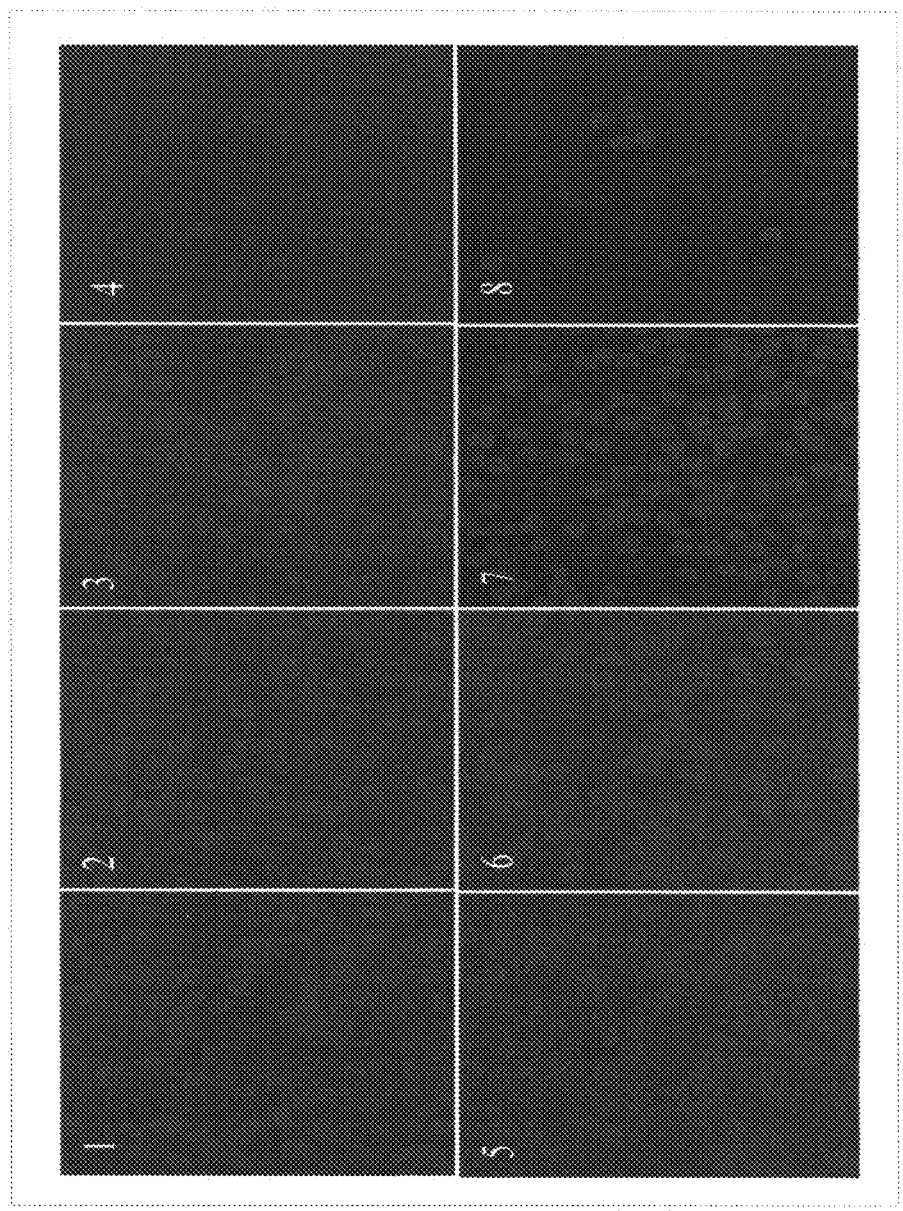
FIG. 17 shows the stains with the DAPI live cell dye for cells incubated with: 1: Control; 2: ODN+IM8; 3: ODN+IM16; 4: ODN+SF; 5: ODN; 6: IM8; 7: IM16; 8: SF.

FIG. 17 shows the results produced with the following samples: 1: Control; 2: ODN+IM8; 3: ODN+IM16; 4: ODN+SF; 5: ODN; 6: IM8; 7: IM16; 8: SF The cells treated either with the CBS-ODN complexes or CBS alone, showed round nuclei with homogenously distributed chromatin, with a similar appearance to that of the untreated control cells. The wells treated with SF (4 and 8) showed a marked cell depletion, making analysis difficult.

Videos

The clearest evidence that a cell is alive is that it moves. Live cells show transitory cell protrusions moving on a crystal surface seeded with fibronectin. The cells treated with CBS showed a movement pattern similar to that of the untreated cells.

Figure 18:
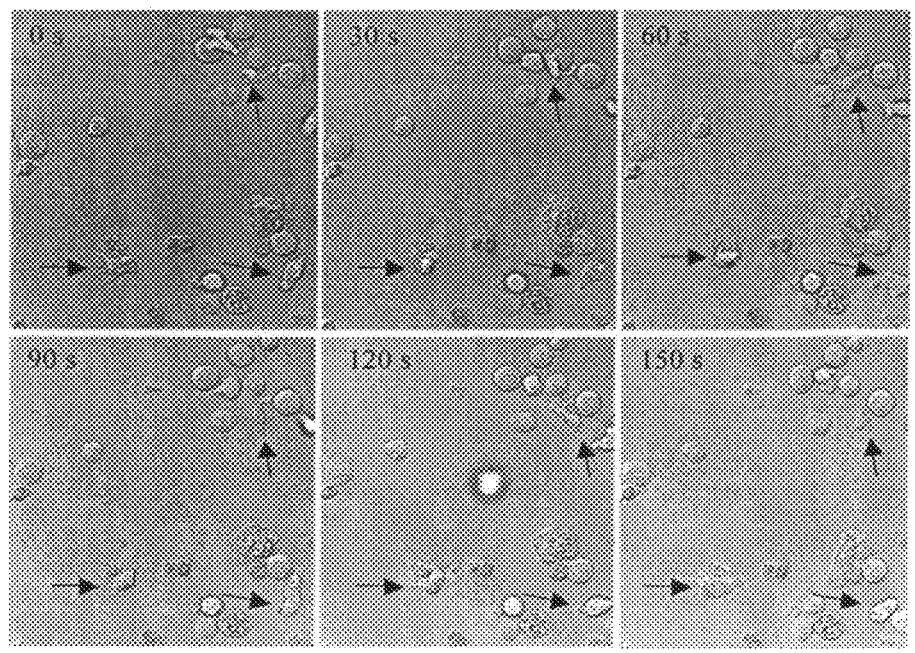
FIG. 18 shows photos taken after 72 hours of incubation of cells with IM8-ODN, after 0, 30, 60, 90, 120 and 150 seconds.

As an Example, FIG. 18 shows a sequence of photos taken after 72 hours of incubation of the cells with CBS IM8-ODN. Some movement details are highlighted with arrows.

In conclusion, the concentrations of use of the dendrimers in the complex formation demonstrated that they were fairly biocompatible, the cells showing similar viability when treated with CBS-ODN complexes as when treated alone.

Antigenic Capacity

It is very important, when one wants to know the biocompatibility profile of a new molecule, to know if it can constitute a non-specific antigenic stimulus. This would be a drawback, as the immune system cells could recognize said molecule as a foreign element against which it would unleash a response which would probably be deleterious for the organism. To do this, a lymphocyte proliferation study was carried out in the presence of different CBS, with the purpose of comparing the capacity of lymphocytic stimulation they would have in comparison with a classic potent stimulus such as phytohemagglutinin (PHA).

Example 41

Proliferative Test

To evaluate the antigenic capacity of CBS dendrimers, a lymphoproliferative test was performed. The experiment was prepared in triplicate in a 96-well flat bottomed plate (100,000 cells per well in 200 μl of complete human AB medium with antibiotics, glutamine and 10% AB serum). The experiment had a negative control proliferation well (untreated cells), a well treated with a dose of habitual use (2 μM) of each dendrimer to test, another with a greater dose very close to cytotoxicity (5 μM) and another positive control of proliferation treated with 1 μg/mL of phytohemagglutinin. After 5 days of incubation at 37° C. with 5% atmosphere of $CO_2$ 100 μl of supernatant was removed, then adding 100 μL of a medium with an isotopic intercalating agent of DNA, tritiated thymidine (prepared with 10% AB medium and Thymidine 1/100). The plate was then filtered using a Harvester passing its content through a filter, which was left to dry overnight (approx. 16 hours). After this period, a sheet of Methylex® containing scintillation medium was heat-melted, and it was read in a gamma camera to evaluate the number of counts (greater the counts, more proliferation). The results, which are shown below in Table 8, are expressed as tritiated thymidine counts per minute (cpm). Each result of each concentration was performed in triplicate, the value which appears in the table being the average of the 3. The PHA and the control were tested 12 times.

TABLE 8

Reading of the number of counts in a lymphoproliferative test

| Antigenic stimulus | Measurement of the scintillation counter | |
|---|---|---|
| Dendrimers | 2 μM | 5 μM |
| IM8 | 144 cpm | 149 cpm |
| IM16 | 175 cpm | 141 cpm |
| NN | 145 cpm | 160 cpm |
| Phe | 146 cpm | 170 cpm |
| Control | 146 cpm | |
| PHA | 10267 cpm | |

Figure 19:
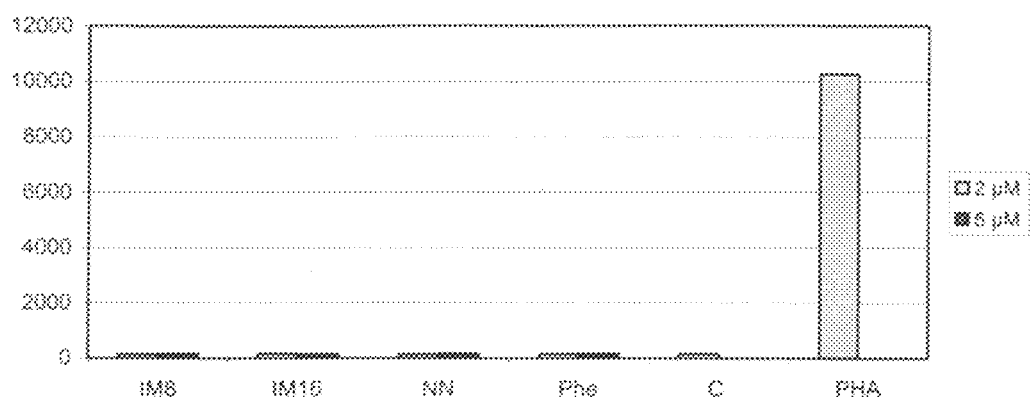
FIG. 19 shows a graphic with the results produced in the scintillation counter in a lymphoproliferative test stimulating the cells with different CBS dendrimers, with PHA and with a control (C).

FIG. 19 shows the graphic representation of this information.

As can be gathered from this test, the CBS dendrimers did not constitute an antigenic stimuli for the PBMC, at any of the concentrations tested.

Transfection Tests

The capacity of the ODN was evaluated to cross the plasma and nuclear membranes of the PBMC, and said capacity was compared with that which said ODN presented forming a complex with the different CBS. The dendrimers of the invention were compared with those of PAMAM type, using confocal microscopy.

Example 42

Transfection Test

Production of PBMC Cells and Incubation with the Samples

The same process explained in previous examples was used.

Prior Treatment of the Cells

Two days before treatment with ODN or with the dendriplexes, the PBMC were stimulated with phytohemagglutinin at a dose between 1-2 μg/ml and with interleukin-2 (IL-2) at a dose of 100 IU/ml, the cell concentration being between 3 and 5 million/ml. On the day of treatment, the cells were resuspended at a concentration of between 300,000-500,000 cells per 340 μl. However, and given that the final volume after the respective subsequent treatments was of 500 μl, IL-2 was added to maintain the cell activation during the course of the experiment at a dose of 50 IU/ml, calculated based on the 500 μl which would constitute the final volume.

Confocal Microscopy

The process described previously in other Examples was used.

Results Obtained with the ODN

Figure 20:
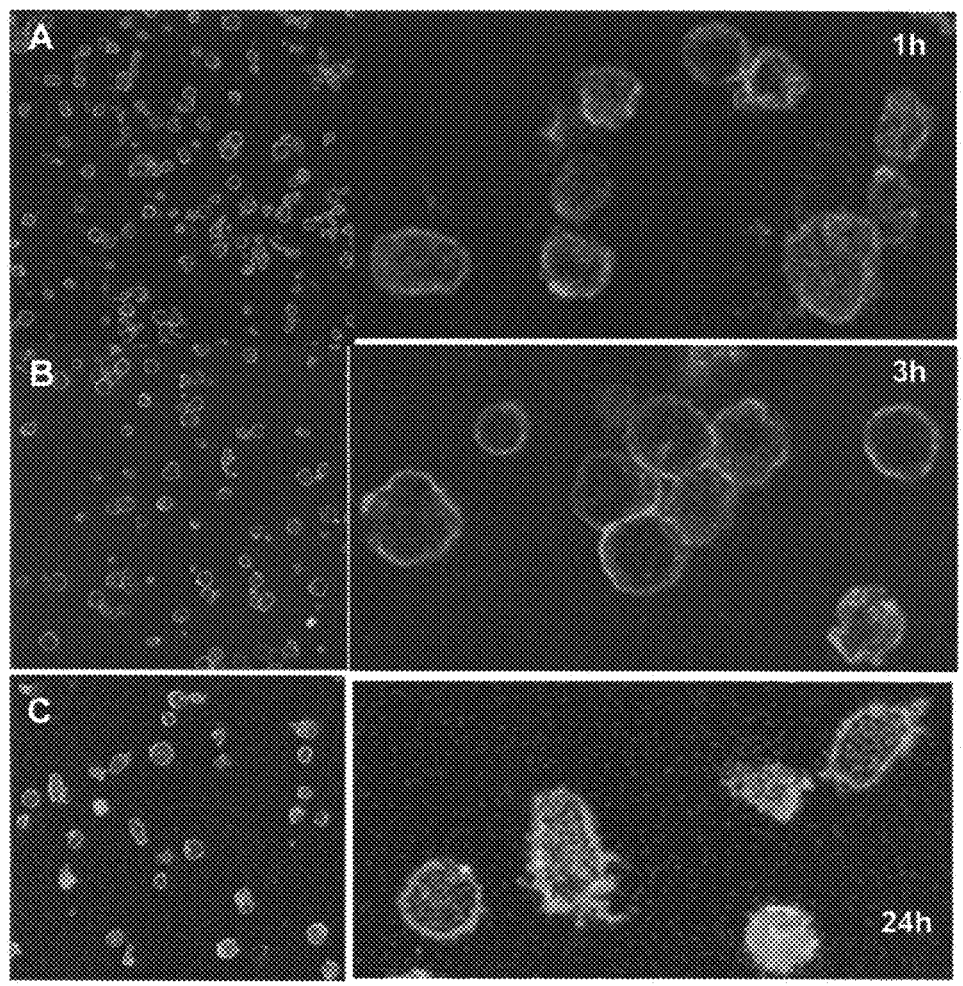
FIG. 20 shows the cell localization of an ODN with which the PBMC were transfected after: A: 1 hours; B: 3 hours; C: 24 hours.

Tests were performed with each one of the ODN of sequences SEQ ID NO:1 to SEQ ID NO:5. The ODN showed, contrary to that previously published, a surprising capacity for crossing the plasma membrane, as well as the nuclear membrane. This process is time-dependent. Thus, after 3 hours, the ODN was found in the cell cytoplasm, and after 24 hours in the nucleus. An example of this can be observed in FIG. 20, where photographs taken after 1, 3 or 24 hours since the start of transfection with ODN RF can be observed.

The fluorescence pattern was diffuse, without formation of aggregates.

Figure 21A:
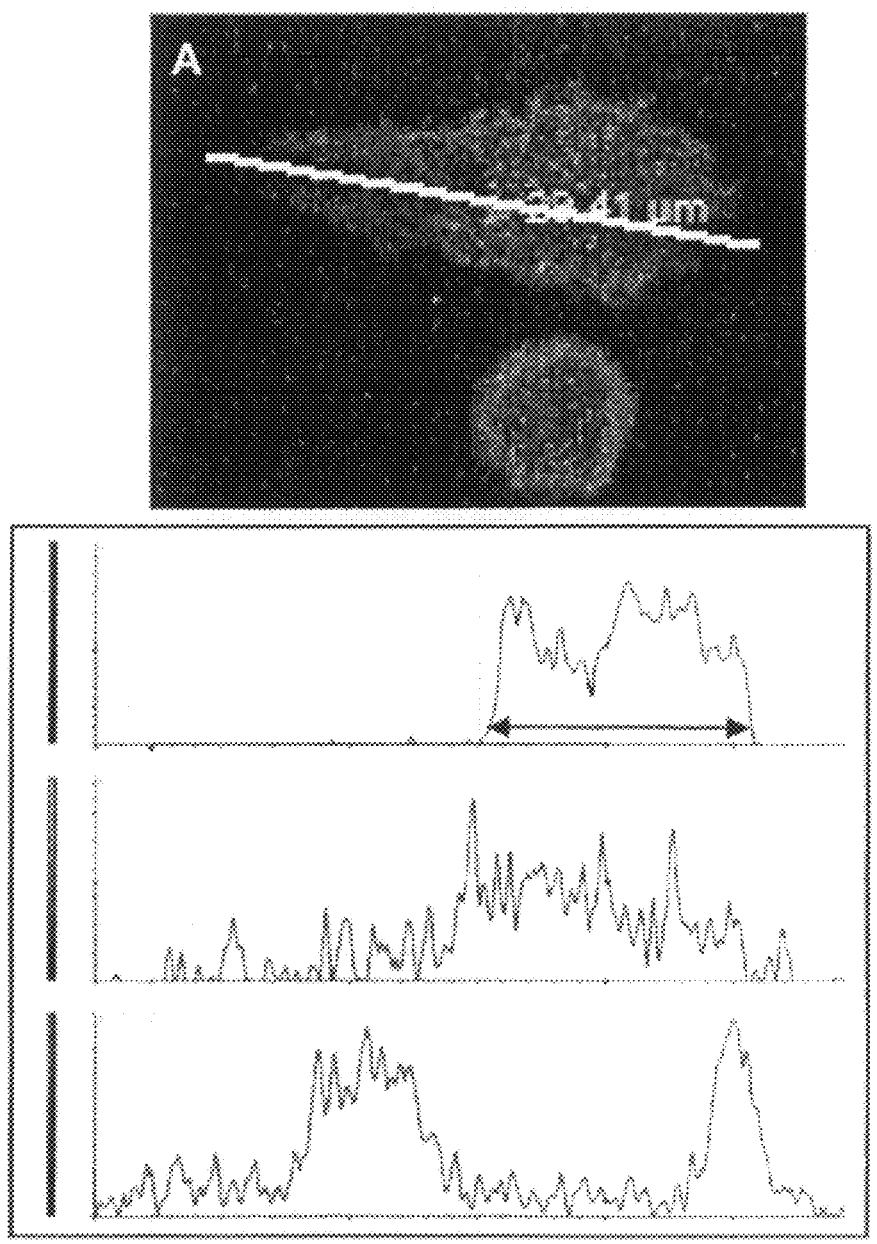
FIG. 21A shows in ordinates the values of fluorescence produced at each point throughout a line which represents an average cut in XY, the top graphic corresponding to blue fluorescence, the middle to green and the bottom to red.
Figure 21:
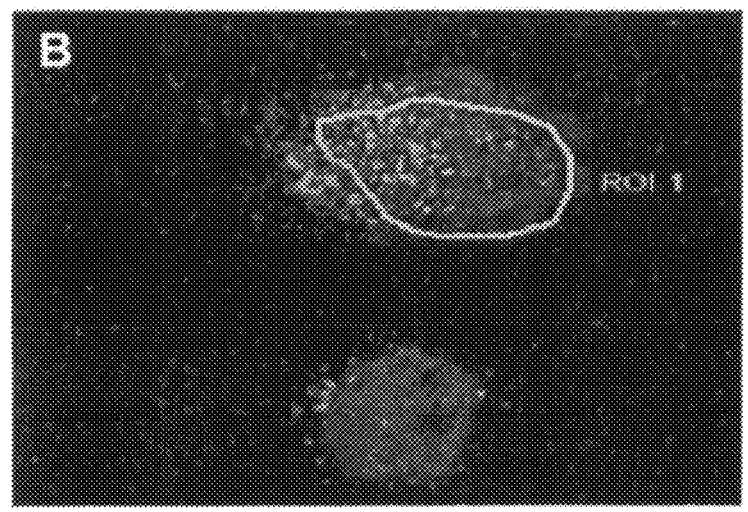
FIG. 21 shows the analysis of the fluorescence present in a cell which has been transfected with an ODN.
Figure 21:
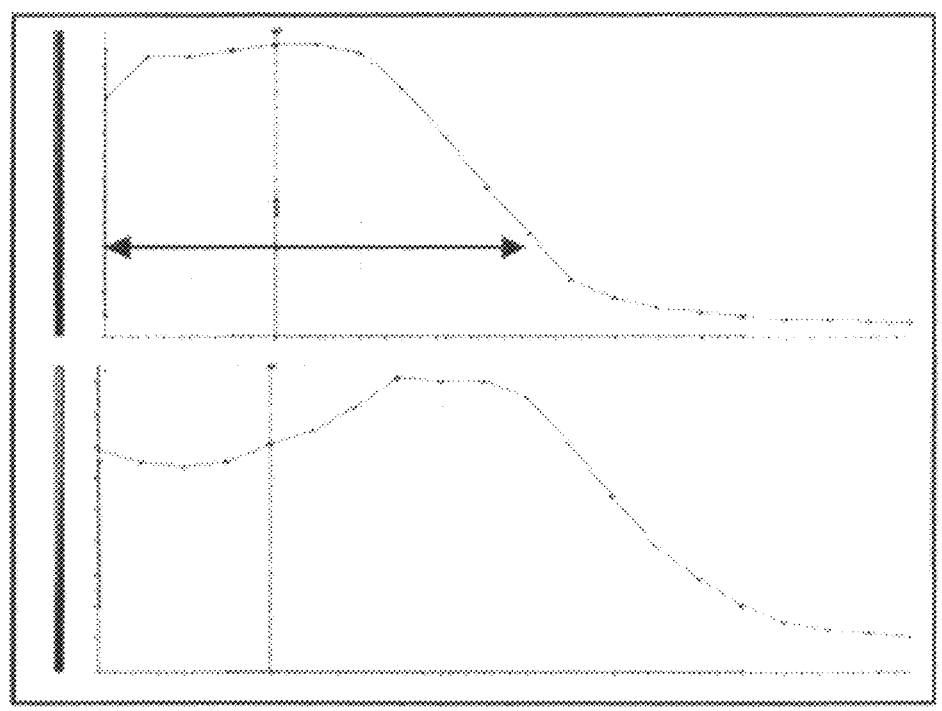

The nuclear localization is even clearer when an XY cut is performed of a cell and the fluorescence present is analysed. A test of this type can be observed in FIG. 21. When the fluorescence present throughout a line in a middle plane is observed (FIG. 21 A), the blue fluorescence represented in the top graphic (nucleus) and the green fluorescence represented in the middle graphic (ODN) colocalize under the red signal represented in the bottom graphic (membrane). When a similar analysis was performed, but taking a region of interest (ROI) (FIG. 21 B) drawn around the nucleus throughout various sections on the Z-axis, it shows how the green (bottom graphic) colocalizes with the blue (top graphic) and is present beyond the cytoplasm until reaching the membrane.

The results were the same irrespective of the length of the ODN tested (from 15 to 28 bases).

Results Produced with ODN+CBS Dendriplexes

Transfection tests were performed using ODN PPT to form dendriplexes with different dendrimers of the invention. Specifically, the following samples were used to transfect: 1: Control; 2: PPT; 3: PPT+IM8; 4: PPT+NN; 5: PPT+Phe; PPT+IM16.

Figure 22:
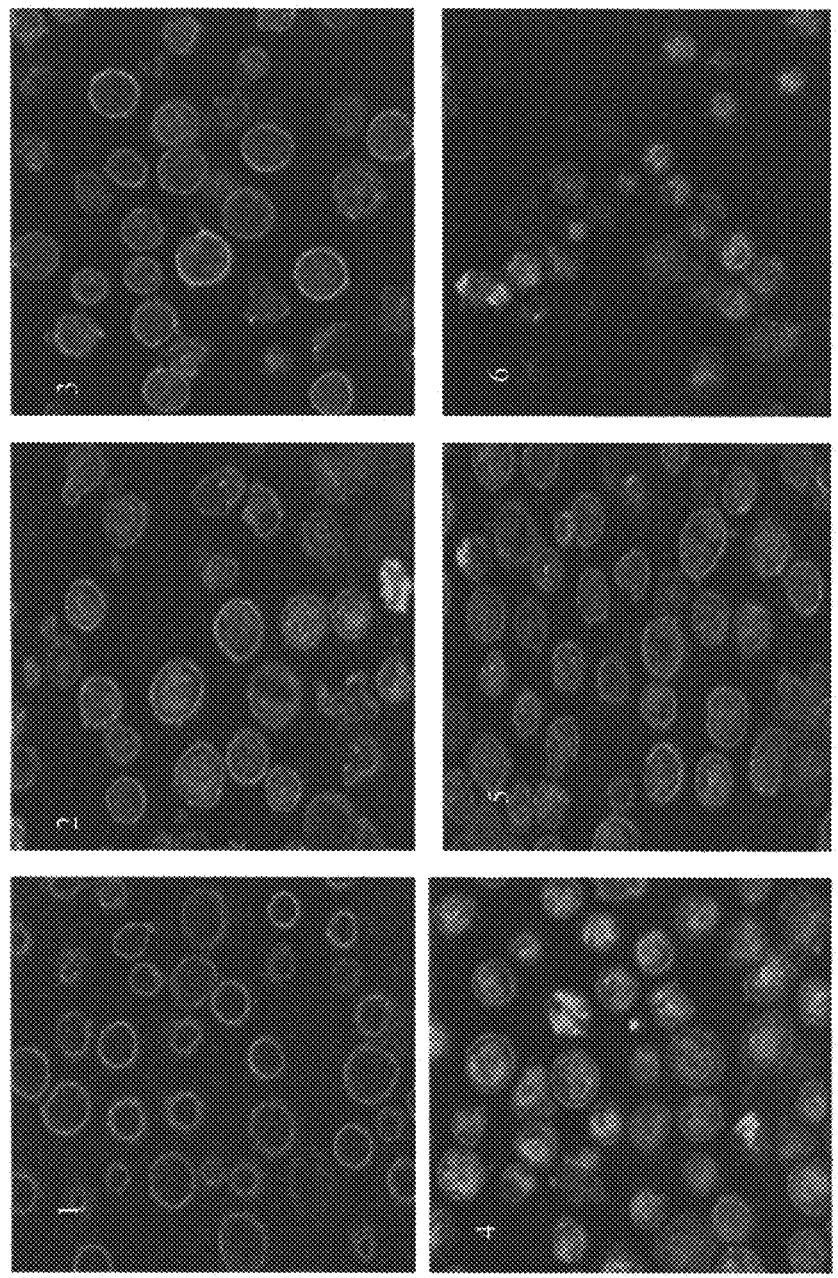
FIG. 22 shows the fluorescence pattern produced after transfection with PPT or dendriplexes of the invention. 1: Control; 2: PPT; 3: PPT+IM8; 4: PPT+NN; 5: PPT+Phe; 6: PPT+IM16.

The results produced after 48 hours are shown in FIG. 22.

Figure 23:
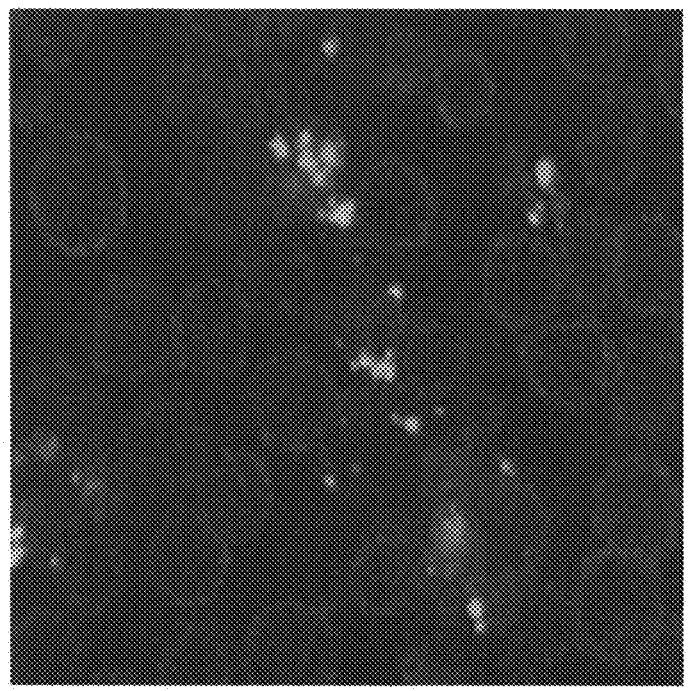
FIG. 23 shows the fluorescence pattern produced after transfection with a ClNH4 and PPT dendriplex.
Figure 24:
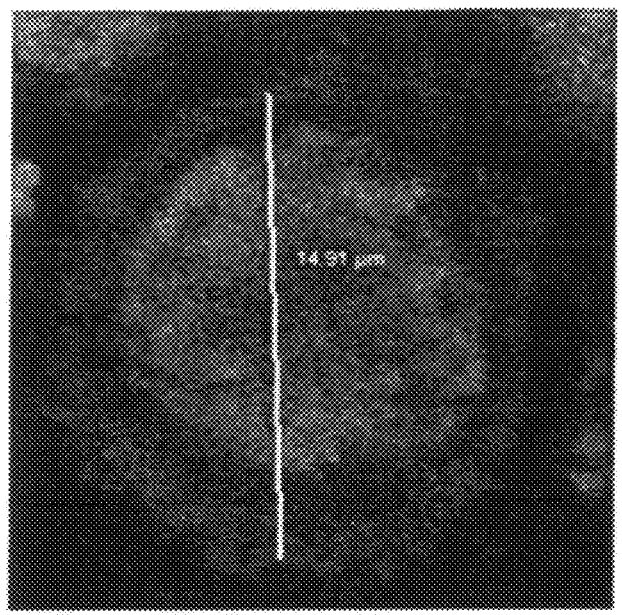
FIG. 24 shows the histogram of the fluorescence in a midplane in XY of a cell treated with PPT+NN, wherein the top graphic shows in ordinates the intensity of green fluorescence which is found throughout the plane, the middle graphic is an analogous analysis corresponding to red fluorescence and the bottom graphic shows an analogous analysis corresponding to blue fluorescence.
Figure 24:
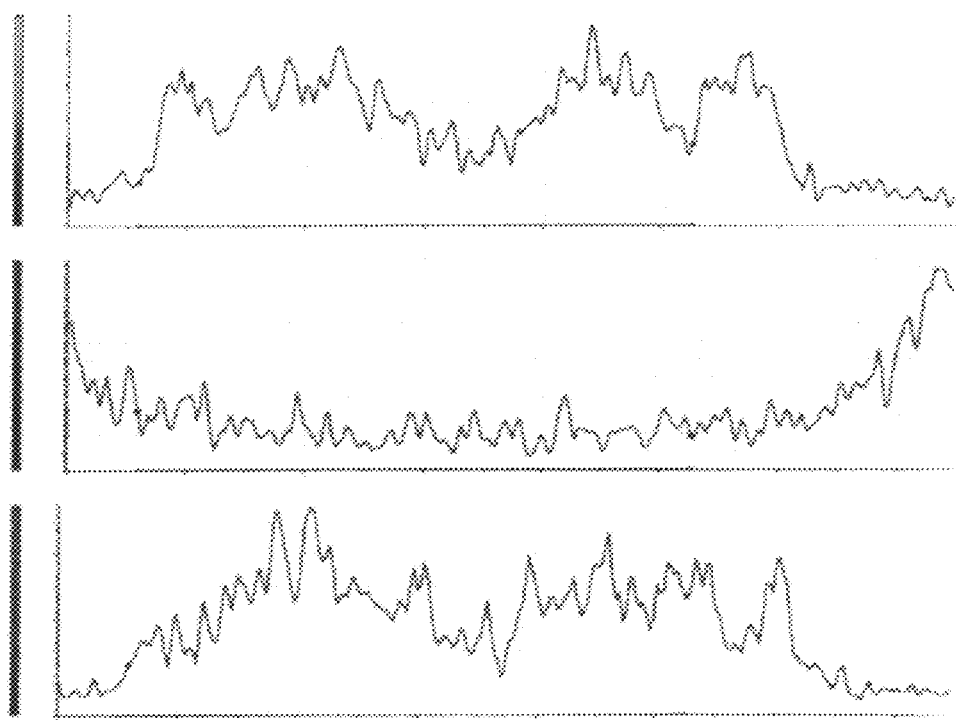

All the dendrimers except $ClNH_4$ achieved a pattern similar to that of the ODN without CBS, i.e. diffuse, nuclear and cytoplasmic. Some of the complexes achieved higher results in arbitrary units of fluorescence than the ODN without CBS (those with NN and Phe) in some of the experiments performed, but this was not repeated with statistical significance in different experiments with repetitions of up to 7 comparative series between complexes and ODN alone. The sample of PPT with ClNH4, however, gave rise to the fluorescence pattern in aggregates which is shown in FIG. 23.

To demonstrate that it is effectively a cytoplasmic and nuclear fluorescence pattern, histograms were performed of a single cell in a mid-plane in XY, similar to that performed with the ODN without CBS. FIG. 23 shows, as an example, one of the analyses on a cell with PPT+NN:

From these data it can be concluded that the CBS dendrimers, with the exception of ClNH4, in no way interfere with the distribution of the ODN in the cell.

Inhibition of Virus or Other Biological Agents by the Dendrimers

Due to the biocompatibility shown in the previous experiments, the dendrimers of the invention would be suitable for the preparation of drug compositions (parenteral or oral) or interference devices (vaginal gels, antiseptics) for the prevention and/or the treatment of biological agents such as the HIV virus or other virus such as hepatitis C or of other biological agents such as prions. With that objective, HIV virus inhibition tests were designed wherein this capacity was studied.

Example 43

HIV Inhibition Tests

Virus Preparation

MT-2 cells were used (human T lymphocytes immortalized with the human lymphocytotropic virus type I). $20 \times 10^6$ MT-2 were washed twice with RPMI 1640 medium supplemented with 10% FCS and they were transferred to 25 ml at a concentration of $2 \times 10^6$ cells/ml in RPMI medium with 10% FCS. The HIVNL4.3 virus strain was then added at a concentration of 1 particle per cell (1 MOI). The MT-2 and the virus were cultured during at least 2 hours at 37° C., stirring the culture every 15-30 minutes. Finally, the cultures (cells-virus) were washed twice to remove the virus which had not integrated in the cell genome. The cells were transferred and cultured in 25 cm$^2$ bottles in the same culture medium.

Every 72-96 hours half of the supernatant was collected taking care not to also collect cells. $40 \times 10^6$ MT-2 were added at the same concentration in RPMI medium with 10% FCS. The supernatant was aliquoted and stored in liquid nitrogen, and later it was tittered.

Virus Titering

The isolated viral HIVNL4.3, established laboratory viral strain, was titered in the MT-2 cell line. $2 \times 10^4$ MT-2 cells were cultured with complete medium in 96-well plates and 40 µl of the viral preparation were added at different concentrations for which the corresponding dilutions are made. All of them were placed in octuplicate and were maintained at 37° C. in CO$_2$ atmosphere during a week. After this time, the titering was read by display of the cytopathic effect and syncyte formation. The titering was calculated by applying Spearman-Karber's formula[30], which serves to quantify the number of particles of virus per ml of medium in a culture in which serial dilutions of the concentrate of virus to titer have been seeded in octuplicate.

In vitro Infection of T Lymphocytes

The PBMC were stimulated during 48 hours with 2 µg/ml of PHA and 100 IU of IL-2, to provoke a polyclonal activation; after 24 hours the cells were washed with PBS. The desired concentration of cells was incubated with the number of particles of HIVNL4.3 per cell calculated in RPMI medium with 10% FCS during 4 hours at 37° C. in an atmosphere humidified with 5% CO$_2$. After this time the culture cells were collected and were washed three times to eliminate the virus adhered to the cell surface, they were deposited again in a 24-well plate in RPMI medium with 10% FCS and 50 IU/ml of IL2 and they are treated with the different dendrimers. The cultures were incubated at 37° C. and they were maintained in a humidified atmosphere with 5% CO$_2$.

Inhibition of HIV by CBS 400,000 PBMC/well of 24-plate were seeded and they were treated with 1, 3 and 5 µM of NN, in a case before infecting them and in another after infecting them at an multiplicity of infection of 0.4 MOI. Cells were collected after 24 h to extract DNA and subsequent quantification of virus copies per cell (following the method for detection and quantification of HIV DNA in infected cells registered with U.S. Pat. No. 2,401,986 of the National Patent Office).

To eliminate the influence of the possible toxicity of the dendrimer on the number of cells and the quantity of viral copies, the number of virus copies was adjusted to the percentage of live cells to be able to make comparisons between different dendrimer concentrations. Nevertheless, dendrimers did not induce a significant mortality at the concentrations used (quantified by FW and SD in flow cytometry).

Figure 25:
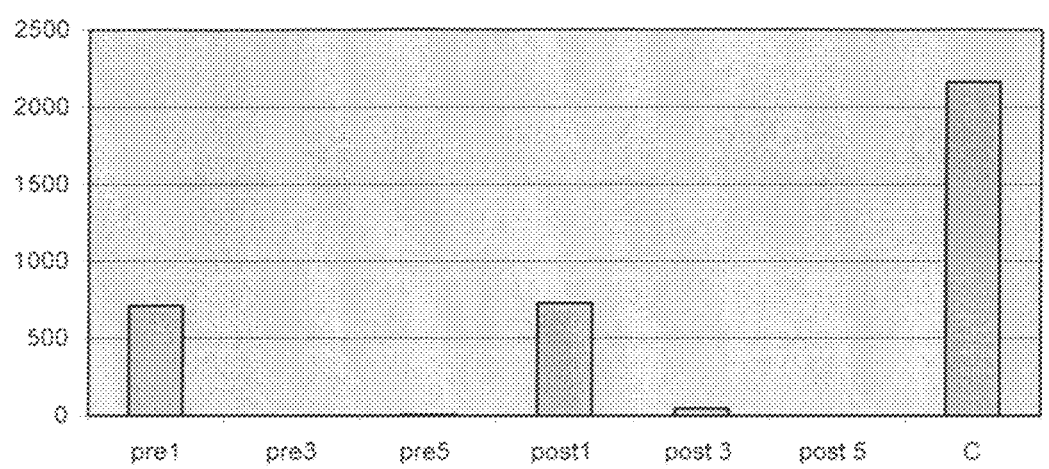
FIG. 25 shows the graphic produced calculating the number of DNA copies of HIV in accordance with the number of cells with different concentrations of NN dendrimer before and after the infection.

The following adjustment was therefore made: no. of DNA HIV copies/10$^6$ of cells per % live cells, producing the following graphic which is shown in FIG. 25, wherein the prefixes pre or post refer to the administration of 1, 3 or 5 µM of NN before or after infection and the bar marked as "C" corresponds to the control.

The results produced indicate that the dendrimer exercises a clear impediment in infection of the PBMC by HIV, both applied previously to the invention and after. Therefore, it should act on both the preintegration and postintegration steps.

Conclusions of the Experiments of Examples 31 to 43

- The CBS dendrimers tested showed a good biocompatibility for the PBMC at the dose used to carry ODN.
- When the toxicity data on lymphocytes and erythrocytes are taken as a whole, the dendrimer which has a better biocompatibility profile is CBS-NN.
- CBS NN, IM8 and IM16 release the ODN over time, having released practically 100% of the ODN after 24 hours. These dendrimers also release the ODN at acid pHs (<5).
- The ODN tested show a high capacity of uptake in the cell by themselves, crossing both the plasma and nuclear membrane in almost 100% of the live cells after 17 hours of having been added to the cell culture, in the presence of 10% FCS.
- All the CBS-ODN dendriplexes tested (with the exception of ClNH4) did not interfere with the internalization of the ODN and its cytoplasmic and nuclear distribution.
- The CBS NN protects the ODN of the bond to plasma proteins, this protection not interfering in the subsequent gradual release of the ODN over time in an aqueous medium in the presence of said proteins. For this reason and the previous ones, the dendrimers of the invention seem suitable for their use in antisense therapies for the inhibition of protein synthesis whose level it is generally convenient to decrease, as it is involved in some disorder, whether of tumoral or viral type or involved in any other form in different human or animal diseases.
- The NN Dendrimer shows a good capacity for preventing the infection of lymphocytes by the HIV virus which, together with the good biocompatibility demonstrated, indicates that it can be used for the prevention and/or the treatment of disorders produced by biological agents such as HIV or other viruses such as hepatitis C, including other biological agents such as prions.
- CBS Phe and ClNH4 show a good capacity for efficiently and long-lastingly fixing the nucleic acids, for which purpose they may be suitable for the generation of RNA or DNA microchips or other devices which require the fixation of nucleic acids since, furthermore, due to the form of DNA fixation (electrostatic with the phosphate groups of the DNA), the CBS here described leave the nucleotidic sequence exposed to the interaction with complementary sequences of other nucleic acids.

Synthesis of Novel Dendrimers

To increase the versatility of the carbosilane dendrimers of the invention, additional dendrimers were synthesized to those whose synthesis is described in Examples 1 to 30, varying both the starting compound used to give rise to the terminal moiety of the branches (Examples 44 to 47) and increasing the concentration of the quaternization reagent quaternization processes of amino groups of dendrimers whose synthesis had already been described in previous examples, to ensure not only the quaternization of the amino group that the ends of terminal moieties can constitute as such but of other amino groups which may be contained in said terminal moieties (Examples 48 and 49).

The Synthesis of these dendrimers is described below:

EXAMPLES 44 to 47

Example 44

Synthesis of 1G-[Si($CH_2$)$_2$$C_6H_3$(OMe)(O($CH_2$)$_2$NMe$_2$)]$_4$. (31)

For the synthesis of this dendrimer and of dendrimer 32, described in the following example, 4-allyl-2-methoxy-1-(N,N-dimethylamino) benzene (($CH_2$=CH—$CH_2$)$C_6H_3$(OMe){O($CH_2$)$_2$NMe$_2$}) was used, a non-commercial compound which it was necessary to synthesize prior to the corresponding hydrosilylation reaction.

Synthesis of ($CH_2$=CH—$CH_2$)$C_6H_3$(OMe){O($CH_2$)$_2$ NMe$_2$}

1 equivalent of Cl$CH_2$$CH_2$NMe$_2$H$^+$Cl$^-$ (7.02 g, 48.7 mmol), 4 equivalents of $K_2CO_3$ (26.93 g, 195 mmol) and 18-Corona-6 ether corona (2.57 g, 9.74 mmol) were added to a solution of 4-allyl-2-methoxyphenol (8.0 g, 48.7 mmol) in acetone. The reaction was maintained at reflux during 48 h. After the vacuum elimination of the solvent, an extraction was performed in $CH_2Cl_2$/$H_2O$ (2×50 ml). The organic phase was dried with $MgSO_4$ during 2 h. It was then filtered and the solvent was eliminated, producing a pale yellow oil which was washed with hexane (2×10 ml) to eliminate the 18-Corona-6 ether corona. The compound was thus produced as a pale yellow oil (5.49 g, 48%).

NMR-$^1$H (CDCl$_3$): δ 6.79 (d, 1H, $C_6H_3$), 6.68 (m, 2H, $C_6H_3$), 5.92 (t, 1H, CH=$CH_2$—$CH_2$-Ph), 5.02 (m, 2H, CH=$CH_2$—$CH_2$-Ph), 4.07 (t, 2H, Ph-O—$CH_2$—$CH_2$—NMe$_2$), 3.81 (s, 3H, CH$_3$O), 2.52 (m, 2H, Si—$CH_2$—$CH_2$—$CH_2$-Ph), 2.74 (t, 2H, Ph-O—$CH_2$—$CH_2$—NMe$_2$), 2.31 (s, 6H, NMe$_2$). NMR-$^{13}$C{$^1$H} (CDCl$_3$): δ 149.51 (Cipso bound to —O($CH_2$)$_2$NMe$_2$), 146.55 (Cipso bound to —OMe), 137.59 (Cipso bound to —$CH_2$), 133.17 (CH=$CH_2$—$CH_2$-Ph), 120.37, 113.76, 112.26 ($C_6H_3$), 115.58 (CH=$CH_2$—$CH_2$-Ph), 67.39 (Ph-O—$CH_2$—$CH_2$—NMe$_2$), 58.12 (Ph-O—$CH_2$—$CH_2$—NMe$_2$), 55.78 (CH$_3$O), 45.94 (NMe$_2$), 39.76 (Si—$CH_2$—$CH_2$—$CH_2$-Ph).

Synthesis of Dendrimer 31

($CH_2$=CH—$CH_2$)$C_6H_3$(OMe){O($CH_2$)$_2$NMe$_2$} (0.9 g, 4.64 mmol) and a drop of Karstedt catalyst (3-3.5% Pt) were added to a 1G-H$_4$ dendrimer solution (0.50 g, 1.16 mmol) in the minimum quantity of THF (3 ml). The reaction mixture was heated to 45° C. in a vacuum ampoule during 12 h. The solution produced was dried by vacuum elimination of the solvent, giving rise to compound 31 as a yellow oil (1.60 g, 100%).

NMR-$^1$H (CDCl$_3$): δ 6.80 (d, 1H, $C_6H_3$), 6.65 (m, 2H, $C_6H_3$), 4.07 (t, 2H, Ph-O—$CH_2$—$CH_2$—NMe$_2$), 3.81 (s, 3H, CH$_3$O), 2.74 (t, 2H, Ph-O—$CH_2$—$CH_2$—NMe$_2$), 2.52 (m, 2H, Si—$CH_2$—$CH_2$—$CH_2$-Ph), 2.31 (s, 6H, NMe$_2$), 1.55 (m broad, 2H, Si—$CH_2$—$CH_2$—$CH_2$-Ph), 1.28 (m broad, 2H, Si—$CH_2$—$CH_2$—$CH_2$—Si), 0.53 (m, 6H, Si—$CH_2$—$CH_2$—$CH_2$—Si), -0.07 (s, 6H, SiMe$_2$), NMR-$^{13}$C{$^1$H} (CDCl$_3$): δ 149.40 ($C_{ipso}$ bound to —O($CH_2$)$_2$NMe$_2$), 146.29 ($C_{ipso}$ bound to —OMe), 136.03 ($C_{ipso}$ bound to —$CH_2$), 120.24, 113.72, 112.30 ($C_6H_3$), 67.47 (Ph-O—$CH_2$—$CH_2$—NMe$_2$), 58.22 (Ph-O—$CH_2$—$CH_2$—NMe$_2$), 55.88 (CH$_3$O), 46.00 (NMe$_2$), 39.67 (Si—$CH_2$—$CH_2$—$CH_2$-Ph), 26.26 (Si—$CH_2$—$CH_2$—$CH_2$-Ph), 20.29, 18.56, 17.53 (Si($CH_2$)$_3$Si), 15.41 (Si—$CH_2$—$CH_2$—$CH_2$-Ph), -3.28 (SiMe$_2$), $^{29}$Si{$^1$H}-NMR (CDCl$_3$): δ (G$_0$-Si) not observed, 1.60 (G$_1$-Si).

Example 45

Synthesis of 2G-[Si($CH_2$)$_2$$C_6H_3$(OMe)(O($CH_2$)$_2$NMe$_2$)]$_8$. (32)

The second generation dendrimer 32 was prepared following a process similar to that described for 31, starting from the dendrimer 2G-H$_8$ (0.32 g, 0.27 mmol), ($CH_2$=CH—$CH_2$)$C_6H_3$(OMe){O($CH_2$)$_2$NMe$_2$}] (0.51 g, 2.17 mmol), 3 ml of THF and a drop of Karstedt catalyst. In this way, 32 was produced as a brown oil (0.38 g, 50%).

NMR-$^1$H (CDCl$_3$): δ 6.80 (d, 2H, $C_6H_3$), 6.66 (m, 4H, $C_6H_3$), 4.08 (t, 4H, Ph-O—$CH_2$—$CH_2$—NMe$_2$), 3.81 (s, 6H, CH$_3$O), 2.74 (t, 4H, Ph-O—$CH_2$—$CH_2$—NMe$_2$), 2.52 (m, 4H, Si—$CH_2$—$CH_2$—$CH_2$-Ph), 2.30 (s, 12H, NMe$_2$), 1.55 (m broad, 4H, Si—$CH_2$—$CH_2$—$CH_2$-Ph), 1.28 (m broad, 6H, Si—$CH_2$—$CH_2$—$CH_2$—Si), 0.53 (m broad, 16H, —$CH_2$ bound to Si), -0.072 (s, 12H, SiMe$_2$), -0.01 (s, 3H, SiMe), NMR-$^{13}$C{$^1$H} (CDCl$_3$): δ 149.37 ($C_{ipso}$ bound to —O($CH_2$)$_2$NMe$_2$), 146.29 ($C_{ipso}$ bound to —OMe), 135.98 ($C_{ipso}$ bound to —$CH_2$), 120.24, 113.69, 112.30 ($C_6H_3$), 67.44 (Ph-O—$CH_2$—$CH_2$—NMe$_2$), 58.19 (Ph-O—$CH_2$—$CH_2$—NMe$_2$), 55.86 (CH$_3$O), 45.98 (NMe$_2$), 39.65 (Si—$CH_2$—$CH_2$—$CH_2$-Ph), 26.23 (Si—$CH_2$—$CH_2$—$CH_2$-Ph), 20.13, 18.81, 18.60 (Si($CH_2$)$_3$Si), 15.38 (Si—$CH_2$—$CH_2$—$CH_2$-Ph), -3.25 (SiMe$_2$), -4.93 (SiMe), $^{29}$Si{$^1$H}-NMR (CDCl$_3$): δ 0.1.00 (G$_1$-Si); 1.70 (G$_2$-Si).

Example 46

Synthesis of 1G-[Si(($CH_2$)$_2$$C_6H_3$(OMe)(O($CH_2$)$_2$NMe$^+$$_3$I$^-$))]$_4$. (33)

0.02 ml of a 2M solution of MeI (0.27 mmol) in diethylene ether were added to a 31 dendrimer solution (0.094 g, 0.068 mmol) in ether (3 ml). The reaction mixture was maintained with constant stirring during 48 h at ambient temperature, then, it was dried to eliminate the excess MeI. The resulting residue was washed with Hexane (2×5 ml) and was vacuum dried to produce dendrimer 33 as a white coloured solid (0.10 g, 83%).

NMR-$^1$H (DMSO): δ 6.94 (d, 1H, $C_6H_3$), 6.75 (m, 2H, $C_6H_3$), 4.34 (t, 2H, Ph-O—$CH_2$—$CH_2$—NMe$_2$), 3.74 (s, 3H, CH$_3$O and t, 2H, Ph-O—$CH_2$—$CH_2$—NMe$^+$$_3$ overlapped), 3.18 (s, 9H, NMe$^+$$_3$), 2.49 (m, 2H, Si—$CH_2$—$CH_2$—$CH_2$-Ph, overlapped with signal of DMSO), 1.51 (m broad, 2H, Si—$CH_2$—$CH_2$—$CH_2$-Ph) 1.28 (m broad, 2H, Si—$CH_2$—$CH_2$—$CH_2$—Si), 0.91 (m, 2H, Si—$CH_2$—$CH_2$—$CH_2$-Ph), 0.51 (m, 4H, Si—$CH_2$—$CH_2$—$CH_2$—Si), -0.07 (s, 6H, SiMe$_2$), NMR-$^{13}$C{$^1$H} (DMSO): δ 148.6 ($C_{ipso}$ bound to —O(CH$_2$)$_2$NMe$_2$), 144.3 ($C_{ipso}$ bound to —OMe), 135.9 ($C_{ipso}$ bound to —$CH_2$), 119.5, 114.2, 111.9 ($C_6H_3$), 63.6 (Ph-O—$CH_2$—$CH_2$—NMe$_2$), 62.6 (Ph-O—$CH_2$—$CH_2$—NMe$_2$), 55.1 (CH$_3$O), 52.7 (NMe$^+$$_3$), 39.0 (Si—$CH_2$—$CH_2$—$CH_2$-Ph, overlapped with the signal of DMSO), 25.3 (Si—$CH_2$—$CH_2$—$CH_2$-Ph), 19.1, 17.6, 16.4 (Si($CH_2$)$_3$Si), 14.3 (Si—$CH_2$—$CH_2$—$CH_2$-Ph), -3.7 (SiMe$_2$).

Example 47

Synthesis of 2G-[Si(($CH_2$)$_2$$C_6H_3$(OMe)(O($CH_2$)$_2$NMe$^+$$_3$I$^-$))]$_8$ (34)

The second generation dendrimer 34 was prepared following a process similar to that described for 33, starting from 32 (0.38 g, 0.13 mmol) and 0.07 ml of a 2M MeI solution in ether (1.04 mmol). In this way, compound 34 was produced as a white coloured solid (0.45 g, 85%).

NMR-$^1$H (DMSO): δ 6.94 (d, 2H, $C_6H_3$), 6.75 (m, 4H, $C_6H_3$), 4.33 (t, 4H, Ph-O—$CH_2$—$CH_2$—NMe$_2$), 3.74 (s, 6H, CH$_3$O and t, 4H, Ph-O—$CH_2$—$CH_2$—NMe$^+$$_3$ overlapped), 3.18 (s, 18H, NMe$^+$$_3$), 3.18 (m, 4H, Si—$CH_2$—$CH_2$—$CH_2$-Ph, overlapped with signal of DMSO), 1.50 (m broad, 4H, Si—$CH_2$—$CH_2$—$CH_2$-Ph) 1.29 (m broad, 6H, Si—$CH_2$—$CH_2$—$CH_2$—Si), 0.50 (m, 16H, CH$_2$Si), -0.09 (s, 12H, SiMe$_2$), -0.11 (s, 3H, SiMe), $^{13}$C{$^1$H}-NMR (DMSO): δ 148.6 ($C_{ipso}$ bound to —O(CH$_2$)$_2$NMe$_2$), 144.3 ($C_{ipso}$ bound to —OMe), 135.9 ($C_{ipso}$ bound to —$CH_2$), 119.5, 114.3, 111.9 ($C_6H_3$), 63.6 (Ph-O—$CH_2$—$CH_2$—NMe$_2$), 62.6 (Ph-O—$CH_2$—$CH_2$—NMe$_2$), 55.1 (CH$_3$O), 52.7 (NMe$^+$$_3$), 39.0 (Si—$CH_2$—$CH_2$—$CH_2$-Ph, overlapped with the signal of DMSO), 25.3 (Si—$CH_2$—$CH_2$—$CH_2$-Ph), 19.0, 17.7, 17.6 (Si($CH_2$)$_3$Si), 14.3 (Si—$CH_2$—$CH_2$—$CH_2$-Ph), -3.8 (SiMe$_2$), -5.4 (SiMe).

EXAMPLES 48 and 49

Example 48

Synthesis of 1G-[(Si(O(CH$_2$)$_2$N(Me)$_2$(CH$_2$)$_2$NMe$_3$$^+$ 2I$^-$)]$_4$ (35)

Dendrimer 35, which has all the nitrogen atoms of its structure quaternized, was prepared from the first generation dendrimer 25 (0.24 g, 0.24 mmol) and 1.2 ml of MeI (2.4 mmol) in diethylene ether as solvent. In this way, dendrimer 35 was produced as a white coloured solid insoluble in diethylene ether (0.49 g, 95%).

NMR-$^1$H (DMSO-d$_6$): δ 4.00 (2H, t, CH$_2$O), 3.93 (4H, m, CH$_2$N(Me)$_2$$^+$), 3.53 (2H, t, CH$_2$N(Me)$_3$$^+$), 3.18 (15H, s broad, N(Me)$_2$$^+$ and N(Me)$_3$$^+$), 1.31 (2H, m, SiCH$_2$CH$_2$CH$_2$SiO), 0.70 (2H, m, SiCH$_2$CH$_2$CH$_2$SiO), 0.55 (2H, m, SiCH$_2$CH$_2$CH$_2$SiO), 0.13 (6H, s, OSiMe$_2$). NMR-$^{13}$C{$^1$H} (DMSO-d$_6$): δ 64.9 (CH$_2$O), 56.3, 55.9, 55.6 (CH$_2$N(Me)$_2$$^+$ and CH$_2$N(Me)$_3$$^+$), 52.5 (NMe$_3$$^+$), 50.9 (NMe$_2$$^+$), 21.2 (SiCH$_2$CH$_2$CH$_2$SiO), 17.8 (SiCH$_2$CH$_2$CH$_2$SiO), 17.2 (SiCH$_2$CH$_2$CH$_2$SiO), −2.6 (OSiMe$_2$). Elemental analysis of C$_{52}$H$_{128}$N$_8$O$_4$Si$_5$I$_8$. Calc. %: C, 39.59; H, 8.18; N, 7.10. Exp. %: C, 38.65; H, 7.98; N, 6.94.

Example 49

Synthesis of 2G-[Si(O(CH$_2$)$_2$N$^+$(Me)$_2$(CH$_2$)$_2$NMe$_3$$^+$ 2I$^-$)]$_8$ (36)

The second generation dendrimer 36 was prepared following a process similar to that described for 35, starting from 26 (0.11 g, 0.04 mmol) and 0.06 ml of MeI (0.91 mmol). In this way, compound 36 was produced as a white coloured solid (0.18 g, 86%).

NMR-$^1$H (DMSO-d$_6$): δ 4.00 (4H, t, CH$_2$O), 3.93 (8H, m, CH$_2$N(Me)$_2$$^+$), 3.59 (4H, t, CH$_2$N(Me)$_3$$^+$), 3.21 (30H, s$_{broad}$, N(Me)$_2$$^+$ and N(Me)$_3$$^+$), 1.35 (6H, m, SiCH$_2$CH$_2$CH$_2$SiO and SiCH$_2$CH$_2$CH$_2$Si), 0.72 (4H, m, SiCH$_2$CH$_2$CH$_2$SiO), 0.56 (8H, m, SiCH$_2$), 0.13 (12H, s, OSiMe$_2$), −0.07 (3H, s, SiMe). NMR-$^{13}$C{$^1$H} (DMSO-d$_6$): δ 64.7 (CH$_2$O), 56.3, 56.0, 55.7 (CH$_2$N(Me)$_2$$^+$ and CH$_2$N(Me)$_3$$^+$), 52.6 (NMe$_3$$^+$), 50.9 (NMe$_2$$^+$), 21.2-17.2 (groups —CH$_2$— of the carbosilane skeleton), −2.5 (OSiMe$_2$), −5.5 (SiMe). Elemental analysis of C$_{128}$H$_{316}$N$_{16}$O$_8$Si$_{13}$I$_{16}$. Calc. %: C, 33.40; H, 6.92; N, 4.87. Exp. %: C, 32.90; H, 6.75; N, 4.57.

This dendrimer, which is used in tests described in the following examples, received the abbreviated name NN16, the name it will be called by hereinafter. It structural formula, molecular weight (Mw) and number of positive charges are those shown below:

NN16:

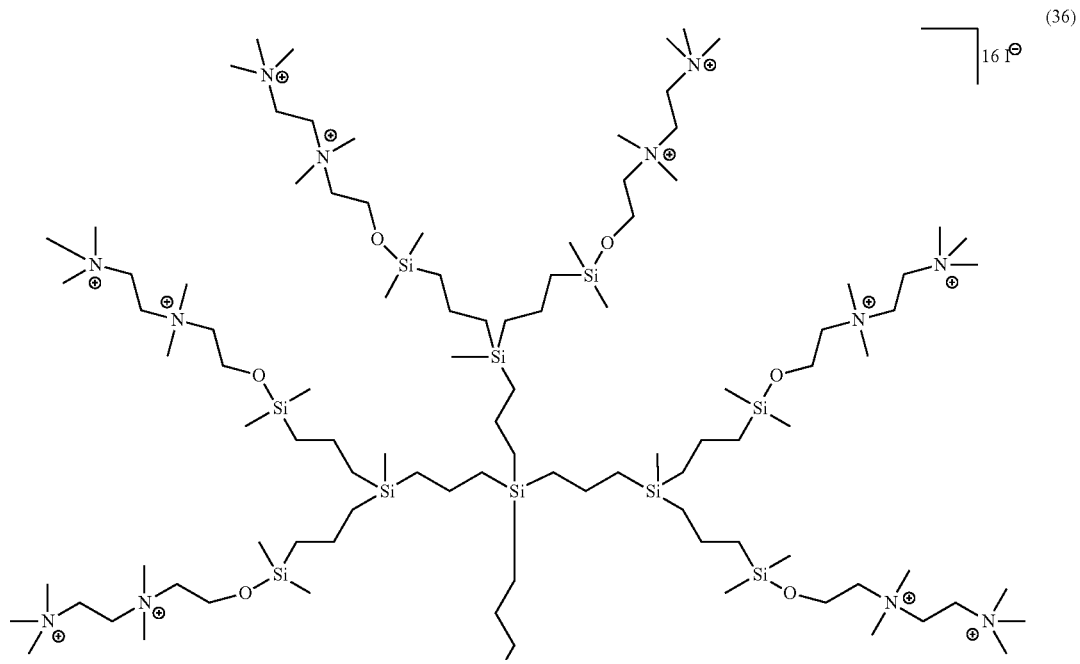

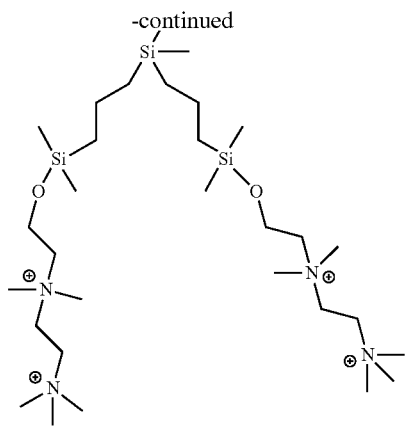

2G-[SiO(CH$_2$)$_2$N$^+$(Me)$_2$(CH$_2$)$_2$NMe$_3{}^+$2I$^-$]$_8$
Mw = 4603.26 g/mol
16 positive charges Binding Tests of Dendrimers to Drugs In order to test the utility of the dendrimers of the invention as drug vehicles which have a negative charge at physiological pH, tests were performed wherein it was checked, in first place, if different dendrimers of the invention were capable of forming complexes with various drugs and, then, it was verified if the bond was reversible, checking if the variation in pH of the medium gave rise to the dissociation of the dendrimer-drug complex. This intended to emulate what would occur in physiological conditions checking, on the one side, that the dendrimers are capable of forming complexes with the drugs which protect them from interaction with plasma proteins or cell membranes during its transport through the blood; on the other hand, with the dissociation tests with the change in pH, it was attempted to reproduce the conditions which the dendrimer-drug complex would find inside the cell, in which it is supposed that the dendrimer-drug complex penetrates or may penetrate by an endosome whose interior, once in the cytoplasm, is acidified by action of H$^+$ type ATPase transport pumps, ambient wherein the dendrimer should capture part of the excess protons and release the molecule transported, which would enable that it exercised its action.

Tests to Determine Dendrimer-drug Bond

The dendrimers chosen to perform the tests were:
NN (2G-[Si(O(CH$_2$)$_2$N(Me)(CH$_2$)$_2$NMe$_3{}^+$I$^-$)]$_8$ (26))
NN16 (2G-[Si(O(CH$_2$)$_2$N$^+$(Me)$_2$(CH$_2$)$_2$NMe$_3{}^+$2I$^-$)]$_8$ (36))
IM16 (2G-[Si(OCH$_2$CH$_2$NMe$_3{}^+$I$^-$)$_2$]$_8$ (19))

The drugs chosen to perform the tests, all with at least one negative charge at physiological pH, were:
Methotrexate (sodium salt):
 1 charge (−)
 Supplying laboratory: Almirall
 Presentation: 25 mg/ml solution
 Excipients: NaCl, NaOH, HCl, double-distilled H$_2$O
Heparin (sodium salt)
 Several charges (−)
 Supplying laboratory: Rovi
 Presentation: 10 mg/ml solution (1000 U)
 Excipients: methyl p-oxybenzoate, propyl p-oxybenzoate, NaCl, double-distilled H$_2$O
Insulin (recombinant human insulin)
 4 charges (−)
 Supplying laboratory: Novo Nordisk
 Product trade name: Actrapid
 Presentation: 3.5 mg/ml solution (100 U)
 Excipients: ZnCl$_2$, HCl, NaOH, double-distilled H$_2$O The determination of the bond and complex formation between the dendrimer and the drug was performed by evaluating the delay in the polyacrylamide gel of the dendrimer bound to drug with respect to the free dendrimer:

Complex formation: It is performed in a final volume of the mixture of 30 μl, which is the maximum volume to load in the gel. To do this, one starts from the necessary quantity of dendrimer that provides a perfectly identifiable band by staining with silver nitrate in the gel once the electrophoresis has been carried out: 20 μl of a 100 μM solution, which corresponds to 1.2×10$^5$ molecules. The drug is added in the 10 μl at different concentrations to produce the chosen (+) and (−) charge ratios, also determining the quantity of drug molecules present in the mixture. An incubation of said mixture was performed at 37° C. during 1 hour to give time for a more thermodynamically stable complex to form, although more time may be needed for its formation. Each complex is performed in duplicate.

Electrophoresis and gel staining: The gels used were 7.5% polyacrylamide/bisacrylamide, prepared with 1.5M Tris pH 8.8. Each electrophoresis was carried out at 90 volts during 4 hours, after which the gel was stained with silver nitrate and photographed. For each test referring to the complex formation between a certain dendrimer and a drug in particular, a previous electrophoresis was performed in a gel wherein the dendrimer was loaded alone, at different concentrations, to check their state, placing each one of the concentrations in duplicate, after which another electrophoresis was performed in another gel wherein the previously incubated dendrimer-drug complexes were loaded, also loading in a pair of wells the incubation control mixtures wherein the dendrimer but not the drug had been added, to be able to verify the existence of delay in the bands produced in the lanes corresponding to the dendrimer and drug mixtures.

The results produced with each one of the dendrimers and the drugs tested are described in Examples 50 to 52.

Example 50

Binding Tests of Drugs to NN Dendrimer

NN dendrimer was dissolved in distilled $H_2O$ at an initial concentration of 576 µM and, from it, dilutions were made to produce concentrations of 100 µM, 10 µM and 1 µM. The previous electrophoresis carried out with aliquots of the solutions corresponding to each one of these concentrations demonstrated that the dendrimer was in good condition in all of them. The concentration of 100 µM was chosen as concentration which permitted viewing the dendrimer in the gel after staining and detecting possible delays in the band produced on being subjected to electrophoresis not in free form, but forming complexes with a drug.

Below, the binding tests with the different drugs are carried out in the following manner:

a) Methotrexate

As has been commented, the methotrexate used in this test is present in the form of aqueous solution at 25 mg/ml, with a molecular weight Mw=476.427 g/mol and 1 (−) charge per molecule. Dendrimer-methotrexate mixtures were prepared and incubated which responded to characteristics shown below in Table 9:

TABLE 9

Characteristics of the NN dendrimer-methotrexate mixture

| | Mixture | | | |
|---|---|---|---|---|
| | 1 | 2 | 3 | 4 |
| Dendrimer/Drug Charge ratio | 1+/1− | 2+/1− | 4+/1− | 8+/1− |
| Dendrimer/Drug Molecules ratio Total | 1/8 | 1/4 | 1/2 | 1/1 |
| Dendrimer | $1.2 \times 10^{15}$ | $1.2 \times 10^{15}$ | $1.2 \times 10^{15}$ | $1.2 \times 10^{15}$ |
| Drug molecules | $8 \times 10^{15}$ | $4 \times 10^{15}$ | $2 \times 10^{15}$ | $1 \times 10^{15}$ |

Figures 26A, 26B:
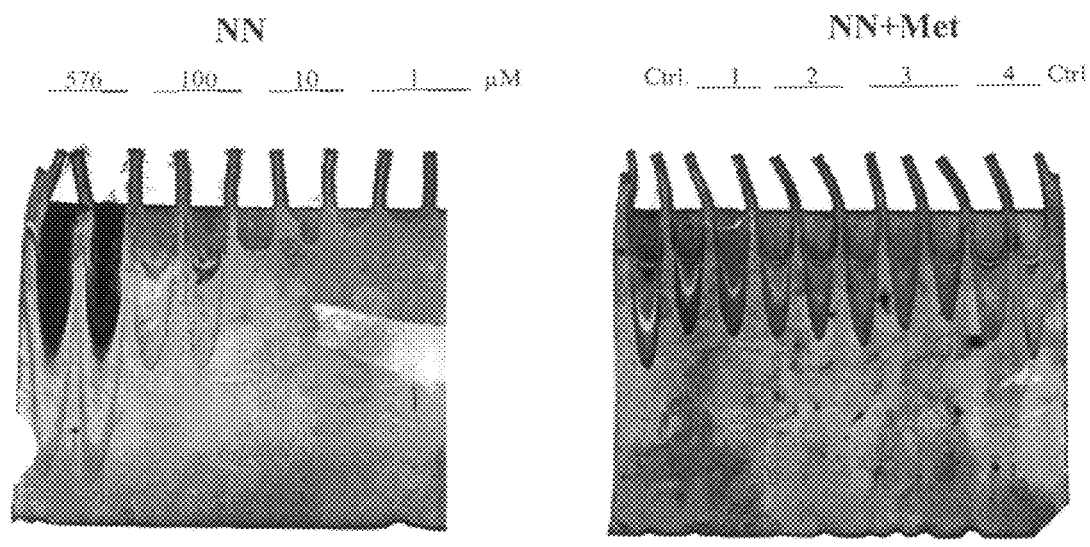
FIG. 26a shows the pattern of bands produced on subjecting the micromolar concentrations (µM) of NN dendrimer which are shown on the lanes to electrophoresis in acrylamide/bisacrylamide.
FIG. 26b shows the pattern of bands produced on subjecting to electrophoresis samples of NN dendrimer incubated with no drug (Ctrl) or samples of said dendrimer incubated with methotrexate in a ratio of dendrimer/drug molecules 1/8 (lanes marked as "1"), 1/4 (lanes marked as "2"), 1/2 (lanes marked as "3") or 1/1 (lanes marked as "4").

The results of subjecting these mixtures to electrophoresis, as well as the dendrimer without drug control, are shown in FIG. 26b, marked as "NN+Met". Here it can be observed how delays of the dendrimers are produced bound against the free one in all complex ratios. Therefore it can be said that the N,N-Methotrexate complex is formed. The delay is not greater when more drug molecules (1) are placed, and less where there is less (4), but to the contrary. This can be due to the fact that the accessibility of the (+) charges of the dendrimer by the methotrexate molecules is not free, i.e. all (+) charges cannot be occupied by methotrexate molecules since it is possible to interfere between them sterically, so that in the presence of a high number of methotrexate molecules in the medium, they compete between themselves by binding to the (+) charges, so that the bonds are not stabilized and the result is a complex wherein there are bound less drug molecules than those theoretically provided per time unit. A dynamic equilibrium was formed.

b) Heparin

Heparin used in the test is presented in aqueous solution, at 10 mg/ml (1000 U). As we do not have its molecular weight, nor the number of negative charges, although it is known that there are several, the bond with the dendrimer was performed by heparin units. Thus, dendrimer-heparin mixtures were prepared and incubated which responded to the characteristics shown below in Table 10.

TABLE 10

Composition of the NN dendrimer-heparin mixture

| Control (Ctrl.) | 1 | 2 | 3 | 4 |
|---|---|---|---|---|
| NN 100 µM ($1.2 \times 10^{15}$ molecules) | $1.2\ 10^{15}$ NN molecules + Heparin 10 U | $1.2\ 10^{15}$ NN molecules + Heparin 1 U | $1.2\ 10^{15}$ NN Molecules + Heparin 0.5 U | $1.2\ 10^{15}$ NN Molecules + Heparin 0.1 U |

Figure 26C:
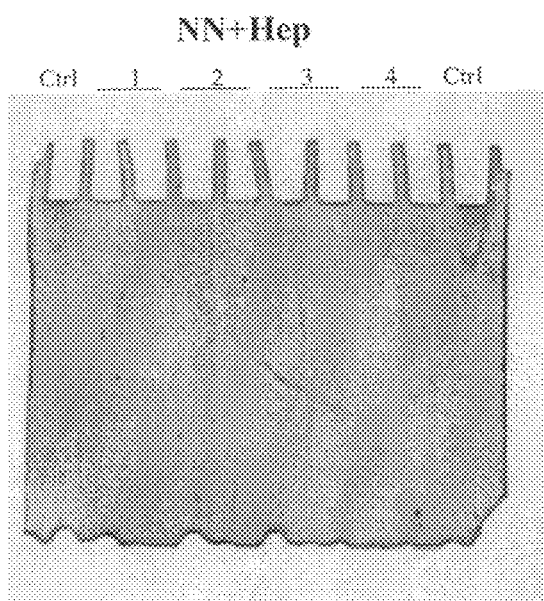
FIG. 26c shows the pattern of bands produced on subjecting to electrophoresis samples of NN dendrimer incubated with no drug (Ctrl) or samples of said dendrimer incubated with different units of heparin: 10 U (lanes marked as "1"), 1 U (lanes marked as "2"), 0.5 U (lanes marked as "3") or 0.1 U (lanes marked as "4").

The results of subjecting these mixtures to electrophoresis, as well as the dendrimer without drug control, are shown in FIG. 26c, marked as "NN+Hep". As can be observed in said Figure, delays occur of the dendrimer incubated with heparin against the control in all the dendrimer/drug ratios; indeed, the dendrimer only migrates a little when it is bound to 0.1 U of heparin. Therefore, it can be said that the N,N-heparin complex is formed.

c) Insulin

The insulin used in the test is presented in aqueous solution, at a concentration of 3.5 mg/ml (100 U). Despite having its molecular weight (5825 g/mol) and establishing an average of 4 (−) charges, the bond with the dendrimer was designed calculating it by units of insulin, thinking that it can be useful with a view to comparing the results with the dose of free insulin used in clinical practice. Thus, dendrimer-insulin mixtures were prepared and incubated which responded to the characteristics shown below in Table 11.

TABLE 11

Characteristics of the NN dendrimer-insulin mixtures

| | Mixture | | | |
|---|---|---|---|---|
| | 1 | 2 | 3 | 4 |
| Units of insulin | 1 U | 0.5 U | 0.1 U | 0.05 U |
| Dendrimer/Drug Drug ratios | 8+/12− | 8+/6− | 32+/4− | 80+/4− |
| Dendrimer/Drug Molecules ratios Total | 1/3 | 1/1.5 | 4/1 | 10/1 |
| Dendrimer | $1.2 \times 10^{15}$ | $1.2 \times 10^{15}$ | $1.2 \times 10^{15}$ | $1.2 \times 10^{15}$ |
| Drug molecules | $3.6 \times 10^{15}$ | $1.8 \times 10^{15}$ | $0.3 \times 10^{15}$ | $0.1 \times 10^{15}$ |

Figure 26D:
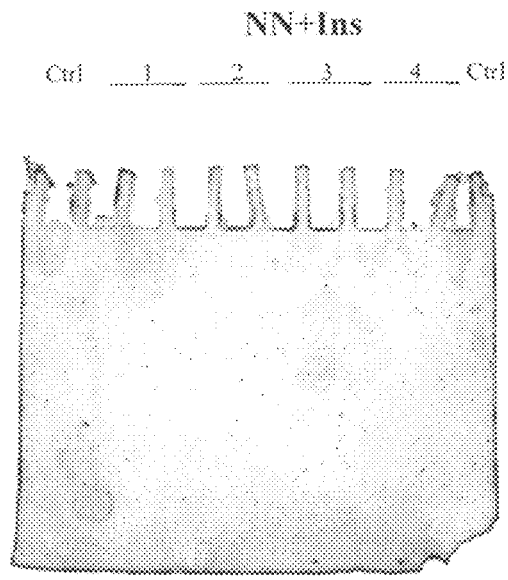
FIG. 26d shows the pattern of bands produced on subjecting to electrophoresis samples of NN dendrimer incubated with no drug (Ctrl) or samples of said dendrimer incubated with insulin in a ratio of dendrimer/drug molecules 1/3 (lanes marked as "1"), 1/1.5 (lanes marked as "2"), 4/1 (lanes marked as "3") or 10/1 (lanes marked as "4").

The results of subjecting these mixtures to electrophoresis, as well as the dendrimer without drug control, are shown in FIG. 26d, marked as "NN+Ins". In this it can be observed that delays occur of the dendrimer incubated with insulin against the control in all the dendrimer/drug ratios; indeed, the dendrimer only migrates a little when it is bound to 0.1 U or 0.05 U of insulin. Therefore, it can be said that a N,N-insulin complex is formed.

Example 51

Binding Tests of Drugs to NN16 Dendrimer

NN dendrimer16 was dissolved in distilled $H_2O$ at an initial concentration of 434 µM and, from it, dilutions were made to produce concentrations of 100 µM, 10 µM and 1 µM. The previous electrophoresis performed with aliquots of the solutions corresponding to each one of these concentrations, to which the gel shown in FIG. 27a corresponds, demonstrated that the dendrimer was in good condition in all of them and that the concentration of 100 μM was suitable for easily viewing the dendrimer in the gel after staining and detecting possible delays in the band produced on being subjected to electrophoresis not in free form, but forming complexes with a drug.

Below, the binding tests with the different drugs are carried out in the following manner:

a) Methotrexate

As has been commented, the methotrexate used in this test is present in the form of 25 mg/ml aqueous solution, with a molecular weight Mw=476.427 g/mol and 1 (−) charge per molecule. Dendrimer-methotrexate mixtures were prepared and incubated which responded to characteristics shown below in Table 12:

TABLE 12

Characteristics of the NN16 dendrimer-methotrexate mixtures

| | Mixture | | | |
|---|---|---|---|---|
| | 1 | 2 | 3 | 4 |
| Dendrimer/Drug Drug ratios | 1+/1− | 2+/1− | 4+/1− | 8+/1− |
| Dendrimer/Drug Molecules ratios Total | 1/16 | 1/8 | 1/4 | 1/2 |
| Dendrimer | $1.2 \times 10^{15}$ | $1.2 \times 10^{15}$ | $1.2 \times 10^{15}$ | $1.2 \times 10^{15}$ |
| Drug molecules | $16 \times 10^{15}$ | $8 \times 10^{15}$ | $4 \times 10^{15}$ | $2 \times 10^{15}$ |

Figures 27A, 27B:
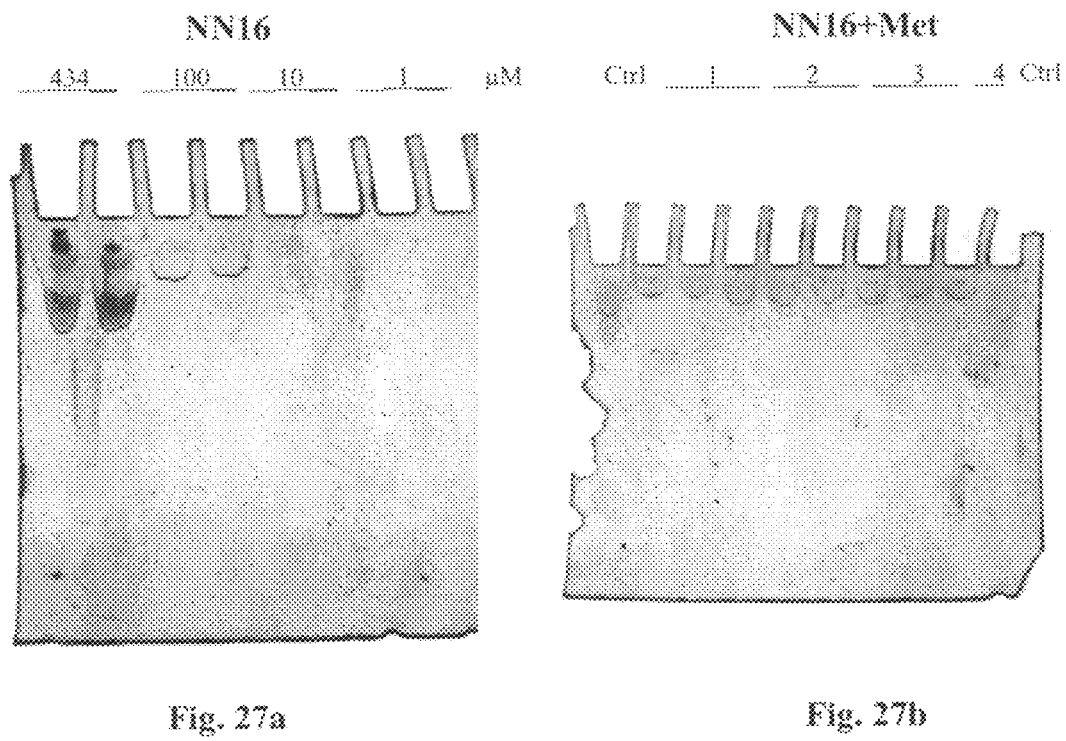
FIG. 27a shows the pattern of bands produced on subjecting the micromolar concentrations (µM) of NN16 dendrimer which are shown on the lanes to electrophoresis in acrylamide/bisacrylamide gel.
FIG. 27b shows the pattern of bands produced on subjecting to electrophoresis samples of NN16 dendrimer incubated with no drug (Ctrl) or samples of said dendrimer incubated with methotrexate in a ratio of dendrimer/drug molecules 1/16 (lanes marked as "1"), 1/8 (lanes marked as "2"), 1/4 (lanes marked as "3") or 1/2 (lanes marked as "4").

The results of subjecting these mixtures to electrophoresis, as well as the dendrimer without drug control, are shown in FIG. 27a, marked as "NN16+Met". In this it can be observed that delays occur, although not very pronounced, of the dendrimer incubated with methotrexate against the control in all the dendrimer/drug ratios. Therefore, it can be said that NN 16-methotrexate complex is formed.

b) Heparin

As in the previous Example, the heparin used in the test is presented in aqueous solution, at 10 mg/ml (1000 U). As we do not have its molecular weight, nor the number of negative charges, although it is known that there are several, the bond with the dendrimer was performed by units of heparin. Thus, dendrimer-heparin mixtures were prepared and incubated which responded to the characteristics shown below in Table 13.

TABLE 13

Composition of the NN16 dendrimer-heparin mixtures

| Control (Ctrl.) | 1 | 2 | 3 | 4 |
|---|---|---|---|---|
| NN16 100 μM ($1.2 \times 10^{15}$ molecules) | $1.2 \times 10^{15}$ NN16 molecules + Heparin 10 U | $1.2 \times 10^{15}$ NN16 molecules + Heparin 1 U | $1.2 \times 10^{15}$ NN16 molecules + Heparin 0.5 U | $1.2 \times 10^{15}$ NN16 molecules + Heparin 0.1 U |

Figure 27C:
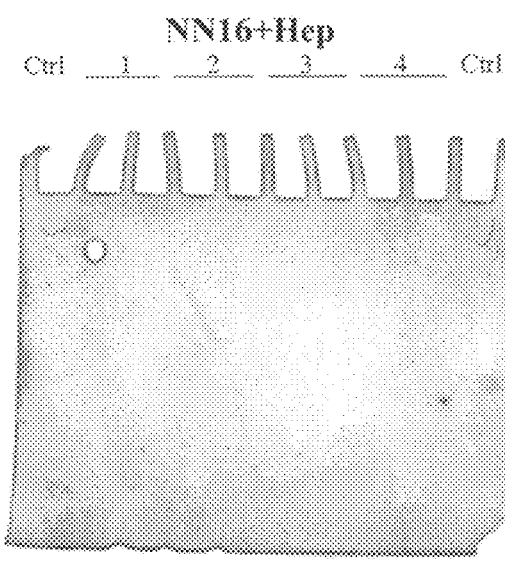
FIG. 27c shows the pattern of bands produced on subjecting to electrophoresis samples of NN16 dendrimer incubated with no drug (Ctrl) or samples of said dendrimer incubated with different units of heparin: 10 U (lanes marked as "1"), 1 U (lanes marked as "2"), 0.5 U (lanes marked as "3") or 0.1 U (lanes marked as "4").

The results of subjecting these mixtures to electrophoresis, as well as the dendrimer without drug control, are shown in FIG. 27c, marked as "NN16+Hep". As can be observed in said Figure, delays occur of the dendrimer incubated with heparin against the control in all the dendrimer/drug ratios; indeed, there is no migration in the dendrimer with heparin wells. Therefore, it can be said that NN16-Heparin complex is formed.

c) Insulin

As in the previous example, the insulin used in the test is presented in aqueous solution, at a concentration of 3.5 mg/ml (100 U). Despite having its molecular weight (5825 g/mol) and establishing an average of 4 (−) charges, the bond with the dendrimer was designed calculating it by units of insulin, thinking that it can be useful with a view to comparing the results with the dose of free insulin used in clinical practice. Thus, dendrimer-insulin mixtures were prepared and incubated which responded to the characteristics shown below in Table 14.

TABLE 14

Characteristics of the NN16 dendrimer-insulin mixtures

| | Mixture | | | |
|---|---|---|---|---|
| | 1 | 2 | 3 | 4 |
| Units of insulin | 1 U | 0.5 U | 0.1 U | 0.05 U |
| Dendrimer/Drug Drug ratios | 16+/12− | 16+/6− | 64+/4− | 160+/4− |
| Dendrimer/Drug Molecules ratios Total | 1/3 | 1/1.5 | 4/1 | 10/1 |
| Dendrimer | $1.2 \times 10^{15}$ | $1.2 \times 10^{15}$ | $1.2 \times 10^{15}$ | $1.2 \times 10^{15}$ |
| Drug molecules | $3.6 \times 10^{15}$ | $1.8 \times 10^{15}$ | $0.3 \times 10^{15}$ | $0.1 \times 10^{15}$ |

Figure 27D:
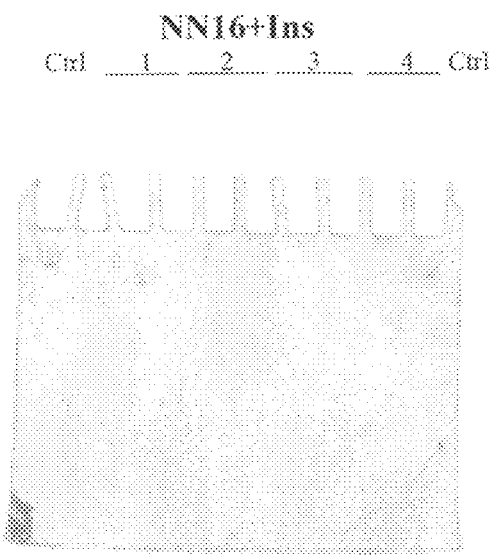
FIG. 27d shows the pattern of bands produced on subjecting to electrophoresis samples of NN16 dendrimer incubated with no drug (Ctrl) or samples of said dendrimer incubated with insulin in a ratio of dendrimer/drug molecules 1/3 (lanes marked as "1"), 1/1.5 (lanes marked as "2"), 4/1 (lanes marked as "3") or 10/1 (lanes marked as "4").

The results of subjecting these mixtures to electrophoresis, as well as the dendrimer without drug control, are shown in FIG. 27d, marked as "NN16+Ins". In this it can be observed that delays occur of the dendrimer incubated with insulin against the control in all the dendrimer/drug ratios; indeed, the dendrimer only migrates a little when it is bound to 0.1 U or 0.05 U of insulin. Therefore, it can be said that NN16-insulin complex is formed.

Example 52

Binding Tests of Drugs to IM16 Dendrimer

Figure 28A:
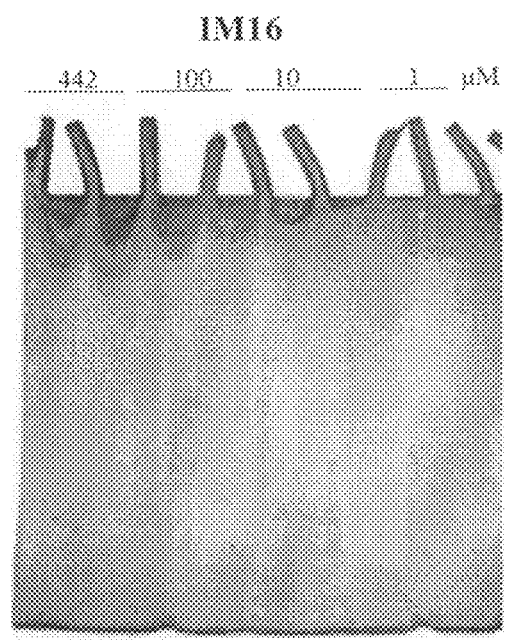
FIG. 28a shows the pattern of bands produced on subjecting the micromolar concentrations (µM) of IM16 dendrimer which are shown on the lanes to electrophoresis in acrylamide/bisacrylamide gel.

IM16 dendrimer was dissolved in distilled $H_2O$ at an initial concentration of 442 μM and, from it, dilutions were performed to produce concentrations of 100 μM, 10 μM and 1 μM. The previous electrophoresis performed with aliquots of the solutions corresponding to each one of these concentrations, to which the gel shown in FIG. 28a corresponds, demonstrated that the dendrimer was in good condition in all of them.

Below, the binding tests with the different drugs are carried out in the following manner:

a) Methotrexate

As has been commented, the methotrexate used in this test is present in the form of aqueous solution at 25 mg/ml, with a molecular weight Mw=476.427 g/mol and 1 (−) charge per molecule. Dendrimer-methotrexate mixtures were prepared and incubated which responded to the characteristics shown below in Table 15:

TABLE 15

Characteristics of IM16 dendrimer-methotrexate mixtures

|  | Mixture | | | |
| --- | --- | --- | --- | --- |
|  | 1 | 2 | 3 | 4 |
| Dendrimer/Drug Drug ratios | 1+/1− | 2+/1− | 4+/1− | 8+/1− |
| Dendrimer/Drug Molecules ratios Total | 1/16 | 1/8 | 1/4 | 1/2 |
| Dendrimer | $1.2 \times 10^{15}$ | $1.2 \times 10^{15}$ | $1.2 \times 10^{15}$ | $1.2 \times 10^{15}$ |
| Drug molecules | $16 \times 10^{15}$ | $8 \times 10^{15}$ | $4 \times 10^{15}$ | $2 \times 10^{15}$ |

Figure 28B:
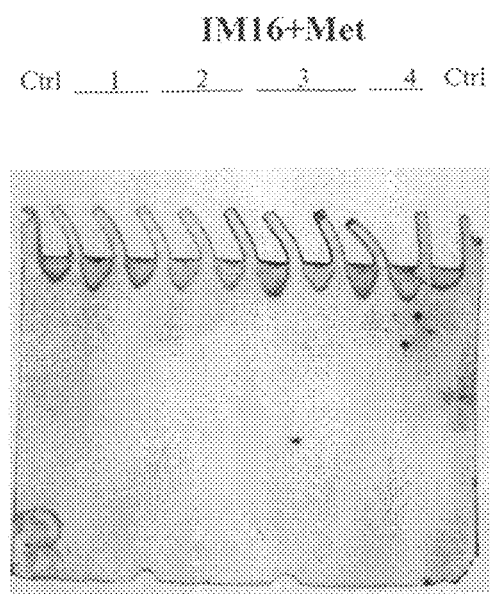
FIG. 28b shows the pattern of bands produced on subjecting to electrophoresis samples of IM16 dendrimer incubated with no drug (Ctrl) or samples of said dendrimer incubated with methotrexate in a ratio of dendrimer/drug molecules 1/16 (lanes marked as "1"), 1/8 (lanes marked as "2"), 1/4 (lanes marked as "3") or 1/2 (lanes marked as "4").

The results of subjecting these mixtures to electrophoresis, as well as the dendrimer without drug control, are shown in FIG. 28b, marked as "IM16+Met". In this it can be observed that no delays occur of the dendrimer incubated with methotrexate against the control in any of the dendrimer/drug ratios. Therefore, it can be said that IM16-methotrexate complex is not formed.

b) Heparin

As in Examples 50 and 51, the heparin used in the test is presented in aqueous solution, at 10 mg/ml (1000 U). As we do not have its molecular weight, nor the number of negative charges, although it is known that there are several, the bond with the dendrimer was performed by heparin units. Thus, dendrimer-heparin mixtures were prepared and incubated which responded to the characteristics shown below in Table 16.

TABLE 16

Composition of IM16 dendrimer-Heparin mixtures

| Control (Ctrl.) | 1 | 2 | 3 | 4 |
| --- | --- | --- | --- | --- |
| IM16 100 μM ($1.2 \times 10^{15}$ molecules) | $1.2 \times 10^{15}$ IM16 molecules + Heparin 10 U | $1.2 \times 10^{15}$ IM16 molecules + Heparin 1 U | $1.2 \times 10^{15}$ IM16 molecules + Heparin 0.5 U | $1.2 \times 10^{15}$ IM16 molecules + Heparin 0.1 U |

Figure 28C:
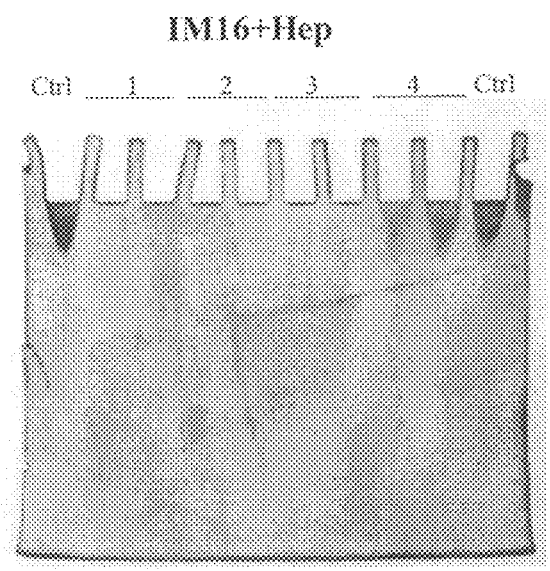
FIG. 28c shows the pattern of bands produced on subjecting to electrophoresis samples of IM 16 dendrimer incubated with no drug (Ctrl) or samples of said dendrimer incubated with different units of heparin: 10 U (lanes marked as "1"), 1 U (lanes marked as "2"), 0.5 U (lanes marked as "3") or 0.1 U (lanes marked as "4").

The results of subjecting these mixtures to electrophoresis, as well as the dendrimer without drug control, are shown in FIG. 28c, marked as "IM16+Hep". As can be observed in said Figure, the band which appear in the lanes corresponding to mixtures of type 4 (0.1 U of heparin) are weaker than those produced with the controls, which indicates that heparin is bound to a small fraction of dendrimer. In the other dendrimer/drug ratios the heparin prevents migration of the dendrimer. Therefore, it can be said that IM16-Heparin complex is formed.

c) Insulin

As in Examples 50 and 51, the insulin used in the test is presented in aqueous solution, at a concentration of 3.5 mg/ml (100 U). Despite having its molecular weight (5825 g/mol) and establishing an average of 4 (−) charges, the bond with the dendrimer was designed calculating it by units of insulin, thinking that it can be useful with a view to comparing the results with the dose of free insulin used in clinical practice. Thus, dendrimer-insulin mixtures were prepared and incubated which responded to the characteristics shown below in Table 17.

TABLE 17

Characteristics of IM16 dendrimer-insulin mixtures

|  | Mixture | | | |
| --- | --- | --- | --- | --- |
|  | 1 | 2 | 3 | 4 |
| Units of insulin | 1 U | 0.5 U | 0.1 U | 0.05 U |
| Dendrimer/Drug Drug ratios | 16+/12− | 16+/6− | 64+/4− | 160+/4− |
| Dendrimer/Drug Molecules ratios Total | 1/3 | 1/1.5 | 4/1 | 10/1 |
| Dendrimer | $1.2 \times 10^{15}$ | $1.2 \times 10^{15}$ | $1.2 \times 10^{15}$ | $1.2 \times 10^{15}$ |
| Drug molecules | $3.6 \times 10^{15}$ | $1.8 \times 10^{15}$ | $0.3 \times 10^{15}$ | $0.1 \times 10^{15}$ |

Figure 28D:
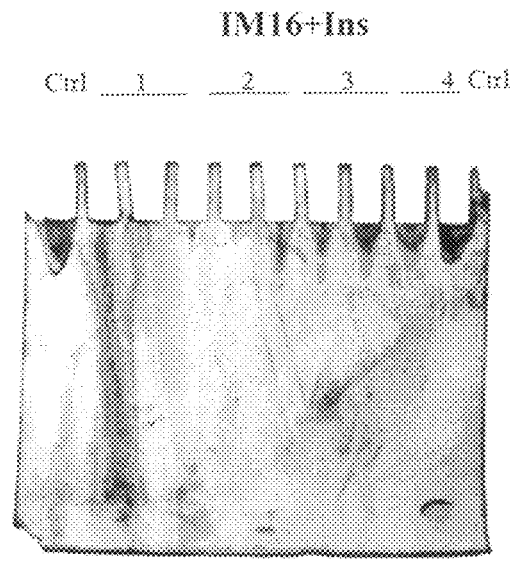
FIG. 28d shows the pattern of bands produced on subjecting to electrophoresis samples of IM 16 dendrimer incubated with no drug (Ctrl) or samples of said dendrimer incubated with insulin in a ratio of dendrimer/drug molecules 1/3 (lanes marked as "1"), 1/1.5 (lanes marked as "2"), 4/1 (lanes marked as "3") or 10/1 (lanes marked as "4").

The results of subjecting these mixtures to electrophoresis, as well as the dendrimer without drug control, are shown in FIG. 28d, marked as "IM16+Ins". In this it can be observed that delays occur of the dendrimer incubated with insulin against the control in all the dendrimer/drug ratios, although in the lanes corresponding to the mixtures which contained 0.05 U or 0.01 U of insulin delays only occur in some dendrimer molecules: the band migrates as in the control but it is weaker. Instead, when the incubation has occurred with 0.5 U of insulin the delay is significant and in the lane corresponding to the dendrimer incubation mixtures with 1 U of insulin no band appears, which indicates that a complex has formed, which does not come to enter the gel. Therefore, it can be said that IM16-insulin complex is formed.

Determination of Stability to pH of the Dendrimer-drug Complexes

Once the binding to the dendrimers of various drugs has been verified, it was attempted to check if the bond was reversible, checking if dissociation of the dendrimer-drug complex occurred to due variation in the medium's pH, attempting to reproduce with it what would happen in physiological conditions, wherein it is supposed that the dendrimer-drug complex would penetrate in the cell by an endosome, whose interior would be acidified on reaching the cytoplasm by the action of $H^+$ pumps, which would give rise to the release of the dendrimer drug on capturing this part of the proton excess.

It is known that the pH reached in an endosome can be between 4.5 and 6.5[77,78,79]. Thus, the pH chosen to perform the test were:

5-6-7.4-9-10

The test on the behaviour of the dendrimer-drug complexes previously formed on varying the medium's pH was again performed by evaluating the delay in polyacrylamide gel of the dendrimer bound to the drug with respect to free dendrimer, following a process similar to that used in the tests to determine the dendrimer-drug bond, although introducing a stage of variation of pH in the complex formation process of prior to electrophoresis, process that was performed in the following way:

Complex formation: It was performed in a final mixture volume of 30 μl, which is the maximum volume for loading in the gel. To do this, we started from the necessary quantity of dendrimer which provides a band perfectly identifiable by staining with silver nitrate in the gel once the electrophoresis has been performed: 20 μl of a 100 μM solution, which correspond to $1.2 \times 10^{15}$ molecules. The drug was added in the remaining 10 μl, choosing for it the minimum concentration which, according to the complex formation tests previously performed, it is capable of producing an evident delay of the dendrimer-drug complex band with respect to the band corresponding to the free dendrimer; the choice of that concentration ensures that a dendrimer-drug complex is formed. An incubation was performed of the dendrimer and drug mixtures at 37° C. during 1 hour to give time for a more thermodynamically stable complex to form, although more time may be needed for its formation. For each pH to test, 2 mixtures were incubated. Next, 10 μl of a 0.1 M buffer were added, which were capable of maintaining the pH sought in each sample at the end concentration of 0.025 M which was attained in it, then maintaining each sample at 37° C. during a further 15 minutes.

Electrophoresis and gel staining: They were performed in the same conditions described in the dendrimer-drug bond determination tests.

Dendrimers:

The tests were performed with IM16 dendrimer:

$(2G-[Si(OCH_2CH_2NMe_3^+I^-)_2]_8$ (19).

Drugs:

Insulin was selected to perform the test, adding 0.5 units (0.5 U) to each reaction mixture.

Buffer solutions

Solutions prepared with different phosphoric acid salts were chosen as buffer solutions. To do this, 0.2 M solutions of each one of the $H_2PO_4Na$, $HPO_4Na_2$ and $PO_4Na_3$ species from which buffer solutions were prepared of each one of the desired pH, all 0.1 M, mixing the volumes of said solutions which are indicated in Table 18 and completing with $H_2O$ to 100 ml.

TABLE 18

Composition of the buffer solutions

| Buffer solution | pH | Volume $H_2PO_4Na$ 0.2M (ml) | Volume $HPO_4Na_2$ 0.2M (ml) | Volume $PO_4Na_3$ 0.2M (ml) | Final volume (ml) |
|---|---|---|---|---|---|
| T5 | 5 | 49.3 | 0.7 | — | 100 |
| T6 | 6 | 43.9 | 6.1 | — | 100 |
| T7.4 | 7.4 | 11.2 | 38.8 | — | 100 |
| T9 | 9 | 0.4 | 49.6 | — | 100 |
| T10 | 10 | — | 49.8 | 0.2 | 100 |

The details of the test and the result are described in the following.

Example 53 pH Stability Test of IM16 Dendrimer-drug Complexes 10 reaction mixtures ("C" samples: complex) were prepared for the dendrimer drug complex formation adding to each one of them 20 μl of the dendrimer solution with 100 μM concentration and 10 μl of an insulin solution which contained 0.5 U thereof. A control sample was prepared for each one of said reaction mixtures ("D": free dendrimer) wherein dendrimer but not drug was added. After 1 hour of incubation, 10 μl of buffer was added to each sample, so that the 20 samples had the composition and characteristics shown below in Table 19:

TABLE 19

Stability test mixtures of IM16-insulin complexes

| pH final | Type of sample | No. of samples | Dendrimer IM16 (100 μM) | Units of insulin | Buffer solution | Buffer Volume (μl) | Final Conc. (mol/l) |
|---|---|---|---|---|---|---|---|
| 5 | D (control) | 2 | 20 μl | 0.5 | T5 | 10 | 0.025 |
|   | C (complex) | 2 | 20 μl | 0.5 | T5 | 10 | 0.025 |
| 6 | D (control) | 2 | 20 μl | 0.5 | T6 | 10 | 0.025 |
|   | C (complex) | 2 | 20 μl | 0.5 | T6 | 10 | 0.025 |
| 7.4 | D (control) | 2 | 20 μl | 0.5 | T7.4 | 10 | 0.025 |
|   | C (complex) | 2 | 20 μl | 0.5 | T7.4 | 10 | 0.025 |
| 9 | D (control) | 2 | 20 μl | 0.5 | T9 | 10 | 0.025 |
|   | C (complex) | 2 | 20 μl | 0.5 | T9 | 10 | 0.025 |
| 10 | D (control) | 2 | 20 μl | 0.5 | T10 | 10 | 0.025 |
|   | C (complex) | 2 | 20 μl | 0.5 | T10 | 10 | 0.025 |

Figure 29:
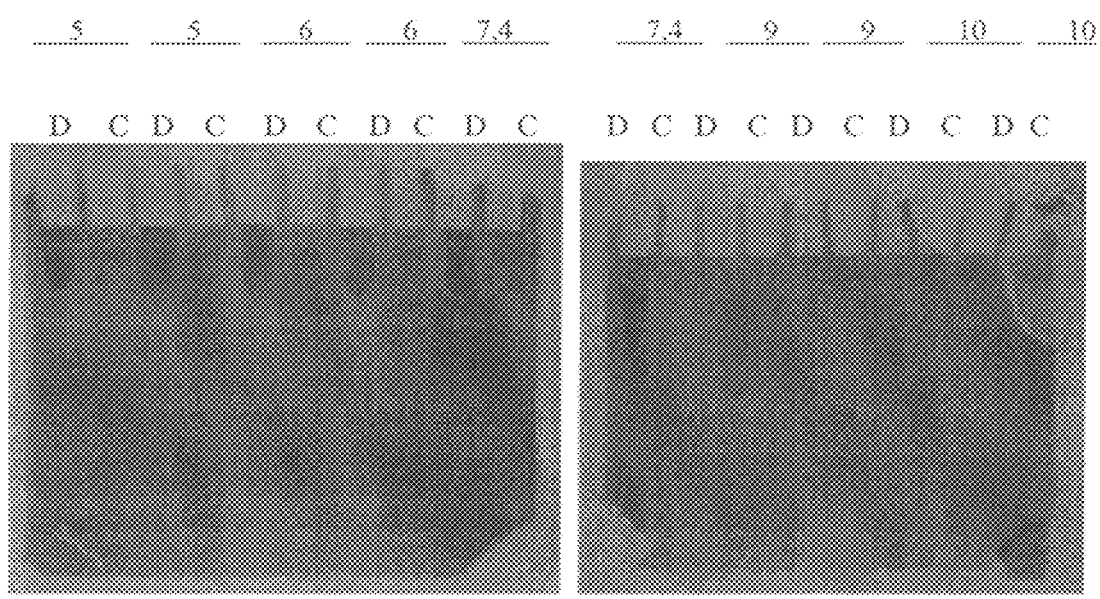
FIG. 29 shows the pattern of bands produced on subjecting to electrophoresis samples of IM16 dendrimer incubated with no drug (lanes marked as "D") or incubated with insulin (lanes marked as "C") wherein the pH was taken to the numerical value indicated on the lanes. Each of the two photographs which appear in figure, on the right and on the left, corresponds to a different gel, produced in the same electrophoresis conditions.

After the waiting time after the addition of the buffer (15 minutes) the samples underwent electrophoresis and staining of the gel, producing the band distribution shown in FIG. 29, wherein the samples appear distributed among two different gels. In said figure it can be observed that at acid pHs the free dendrimer is maintained stable, whilst in the lanes with complex the appearance of bands is observed, for which purpose it is gathered that the partial dissociation of the complexes has occurred and the drug has been released from the dendrimer, leaving the latter free. At alkaline pHs, the dendrimer is unstable and does not degrade, which leads to dissociation of the complex.

The conclusion is that IM16 dendrimer-insulin complex is dissociated at acid pH, which makes it conceivable that other dendrimer-drug complexes may also show a similar behaviour.

Therefore, the tests described in Examples 50 to 53 support the utility of the dendrimers as drug vehicles with negative charge in the blood and that, furthermore, the bond is reversible, the release of the drug being possible inside the cell at acid pH which is reached in the uptake endosome.

Transfection of Cells Derived from the Nervous System with Oligonucleotides Transported by Dendrimers Since the tests performed with the PBMC demonstrate that the dendrimer-ODN complexes may penetrate in the cell and become dissociated in it, tests were performed to check if the dendrimers could serve as transfection vehicles of ODN or other molecules of polyanionic character such as RNAi in cells wherein said molecules give rise to low transfection rate, increasing it. Therefore, two lines were chosen derived from the nervous system, SK-N-MC (neuroblastoma: ATCC HTB10) and U87-MG (astroglioma: ICLC HTL 00013) and it was verified, in first place, that the carbosilane dendrimers of the invention were not toxic, therefore, do not lead to proliferation, after which it was tested if the transfection rate of ODN in these cells could increase on their penetrating the same forming complexes with dendrimers of the invention. The tests were performed with the dendrimers NN (2G-[Si(O (CH$_2$)$_2$N(Me)(CH$_2$)$_2$NMe$_3$$^+$I$^-$)]$_8$ (26)) and NN16 (2G-[Si(O (CH$_2$)$_2$N$^+$(Me)$_2$(CH$_2$)$_2$NMe$_3$$^+$2I$^-$)]$_8$ (36)). The transfection tests were performed with the anti-rev RF ODN (SEQ ID NO:2). The culture medium was DMEM+10% bovine foetal serum.

Example 54

Proliferation of SK-N-MC and U-87-MG Cells Incubated with Dendrimers

Different experiments were performed, one with SK-N-MC cells and another with U-87-MG cells, which studied the effect of the dendrimers on the proliferation of said lines. For this, 7000 cells/well were plated of the corresponding in a 96-well dish. The cells were incubated with different concentrations (1 µM, 5 µM and 10 µM) or NN dendrimer or NN16 dendrimer, during 3 days. As positive proliferation control, cells were incubated with 20 µg/ml of LPS and, as positive death induction control, cells were used incubated with 7% DMSO. As negative control untreated cells were used. After 3 days of incubation cell proliferation was measured using the CellTiter 96 Aqueous One Solution Cell Proliferation Test Kit from Promega, which permits quantifying cell proliferation from the evaluation of the cell reducing capacity, determined from the colorimetric change produced by the bioreduction of MTS (3-(4,5-dimethylthiazol-2-yl)-5-(3-carboximethoxyphenyl)-2-(4-sulfophenyl)-2H-tetrazolium in combination with the electron coupling reagent PES (Phenazine ethosulfate). At the absorbance value obtained 490 nm for the negative control it was given the value 1 and the moiety of the absorbencies produced was used to refer thereto.

Figure 30:
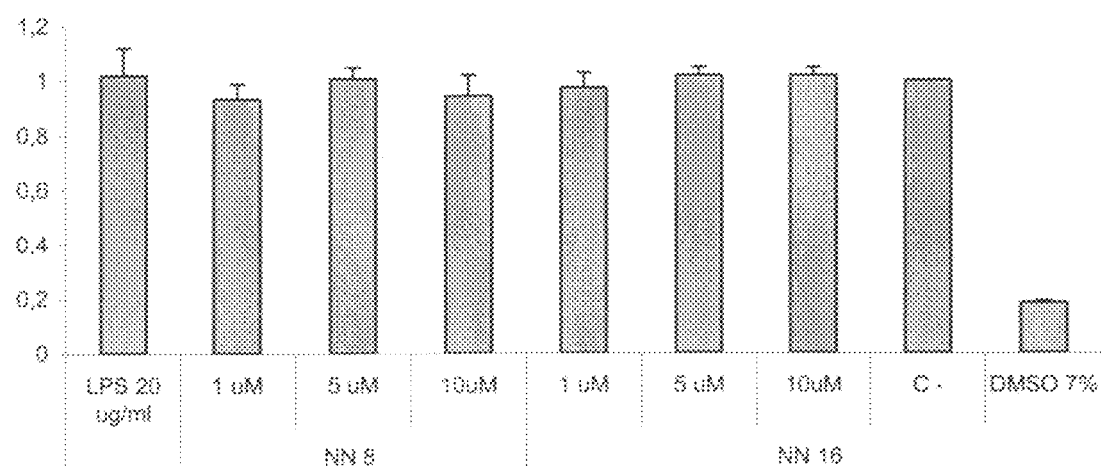
FIG. 30 shows graphics of bars wherein, in ordinates, it shows the value of the proliferation factor, referred to the control ("C–") produced on incubating U87-MG cells (top graphic, marked as "A") or SK-N-MC cells (bottom graphic, marked as "B") with the compounds which are indicated under each bar, at the concentrations indicated. C–: negative control, corresponding to samples only incubated with culture medium without additional compounds.
Figure 30:
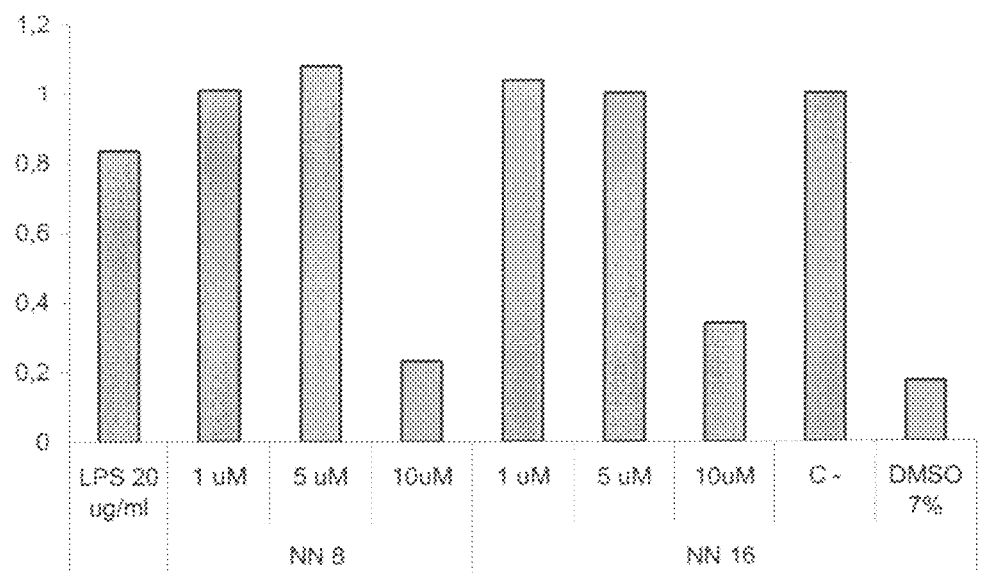

The upper part of FIG. 30, marked as "A", shows a graphic with the results obtained in U87-MG cells. It is observed that the bars corresponding to the samples incubated with the dendrimers indicate a proliferation of cells therein very similar to that of the negative control (C−), for which purpose it can be said that dendrimers NN and NN16 neither induce proliferation nor cell death after incubating them for three days with the U87-MG cell line.

The lower part of FIG. 30, marked as "B", shows a graphic with the results produced in SK-N-MC cells. Therein it can be observed that both dendrimers NN and NN16 are toxic for the SK-N-MC cell line at a concentration of 10 µM. In contrast, the concentrations of 1 µM and 5 µM do not produce toxicity nor cell proliferation.

Example 55

Toxicity Study of Dendrimers in U-87-MG Cells

Tests with MTT
A test with U-87-MG cells was performed, wherein the effect of the dendrimers on the viability of said lines was studied at different times. To do this, 15000 (24 hour incubations), 7000 (3 day incubations) or 1500 (7 day incubations) cells per well were plated in 96-well plates. The cells were incubated with different concentrations (1 µM, 5 µM and 10 µM) either NN dendrimer or NN16 dendrimer, during 24 hours, 3 days and 7 days. Two different negative controls were used: untreated cells (C−) and additionally, cells incubated with different concentrations (1 µM, 5 µM and 10 µM) of dextran, a macromolecule which is typically used as negative control of cytotoxicity in new biomaterial tests. Two different positive controls were also used: cells treated with 7% DMSO and cells treated with 1% Triton X-100.

To be able to have other reference studies, the toxicity of the commercial dendrimers Superfect® and Polyfect® (both from Qiagen) were also studied after 24 hours, 3 and 7 days. In the case of Superfect, three doses were tested, the optimum dose recommended by the manufacturer (2.5 µl), a lower dose (1.25 µl) and another higher dose (5 µl). With regard to Polyfect, specifically designed for adherent cells, the three doses tested were: optimum dose (0.6 µl), lower dose (0.3 µl) and higher dose (1.2 µl).

After each corresponding incubation time, a test was performed with MTT analogous to that described in Example 38. At the absorbance value obtained in the untreated cells (C−) it was given the value of 1 and the moiety of the absorbencies produced was used to refer to it.

Figure 31:
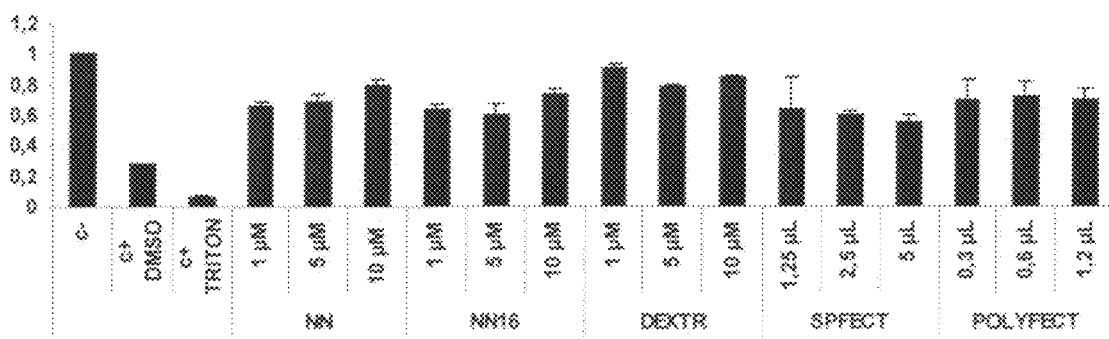
FIG. 31 shows graphics of bars wherein, in ordinates, it shows value of the viability factor, calculated as percentage with respect to that of the control ("C–"), produced on performing tests with MTT in U87-MG cells incubated with the compounds which are indicated under the bars, at the concentrations and volumes indicated, during times of 24 hours (24H) (top graphic, marked as "A"), 3 days (3D) (middle graphic, marked as "B") or 7 days (7D) (bottom graphic, marked as "C"). Dextr: Dextran; Spfect: Superfect.
Figure 31:
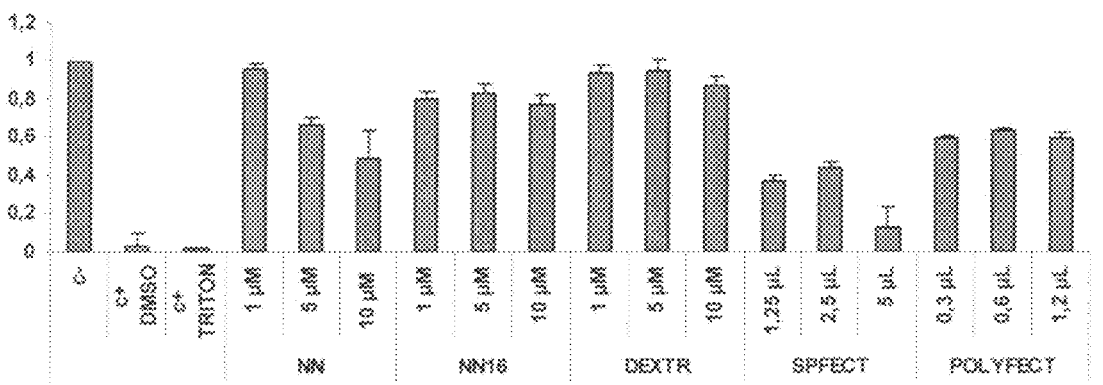
Figure 31:
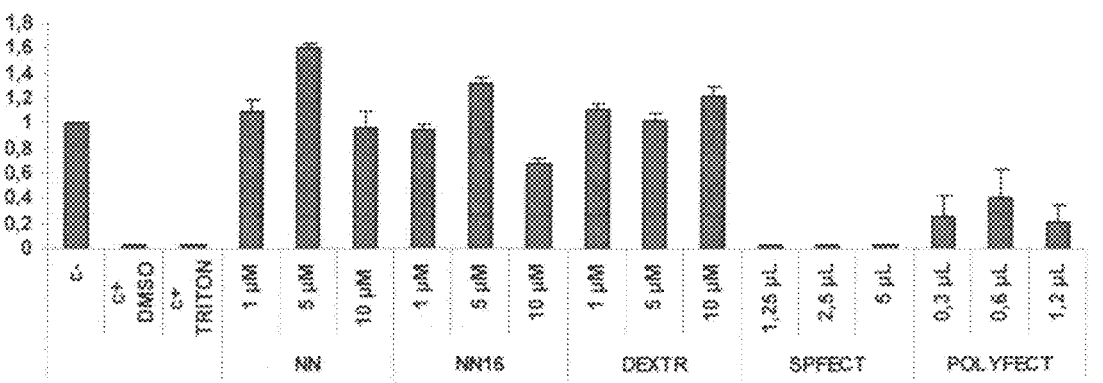

FIG. 31 permits observing the results produced with U87-MG cells. The graphic of the upper part, marked as "A" corresponds to the values produced after 24 hours of incubation; the graphic located in the middle area, marked as "B", corresponds to the values produced after 3 days of incubation; finally, the graphic situated in the lower part, marked as "C", corresponds to the values produced after 7 days of incubation.

In said graphics, it can be observed that the cells treated with dextran, both after 24 hours and after 3 and 7 days had viability values equal to or greater than 0.8.

The commercial dendrimer Superfect, after 24 hours of incubation, gave rise to a similar viability of the cells in any of the concentrations, equal to 0.7. This value has been decreased after three days even at a lower dose (1.25 µl), coming to have a value of up to 0.4. After 7 days of incubation with Superfect, the cells are dead at any one of the three doses used.

The Polyfect dendrimer had less toxicity than Superfect at any one of the three doses tested.

With regard to the dendrimers of the invention NN and NN16, the viabilities produced after 24 hours were similar to one another and are found in a range of between 0.6 and 0.75 with respect to the negative control. The cell viability after 3 days, in the case of NN dendrimer, decreases on increasing the concentration passing from values of 0.95, at a concentration of 1 µM, to values of 0.5 at 10 µM. With regard to the NN16 dendrimer, it has values close to 0.8 at any one of the three concentrations studied. After 7 days of incubation with carbosilane dendrimers, U87-MG has viabilities close to or over those of the negative control except in the case of NN16 at a concentration of 10 µM, whose viability is 0.7.

Measurement of the Lactate Dehydrogenase Concentration (LDH) in the Supernatant

Another form of evaluating cell toxicity that may be induced by the dendrimers is by quantification of the concentration of LDH in the cell culture supernatant, which is considered a direct measure of the cytotoxicity of a certain compound or molecule and gives an idea of the damage the cells have undergone in the membrane. Therefore, a viability test was performed in U87-MG cells similar to that of determination by MTT, although in this case the viability was determined by measuring the concentration of LDH in the cell supernatant culture after 24 hours of incubation in culture medium whereto dextran had been added, the commercial dendrimers Superfect or Polyfect, the dendrimers of the invention NN or NN16, DMSO or Triton X-100. The concentrations and volumes of each one of these compounds were the same used in the test performed with MTT. The commercial kit Cytotoxicity Detection KitPLUS (LDH), from Roche Applied Science was used to determine lactate dehydrogenase, following the manufacturer's instructions.

To evaluate the results, the value of 1 was assigned to negative control (untreated cells), calculating from it the values of cytotoxicity of each one of the compounds with which the cells were incubated.

Figure 32:
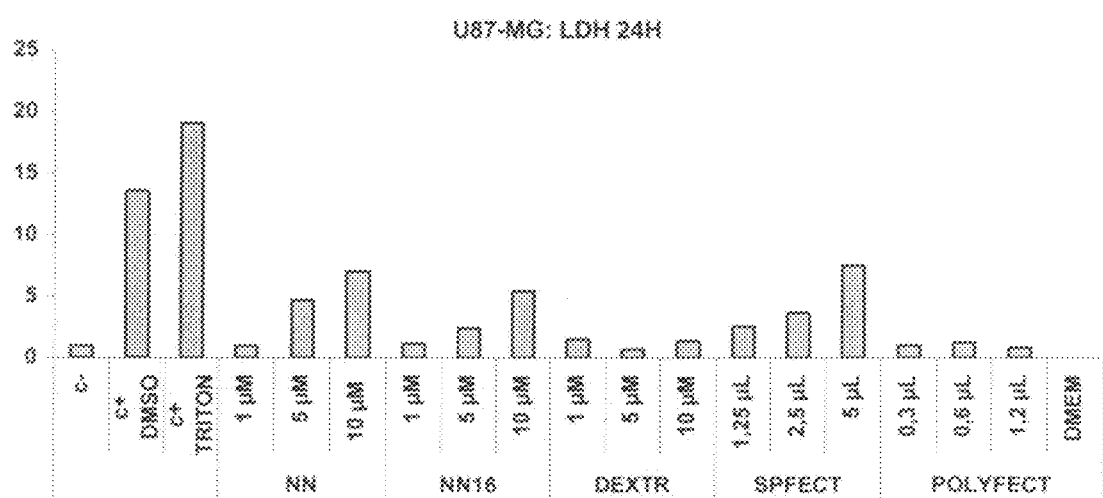
FIG. 32 shows a graphic of bars wherein, in ordinates, it shows the value of the cytotoxicity factor, expressed as percentage with respect to that of the control ("C–"), produced after the quantification of lactate dehydrogenase (LDH) in the U87-MG cell culture supernatant incubated during 24 hours (24H) with the compounds indicated under the bars, in the concentrations and volumes indicated. Dextr: Dextran; Spfect: Superfect. DMEM: value corresponding to culture medium without cells.

The results produced, which are shown in FIG. 32, demonstrate that, as was observed in the test performed with MTT, Polyfect is the commercial dendrimer which has least toxicity at any of the concentrations, whilst Superfect produces greater damage in the membrane as the concentration increases, coming to produce up to 5 times more cytotoxicity than the negative control at the maximum dose (5 µl).

NN and NN16 dendrimers have greater cytotoxicity as their concentration increases. Comparing one with another, NN16 is less toxic than NN.

Example 56

Toxicity Studies of Dendrimers in SK-N-MC Cells

Tests analogous to those described in Example 55 were performed in SK-N-MC cells for U87-MG cells (evaluation of cell viability by tests performed with MTT and quantification of LDH in the cell supernatant): the cells were incubated with the same compounds at the same concentrations, although in this case the measurements with MTT alone were performed after 24 hours of incubation.

Figure 33:
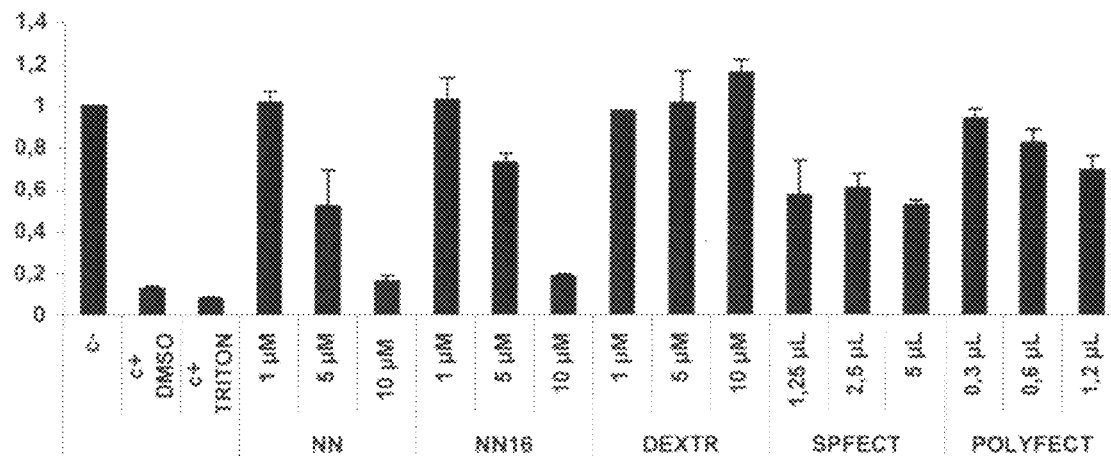
FIG. 33 shows graphics of bars wherein, in ordinates, it shows the value of the percentage with respect to the control ("C") corresponding to the results produced on performing tests with MTT (top graphic, marked as "A") or of quantification of lactate dehydrogenase (LDH) in the culture supernatant (bottom graphic, marked as "B") in SK-N-MC cells incubated during 24 hours (24H) with the compounds which are indicated under the bars, in the concentrations and volumes indicated. Dextr: Dextran; Spfect: Superfect. DMEM: value corresponding to the culture medium without cells
Figure 33:
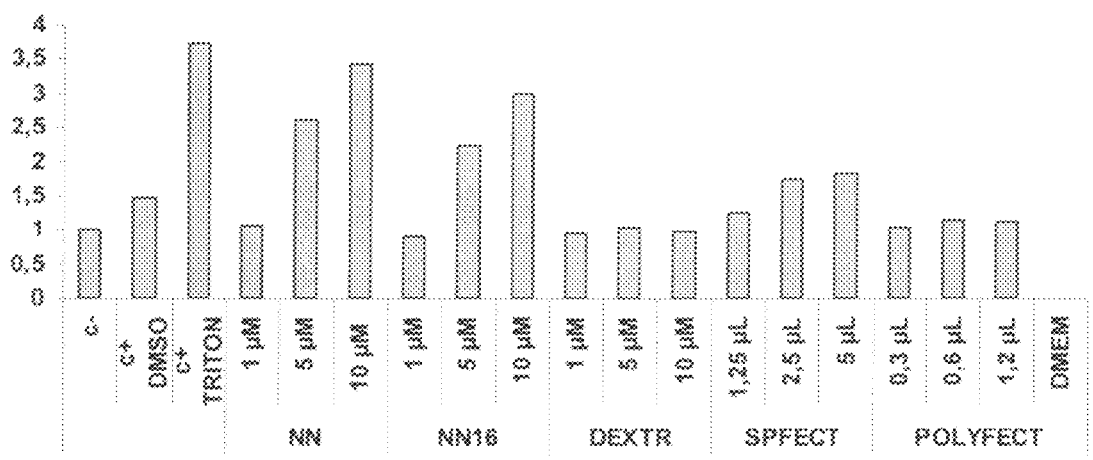

As in Example 55, the absorbance values produced in the test with MTT were indexed to the negative control, producing the results shown in the upper part of FIG. 33 (A).

According to these results, the cells incubated with dextran showed viability values equal to or greater than those of the negative control at any one of the concentrations used.

The cells treated with Polyfect had viabilities over 0.7 in any of the three concentrations used, contrary to what occurs when the cells were treated with Superfect, which gave rise to viabilities around 0.5.

With regard to the dendrimers of the invention it is observed that, contrary to what occurs in the U87-MG line, the changes in dendrimer concentrations gave rise to very acute variations in cell viability. Of the two dendrimers of the invention tested (NN and NN16), NN16 was the one with least toxicity.

In the LDH quantification test, the value of 1 was assigned to the negative control, calculating the other cytotoxicity values from said value and producing the results shown in the lower part of FIG. 33 (B). The results produced confirm the observations made with respect to the test with MTT.

Example 57

Transfection of U87-MG and SK-N-MC Cells Mediated by Dendrimers 100000 cells/well were plated of the corresponding cell line in a 24-well plate with 500 µl of medium.

Dendriplexes were formed with dendrimers NN and NN16 and the fluorescent anti-rev antisense oligonucleotide in a total volume of 75 µl of medium without serum, wherein the anti-rev oligonucleotide was mixed at a concentration 250 nM and the corresponding dendrimer in different proportions, so that different − charge/+ charge ratios were obtained: 1:1, 1:2, 1:4 and 1:8. The mixture was incubated during half an hour at ambient temperature and then it was added to the corresponding well to incubate the cells with dendriplexes.

After 24 hours of incubation, the cells were removed from the well, they were washed twice with PBS, they were incubated for 1 minute with acid glycine to remove the possible moieties of dendriplexes which may have remained adhered on the cell membrane, and a final wash was performed with PBS. Finally, the cells were resuspended in 500 µl of PBS and the quantity of fluorescent oligonucleotide inside the cell was quantified by flow cytometry.

Figure 34A:
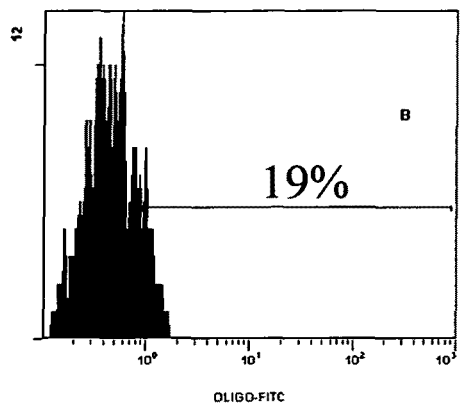
FIG. 34a shows the graphics produced in a flow cytometer on analysing U87-MG cells incubated with the anti-rev oligonucleotide labelled with fluorescein (Oligo-FITC) in the absence of dendrimer (graphic marked as "Ctrl", control) or with complexes formed between the oligonucleotide and NN dendrimer in proportions which give rise to the – charge/+ charge ratios indicated on each graphic: 1:1, 1:2, 1:4 and 1:8.
Figure 34A:
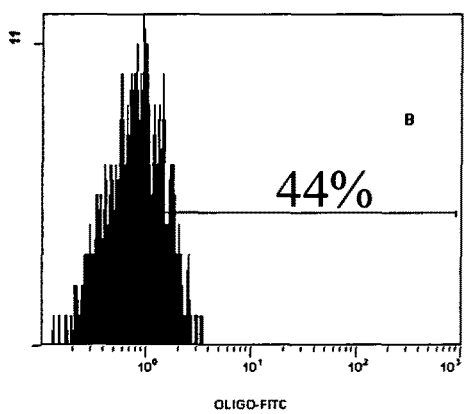
Figure 34A:
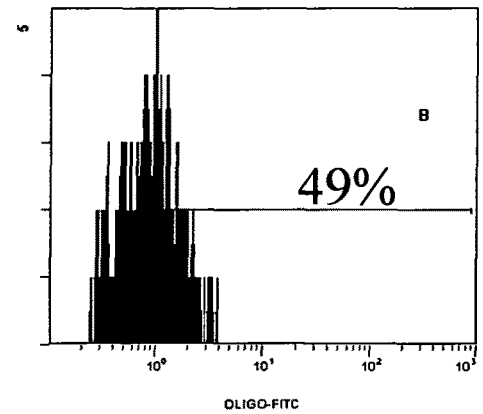
Figure 34A:
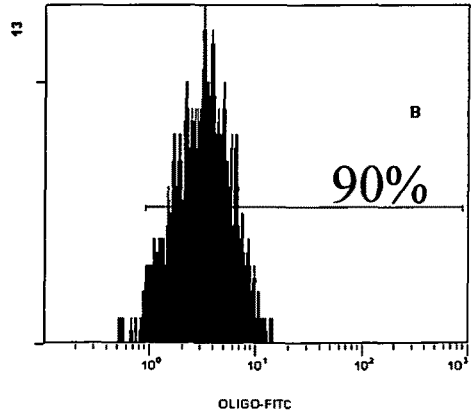
Figure 34A:
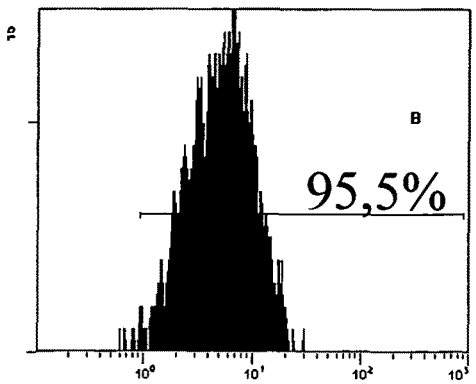
Figure 34B:
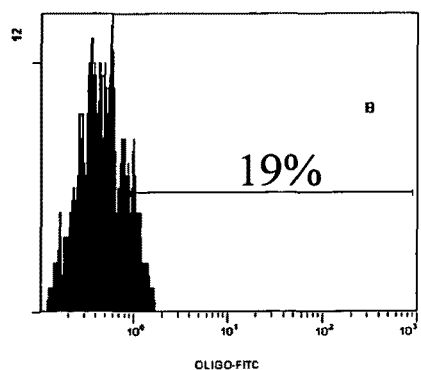
FIG. 34b shows the graphics produced in a flow cytometer on analysing U87-MG cells incubated with the anti-rev oligonucleotide labelled with fluorescein (Oligo-FITC) in the absence of dendrimer (graphic marked as "Ctrl", control) or with complexes formed between the oligonucleotide and NN16 dendrimer in proportions which give rise to the – charge/+ charge ratios indicated on each graphic: 1:1, 1:2, 1:4 and 1:8.
Figure 34B:
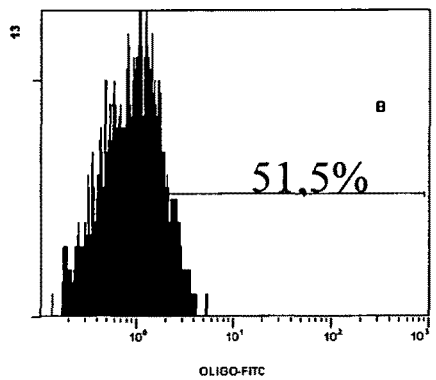
Figure 34B:
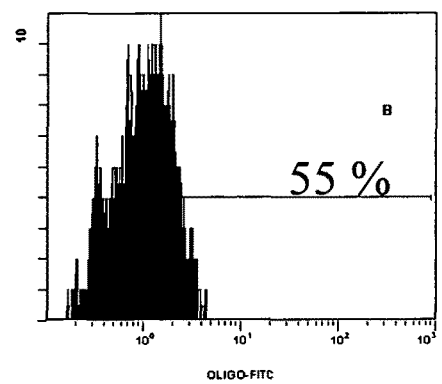
Figure 34B:
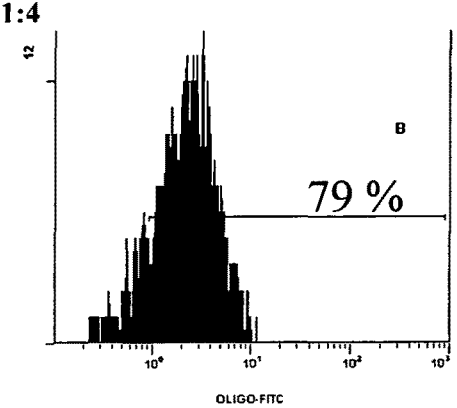
Figure 34B:
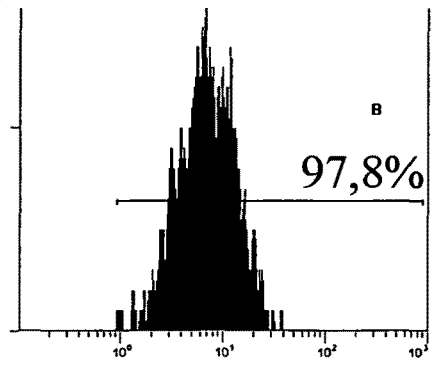

FIGS. 34a and 34b show the results produced with the U87-MG cell line. The graphics correspond to the results produced with cells incubated with the oligonucleotide without dendrimer (Ctrl) or with complexes formed with one of the dendrimers and the anti-rev oligonucleotide in proportions which gave rise to − charge/+ charge ratios indicated on each graphic: 1:1, 1:2, 1:4 and 1:8. FIG. 34a, corresponds to the tests performed with NN dendrimer, whilst FIG. 34b, corresponds to the tests performed with NN16 dendrimer. In both cases, the graphics permit observing that the incubation of the U87-MG cells with complexes formed with greater quantity of dendrimer gives rise to an increase in transfection, passing from 19% produced in the case of incubation of the cells only with the oligonucleotide (Ctrl) to 95% when the dendriplex formed with a − charge/+ charge ratio 1:8 and 97.8% in the case of the dendriplex formed with NN16 dendrimer also with a − charge/+ charge ratio 1:8 were incubated. The results demonstrate, therefore, that an increase in dendrimer with respect to the oligonucleotide produces an increase in the percentage of cells transfected, coming to reach a maximum transfection point when the − charge/+ charge ratio is 1:8.

Figure 35:
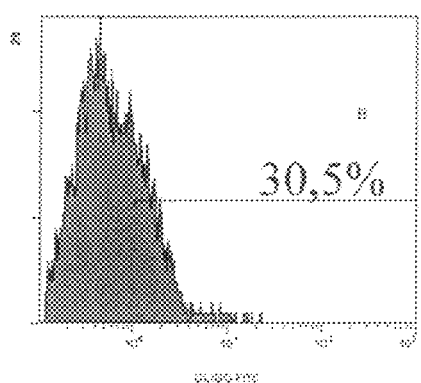
FIG. 35 shows the graphics produced in a flow cytometer on analysing SK-N-MC cells the anti-rev oligonucleotide labelled with fluorescein (Oligo-FITC) in the absence of dendrimer (graphic marked as "Ctrl", control) or with complexes formed between the oligonucleotide and NN16 dendrimer in proportions which give rise to the – charge/+ charge ratios indicated on each graphic: 1:1, 1:2, 1:4 and 1:8.
Figure 35:
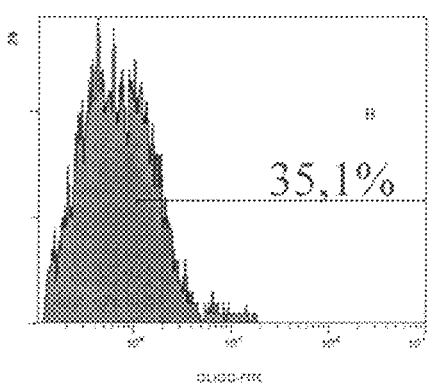
Figure 35:
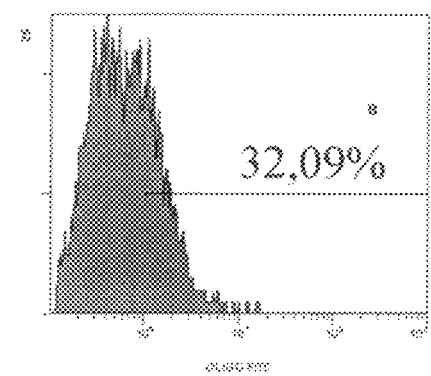
Figure 35:
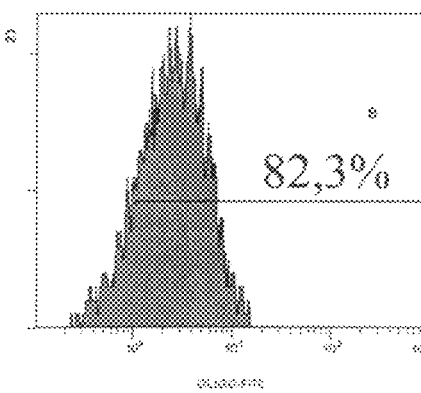
Figure 35:
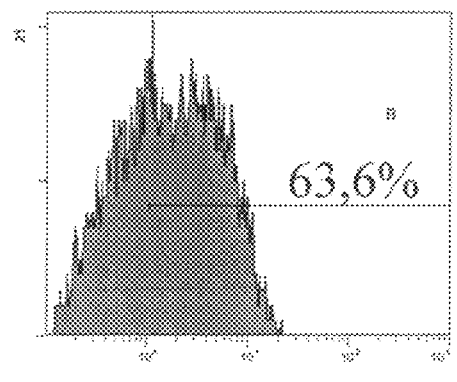

FIG. 35 shows the results produced with the SK-N-MC cell line with NN16 dendrimer. In this case, the maximum transfection is produced with dendriplexes formed with a − charge/+ charge ratio 1:4 (82.3%).

Both in one cell line and in the other, an increase is produced in the transfection percentage occurring on incubating the cells with dendriplexes with respect to that produced when incubated with the nucleotide alone, especially when the − charge/+ charge proportions are 1:4 or 1:8, i.e. when the dendrimer proportion increases with respect to any other oligonucleotide, composed of ribonucleotides or by deoxyribonucleotides, gave rise to similar results, although the optimum − charge/+ charge ratios could be different according to the type of cell to transfect and the specific dendrimer and the oligonucleotide which form the dendriplex. In any case, the tests described support the utility of the carbosilane dendrimers of the invention as vehicles to increase transfection of polyanionic molecules such as oligonucleotides, oligodeoxyribonucleotides (ODN) or interference RNA (RNAi).

4. BIBLIOGRAPHY

1. M. Fischer, F. Vögtle, *Angew. Chem.* 1999, 111, 934-955; *Angew. Chem. Int. Ed.* 1999, 38, 884-905 and references included therein.
2. Hacein-Bey-Abina S. et al. N Engl J. Med. 2003 Jan. 16; 348(3):255
3. P. L. Felgner, t. R. Gadek, M. Holm, R. Roman, H. W. Chan, M. Wenz, J. P. Northrop, G. M. Ringold, M. Danielsen, *Proc. Natl. Acad. Sci. USA,* 1987, 84, 7413-7417.
4. G McLachlan, B. J. Stevenson, D. J. Davidson, D. J. Porteous. *Gene Ther.* 2000 March; 7(5):384-92.
5. T. V. Chirila, P. E. Rakoczy, K. L. Garret, X. Lou, I. J. Constable, *Biomaterials* 2002, 23, 321-342.
6. J. Haensler, F. C. Szoka Jr., *Bioconjugate Chem.* 1993, 4, 372-379.

7. A. U. Bielinska, C. Chen, J. Johnson, J. R. Baker jr., *Bioconjugate Chem.* 1999, 10, 843-850.
8. C. Loup, M. A. Zanta, A. M. Caminade, J. P. Majoral, B. Meunier, *Chem. Eur. J.* 1999, 5, 3644-3650.
9. B. H. Zinselmeyer, S. P. Mackay, A. G. Schatzlein, I. F. Uchegbu, *Pharm. Res.* 2002, 19, 960-967.
10. T. Nidome, M. Wakamatsu, A. Wada, T. Hirayama, H. Aoyagi, *J. Pep. Sci.* 2000, 271-279.
11. R. Hogrefe. Antisense and Nucleic Acid Drug Development, 9, 351-357 1999. Updated 2002.
12. D A Jabs et al. Am J Opthalmol. 2002 April; 133(4): 552-6.
13. S. Agrawal et al. Int J Oncol. 2002 July; 21(1):65-72.
14. N. Sato et al. Clin Cancer Res 2001 November; 7(11): 3606-12
15. C. Giovannangeli, et al. Proc. Natl. Acad. Sci. USA. 1997. January Vol. 94, pp. 79-84,
16. D. M. Klinman D M. Expert Opin Biol Ther. 2004 June; 4(6):93746.
17. B. Tavitian. Gut. 2003; 52 (Suppl IV):iv40-iv47.
18. P. Fiset, and A. S. Gounni. Reviews in Biology and Biotechnology Vol. 1, No 2, May 2001. pp. 27-33. Antisense ODNnucleotides: problems with use and solutions.
19. M Witvrouw et al. Mol. Pharmacol. 2000 58:1100-1108.
20. S. Supattapone, H. B. Nguyen, F. E. Cohen, S. B. Prusiner and M. R. Scott. PNAS. 1999. Dec. 7. Vol. 96, Issue 25, 14529-14534.
21. N. Malik, R. Wiwattanapatapee, K. Klopsch, K. Lorenz, H. Frey, J. W. Weener, E. W. Meijer, W. Paulus, R. Duncan, *J. Control., Rel.* 2000, 65, 133-148.
22. S. W. Krska, D. Seyferth, *J. Am. Chem. Soc.* 1998, 120, 3604-3612.
23. B. Luhmann, H. Lang, K. Bruning, *Phosph. Sulf Silic. Relat. Element.* 2001, 168, 481-484.
24. A. W. Kleij, R. van de Coevering, R. J. M. Klein Gebbink, A. M. Noordman, A. L. Spek, G. van Koten, *Chem. Eur. J.* 2001, 7, 181-192.
25. A. W. van der Made, P. W. N. M. van Leeuwen, *J. Chem. Soc., Chem. Commun.* 1992, 1400-1401.
26. K. Lorenz, R. Mülhaupt, H. Frey, U. Rapp, F. J. Mayer-Posner, *Macromolecules* 1995, 28, 6657-6661.
27. C. Kim, I. Jung, *J. Organomet. Chem.* 1999, 588, 9-19.
28. Karstedt, B. D. U.S. Pat. No. 3,775,452, 1973.
29. S. W. Krska, D. Seyferth, *J. Am. Chem. Soc.* 1998, 120, 3604-3612.
30. Hamilton, M. A., R. C. Russo, y R. V. Thurston, *Environ. Sci. Technol.* 1977, 11(7): 714-719; Correction 1978, 12(4):417.
31. *Dendrimers and other dendritic polymers*. Eds. J. M. Fréchet, D. A. Tomalia. Wiley Series in Polymer Science 2001. J. Wiley & Sons, Ltd.
32. *Dendrimers and Dendrons: Concepts, Syntheses, Applications*. Ed. G. R. Newkome, C. N. Moorefield, F. Vögtle, Wiley-VCH, 2001.
33. G. E. Ossterom, J. N. H. Reek, P. C. J. Kamer, P. W. N. M. van Leeuwen, *Angew. Chem. Int. Ed.* 2001, 40, 1828-1849.
34. D. Astruc, F. Chardac, *Chem. Rev.* 2001, 101, 2991-3023.
35. S. M. Grayson, J. M. J. Fréchet, *Chem. Rev.* 2001, 101, 3819-3867.
36. S. E. Stiriba, H. Frey, R. Haag, *Angew. Chem. Int. Ed.* 2002, 41, 1329-1334.
37. F. Aulenta, W. Hayes, S. Rannard, *Eur. Polym. J.* 2003, 39, 1741-1771.
38. U. Boas, P. M. H. Heegaard, *Chem. Soc. Rev.*, 2003, 33, 43-63.
39. J. Dennig, E. Duncan, *Rev. Mol. Biotech.* 2002, 90, 339-347.
40. J. Dennig, *Top. Curr. Chem.* 2003, 228, 227-236.
41. M. Ohraki, T. Okuda, A. Wada, T. Hirayama, T. Nidome, H. Aoyagi, *Bioconjugate Chem.* 2002, 13, 510-517.
42. A. W. van der Made, P. W. N. M. van Leeuwen. J. C. de Wilde, R. A. C. Brandes, *Adv. Mater.* 1993, 5, 466-468.
43. J. Roovers, P. M. Toporowski, L. L. Zhou, *Polym. Prep.* (J. Am. Chem. Soc., Div. Polym. Chem.), 1992, 33, 182.
44. L. L. Zhou, J. Roovers, *Macromolecules* 1993, 26, 963-968.
45. D. Seyferth, D. Y. Son, A. L. Rheingold, R. L. Ostrander, *Organometallics* 1994, 13, 2682-2690.
46. I. Cuadrado, M. Moran, J. Losada, C. M. Casado, C. Pascual, B. Alonso, F. Lobete, in *Advances in Dendritic Macromolecules*; Eds.; G. R. Newkomone, JAI Press Inc: Greenwich Conn., 1999, Vol. 3, pp 151-191.
47. M. Veith, R. Elsässer, R. P. Krüger, *Organometallics* 1999, 18, 656-661.
48. C. Kim, I. Jung, *J. Organomet. Chem.* 2000, 599, 208-215.
49. S. Arévalo, E. de Jesús, F. J. de la Mata, J: C. Flores, R. Gómez, *Organometallics* 2001, 20, 2583-2592
50. N. Bourne, et al. *Antimicrob Agents Chemother*, 2000, 44(9), 2471-2474.
51. Y. Gong, et al., *Antiviral Res*, 2002, 55(2), 319-329.
52. M. Witvrouw, et al., *Med Chem,* 2000, 43(5), 778-783.
53. C. Z. Chen, y S. L. Cooper, *Biomaterials,* 2002, 23, 3359-3368.
54. C. Z. Chen, N. C. Beck-Tan, P. Dhurjati, T. K. van Dyk, R. A. LaRossa, S. L. Cooper, *Biomacromolecules,* 2000, 1(3), 473-480.
55. D. J. Selkoe, *Science,* 1997, 275(5300), 630-631.
56. J. Hardy y D J Selkoe, *Science,* 2002, 297, 353-356.
57. K. Sadler, y J. P. Tam, *J Biotechnol,* 2002, 90(34), 195-229.
58. J. C. Spetzler, y J. P. Tam, *Pept Res,* 1996, 9(6), 290-296.
59. C. A. Moreno, et al., *Vaccine,* 1999, 18(1-2): 89-99.
60. S. Ota, et al., *Cancer Res,* 2002, 62(5), 1471-1476.
61. R. A. Benkeser, J. Kang, *J. Organomet. Chem.,* 1980, 185, C9.
62. J. L. Speier, J. A. Webster, G. H. Barnes, *J. Amer. Chem. Soc.* 1957, 79, 974.
63. V. Le Berre, E. Trévisiol, A. Dagkessamanskaia, S. Sokol, A. M. Caminade, J. P. Majoral, B. Meunier y J. François, *Nucl. Acids Res.,* 2003, 31, e88.
64. P. Veprek y J. Jezek, *J Pept Sci,* 1999, 5(5), 203-220.
65. S. Andre, et al., *Chembiochem,* 2001, 2(11), 822-830.
66. R. Roy, M. G. Baek, K. Rittenhouse-Olson, *J. Am. Chem. Socj,* 2001, 123, 1809-1816.
67. R. Roy, *Curr. Opin. Struct Biol.,* 1996, 6, 692-702.
68. J. F. G. A. Jansen, E. W. Meijer, E. M. M. de Brabander-van den Berg, *Macromol. Symp.,* 1996, 102, 27-33.
69. T. P. Devasagayam y J. P. Kamat, *Indian J Exp Biol,* 2002, 40(6), 680-692.
70. S. H. Battah, et al., *Bioconjug Chem,* 2001, 12(6), 980-988.
71. N. Nishiyama, et al., *Bioconjug Chem,* 2003, 14(1), 58-66.

72. A. S. Chauhan, S. Sridevi, K. B. Chalasani., A. K. Jain., S. K. Jain, N. K. Jain, P. V. Diwan, *J. Control. Rel.*, 2003, 90, 335-343.
73. K. Kono, M. Liu y J. M. Frechet, *Bioconjug Chem*, 1999, 10(6), 1115-1121.
74. A. Quintana, et al., *Pharm Res*, 2002, 19(9), 1310-1316.
75. S. Shukla, et al., *Bioconjugate Chem*, 2003, 14, 158-167.
76. N. Malik, E. G. Evagorou y R. Duncan, *Anticancer Drugs*, 1999, 57, 249-257.
77. R. F. Murphy et al., *The Journal of Cell Biology*, 1984, 98, 1757-1762.
78. O. Seksek et al., *The Journal of Biological Chemistry*, 1996, 271(26), 15542-15548.
79. http://www.cytochemistry.net/Cell-biology/lysosome.htm

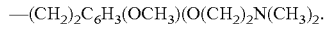

The invention claimed is:

1. A branched carbosilane dendrimer with terminal moieties at ends of their branches which contain primary, secondary, tertiary or quaternary amino groups, and said carbosilane dendrimer is described by any one of the formulas:

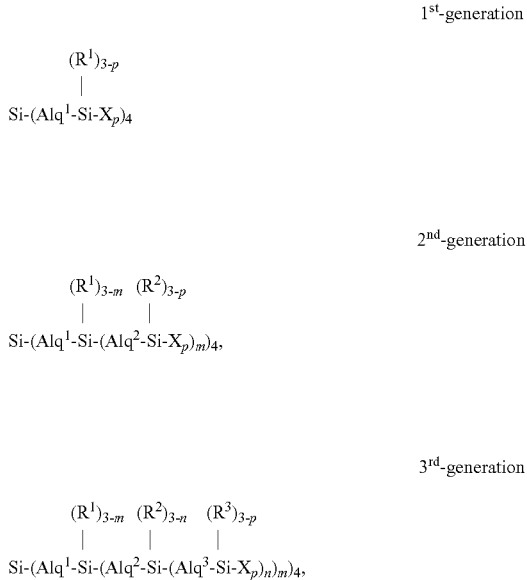

1st-generation $Si\text{-}(Alq^1\text{-}Si\text{-}X_p)_4$
$(R^1)_{3-p}$

2nd-generation $Si\text{-}(Alq^1\text{-}Si\text{-}(Alq^2\text{-}Si\text{-}X_p)_m)_4$,
$(R^1)_{3-m}\ (R^2)_{3-p}$ 3rd-generation $Si\text{-}(Alq^1\text{-}Si\text{-}(Alq^2\text{-}Si\text{-}(Alq^3\text{-}Si\text{-}X_p)_n)_m)_4$,
$(R^1)_{3-m}\ (R^2)_{3-n}\ (R^3)_{3-p}$ or by the corresponding analogous formulas in the case of later generations, wherein the formula corresponding to later generation (i) results from substituting $X_p$ in the formula corresponding to the previous generation (i−1) by a new block of the type:

$Alq^i\text{-}Si\text{-}X_p$
$(R^i)_{3-p}$ passing the group bound to the same silicon atom as this substitutory block from being represented by $(R^{i-1})_{3-p}$ to being represented by $(R^{i-1})_{3-z}$, formulas, and wherein:

$Alq^1$, $Alq^2$, $Alq^3$, ..., $Alq^{i-1}$, $Alq^i$ represent alkylene moieties of 2 to 4 carbons which are chosen independently from one another according to the length of the branches in each generation;

$R^1$, $R^2$, $R^3$, ..., $R^{i-1}$, $R^i$ each independently represent methyl and/or phenyl;

X is a moiety comprising at least one primary, secondary, tertiary or quaternary amino group;

p and m, n, ..., z are each independently as integer of 1 to 3; and wherein the terminal moiety of the branches comprising at least one amino group is bound to the dendrimer by (1) an —O— group formed from the —OH group of an alcohol-amine; or by (2) a —CH$_2$— group formed from a terminal carbon which was forming part of a carbon-carbon double bond in a compound which contains at least one amino group with which the dendrimer is made to react to produce terminal moieties of branches.

2. The carbosilane dendrimer according to claim 1, wherein the moieties $Alq^1$, $Alq^2$, $Alq^3$, ..., $Alq^i$ are selected independently among ethylene or propylene.

3. The carbosilane dendrimer according to claim 2, wherein the moieties $Alq^1$, $Alq^2$, $Alq^3$, ..., $Alq^i$ are all identical and correspond to propylene moieties.

4. The carbosilane dendrimer according to claim 1, wherein the whole numbers m, n, ..., z are identical to one another and have the value 2.

5. The carbosilane dendrimer according to claim 1, wherein the moieties $R^1$, $R^2$, $R^3$, ... $R^{i-1}$, $R^i$ are all identical and correspond to methyl moieties.

6. The carbosilane dendrimer according to claim 1 wherein the moieties $Alq^1$, $Alq^2$, $Alq^3$, ..., $Alq^i$ are identical to one another and correspond to propylene moieties; the whole numbers m, n, ..., j are identical to one another and have the value 2 and the moieties $R^1$, $R^2$, $R^3$ ..., $R^{i-1}$, $R^i$ are all identical and correspond to methyl moieties.

7. The carbosilane dendrimer according to claim 1, wherein the terminal moiety of the branches which contains at least one amino group is chosen among the moieties consisting of —OCH$_2$CH$_2$N(CH$_3$)$_2$, —OCH$_2$—(C$_6$H$_3$)-3,5-(OCH$_2$CH$_2$N(CH$_3$)$_2$) and —OCH$_2$CH$_2$N(CH$_3$)CH$_2$CH$_2$N(CH$_3$)$_2$.

8. The carbosilane dendrimer according to claim 7, wherein the terminal moiety of the branches which contains at least one amino group is the moiety —OCH$_2$CH$_2$N(CH$_3$)$_2$.

9. The carbosilane dendrimer according to claim 8, wherein the "p" index takes the value 1 and each branch ends with a single —OCH$_2$CH$_2$N(CH$_3$)$_2$ moiety.

10. The carbosilane dendrimer according to claim 9 which is of first, second or third generation.

11. The carbosilane dendrimer according to claim 8, wherein the "p" index takes the value 2 and each branch ends with two —OCH$_2$CH$_2$N(CH$_3$)$_2$ moieties.

12. The carbosilane dendrimer according to claim 11, which is of first, second or third generation.

13. The carbosilane dendrimer according to claim 7, wherein the terminal moiety of the branches which contains at least one amino group is the moiety —OCH$_2$—(C$_6$H$_3$)-3,5-(OCH$_2$CH$_2$N(CH$_3$)$_2$).

14. The carbosilane dendrimer according to claim 13, wherein the "p" index takes the value 1 and each branch ends with a single —OCH$_2$—(C$_6$H$_3$)-3,5-(OCH$_2$CH$_2$N(CH$_3$)$_2$OCH$_2$)$_2$ moiety.

15. The carbosilane dendrimer according to claim 14, which is of first, second or third generation.

16. The carbosilane dendrimer according to claim 13, wherein the "p" index takes the value 2 and each branch ends with two —OCH$_2$—(C$_6$H$_3$)-3,5-OCH$_2$CH$_2$N(CH$_3$)$_2$OCH$_2$)$_2$ moieties.

17. The carbosilane dendrimer according to claim 16, which is of first, second or third generation.

18. The carbosilane dendrimer according to claim 7, wherein the terminal moiety of the branches which contains at least one amino group is the moiety —OCH$_2$CH$_2$N(CH$_3$)CH$_2$CH$_2$N(CH$_3$)$_2$.

19. The carbosilane dendrimer according to claim 18, wherein the "p" index takes the value 1 and each branch ends with a single —OCH$_2$CH$_2$N(CH$_3$)CH$_2$CH$_2$N(CH$_3$)$_2$ moiety.

20. The carbosilane dendrimer according to claim 19, which is of first, second or third generation.

21. The carbosilane dendrimer according to claim 18, wherein the "p" index takes the value 2 and each branch ends with two —OCH$_2$CH$_2$N(CH$_3$)CH$_2$CH$_2$N(CH$_3$)$_2$ moieties.

22. The carbosilane dendrimer according to claim 21, which is of first, second or third generation.

23. The carbosilane dendrimer according to claim 1, wherein the terminal moiety of the branches corresponds to the formula —$CH_2CH_2(CH_2)_e$—$NH_2$, where "e" is a number between 0 and 2.

24. The carbosilane dendrimer according to claim 23, wherein "e" takes the value 1, the terminal moiety of the branches which contains at least one amino group corresponding to the formula —$CH_2CH_2CH_2$—$NH_2$.

25. The carbosilane dendrimer according to claim 24, wherein the "p" index takes the value 1 and each branch ends with a single —$CH_2CH_2CH_2$—$NH_2$ moiety.

26. The carbosilane dendrimer according to claim 25, wherein the carbosilane dendrimer is of first, second or third generation.

27. The carbosilane dendrimer according to claim 6, wherein part or all of the amino groups present in the terminal moieties of the branches are quaternized.

28. The carbosilane dendrimer according to claim 27, wherein the terminal moiety of the branches which contains at least one quaternized amino group is chosen among the moieties consisting of —$OCH_2CH_2N^+(CH_3)_3$—$I^-$—, —$OCH_2$—$(C_6H_3)$-3,5-$(OCH_2CH_2N^+(CH_3)_3)I^-)_2$ and —$OCH_2CH_2N(CH_3)CH_2CH_2N^+(CH_3)_3I^-$.

29. The carbosilane dendrimer according to claim 28, wherein the terminal moiety of the branches which contains at least one quaternized amino group is the moiety —$OCH_2CH_2N^{30}(CH_3)_3I^-$.

30. The carbosilane dendrimer according to claim 29, wherein the "p" index takes the value 1 and each branch ends with a single —$OCH_2CH_2N^+(CH_3)_3I^-$moiety.

31. The carbosilane dendrimer according to claim 30, which is of first, second or third generation.

32. The carbosilane dendrimer according to claim 29, wherein the "p" index takes the value 2 and each branch ends with two —$OCH_2CH_2N^+(CH_3)_3I^-$moieties.

33. The carbosilane dendrimer according to claim 32, which is of first, second or third generation.

34. The carbosilane dendrimer according to claim 28, wherein the terminal moiety of the branches which contains at least one quaternized amino group is the moiety —$OCH_2$—$(C_6H_3)$-3,5-$(OCH_2CH_2N^+(CH_3)_3)I^-)_2$.

35. The carbosilane dendrimer according to claim 34, wherein the "p" index takes the value 1 and each branch ends with a single —$OCH_2$—$(C_6H_3)$-3,5-$(OCH_2CH_2N^+(CH_3)_3)I^-)_2$ moiety.

36. The carbosilane dendrimer according to claim 35, which is of first, second or third generation.

37. The carbosilane dendrimer according to claim 34, wherein the "p" index takes the value 2 and each branch ends with two —$OCH_2$—$(C_6H_3)$-3,5-$(OCH_2CH_2N^+(CH_3)_3)I^-)_2$ moieties.

38. The carbosilane dendrimer according to claim 37, which is of first, second or third generation.

39. The carbosilane dendrimer according to claim 28, wherein the terminal moiety of the branches which contains at least one quaternized amino group is the moiety —$OCH_2CH_2N(CH_3)CH_2CH_2N^+(CH_3)_3I^-$.

40. The carbosilane dendrimer according to claim 39, wherein the "p" index takes the value 1 and each branch ends with a single —$OCH_2CH_2N(CH_3)CH_2CH_2N^+(CH_3)_3I^-$ moiety.

41. The carbosilane dendrimer according to claim 40, which is of first, second or third generation.

42. The carbosilane dendrimer according to claim 39, wherein the "p" index takes the value 2 and each branch ends with two —$OCH_2CH_2N(CH_3)CH_2CH_2N^+(CH_3)_3I^-$ moieties.

43. The carbosilane dendrimer according to claim 42, which is of first, second or third generation.

44. The carbosilane dendrimer according to claim 27, wherein the terminal moiety of the branches which contains at least one quaternized amino group corresponds to the formula —$CH_2CH_2(CH_2)_e$—$N^+H_3Cl^-$, wherein "e" is a whole number between 0 and 2.

45. The carbosilane dendrimer according to claim 44, wherein "e" takes the value 1, the terminal moiety of the branches which contains at least one quaternized amino group corresponding to the formula —$CH_2CH_2(CH_2)_e$—$N^+H_3Cl^-$.

46. The carbosilane dendrimer according to claim 45, wherein the "p" index takes the value 1 and each branch ends with a single —$CH_2CH_2(CH_2)_e$—$N^+H_3Cl^-$ moiety.

47. The carbosilane dendrimer according to claim 46, wherein the carbosilane dendrimer is of first, second or third generation.

48. The carbosilane dendrimer according to claim 6, wherein the terminal moiety which contains at least one amino group forms part of an antigenic moiety.

49. The carbosilane dendrimer according to claim 48, wherein the mine moiety forms part of a peptide.

50. A composition which contains at least one carbosilane dendrimer according to claim 1.

51. The composition according to claim 50, which further contains at least one molecule of anionic or polyanionic character.

52. The composition according to claim 51, wherein the molecule of polyanionic character is a sequence of a nucleic acid or a derivative thereof.

53. The composition according to claim 52, wherein the sequence of nucleic acid or derivative thereof is an antisense DNA.

54. The composition according to claim 53, wherein at least one of the carbosilane dendrimers present have the purpose of acting as vehicle of antisense DNA or of a derivative thereof to decrease the possibilities of interaction of the antisense DNA with plasma proteins or with cell surfaces.

55. The composition according to claim 54, wherein at least one of the carbosilane dendrimers present has the purpose of facilitating the controlled release of at least one antisense DNA present therein or a derivative thereof.

56. The composition according to claim 55, wherein at least one of the carbosilane dendrimers chosen from NN, IM8 and/or IM dendrimers.

57. The composition according to claim 53, wherein the antisense DNA has the sequence SEQ ID NO: 1.

58. The composition according to claim 53, wherein the antisense DNA has the sequence SEQ ID NO:2.

59. The composition according to claim 53, wherein the antisense DNA has the sequence SEQ ID NO:3.

60. The composition according to claim 53, wherein the antisense DNA has the sequence SEQ ID NO:4.

61. The composition according to claim 53, wherein the antisense DNA has the sequence SEQ ID NO:5.

62. The composition according to claim 52, wherein the sequence of nucleic acid or derivative thereof is a two-stranded DNA sequence.

63. The composition according to claim 62, wherein the sequence of nucleic acid or derivative thereof is a plasmid or DNA derivative of a virus.

64. The composition according to claim 51, wherein the molecule of polyanionic character is an interference RNA or a derivative thereof.

65. The composition according to claim 64, wherein the molecule of the interference RNA contains the sequence SEQ ID NO:6.

66. The composition according to claim 51, wherein the molecule of anionic character is a drug with negative charge at physiological pH.

67. The composition according to claim 66, wherein the drug with negative charge is acetylsalicylic acid, indomethacin, fiuosemide, penicillin, phenytoin, tolbutamide, warfarin, nalidixic acid or chlorothiazide.

68. The composition according to claim 50, wherein at least one of the carbosilane dendrimers present has the purpose of acting as active substance designed to prevent and/or treat diseases caused by virus or by prions in whose life cycle it is capable of interfering.

69. The composition according to claim 68, wherein the disease attempted to prevent or treat is caused by the HIV virus.

70. The composition according to claim 56, wherein at least the NN dendrimer is present.

71. The composition according to claim 50, wherein at least one of the carbosilane dendrimers present has the purpose of acting as active substance designed to prevent and/or treat a disease caused by bacteria or- by fungi whose cell membranes or walls are susceptible of being altered by said dendrimer.

72. The composition according to claim 50, wherein at least one of the carbosilane dendrimers present has the purpose of acting as an active substance designed to interfere in the formation of or facilitate the dissolution of protein aggregates such as those which appear in Alzheimer's disease or in the encephalopathies caused by prions.

73. The composition which contains at least one carbosilane dendrimer according to claim 48, designed to unleash an immune response, prevents or protects the individual to whom it is supplied against a disease caused by an organism which contains the peptide or antigenic moiety bound to the dendrimer.

74. The composition according claim 51, designed to be administered by iontophoresis, by transdermal route or inhalation.

75. The composition according to claim 51, designed to be injected.

76. The composition according to claim 51, designed to form with it films to coat prosthesis structures or stent meshes so that the controlled release is produced from them of at least one dendrimer of the invention or of at least one substance present in the composition.

77. The composition which contains at least one carbosilane dendrimer according to claim 50, designed to be used in the fixation of nucleic acid molecules to surfaces.

78. The composition according to claim 77, wherein the dendrimer is Phe and/or ClNH$_4$ dendrimers.

79. The carbosilane dendrimer according to claim 1, wherein the terminal moiety of the branches corresponds to the formula:

—(CH$_2$)$_2$C$_6$H$_3$(OCH$_3$)(O(CH$_2$)$_2$N(CH$_3$)$_2$.

80. The carbosilane dendrimer according to claim 79, wherein the "p" index takes the value 1 and each branch ends with a single —(CH$_2$)$_2$C$_6$H3(OCH$_3$)(O(CH$_2$)$_2$N(CH$_3$)$_2$ moiety.

81. The carbosilane dendrimer according to claim 80, which is of first or second generation.

82. The carbosilane dendrimer according to claim 27, wherein the terminal moiety of the branches which contains at least one quaternized amino group is the moiety —(CH$_2$)$_2$C$_6$H$_3$(OCH$_3$)(O(CH$_2$)$_2$N$^+$(CH$_3$)$_3$I$^-$.

83. The carbosilane dendrimer according to claim 82, wherein the "p" index takes the value 1 and each branch ends with a single —(CH$_2$)$_2$C$_6$H$_3$(OCH$_3$)(O(CH$_2$)$_2$N$^+$(CH$_3$)$_3$I$^-$ moiety.

84. The carbosilane dendrimer according to claim 83, which is of first or second generation.

85. The carbosilane dendrimer according to claim 27, wherein the terminal moiety of the branches which contains at least one quaternized amino group is the moiety —O(CH$_2$)$_2$ N(CH$_3$)$_2$(CH$_2$)$_2$NMe$_3$$^+$2I$^-$.

86. The carbosilane dendrimer according to claim 85, wherein the "p" index takes the value 1 and each branch ends with a single —O(CH$_2$)$_2$N(CH$_3$)$_2$(CH$_2$)$_2$NMe$_3$$^+$2I$^-$ moiety.

87. The carbosilane dendrimer according to claim 86, which is of first or second generation.

88. The composition according to claim 66, wherein the drug with negative charge is selected from the group consisting of methotrexate, heparin or insulin.

89. The composition according to claim 88, wherein the carbosilane dendrimer present is selected from the group consisting of NN, NN16 or IM16 dendrimers.

90. The composition according to claim 89, wherein the carbosilane dendrimer present is the NN16 dendrimers and the drug is insulin.

91. A kit to increase the transfection rate of a molecule of anionic or polyanionic character at physiological pH which comprises at least one carbosilane dendrimer according to claim 1 with which the molecule of anionic or polyanionic character is capable of forming a complex at physiological pH.

92. The kit according to claim 91, wherein the cells to transfect are cells of the nervous system or cells of cell lines derived from the nervous system.

93. The kit according to claim 92, wherein the molecule of anionic or polyanionic character at physiological pH whose transfection rate one wants to increase is a nucleic acid or a derivative thereof.

94. The kit according to claim 93, wherein the nucleic acid is an antisense DNA or interference RNA.

95. The kit according to claim 93, wherein the nucleic acid is also included in the kit.

96. The kit according to claim 95, wherein the nucleic acid is included in the kit in a composition separate from the composition of which the carbosilane dendrimer forms part.

97. The kit according to claim 95, wherein the nucleic acid is included in the kit in the same composition of which the carbosilane dendrimer forms part.

98. The kit according to claim 97, wherein the nucleic acid is included in the kit in the same composition of which the dendrimer forms part in a negative charges:positive charges ratio which varies between 1:1 and 1:8.

99. The kit according to claim 91, wherein the carbosilane dendrimer is selected from the group consisting of NN and NN16.

SEQUENCE LISTING

<160> NUMBER OF SEQ ID NOS: 5

<210> SEQ ID NO 1
<211> LENGTH: 25
<212> TYPE: DNA
<213> ORGANISM: Artificial sequence
<220> FEATURE:
<223> OTHER INFORMATION: Antisense oligonucleotide, GF, Anti-gag, phosphorothioate bonds between nucleotides, fluorescein at 5'

<400> SEQUENCE: 1
ctctcgcacc catctctctc cttct                                        25

<210> SEQ ID NO 2
<211> LENGTH: 28
<212> TYPE: DNA
<213> ORGANISM: Artificial sequence
<220> FEATURE:
<223> OTHER INFORMATION: antisense oligonucleotide, RF, Anti-Rev, phosphorothioate between nucleotides, fluoroscein at 5' end

<400> SEQUENCE: 2
tcgtcgctgt ctccgcttct tcctgcca                                     28

<210> SEQ ID NO 3
<211> LENGTH: 18
<212> TYPE: DNA
<213> ORGANISM: Artificial sequence
<220> FEATURE:
<223> OTHER INFORMATION: antisense oligonucleotide, PPT, Anti-mRNA, phosphorothioate between nucleotides,

<400> SEQUENCE: 3
aattttcttt tccccct                                                 18

<210> SEQ ID NO 4
<211> LENGTH: 15
<212> TYPE: DNA
<213> ORGANISM: Artificial sequence
<220> FEATURE:
<223> OTHER INFORMATION: antisense oligonucleotide, PPT-TFO, Triple helix former, phosphorothioate between nucleotides,

<400> SEQUENCE: 4
ttttcttttg ggggg                                                   15

<210> SEQ ID NO 5
<211> LENGTH: 21
<212> TYPE: DNA
<213> ORGANISM: Artificial sequence
<220> FEATURE:
<223> OTHER INFORMATION: Interference RNA, ipRNA anti-CD4

<400> SEQUENCE: 5
gaucaagaga cuccucagug a                                            21